(12) United States Patent
Kortesmaa et al.

(10) Patent No.: US 6,638,907 B1
(45) Date of Patent: Oct. 28, 2003

(54) LAMININ 8 AND METHODS FOR ITS USE

(75) Inventors: Jarrko Kortesmaa, Stockholm (SE); Karl Tryggvason, Stockholm (SE)

(73) Assignee: BioStratum, Inc., Durham, NC (US)

( * ) Notice: Subject to any disclaimer, the term of this patent is extended or adjusted under 35 U.S.C. 154(b) by 0 days.

(21) Appl. No.: 09/561,818

(22) Filed: Apr. 28, 2000

Related U.S. Application Data

(60) Provisional application No. 60/182,012, filed on Feb. 11, 2000, provisional application No. 60/155,945, filed on Sep. 24, 1999, provisional application No. 60/149,738, filed on Aug. 21, 1999, and provisional application No. 60/131,720, filed on Apr. 30, 1999.

(51) Int. Cl.$^7$ ............................................. C07K 14/00
(52) U.S. Cl. ............................ 514/2; 530/300; 530/350
(58) Field of Search ................................ 530/350, 300; 514/2

(56) References Cited

U.S. PATENT DOCUMENTS

| | | |
|---|---|---|
| 5,019,087 A | 5/1991 | Nichols |
| 5,229,365 A | 7/1993 | Poltter et al. |
| 5,422,264 A | 6/1995 | Quaranta et al. |
| 5,444,158 A | 8/1995 | Engvall et al. |
| 5,510,263 A | 4/1996 | Quaranta et al. |
| 5,541,106 A | 7/1996 | Jones |
| 5,585,267 A | 12/1996 | Jones et al. |
| 5,624,905 A | 4/1997 | Engvall et al. |
| 5,658,789 A | 8/1997 | Quaranta et al. |
| 5,672,361 A | 9/1997 | Halberstadt et al. |
| 5,681,587 A | 10/1997 | Halberstadt et al. |
| 5,770,562 A | 6/1998 | Burgeson et al. |
| 5,863,743 A | 1/1999 | Campbell et al. |
| 5,872,231 A | 2/1999 | Engvall et al. |

FOREIGN PATENT DOCUMENTS

| | | |
|---|---|---|
| EP | 0204302 | 12/1986 |
| EP | 0537654 | 4/1993 |
| EP | 0704532 | 4/1996 |
| WO | WO 90/02556 | 3/1990 |
| WO | WO 98/27202 | 6/1998 |

OTHER PUBLICATIONS

Altschul, et al., J. Mol. Biol., 215, 1990, pp. 403–410.
Altschul, et al., Nucleic Acids. Res., 25, 1997, pp. 3389–3402.
Assoain, R. K. and Marcantonio, E. E., J. Clin. Invest., 100(11), 1997, pp. S15–S18.
Aumailley, M. and Krieg, T., J. Invest. Dermatol., 106, 1996, pp. 209–214.
Aumailley et al., In The Laminins, Timpl and Ekblom, eds., Harwood Academic Publishers, Amsterdam (1996), pp. 127–158.
Bailey, S. B., et al., J. Neurocytology, 22, 1993, pp. 176–184.
Bates, C. A. and Meyer, R. L., Dev. Biol., 181, 1997, pp. 91–101.
Bernier et al., Matrix Biol., 14, 1995, pp. 447–455.
Bowie, J. U. et al., Science, 247, 1990 pp. 1306–1310.
Brown, J. C., et al., J. Cell Sci., 107, 1994, pp. 329–338.
Cleland et al., Crit. Rev. Therapeutic Drug Carrier Systems, 10, 1993, pp. 307–377.
Colognato, H., et al., J. Cell Biol., 145(3), 1999, pp. 619–631.
Cunningham and Wells, Science, 244, 1989, pp. 1081–1085.
Dobeli, et al., J. Biotechnology, 7, 1988 pp. 199–216.
Donaldson, D. J., and Mahan, J. T., Cell Tissue Res., 235, 1984, pp. 221–224.
Gayle, et al., J. Biol. Chem., 268, 1993, pp. 22105–22111.
Glukhova, M., et al., Dev. Biol., 157, 1993, pp. 437–447.
Grant, D. S. and Kleinman, H. K., Regulation of Angiogenesis, Goldberg I.D., and Rosen, E.M., eds., Birkhauser Verlag, Basel, Switzerland, 1997, pp. 317–333.
Hedin, U., et al., J. Cell Biol., 107, 1988, pp. 307–319.
Kamiguchi, H., et al., Annu. Rev. Neurosci. 21, 1998, pp. 97–125.
Karlin and Altschul, Proc. Natl. Acad. Sci. USA, 87, 1990, pp. 2264–2268.
Karlin and Altschul, Proc. Natl. Acad. Sci. USA, 90, 1993, pp. 5873–5877.
Lefebvre, O., et al., Dev. Biol., 210, 1999, pp. 135–150.
Malinda, K. M. and Kleinman, H. K., Int. J. Biochem. Cell Biol., 28(9), 1996, pp. 957–959.
Malinda, K. M., et al., FASEB J., 13, 1999, pp. 53–62.
Miner, J. H. and Patton, B. L., Int. J. Biochem. Cell Biol., 31, 1999, pp. 811–816.
Nomizu, M., et al., J. Biol. Chem., 272(51), 1997, pp. 32198–32205.
Olsen, D., et al., Lab. Invest., 60(6), 1989, pp. 772–782.
Patton, B. L., et al., Neuromusc. Disord., 9, 1999, pp. 423–433.
Pinckard et al., Clin. Exp. Immunol., 2, 1967, pp. 331–340.
Ponce, M. L., et al., Circ. Res., 84, 1999, pp. 688–694.
Robbins et al., Diabetes, 36, 1987, pp. 838–845.
Ron, et al., J. Biol. Chem., 268, 1993, pp. 2984–2988.
Ryan, M. C. and Christiano, A. M., Matrix Biol., 15, 1996, pp. 369–381.
Thyberg, J., et al., J. Histochem. Cytochem., 45(6), 1997, pp. 837–846.
Thyberg, J. and Hultgårdh–Nilsson, A., Cell Tissue Res., 276, 1994, pp. 263–271.
Wewer, U. M. and Engvall, E., Neuromusc. Disord., 6, 1996, pp. 409–418.
Kortesmaa, et al., J. Biol. Chem., 2000; 275(20): 14853–14559.

(List continued on next page.)

Primary Examiner—Karen Cochrane Carlson
(74) Attorney, Agent, or Firm—McDonnell Boehnen Hulbert & Berghoff; David S. Harper

(57) ABSTRACT

The present invention provides substantially purified laminin 8, methods for making recombinant laminin 8, cells that express recombinant laminin 8, and methods for using the recombinant laminin 8 to accelerate the healing of injuries to vascular tissue and tissue of mesenchymal origin, and to promote cell attachment and migration.

3 Claims, 4 Drawing Sheets

OTHER PUBLICATIONS

Bonfil R. D., et al., *Int. J. Cancer*, 58, 1994, pp. 223–239.
Colin, et al., *Journal of Dental Research*, Jul., 1984, pp. 987–993.
Conforti et. al., *Cell Adhes. Commun.* 1(4), 1994, pp. 279–293.
Delwel et al., *J. Biol. Chem.*, 268(34), 1993, pp. 25865–25875.
Delwel et al., *Mol. Biol. Cell*, 5(2), 1994, pp. 203–215.
Durbeej et al. *J. Histochem. Cytochem.* 46(4), 1998, pp. 449–457.
Ervasti and Campbell, *J. Cell Biol.*, 122(4), 1993, pp. 809–823.
Frieser, M., et al., *Eur. J. Biochem.*, 246, 1997, pp. 727–735.
Geberhiwot, T., et al., *Exp. Cell Res.*, 253, 1999, pp. 723–732.
Georges–Labouesse et al, *Nat. Genet.* 13(3), 1996, pp. 370–373.
Gu, B.-Y., et al., *Blood*, 93(8), 1999, pp. 2533–2542.
Iivanainen, A., et al., *FEBS Lett.*, 365, 1995, pp. 183–188.
Iivanainen, A., et al., *J. Biol. Chem.*, 272(44), 1997, pp. 27862–27868.
Kallunki, T., et al., *J. Biol. Chem.*, 266(1), 1991, pp. 221–228.
Kanda et al., *Exp. Cell Res.*, 248(1), 1999, pp. 203–213.
Klein et al., *Mol. Biol. Cell* 4(10), 1993, pp. 973–982.
Kortesmaa, et al., *J. Biol. Chem.*, 2000; 275(20): 14853–14559.
Liu, J. and Mayne, R., *Matrix Biol.*, 15, 1996, pp. 433–437.
McDearmon et al., *J. Biol. Chem.* 273(37), 1998, pp. 24139–44.
Molander, et al. *Biomaterials*, 4, Oct, 1983, pp. 276–280.
Nicosia, R. F., et al., *Dev. Biol.*, 164, 1994, pp. 197–206.
Niessen et al., *Exp. Cell Res.*, 211(2), 1994, pp. 360–367.
Niimi, T., et al., *Matrix Biol.*, 16, 1997, pp. 223–230.
Nyilas, et al., *Trans. Soc. Biomater.*, 6, 1983, 85.
Patton et al, *J. Cell Biol.*, 139(6);Dec. 15, 1997, pp. 1507–1521.
Pierschbacher and Ruoslahti, 1984, *Nature* 309(5963), pp. 30–33.
Pikkarainen, T., et al., *J. Biol. Chem.*, 262(22), 1987, pp. 10454–10462.
Richards, A., et al., *Eur. J. Biochem.*, 238, 1996, pp. 813–821.
Ringelmann et al., *Exp. Cell Res.*, 246(1); Jan. 10, 1999, pp. 165–182.
Sasaki et al., *J. Biol. Chem.*, 263, 1988, pp. 16536–16544.
Sasaki and Yamada, *J. Biol. Chem.*, 262, 1987, pp. 17111–17117.
Sasaki et al., *Proc. Natl. Acad. Sci.*, 84, 1987, pp. 935–939.
Shimizu et al., *J. Biol. Chem.* 274(17), 1999, pp. 11995–2000.
Sonnenberg et al., *J. Cell Sci.* 96(Pt 2), 1990, pp. 207–217.
Sonnenberg et al., *J. Cell Sci.*, 106(Pt 4), 1993, pp. 1083–1102.
Vachon et al, *J. Clin. Invest.* 100(7), 1997, pp. 1870–1881.
van der Neut et al., *Nat. Genet.* 13(3), 1996, pp. 366–369.
Vuolteenaho et al., *J. Biol. Chem.*, 265, 1990, pp. 15611–15616.
Wayner et al., *J. Cell Biol.* 121(5), 1993, pp. 1141–1152.
Yurchenco, P. D., et al., *Proc. Natl. Acad. Sci. USA*, 94, 1997, pp. 10189–10194.
Miner et al. 1997; J. Cell Biol. 137(3):685–701.*
Pikkarainen et al. 1988; J. Biol. Chem. 263(14):6751–6758.*

* cited by examiner

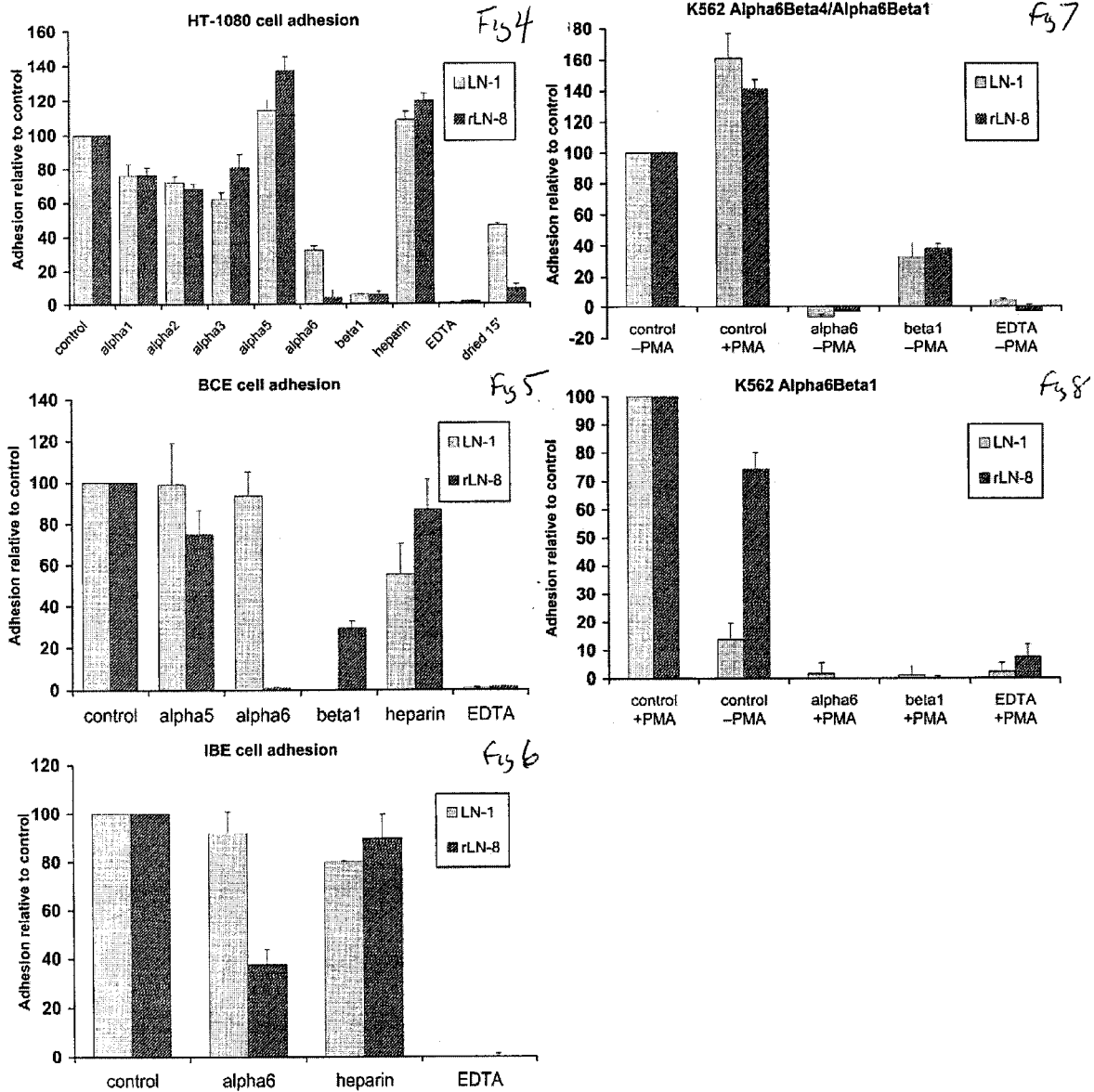

SEQUENCE LISTING

```
<160> NUMBER OF SEQ ID NOS: 28

<210> SEQ ID NO 1
<211> LENGTH: 6204
<212> TYPE: DNA
<213> ORGANISM: Homo sapiens
<220> FEATURE:
<221> NAME/KEY: CDS
<222> LOCATION: (191)..(5638)
<221> NAME/KEY: sig_peptide
<222> LOCATION: (191)..(262)

<400> SEQUENCE: 1
tagcgctggc ggggcctcac cccaatccgt ctgccttttg atgccgtact ctgctggttg     60
cgcacgcacc tcgggatact gcacacggag aggagggaaa ataagcgagg caccgccgca    120
ccacgcggag acctacggag acccacagcg cccgagccct ggaagagcac tactggatgt    180
cagcggagaa atg gct ttg agc tca gcc tgg cgc tcg gtt ctg cct ctg       229
```

```
            Met Ala Leu Ser Ser Ala Trp Arg Ser Val Leu Pro Leu
             1               5                  10 tgg ctc ctc tgg agc gct gcc tgc tcc cgc gcc gcg tcc ggg gac gac        277
Trp Leu Leu Trp Ser Ala Ala Cys Ser Arg Ala Ala Ser Gly Asp Asp
 15                  20                  25 aac gct ttt cct ttt gac att gaa ggg agc tca gcg gtt ggc agg caa        325
Asn Ala Phe Pro Phe Asp Ile Glu Gly Ser Ser Ala Val Gly Arg Gln
 30                  35                  40                  45 gac ccg cct gag acg agc gaa ccc cgc gtg gct ctg gga cgc ctg ccg        373
Asp Pro Pro Glu Thr Ser Glu Pro Arg Val Ala Leu Gly Arg Leu Pro
                 50                  55                  60 cct gcg gcc gag aaa tgc aat gct gga ttc ttt cac acc ctg tcg gga        421
Pro Ala Ala Glu Lys Cys Asn Ala Gly Phe Phe His Thr Leu Ser Gly
                 65                  70                  75 gaa tgt gtg ccc tgc gac tgt aat ggc aat tcc aac gag tgt ttg gac        469
Glu Cys Val Pro Cys Asp Cys Asn Gly Asn Ser Asn Glu Cys Leu Asp
                 80                  85                  90 ggc tca gga tac tgt gtg cac tgc cag cgg aac aca aca gga gag cac        517
Gly Ser Gly Tyr Cys Val His Cys Gln Arg Asn Thr Thr Gly Glu His
                 95                 100                 105 tgt gaa aag tgt ctg gat ggt tat atc gga gat tcc atc agg gga gca        565
Cys Glu Lys Cys Leu Asp Gly Tyr Ile Gly Asp Ser Ile Arg Gly Ala
110                 115                 120                 125 ccc caa ttc tgc cag ccg tgc ccc tgt ccc ctg ccc cac ttg gcc aat        613
Pro Gln Phe Cys Gln Pro Cys Pro Cys Pro Leu Pro His Leu Ala Asn
                130                 135                 140 ttt cca gaa tcc tgc tat agg aaa aat gga gct gtt cgg tgc att tgt        661
Phe Pro Glu Ser Cys Tyr Arg Lys Asn Gly Ala Val Arg Cys Ile Cys
                145                 150                 155 aac gaa aat tat gct gga cct aac tgt gaa aga tgt gct ccc ggt tac        709
Asn Glu Asn Tyr Ala Gly Pro Asn Cys Glu Arg Cys Ala Pro Gly Tyr
                160                 165                 170 tat gga aac ccc ttc ctc att gga agc acc tgt aag aaa tgt gac tgc        757
Tyr Gly Asn Pro Phe Leu Ile Gly Ser Thr Cys Lys Lys Cys Asp Cys
                175                 180                 185 agt gga aat tca gat ccc aac ctg atc ttt gaa gat tgt gat gaa gtc        805
Ser Gly Asn Ser Asp Pro Asn Leu Ile Phe Glu Asp Cys Asp Glu Val
190                 195                 200                 205 act ggc cag tgt agg aat tgc tta cgc aac acc acc gga ttc aag tgt        853
Thr Gly Gln Cys Arg Asn Cys Leu Arg Asn Thr Thr Gly Phe Lys Cys
                210                 215                 220 gaa cgt tgc gct cct ggc tac tat ggg gac gcc agg ata gcc aag aac        901
Glu Arg Cys Ala Pro Gly Tyr Tyr Gly Asp Ala Arg Ile Ala Lys Asn
                225                 230                 235 tgt gca gtg tgc aac tgc ggg gga ggc cca tgt gac agt gta acc gga        949
Cys Ala Val Cys Asn Cys Gly Gly Gly Pro Cys Asp Ser Val Thr Gly
                240                 245                 250 gaa tgc ttg gaa gaa ggt ttt gaa ccc cct aca ggc tgt gat aag tgc        997
Glu Cys Leu Glu Glu Gly Phe Glu Pro Pro Thr Gly Cys Asp Lys Cys
255                 260                 265 gtc tgg gac ctg act gat gac ctg cgg tta gca gcg ctc tcc atc gag       1045
Val Trp Asp Leu Thr Asp Asp Leu Arg Leu Ala Ala Leu Ser Ile Glu
270                 275                 280                 285 gaa ggc aaa tcc ggg gtg ctg agc gta tcc tct ggg gcc gcc gct cat       1093
Glu Gly Lys Ser Gly Val Leu Ser Val Ser Ser Gly Ala Ala Ala His
                290                 295                 300 agg cac gtg aat gaa atc aac gcc acc atc tac ctc ctc aaa aca aaa       1141
Arg His Val Asn Glu Ile Asn Ala Thr Ile Tyr Leu Leu Lys Thr Lys
                305                 310                 315
```

| | |
|---|---|
| ttg tca gaa aga gaa aac caa tac gcc cta aga aag ata caa atc aac<br>Leu Ser Glu Arg Glu Asn Gln Tyr Ala Leu Arg Lys Ile Gln Ile Asn<br>320                   325                   330 | 1189 |
| aat gct gag aac acg atg aaa agc ctt ctg tct gac gta gag gaa tta<br>Asn Ala Glu Asn Thr Met Lys Ser Leu Leu Ser Asp Val Glu Glu Leu<br>335                   340                   345 | 1237 |
| gtt gaa aag gaa aat caa gcc tcc aga aaa gga caa ctt gtt cag aag<br>Val Glu Lys Glu Asn Gln Ala Ser Arg Lys Gly Gln Leu Val Gln Lys<br>350                   355                   360                   365 | 1285 |
| gaa agc atg gac acc att aac cac gca agt cag ctg gta gag caa gcc<br>Glu Ser Met Asp Thr Ile Asn His Ala Ser Gln Leu Val Glu Gln Ala<br>                 370                   375                   380 | 1333 |
| cat gat atg agg gat aaa atc caa gag atc aac aac aag atg ctc tat<br>His Asp Met Arg Asp Lys Ile Gln Glu Ile Asn Asn Lys Met Leu Tyr<br>385                   390                   395 | 1381 |
| tat ggg gaa gag cat gaa ctt agc ccc aag gaa atc tct gag aag ctg<br>Tyr Gly Glu Glu His Glu Leu Ser Pro Lys Glu Ile Ser Glu Lys Leu<br>      400                   405                   410 | 1429 |
| gtg ttg gcc cag aag atg ctt gaa gag att aga agc cgt caa cca ttt<br>Val Leu Ala Gln Lys Met Leu Glu Glu Ile Arg Ser Arg Gln Pro Phe<br>415                   420                   425 | 1477 |
| ttc acc caa cgg gag ctc gtg gat gag gag gca gat gag gct tac gaa<br>Phe Thr Gln Arg Glu Leu Val Asp Glu Glu Ala Asp Glu Ala Tyr Glu<br>430                   435                   440                   445 | 1525 |
| cta ctg agc cag gct gag agc tgg cag cgg ctg cac aat gag acc cgc<br>Leu Leu Ser Gln Ala Glu Ser Trp Gln Arg Leu His Asn Glu Thr Arg<br>                 450                   455                   460 | 1573 |
| act ctg ttt cct gtc gtc ctg gag cag ctg gat gac tac aat gct aag<br>Thr Leu Phe Pro Val Val Leu Glu Gln Leu Asp Asp Tyr Asn Ala Lys<br>                 465                   470                   475 | 1621 |
| ttg tca gat ctc cag gaa gca ctt gac cag gcc ctt aac tat gtc agg<br>Leu Ser Asp Leu Gln Glu Ala Leu Asp Gln Ala Leu Asn Tyr Val Arg<br>480                   485                   490 | 1669 |
| gat gcc gaa gac atg aac agg gcc aca gca gcc agg cag cgg gac cat<br>Asp Ala Glu Asp Met Asn Arg Ala Thr Ala Ala Arg Gln Arg Asp His<br>495                   500                   505 | 1717 |
| gag aaa caa cag gaa aga gtg agg gaa caa atg gaa gtg gtg aac atg<br>Glu Lys Gln Gln Glu Arg Val Arg Glu Gln Met Glu Val Val Asn Met<br>510                   515                   520                   525 | 1765 |
| tct ctg agc aca tct gcg gac tct ctg aca aca cct cgt cta act ctt<br>Ser Leu Ser Thr Ser Ala Asp Ser Leu Thr Thr Pro Arg Leu Thr Leu<br>                 530                   535                   540 | 1813 |
| tca gaa ctt gat gat ata ata aag aat gcg tca ggg att tat gca gaa<br>Ser Glu Leu Asp Asp Ile Ile Lys Asn Ala Ser Gly Ile Tyr Ala Glu<br>                 545                   550                   555 | 1861 |
| ata gat gga gcc aaa agt gaa cta caa gta aaa cta tct aac cta agt<br>Ile Asp Gly Ala Lys Ser Glu Leu Gln Val Lys Leu Ser Asn Leu Ser<br>                 560                   565                   570 | 1909 |
| aac ctc agc cat gat tta gtc caa gaa gct att gac cat gca cag gac<br>Asn Leu Ser His Asp Leu Val Gln Glu Ala Ile Asp His Ala Gln Asp<br>575                   580                   585 | 1957 |
| ctt caa caa gaa gct aat gaa ttg agc agg aag ttg cac agt tca gat<br>Leu Gln Gln Glu Ala Asn Glu Leu Ser Arg Lys Leu His Ser Ser Asp<br>590                   595                   600                   605 | 2005 |
| atg aac ggg ctg gta cag aag gct ttg gat gca tca aat gtc tat gaa<br>Met Asn Gly Leu Val Gln Lys Ala Leu Asp Ala Ser Asn Val Tyr Glu<br>                 610                   615                   620 | 2053 |
| aat att gtt aat tat gtt agt gaa gcc aat gaa aca gca gaa ttt gct<br>Asn Ile Val Asn Tyr Val Ser Glu Ala Asn Glu Thr Ala Glu Phe Ala<br>                 625                   630                   635 | 2101 |

```
ttg aac acc act gac cga att tat gat gcg gtg agt ggg att gat act      2149
Leu Asn Thr Thr Asp Arg Ile Tyr Asp Ala Val Ser Gly Ile Asp Thr
            640                 645                 650 caa atc att tac cat aaa gat gaa agt gag aac ctc ctc aat caa gcc      2197
Gln Ile Ile Tyr His Lys Asp Glu Ser Glu Asn Leu Leu Asn Gln Ala
            655                 660                 665 aga gaa ctg caa gca aag gca gag tct agc agt gat gaa gca gtg gct      2245
Arg Glu Leu Gln Ala Lys Ala Glu Ser Ser Ser Asp Glu Ala Val Ala
670                 675                 680                 685 gac act agc agg cgt gtg ggt gga gcc cta gca agg aaa agt gcc ctt      2293
Asp Thr Ser Arg Arg Val Gly Gly Ala Leu Ala Arg Lys Ser Ala Leu
                690                 695                 700 aaa acc aga ctc agt gat gcc gtt aag caa cta caa gca gca gag aga      2341
Lys Thr Arg Leu Ser Asp Ala Val Lys Gln Leu Gln Ala Ala Glu Arg
            705                 710                 715 ggg gat gcc cag cag cgc ctg ggg cag tct aga ctg atc acc gag gaa      2389
Gly Asp Ala Gln Gln Arg Leu Gly Gln Ser Arg Leu Ile Thr Glu Glu
            720                 725                 730 gcc aac agg acg acg atg gag gtg cag cag gcc act gcc ccc atg gcc      2437
Ala Asn Arg Thr Thr Met Glu Val Gln Gln Ala Thr Ala Pro Met Ala
735                 740                 745 aac aat cta acc aac tgg tca cag aat ctt caa cat ttt gac tct tct      2485
Asn Asn Leu Thr Asn Trp Ser Gln Asn Leu Gln His Phe Asp Ser Ser
750                 755                 760                 765 gct tac aac act gca gtg aac tct gct agg gat gca gta aga aat ctg      2533
Ala Tyr Asn Thr Ala Val Asn Ser Ala Arg Asp Ala Val Arg Asn Leu
                770                 775                 780 acc gag gtt gtc cct cag ctc ctg gat cag ctt cgt acg gtt gag cag      2581
Thr Glu Val Val Pro Gln Leu Leu Asp Gln Leu Arg Thr Val Glu Gln
            785                 790                 795 aag cga cct gca agc aac gtt tct gcc agc atc cag agg atc cga gag      2629
Lys Arg Pro Ala Ser Asn Val Ser Ala Ser Ile Gln Arg Ile Arg Glu
            800                 805                 810 ctc att gct cag acc aga agt gtt gcc agc aag atc caa gtc tcc atg      2677
Leu Ile Ala Gln Thr Arg Ser Val Ala Ser Lys Ile Gln Val Ser Met
815                 820                 825 atg ttt gat ggc cag tca gct gtg gaa gtg cac tcg aga acc agt atg      2725
Met Phe Asp Gly Gln Ser Ala Val Glu Val His Ser Arg Thr Ser Met
830                 835                 840                 845 gat gac tta aag gcc ttc acg tct ctg agc ctg tac atg aaa ccc cct      2773
Asp Asp Leu Lys Ala Phe Thr Ser Leu Ser Leu Tyr Met Lys Pro Pro
                850                 855                 860 gtg aag cgg ccg gaa ctg acc gag act gca gat cag ttt atc ctg tac      2821
Val Lys Arg Pro Glu Leu Thr Glu Thr Ala Asp Gln Phe Ile Leu Tyr
            865                 870                 875 ctc gga agc aaa aac gcc aaa aaa gag tat atg ggt ctt gca atc aaa      2869
Leu Gly Ser Lys Asn Ala Lys Lys Glu Tyr Met Gly Leu Ala Ile Lys
            880                 885                 890 aat gat aat ctg gta tac gtc tat aat ttg gga act aaa gat gtg gag      2917
Asn Asp Asn Leu Val Tyr Val Tyr Asn Leu Gly Thr Lys Asp Val Glu
895                 900                 905 att ccc ctg gac tcc aag ccc gtc agt tcc tgg cct gct tac ttc agc      2965
Ile Pro Leu Asp Ser Lys Pro Val Ser Ser Trp Pro Ala Tyr Phe Ser
910                 915                 920                 925 att gtc aag att gaa agg gtg gga aaa cat gga aag gtg ttt tta aca      3013
Ile Val Lys Ile Glu Arg Val Gly Lys His Gly Lys Val Phe Leu Thr
                930                 935                 940 gtc ccg agt cta agt agc aca gca gag gaa aag ttc att aaa aag ggg      3061
Val Pro Ser Leu Ser Ser Thr Ala Glu Glu Lys Phe Ile Lys Lys Gly
```

-continued

| | |
|---|---|
| gaa ttt tcg gga gat gac tct ctg ctg gac ctg gac cct gag gac aca<br>Glu Phe Ser Gly Asp Asp Ser Leu Leu Asp Leu Asp Pro Glu Asp Thr<br>            960                            965                            970 | 3109 |
| gtg ttt tat gtt ggt gga gtg cct tcc aac ttc aag ctc cct acc agc<br>Val Phe Tyr Val Gly Gly Val Pro Ser Asn Phe Lys Leu Pro Thr Ser<br>    975                            980                          985 | 3157 |
| tta aac ctg cct ggc ttt gtt ggc tgc ctg gaa ctg gcc act ttg aat<br>Leu Asn Leu Pro Gly Phe Val Gly Cys Leu Glu Leu Ala Thr Leu Asn<br>990                       995                    1000                1005 | 3205 |
| aat gat gtg atc agc ttg tac aac ttt aag cac atc tat aat atg gac<br>Asn Asp Val Ile Ser Leu Tyr Asn Phe Lys His Ile Tyr Asn Met Asp<br>          1010                    1015                    1020 | 3253 |
| ccc tcc aca tca gtg cca tgt gcc cga gat aag ctg gcc ttc act cag<br>Pro Ser Thr Ser Val Pro Cys Ala Arg Asp Lys Leu Ala Phe Thr Gln<br>                1025                    1030                    1035 | 3301 |
| agt cgg gct gcc agt tac ttc ttc gat ggc tcc ggt tat gcc gtg gtg<br>Ser Arg Ala Ala Ser Tyr Phe Phe Asp Gly Ser Gly Tyr Ala Val Val<br>          1040                    1045                    1050 | 3349 |
| aga gac ata cca agg aga ggg aaa ttt ggt cag gtg act cgc ttt gac<br>Arg Asp Ile Pro Arg Arg Gly Lys Phe Gly Gln Val Thr Arg Phe Asp<br>1055                    1060                    1065 | 3397 |
| ata gaa gtt cga aca cca gct gac aac ggc ctt att ctc ctg atg gtc<br>Ile Glu Val Arg Thr Pro Ala Asp Asn Gly Leu Ile Leu Leu Met Val<br>1070                    1075                    1080                    1085 | 3445 |
| aat gga agt atg ttt ttc aga ctg gaa atg cgc aat ggt tac cta cat<br>Asn Gly Ser Met Phe Phe Arg Leu Glu Met Arg Asn Gly Tyr Leu His<br>          1090                    1095                    1100 | 3493 |
| gtg ttc tat gat ttt gga ttc agc agt ggc cgt gtg cat ctt gaa gat<br>Val Phe Tyr Asp Phe Gly Phe Ser Ser Gly Arg Val His Leu Glu Asp<br>                1105                    1110                    1115 | 3541 |
| acg tta aag aaa gct caa att aat gat gca aaa tac cat gag atc tca<br>Thr Leu Lys Lys Ala Gln Ile Asn Asp Ala Lys Tyr His Glu Ile Ser<br>          1120                    1125                    1130 | 3589 |
| atc att tac cac aat gat aag aaa atg atc ttg gta gtt gac aga agg<br>Ile Ile Tyr His Asn Asp Lys Lys Met Ile Leu Val Val Asp Arg Arg<br>          1135                    1140                    1145 | 3637 |
| cat gtc aag agc atg gat aat gaa aag atg aaa ata cct ttt aca gat<br>His Val Lys Ser Met Asp Asn Glu Lys Met Lys Ile Pro Phe Thr Asp<br>1150                    1155                    1160                    1165 | 3685 |
| ata tac att gga gga gct cct cca gaa atc tta caa tcc agg gcc ctc<br>Ile Tyr Ile Gly Gly Ala Pro Pro Glu Ile Leu Gln Ser Arg Ala Leu<br>          1170                    1175                    1180 | 3733 |
| aga gca cac ctt ccc cta gat atc aac ttc aga gga tgc atg aag ggc<br>Arg Ala His Leu Pro Leu Asp Ile Asn Phe Arg Gly Cys Met Lys Gly<br>          1185                    1190                    1195 | 3781 |
| ttc cag ttc caa aag aag gac ttc aat tta ctg gag cag aca gaa acc<br>Phe Gln Phe Gln Lys Lys Asp Phe Asn Leu Leu Glu Gln Thr Glu Thr<br>1200                    1205                    1210 | 3829 |
| ctg gga gtt ggt tat gga tgc cca gaa gac tca ctt ata tct cgc aga<br>Leu Gly Val Gly Tyr Gly Cys Pro Glu Asp Ser Leu Ile Ser Arg Arg<br>    1215                            1220                    1225 | 3877 |
| gca tat ttc aat gga cag agc ttc att gct tca att cag aaa ata tct<br>Ala Tyr Phe Asn Gly Gln Ser Phe Ile Ala Ser Ile Gln Lys Ile Ser<br>1230                    1235                    1240                    1245 | 3925 |
| ttc ttt gat ggc ttt gaa gga ggt ttt aat ttc cga aca tta caa cca<br>Phe Phe Asp Gly Phe Glu Gly Gly Phe Asn Phe Arg Thr Leu Gln Pro<br>          1250                    1255                    1260 | 3973 |
| aat ggg tta cta ttc tat tat gct tca ggg tca gac gtg ttc tcc atc | 4021 |

-continued

```
                Asn Gly Leu Leu Phe Tyr Tyr Ala Ser Gly Ser Asp Val Phe Ser Ile
                    1265                1270                1275 tca ctg gat aat ggt act gtc atc atg gat gta aag gga atc aaa gtt              4069
Ser Leu Asp Asn Gly Thr Val Ile Met Asp Val Lys Gly Ile Lys Val
    1280                1285                1290 cag tca gta gat aag cag tac aat gat ggg ctg tcc cac ttc gtc att              4117
Gln Ser Val Asp Lys Gln Tyr Asn Asp Gly Leu Ser His Phe Val Ile
    1295                1300                1305 agc tct gtc tca ccc aca aga tat gaa ctg ata gta gat aaa agc aga              4165
Ser Ser Val Ser Pro Thr Arg Tyr Glu Leu Ile Val Asp Lys Ser Arg
1310                1315                1320                1325 gtt ggg agt aag aat cct acc aaa ggg aaa ata gaa cag aca caa gca              4213
Val Gly Ser Lys Asn Pro Thr Lys Gly Lys Ile Glu Gln Thr Gln Ala
        1330                1335                1340 agt gaa aag aag ttt tac ttc ggt ggc tca cca atc agt gct cag tat              4261
Ser Glu Lys Lys Phe Tyr Phe Gly Gly Ser Pro Ile Ser Ala Gln Tyr
    1345                1350                1355 gct aat ttc act ggc tgc ata agt aat gcc tac ttt acc agg gtg gat              4309
Ala Asn Phe Thr Gly Cys Ile Ser Asn Ala Tyr Phe Thr Arg Val Asp
    1360                1365                1370 aga gat gtg gag gtt gaa gat ttc caa cgg tat act gaa aag gtc cac              4357
Arg Asp Val Glu Val Glu Asp Phe Gln Arg Tyr Thr Glu Lys Val His
    1375                1380                1385 act tct ctt tat gag tgt ccc att gag tct tca cca ttg ttt ctc ctc              4405
Thr Ser Leu Tyr Glu Cys Pro Ile Glu Ser Ser Pro Leu Phe Leu Leu
1390                1395                1400                1405 cat aaa aaa gga aaa aat tta tcc aag cct aaa gca agt cag aat aaa              4453
His Lys Lys Gly Lys Asn Leu Ser Lys Pro Lys Ala Ser Gln Asn Lys
        1410                1415                1420 aag gga ggg aaa agt aaa gat gca cct tca tgg gat cct gtt gct ctg              4501
Lys Gly Gly Lys Ser Lys Asp Ala Pro Ser Trp Asp Pro Val Ala Leu
    1425                1430                1435 aaa ctc cca gag cgg aat act cca aga aac tct cat tgc cac ctt tcc              4549
Lys Leu Pro Glu Arg Asn Thr Pro Arg Asn Ser His Cys His Leu Ser
        1440                1445                1450 aac agc cct aga gca ata gag cac gcc tat caa tat gga gga aca gcc              4597
Asn Ser Pro Arg Ala Ile Glu His Ala Tyr Gln Tyr Gly Gly Thr Ala
    1455                1460                1465 aac agc cgc caa gag ttt gaa cac tta aaa gga gat ttt ggt gcc aaa              4645
Asn Ser Arg Gln Glu Phe Glu His Leu Lys Gly Asp Phe Gly Ala Lys
1470                1475                1480                1485 tct cag ttt tcc att cgt ctg aga act cgt tcc tcc cat ggc atg atc              4693
Ser Gln Phe Ser Ile Arg Leu Arg Thr Arg Ser Ser His Gly Met Ile
        1490                1495                1500 ttc tat gtc tca gat caa gaa gag aat gac ttc atg act cta ttt ttg              4741
Phe Tyr Val Ser Asp Gln Glu Glu Asn Asp Phe Met Thr Leu Phe Leu
    1505                1510                1515 gcc cat ggc cgc ttg gtt tac atg ttt aat gtt ggt cac aaa aaa ctg              4789
Ala His Gly Arg Leu Val Tyr Met Phe Asn Val Gly His Lys Lys Leu
    1520                1525                1530 aag att aga agc cag gag aaa tac aat gat ggc ctg tgg cat gat gtg              4837
Lys Ile Arg Ser Gln Glu Lys Tyr Asn Asp Gly Leu Trp His Asp Val
    1535                1540                1545 ata ttt att cga gaa agg agc agt ggc cga ctg gta att gat ggt ctc              4885
Ile Phe Ile Arg Glu Arg Ser Ser Gly Arg Leu Val Ile Asp Gly Leu
1550                1555                1560                1565 cga gtc cta gaa gaa agt ctt cct cct act gaa gct acc tgg aaa atc              4933
Arg Val Leu Glu Glu Ser Leu Pro Pro Thr Glu Ala Thr Trp Lys Ile
        1570                1575                1580
```

```
aag ggt ccc att tat ttg gga ggt gtg gct cct gga aag gct gtg aaa    4981
Lys Gly Pro Ile Tyr Leu Gly Gly Val Ala Pro Gly Lys Ala Val Lys
        1585                1590                1595 aat gtt cag att aac tcc atc tac agt ttt agt ggc tgt ctc agc aat    5029
Asn Val Gln Ile Asn Ser Ile Tyr Ser Phe Ser Gly Cys Leu Ser Asn
    1600                1605                1610 ctc cag ctc aat ggg gcc tcc atc acc tct gct tct cag aca ttc agt    5077
Leu Gln Leu Asn Gly Ala Ser Ile Thr Ser Ala Ser Gln Thr Phe Ser
1615                1620                1625 gtg acc cct tgc ttt gaa ggc ccc atg gaa aca gga act tac ttt tca    5125
Val Thr Pro Cys Phe Glu Gly Pro Met Glu Thr Gly Thr Tyr Phe Ser
1630                1635                1640                1645 aca gaa gga gga tac gtg gtt cta gat gaa tct ttc aat att gga ttg    5173
Thr Glu Gly Gly Tyr Val Val Leu Asp Glu Ser Phe Asn Ile Gly Leu
        1650                1655                1660 aag ttt gaa att gca ttt gaa gtc cgt ccc aga agc agt tcc gga acc    5221
Lys Phe Glu Ile Ala Phe Glu Val Arg Pro Arg Ser Ser Ser Gly Thr
    1665                1670                1675 ctg gtc cac ggc cac agt gtc aat ggg gag tac cta aat gtt cac atg    5269
Leu Val His Gly His Ser Val Asn Gly Glu Tyr Leu Asn Val His Met
1680                1685                1690 aaa aat gga cag gtc ata gtg aaa gtc aat aat ggc atc aga gat ttt    5317
Lys Asn Gly Gln Val Ile Val Lys Val Asn Asn Gly Ile Arg Asp Phe
        1695                1700                1705 tcc acc tca gta aca ccc aag cag agt ctc tgt gat ggc aga tgg cac    5365
Ser Thr Ser Val Thr Pro Lys Gln Ser Leu Cys Asp Gly Arg Trp His
1710                1715                1720                1725 aga att aca gtt att aga gat tct aat gtg gtt cag ttg gat gtg gac    5413
Arg Ile Thr Val Ile Arg Asp Ser Asn Val Val Gln Leu Asp Val Asp
        1730                1735                1740 tct gaa gtg aac cat gtg gtt gga ccc ctg aat cca aaa cca att gat    5461
Ser Glu Val Asn His Val Val Gly Pro Leu Asn Pro Lys Pro Ile Asp
    1745                1750                1755 cac agg gag cct gtg ttt gtt gga ggt gtt cca gaa tct cta ctg aca    5509
His Arg Glu Pro Val Phe Val Gly Gly Val Pro Glu Ser Leu Leu Thr
1760                1765                1770 cca cgc ttg gcc ccc agc aaa ccc ttc aca ggc tgc ata cgc cac ttt    5557
Pro Arg Leu Ala Pro Ser Lys Pro Phe Thr Gly Cys Ile Arg His Phe
        1775                1780                1785 gtg att gat gga cac cca gtg agc ttc agt aaa gca gcc ctg gtc agc    5605
Val Ile Asp Gly His Pro Val Ser Phe Ser Lys Ala Ala Leu Val Ser
1790                1795                1800                1805 ggc gcc gta agc atc aac tcc tgt cca gca gcc tgacatgaca gagcacagct    5658
Gly Ala Val Ser Ile Asn Ser Cys Pro Ala Ala
        1810                1815 gcccaaatac aaagttcttt agagcactga agaaacaca aagccagcca ggaggaacag    5718
taactcttcc ttcgggtgga agctttcatc gagttgaaca ggacttaaac gaatcatcag    5778
ggaccggata tttcttatt ctcatttgga ttcttaacct tgaatccaaa gtgtctgcaa    5838
tggacaacaa ttgaaggaga ggcaaactta cttgtattga gagcacacgc aattcctact    5898
ggtgaaatta ctgtttctgt ttctaataaa atagaaggga ttccaaataa acacttgcac    5958
acatttttga agtgcggcta gattctcaga ttcaccttttc ttccagggaa gataactttc    6018
aatctatata aaaatctctg tcctaaaact acctttcttt attttgaaga gacttactaa    6078
cttacatata atctaaatta gatgatagat ttcttttttag ccctttttgtt tggtctatca    6138 gtataagaag aatattttag gtttatagct gaagttatca aggtttaata aagtaaattt    6198
ctaaca                                                              6204
```

```
<210> SEQ ID NO 2
<211> LENGTH: 1816
<212> TYPE: PRT
<213> ORGANISM: Homo sapiens

<400> SEQUENCE: 2
```

| | | | | | | | | | | | | | | |
|---|---|---|---|---|---|---|---|---|---|---|---|---|---|---|
| Met | Ala | Leu | Ser | Ser | Ala | Trp | Arg | Ser | Val | Leu | Pro | Leu | Trp | Leu | Leu |
| 1 | | | | 5 | | | | | 10 | | | | | 15 | |

Trp Ser Ala Ala Cys Ser Arg Ala Ala Ser Gly Asp Asp Asn Ala Phe
            20                  25                  30

Pro Phe Asp Ile Glu Gly Ser Ser Ala Val Gly Arg Gln Asp Pro Pro
        35                  40                  45

Glu Thr Ser Glu Pro Arg Val Ala Leu Gly Arg Leu Pro Pro Ala Ala
    50                  55                  60

Glu Lys Cys Asn Ala Gly Phe Phe His Thr Leu Ser Gly Glu Cys Val
65                  70                  75                  80

Pro Cys Asp Cys Asn Gly Asn Ser Asn Glu Cys Leu Asp Gly Ser Gly
                85                  90                  95

Tyr Cys Val His Cys Gln Arg Asn Thr Thr Gly Glu His Cys Glu Lys
            100                 105                 110

Cys Leu Asp Gly Tyr Ile Gly Asp Ser Ile Arg Gly Ala Pro Gln Phe
        115                 120                 125

Cys Gln Pro Cys Pro Cys Pro Leu Pro His Leu Ala Asn Phe Pro Glu
    130                 135                 140

Ser Cys Tyr Arg Lys Asn Gly Ala Val Arg Cys Ile Cys Asn Glu Asn
145                 150                 155                 160

Tyr Ala Gly Pro Asn Cys Glu Arg Cys Ala Pro Gly Tyr Tyr Gly Asn
                165                 170                 175

Pro Phe Leu Ile Gly Ser Thr Cys Lys Lys Cys Asp Cys Ser Gly Asn
            180                 185                 190

Ser Asp Pro Asn Leu Ile Phe Glu Asp Cys Asp Glu Val Thr Gly Gln
        195                 200                 205

Cys Arg Asn Cys Leu Arg Asn Thr Thr Gly Phe Lys Cys Glu Arg Cys
    210                 215                 220

Ala Pro Gly Tyr Tyr Gly Asp Ala Arg Ile Ala Lys Asn Cys Ala Val
225                 230                 235                 240

Cys Asn Cys Gly Gly Pro Cys Asp Ser Val Thr Gly Glu Cys Leu
                245                 250                 255

Glu Glu Gly Phe Glu Pro Pro Thr Gly Cys Asp Lys Cys Val Trp Asp
            260                 265                 270

Leu Thr Asp Asp Leu Arg Leu Ala Ala Leu Ser Ile Glu Glu Gly Lys
        275                 280                 285

Ser Gly Val Leu Ser Val Ser Ser Gly Ala Ala His Arg His Val
    290                 295                 300

Asn Glu Ile Asn Ala Thr Ile Tyr Leu Leu Lys Thr Lys Leu Ser Glu
305                 310                 315                 320

Arg Glu Asn Gln Tyr Ala Leu Arg Lys Ile Gln Ile Asn Asn Ala Glu
                325                 330                 335

Asn Thr Met Lys Ser Leu Leu Ser Asp Val Glu Leu Val Glu Lys
            340                 345                 350

Glu Asn Gln Ala Ser Arg Lys Gly Gln Leu Val Gln Lys Glu Ser Met
        355                 360                 365

Asp Thr Ile Asn His Ala Ser Gln Leu Val Glu Gln Ala His Asp Met

-continued

```
            370                 375                 380
Arg Asp Lys Ile Gln Glu Ile Asn Asn Lys Met Leu Tyr Tyr Gly Glu
385                 390                 395                 400

Glu His Glu Leu Ser Pro Lys Glu Ile Ser Glu Lys Leu Val Leu Ala
                405                 410                 415

Gln Lys Met Leu Glu Glu Ile Arg Ser Arg Gln Pro Phe Phe Thr Gln
                420                 425                 430

Arg Glu Leu Val Asp Glu Glu Ala Asp Glu Ala Tyr Glu Leu Leu Ser
                435                 440                 445

Gln Ala Glu Ser Trp Gln Arg Leu His Asn Glu Thr Arg Thr Leu Phe
450                 455                 460

Pro Val Val Leu Glu Gln Leu Asp Asp Tyr Asn Ala Lys Leu Ser Asp
465                 470                 475                 480

Leu Gln Glu Ala Leu Asp Gln Ala Leu Asn Tyr Val Arg Asp Ala Glu
                485                 490                 495

Asp Met Asn Arg Ala Thr Ala Ala Arg Gln Arg Asp His Glu Lys Gln
                500                 505                 510

Gln Glu Arg Val Arg Glu Gln Met Glu Val Val Asn Met Ser Leu Ser
                515                 520                 525

Thr Ser Ala Asp Ser Leu Thr Thr Pro Arg Leu Thr Leu Ser Glu Leu
530                 535                 540

Asp Asp Ile Ile Lys Asn Ala Ser Gly Ile Tyr Ala Glu Ile Asp Gly
545                 550                 555                 560

Ala Lys Ser Glu Leu Gln Val Lys Leu Ser Asn Leu Ser Asn Leu Ser
                565                 570                 575

His Asp Leu Val Gln Glu Ala Ile Asp His Ala Gln Asp Leu Gln Gln
                580                 585                 590

Glu Ala Asn Glu Leu Ser Arg Lys Leu His Ser Ser Asp Met Asn Gly
                595                 600                 605

Leu Val Gln Lys Ala Leu Asp Ala Ser Asn Val Tyr Glu Asn Ile Val
610                 615                 620

Asn Tyr Val Ser Glu Ala Asn Glu Thr Ala Glu Phe Ala Leu Asn Thr
625                 630                 635                 640

Thr Asp Arg Ile Tyr Asp Ala Val Ser Gly Ile Asp Thr Gln Ile Ile
                645                 650                 655

Tyr His Lys Asp Glu Ser Glu Asn Leu Leu Asn Gln Ala Arg Glu Leu
                660                 665                 670

Gln Ala Lys Ala Glu Ser Ser Ser Asp Glu Ala Val Ala Asp Thr Ser
                675                 680                 685

Arg Arg Val Gly Gly Ala Leu Ala Arg Lys Ser Ala Leu Lys Thr Arg
                690                 695                 700

Leu Ser Asp Ala Val Lys Gln Leu Gln Ala Ala Glu Arg Gly Asp Ala
705                 710                 715                 720

Gln Gln Arg Leu Gly Gln Ser Arg Leu Ile Thr Glu Glu Ala Asn Arg
                725                 730                 735

Thr Thr Met Glu Val Gln Gln Ala Thr Ala Pro Met Ala Asn Asn Leu
                740                 745                 750

Thr Asn Trp Ser Gln Asn Leu Gln His Phe Asp Ser Ser Ala Tyr Asn
                755                 760                 765

Thr Ala Val Asn Ser Ala Arg Asp Ala Val Arg Asn Leu Thr Glu Val
                770                 775                 780

Val Pro Gln Leu Leu Asp Gln Leu Arg Thr Val Glu Gln Lys Arg Pro
785                 790                 795                 800
```

-continued

```
Ala Ser Asn Val Ser Ala Ser Ile Gln Arg Ile Arg Glu Leu Ile Ala
            805                 810                 815
Gln Thr Arg Ser Val Ala Ser Lys Ile Gln Val Ser Met Met Phe Asp
            820                 825                 830
Gly Gln Ser Ala Val Glu Val His Ser Arg Thr Ser Met Asp Asp Leu
            835                 840                 845
Lys Ala Phe Thr Ser Leu Ser Leu Tyr Met Lys Pro Pro Val Lys Arg
            850                 855                 860
Pro Glu Leu Thr Glu Thr Ala Asp Gln Phe Ile Leu Tyr Leu Gly Ser
865                 870                 875                 880
Lys Asn Ala Lys Lys Glu Tyr Met Gly Leu Ala Ile Lys Asn Asp Asn
            885                 890                 895
Leu Val Tyr Val Tyr Asn Leu Gly Thr Lys Asp Val Glu Ile Pro Leu
            900                 905                 910
Asp Ser Lys Pro Val Ser Ser Trp Pro Ala Tyr Phe Ser Ile Val Lys
            915                 920                 925
Ile Glu Arg Val Gly Lys His Gly Lys Val Phe Leu Thr Val Pro Ser
            930                 935                 940
Leu Ser Ser Thr Ala Glu Glu Lys Phe Ile Lys Lys Gly Glu Phe Ser
945                 950                 955                 960
Gly Asp Asp Ser Leu Leu Asp Leu Asp Pro Glu Asp Thr Val Phe Tyr
            965                 970                 975
Val Gly Gly Val Pro Ser Asn Phe Lys Leu Pro Thr Ser Leu Asn Leu
            980                 985                 990
Pro Gly Phe Val Gly Cys Leu Glu Leu Ala Thr Leu Asn Asn Asp Val
            995                 1000                1005
Ile Ser Leu Tyr Asn Phe Lys His Ile Tyr Asn Met Asp Pro Ser Thr
            1010                1015                1020
Ser Val Pro Cys Ala Arg Asp Lys Leu Ala Phe Thr Gln Ser Arg Ala
1025                1030                1035                1040
Ala Ser Tyr Phe Phe Asp Gly Ser Gly Tyr Ala Val Val Arg Asp Ile
            1045                1050                1055
Pro Arg Arg Gly Lys Phe Gly Gln Val Thr Arg Phe Asp Ile Glu Val
            1060                1065                1070
Arg Thr Pro Ala Asp Asn Gly Leu Ile Leu Leu Met Val Asn Gly Ser
            1075                1080                1085
Met Phe Phe Arg Leu Glu Met Arg Asn Gly Tyr Leu His Val Phe Tyr
            1090                1095                1100
Asp Phe Gly Phe Ser Ser Gly Arg Val His Leu Glu Asp Thr Leu Lys
1105                1110                1115                1120
Lys Ala Gln Ile Asn Asp Ala Lys Tyr His Glu Ile Ser Ile Ile Tyr
            1125                1130                1135
His Asn Asp Lys Lys Met Ile Leu Val Val Asp Arg Arg His Val Lys
            1140                1145                1150
Ser Met Asp Asn Glu Lys Met Lys Ile Pro Phe Thr Asp Ile Tyr Ile
            1155                1160                1165
Gly Gly Ala Pro Pro Glu Ile Leu Gln Ser Arg Ala Leu Arg Ala His
            1170                1175                1180
Leu Pro Leu Asp Ile Asn Phe Arg Gly Cys Met Lys Gly Phe Gln Phe
1185                1190                1195                1200
Gln Lys Lys Asp Phe Asn Leu Leu Glu Gln Thr Glu Thr Leu Gly Val
            1205                1210                1215
```

-continued

```
Gly Tyr Gly Cys Pro Glu Asp Ser Leu Ile Ser Arg Arg Ala Tyr Phe
            1220                1225                1230
Asn Gly Gln Ser Phe Ile Ala Ser Ile Gln Lys Ile Ser Phe Phe Asp
        1235                1240                1245
Gly Phe Glu Gly Gly Phe Asn Phe Arg Thr Leu Gln Pro Asn Gly Leu
    1250                1255                1260
Leu Phe Tyr Tyr Ala Ser Gly Ser Asp Val Phe Ser Ile Ser Leu Asp
1265                1270                1275                1280
Asn Gly Thr Val Ile Met Asp Val Lys Gly Ile Lys Val Gln Ser Val
            1285                1290                1295
Asp Lys Gln Tyr Asn Asp Gly Leu Ser His Phe Val Ile Ser Ser Val
        1300                1305                1310
Ser Pro Thr Arg Tyr Glu Leu Ile Val Asp Lys Ser Arg Val Gly Ser
    1315                1320                1325
Lys Asn Pro Thr Lys Gly Lys Ile Glu Gln Thr Gln Ala Ser Glu Lys
1330                1335                1340
Lys Phe Tyr Phe Gly Gly Ser Pro Ile Ser Ala Gln Tyr Ala Asn Phe
1345                1350                1355                1360
Thr Gly Cys Ile Ser Asn Ala Tyr Phe Thr Arg Val Asp Arg Asp Val
            1365                1370                1375
Glu Val Glu Asp Phe Gln Arg Tyr Thr Glu Lys Val His Thr Ser Leu
        1380                1385                1390
Tyr Glu Cys Pro Ile Glu Ser Ser Pro Leu Phe Leu Leu His Lys Lys
    1395                1400                1405
Gly Lys Asn Leu Ser Lys Pro Lys Ala Ser Gln Asn Lys Lys Gly Gly
1410                1415                1420
Lys Ser Lys Asp Ala Pro Ser Trp Asp Pro Val Ala Leu Lys Leu Pro
1425                1430                1435                1440
Glu Arg Asn Thr Pro Arg Asn Ser His Cys His Leu Ser Asn Ser Pro
            1445                1450                1455
Arg Ala Ile Glu His Ala Tyr Gln Tyr Gly Gly Thr Ala Asn Ser Arg
        1460                1465                1470
Gln Glu Phe Glu His Leu Lys Gly Asp Phe Gly Ala Lys Ser Gln Phe
    1475                1480                1485
Ser Ile Arg Leu Arg Thr Arg Ser Ser His Gly Met Ile Phe Tyr Val
1490                1495                1500
Ser Asp Gln Glu Glu Asn Asp Phe Met Thr Leu Phe Leu Ala His Gly
1505                1510                1515                1520
Arg Leu Val Tyr Met Phe Asn Val Gly His Lys Lys Leu Lys Ile Arg
            1525                1530                1535
Ser Gln Glu Lys Tyr Asn Asp Gly Leu Trp His Asp Val Ile Phe Ile
        1540                1545                1550
Arg Glu Arg Ser Ser Gly Arg Leu Val Ile Asp Gly Leu Arg Val Leu
    1555                1560                1565
Glu Glu Ser Leu Pro Pro Thr Glu Ala Thr Trp Lys Ile Lys Gly Pro
1570                1575                1580
Ile Tyr Leu Gly Gly Val Ala Pro Gly Lys Ala Val Lys Asn Val Gln
1585                1590                1595                1600
Ile Asn Ser Ile Tyr Ser Phe Ser Gly Cys Leu Ser Asn Leu Gln Leu
            1605                1610                1615
Asn Gly Ala Ser Ile Thr Ser Ala Ser Gln Thr Phe Ser Val Thr Pro
        1620                1625                1630
Cys Phe Glu Gly Pro Met Glu Thr Gly Thr Tyr Phe Ser Thr Glu Gly
```

```
                1635                1640                1645
Gly Tyr Val Val Leu Asp Glu Ser Phe Asn Ile Gly Leu Lys Phe Glu
    1650                1655                1660

Ile Ala Phe Glu Val Arg Pro Arg Ser Ser Gly Thr Leu Val His
1665                1670                1675                1680

Gly His Ser Val Asn Gly Glu Tyr Leu Asn Val His Met Lys Asn Gly
                1685                1690                1695

Gln Val Ile Val Lys Val Asn Asn Gly Ile Arg Asp Phe Ser Thr Ser
            1700                1705                1710

Val Thr Pro Lys Gln Ser Leu Cys Asp Gly Arg Trp His Arg Ile Thr
        1715                1720                1725

Val Ile Arg Asp Ser Asn Val Val Gln Leu Asp Val Asp Ser Glu Val
    1730                1735                1740

Asn His Val Val Gly Pro Leu Asn Pro Lys Pro Ile Asp His Arg Glu
1745                1750                1755                1760

Pro Val Phe Val Gly Gly Val Pro Glu Ser Leu Leu Thr Pro Arg Leu
                1765                1770                1775

Ala Pro Ser Lys Pro Phe Thr Gly Cys Ile Arg His Phe Val Ile Asp
            1780                1785                1790

Gly His Pro Val Ser Phe Ser Lys Ala Ala Leu Val Ser Gly Ala Val
        1795                1800                1805

Ser Ile Asn Ser Cys Pro Ala Ala
    1810                1815

<210> SEQ ID NO 3
<211> LENGTH: 5942
<212> TYPE: DNA
<213> ORGANISM: Homo sapiens
<220> FEATURE:
<221> NAME/KEY: CDS
<222> LOCATION: (1)..(5376)

<400> SEQUENCE: 3 gcg tcc ggg gac gac aac gct ttt cct ttt gac att gaa ggg agc tca      48
Ala Ser Gly Asp Asp Asn Ala Phe Pro Phe Asp Ile Glu Gly Ser Ser
 1               5                  10                  15 gcg gtt ggc agg caa gac ccg cct gag acg agc gaa ccc cgc gtg gct      96
Ala Val Gly Arg Gln Asp Pro Pro Glu Thr Ser Glu Pro Arg Val Ala
             20                  25                  30 ctg gga cgc ctg ccg cct gcg gcc gag aaa tgc aat gct gga ttc ttt     144
Leu Gly Arg Leu Pro Pro Ala Ala Glu Lys Cys Asn Ala Gly Phe Phe
         35                  40                  45 cac acc ctg tcg gga gaa tgt gtg ccc tgc gac tgt aat ggc aat tcc     192
His Thr Leu Ser Gly Glu Cys Val Pro Cys Asp Cys Asn Gly Asn Ser
     50                  55                  60 aac gag tgt ttg gac ggc tca gga tac tgt gtg cac tgc cag cgg aac     240
Asn Glu Cys Leu Asp Gly Ser Gly Tyr Cys Val His Cys Gln Arg Asn
 65                  70                  75                  80 aca aca gga gag cac tgt gaa aag tgt ctg gat ggt tat atc gga gat     288
Thr Thr Gly Glu His Cys Glu Lys Cys Leu Asp Gly Tyr Ile Gly Asp
                 85                  90                  95 tcc atc agg gga gca ccc caa ttc tgc cag ccg tgc ccc tgt ccc ctg     336
Ser Ile Arg Gly Ala Pro Gln Phe Cys Gln Pro Cys Pro Cys Pro Leu
            100                 105                 110 ccc cac ttg gcc aat ttt cca gaa tcc tgc tat agg aaa aat gga gct     384
Pro His Leu Ala Asn Phe Pro Glu Ser Cys Tyr Arg Lys Asn Gly Ala
        115                 120                 125 gtt cgg tgc att tgt aac gaa aat tat gct gga cct aac tgt gaa aga     432
```

```
                                             Val Arg Cys Ile Cys Asn Glu Asn Tyr Ala Gly Pro Asn Cys Glu Arg
                                                 130                 135                 140 tgt gct ccc ggt tac tat gga aac ccc ttc ctc att gga agc acc tgt       480
Cys Ala Pro Gly Tyr Tyr Gly Asn Pro Phe Leu Ile Gly Ser Thr Cys
145                 150                 155                 160 aag aaa tgt gac tgc agt gga aat tca gat ccc aac ctg atc ttt gaa       528
Lys Lys Cys Asp Cys Ser Gly Asn Ser Asp Pro Asn Leu Ile Phe Glu
                165                 170                 175 gat tgt gat gaa gtc act ggc cag tgt agg aat tgc tta cgc aac acc       576
Asp Cys Asp Glu Val Thr Gly Gln Cys Arg Asn Cys Leu Arg Asn Thr
            180                 185                 190 acc gga ttc aag tgt gaa cgt tgc gct cct ggc tac tat ggg gac gcc       624
Thr Gly Phe Lys Cys Glu Arg Cys Ala Pro Gly Tyr Tyr Gly Asp Ala
        195                 200                 205 agg ata gcc aag aac tgt gca gtg tgc aac tgc ggg gga ggc cca tgt       672
Arg Ile Ala Lys Asn Cys Ala Val Cys Asn Cys Gly Gly Gly Pro Cys
    210                 215                 220 gac agt gta acc gga gaa tgc ttg gaa gaa ggt ttt gaa ccc cct aca       720
Asp Ser Val Thr Gly Glu Cys Leu Glu Glu Gly Phe Glu Pro Pro Thr
225                 230                 235                 240 ggc tgt gat aag tgc gtc tgg gac ctg act gat gac ctg cgg tta gca       768
Gly Cys Asp Lys Cys Val Trp Asp Leu Thr Asp Asp Leu Arg Leu Ala
                245                 250                 255 gcg ctc tcc atc gag gaa ggc aaa tcc ggg gtg ctg agc gta tcc tct       816
Ala Leu Ser Ile Glu Glu Gly Lys Ser Gly Val Leu Ser Val Ser Ser
            260                 265                 270 ggg gcc gcc gct cat agg cac gtg aat gaa atc aac gcc acc atc tac       864
Gly Ala Ala Ala His Arg His Val Asn Glu Ile Asn Ala Thr Ile Tyr
        275                 280                 285 ctc ctc aaa aca aaa ttg tca gaa aga gaa aac caa tac gcc cta aga       912
Leu Leu Lys Thr Lys Leu Ser Glu Arg Glu Asn Gln Tyr Ala Leu Arg
    290                 295                 300 aag ata caa atc aac aat gct gag aac acg atg aaa agc ctt ctg tct       960
Lys Ile Gln Ile Asn Asn Ala Glu Asn Thr Met Lys Ser Leu Leu Ser
305                 310                 315                 320 gac gta gag gaa tta gtt gaa aag gaa aat caa gcc tcc aga aaa gga      1008
Asp Val Glu Glu Leu Val Glu Lys Glu Asn Gln Ala Ser Arg Lys Gly
                325                 330                 335 caa ctt gtt cag aag gaa agc atg gac acc att aac cac gca agt cag      1056
Gln Leu Val Gln Lys Glu Ser Met Asp Thr Ile Asn His Ala Ser Gln
            340                 345                 350 ctg gta gag caa gcc cat gat atg agg gat aaa atc caa gag atc aac      1104
Leu Val Glu Gln Ala His Asp Met Arg Asp Lys Ile Gln Glu Ile Asn
        355                 360                 365 aac aag atg ctc tat tat ggg gaa gag cat gaa ctt agc ccc aag gaa      1152
Asn Lys Met Leu Tyr Tyr Gly Glu Glu His Glu Leu Ser Pro Lys Glu
    370                 375                 380 atc tct gag aag ctg gtg ttg gcc cag aag atg ctt gaa gag att aga      1200
Ile Ser Glu Lys Leu Val Leu Ala Gln Lys Met Leu Glu Glu Ile Arg
385                 390                 395                 400 agc cgt caa cca ttt ttc acc caa cgg gag ctc gtg gat gag gag gca      1248
Ser Arg Gln Pro Phe Phe Thr Gln Arg Glu Leu Val Asp Glu Glu Ala
                405                 410                 415 gat gag gct tac gaa cta ctg agc cag gct gag agc tgg cag cgg ctg      1296
Asp Glu Ala Tyr Glu Leu Leu Ser Gln Ala Glu Ser Trp Gln Arg Leu
            420                 425                 430 cac aat gag acc cgc act ctg ttt cct gtc gtc ctg gag cag ctg gat      1344
His Asn Glu Thr Arg Thr Leu Phe Pro Val Val Leu Glu Gln Leu Asp
        435                 440                 445
```

| | |
|---|---|
| gac tac aat gct aag ttg tca gat ctc cag gaa gca ctt gac cag gcc<br>Asp Tyr Asn Ala Lys Leu Ser Asp Leu Gln Glu Ala Leu Asp Gln Ala<br>450                            455                        460 | 1392 |
| ctt aac tat gtc agg gat gcc gaa gac atg aac agg gcc aca gca gcc<br>Leu Asn Tyr Val Arg Asp Ala Glu Asp Met Asn Arg Ala Thr Ala Ala<br>465                            470                        475                        480 | 1440 |
| agg cag cgg gac cat gag aaa caa cag gaa aga gtg agg gaa caa atg<br>Arg Gln Arg Asp His Glu Lys Gln Gln Glu Arg Val Arg Glu Gln Met<br>                    485                        490                        495 | 1488 |
| gaa gtg gtg aac atg tct ctg agc aca tct gcg gac tct ctg aca aca<br>Glu Val Val Asn Met Ser Leu Ser Thr Ser Ala Asp Ser Leu Thr Thr<br>               500                        505                        510 | 1536 |
| cct cgt cta act ctt tca gaa ctt gat gat ata ata aag aat gcg tca<br>Pro Arg Leu Thr Leu Ser Glu Leu Asp Asp Ile Ile Lys Asn Ala Ser<br>               515                        520                        525 | 1584 |
| ggg att tat gca gaa ata gat gga gcc aaa agt gaa cta caa gta aaa<br>Gly Ile Tyr Ala Glu Ile Asp Gly Ala Lys Ser Glu Leu Gln Val Lys<br>     530                        535                        540 | 1632 |
| cta tct aac cta agt aac ctc agc cat gat tta gtc caa gaa gct att<br>Leu Ser Asn Leu Ser Asn Leu Ser His Asp Leu Val Gln Glu Ala Ile<br>545                            550                        555                        560 | 1680 |
| gac cat gca cag gac ctt caa caa gaa gct aat gaa ttg agc agg aag<br>Asp His Ala Gln Asp Leu Gln Gln Glu Ala Asn Glu Leu Ser Arg Lys<br>                    565                        570                        575 | 1728 |
| ttg cac agt tca gat atg aac ggg ctg gta cag aag gct ttg gat gca<br>Leu His Ser Ser Asp Met Asn Gly Leu Val Gln Lys Ala Leu Asp Ala<br>               580                        585                        590 | 1776 |
| tca aat gtc tat gaa aat att gtt aat tat gtt agt gaa gcc aat gaa<br>Ser Asn Val Tyr Glu Asn Ile Val Asn Tyr Val Ser Glu Ala Asn Glu<br>                    595                        600                        605 | 1824 |
| aca gca gaa ttt gct ttg aac acc act gac cga att tat gat gcg gtg<br>Thr Ala Glu Phe Ala Leu Asn Thr Thr Asp Arg Ile Tyr Asp Ala Val<br>610                            615                        620 | 1872 |
| agt ggg att gat act caa atc att tac cat aaa gat gaa agt gag aac<br>Ser Gly Ile Asp Thr Gln Ile Ile Tyr His Lys Asp Glu Ser Glu Asn<br>625                            630                        635                        640 | 1920 |
| ctc ctc aat caa gcc aga gaa ctg caa gca aag gca gag tct agc agt<br>Leu Leu Asn Gln Ala Arg Glu Leu Gln Ala Lys Ala Glu Ser Ser Ser<br>                         645                        650                        655 | 1968 |
| gat gaa gca gtg gct gac act agc agg cgt gtg ggt gga gcc cta gca<br>Asp Glu Ala Val Ala Asp Thr Ser Arg Arg Val Gly Gly Ala Leu Ala<br>               660                        665                        670 | 2016 |
| agg aaa agt gcc ctt aaa acc aga ctc agt gat gcc gtt aag caa cta<br>Arg Lys Ser Ala Leu Lys Thr Arg Leu Ser Asp Ala Val Lys Gln Leu<br>                    675                        680                        685 | 2064 |
| caa gca gca gag aga ggg gat gcc cag cag cgc ctg ggg cag tct aga<br>Gln Ala Ala Glu Arg Gly Asp Ala Gln Gln Arg Leu Gly Gln Ser Arg<br>               690                        695                        700 | 2112 |
| ctg atc acc gag gaa gcc aac agg acg acg atg gag gtg cag cag gcc<br>Leu Ile Thr Glu Glu Ala Asn Arg Thr Thr Met Glu Val Gln Gln Ala<br>705                            710                        715                        720 | 2160 |
| act gcc ccc atg gcc aac aat cta acc aac tgg tca cag aat ctt caa<br>Thr Ala Pro Met Ala Asn Asn Leu Thr Asn Trp Ser Gln Asn Leu Gln<br>                    725                        730                        735 | 2208 |
| cat ttt gac tct tct gct tac aac act gca gtg aac tct gct agg gat<br>His Phe Asp Ser Ser Ala Tyr Asn Thr Ala Val Asn Ser Ala Arg Asp<br>               740                        745                        750 | 2256 |
| gca gta aga aat ctg acc gag gtt gtc cct cag ctc ctg gat cag ctt<br>Ala Val Arg Asn Leu Thr Glu Val Val Pro Gln Leu Leu Asp Gln Leu<br>               755                        760                        765 | 2304 |

```
cgt acg gtt gag cag aag cga cct gca agc aac gtt tct gcc agc atc    2352
Arg Thr Val Glu Gln Lys Arg Pro Ala Ser Asn Val Ser Ala Ser Ile
    770                 775                 780 cag agg atc cga gag ctc att gct cag acc aga agt gtt gcc agc aag    2400
Gln Arg Ile Arg Glu Leu Ile Ala Gln Thr Arg Ser Val Ala Ser Lys
785                 790                 795                 800 atc caa gtc tcc atg atg ttt gat ggc cag tca gct gtg gaa gtg cac    2448
Ile Gln Val Ser Met Met Phe Asp Gly Gln Ser Ala Val Glu Val His
                805                 810                 815 tcg aga acc agt atg gat gac tta aag gcc ttc acg tct ctg agc ctg    2496
Ser Arg Thr Ser Met Asp Asp Leu Lys Ala Phe Thr Ser Leu Ser Leu
            820                 825                 830 tac atg aaa ccc cct gtg aag cgg ccg gaa ctg acc gag act gca gat    2544
Tyr Met Lys Pro Pro Val Lys Arg Pro Glu Leu Thr Glu Thr Ala Asp
        835                 840                 845 cag ttt atc ctg tac ctc gga agc aaa aac gcc aaa aaa gag tat atg    2592
Gln Phe Ile Leu Tyr Leu Gly Ser Lys Asn Ala Lys Lys Glu Tyr Met
    850                 855                 860 ggt ctt gca atc aaa aat gat aat ctg gta tac gtc tat aat ttg gga    2640
Gly Leu Ala Ile Lys Asn Asp Asn Leu Val Tyr Val Tyr Asn Leu Gly
865                 870                 875                 880 act aaa gat gtg gag att ccc ctg gac tcc aag ccc gtc agt tcc tgg    2688
Thr Lys Asp Val Glu Ile Pro Leu Asp Ser Lys Pro Val Ser Ser Trp
                885                 890                 895 cct gct tac ttc agc att gtc aag att gaa agg gtg gga aaa cat gga    2736
Pro Ala Tyr Phe Ser Ile Val Lys Ile Glu Arg Val Gly Lys His Gly
            900                 905                 910 aag gtg ttt tta aca gtc ccg agt cta agt agc aca gca gag gaa aag    2784
Lys Val Phe Leu Thr Val Pro Ser Leu Ser Ser Thr Ala Glu Glu Lys
        915                 920                 925 ttc att aaa aag ggg gaa ttt tcg gga gat gac tct ctg ctg gac ctg    2832
Phe Ile Lys Lys Gly Glu Phe Ser Gly Asp Asp Ser Leu Leu Asp Leu
    930                 935                 940 gac cct gag gac aca gtg ttt tat gtt ggt gga gtg cct tcc aac ttc    2880
Asp Pro Glu Asp Thr Val Phe Tyr Val Gly Gly Val Pro Ser Asn Phe
945                 950                 955                 960 aag ctc cct acc agc tta aac ctg cct ggc ttt gtt ggc tgc ctg gaa    2928
Lys Leu Pro Thr Ser Leu Asn Leu Pro Gly Phe Val Gly Cys Leu Glu
                965                 970                 975 ctg gcc act ttg aat aat gat gtg atc agc ttg tac aac ttt aag cac    2976
Leu Ala Thr Leu Asn Asn Asp Val Ile Ser Leu Tyr Asn Phe Lys His
            980                 985                 990 atc tat aat atg gac ccc tca aca tca gtg cca tgt gcc cga gat aag    3024
Ile Tyr Asn Met Asp Pro Ser Thr Ser Val Pro Cys Ala Arg Asp Lys
        995                 1000                1005 ctg gcc ttc act cag agt cgg gct gcc agt tac ttc ttc gat ggc tcc    3072
Leu Ala Phe Thr Gln Ser Arg Ala Ala Ser Tyr Phe Phe Asp Gly Ser
    1010                1015                1020 ggt tat gcc gtg gtg aga gac ata cca agg aga ggg aaa ttt ggt cag    3120
Gly Tyr Ala Val Val Arg Asp Ile Pro Arg Arg Gly Lys Phe Gly Gln
1025                1030                1035                1040 gtg act cgc ttt gac ata gaa gtt cga aca cca gct gac aac ggc ctt    3168
Val Thr Arg Phe Asp Ile Glu Val Arg Thr Pro Ala Asp Asn Gly Leu
                1045                1050                1055 att ctc ctg atg gtc aat gga agt atg ttt ttc aga ctg gaa atg cgc    3216
Ile Leu Leu Met Val Asn Gly Ser Met Phe Phe Arg Leu Glu Met Arg
            1060                1065                1070 aat ggt tac cta cat gtg ttc tat gat ttt gga ttc agc agt ggc cgt    3264
Asn Gly Tyr Leu His Val Phe Tyr Asp Phe Gly Phe Ser Ser Gly Arg
```

```
                1075              1080              1085
gtg cat ctt gaa gat acg tta aag aaa gct caa att aat gat gca aaa    3312
Val His Leu Glu Asp Thr Leu Lys Lys Ala Gln Ile Asn Asp Ala Lys
   1090              1095              1100 tac cat gag atc tca atc att tac cac aat gat aag aaa atg atc ttg    3360
Tyr His Glu Ile Ser Ile Ile Tyr His Asn Asp Lys Lys Met Ile Leu
1105              1110              1115              1120 gta gtt gac aga agg cat gtc aag agc atg gat aat gaa aag atg aaa    3408
Val Val Asp Arg Arg His Val Lys Ser Met Asp Asn Glu Lys Met Lys
            1125              1130              1135 ata cct ttt aca gat ata tac att gga gga gct cct cca gaa atc tta    3456
Ile Pro Phe Thr Asp Ile Tyr Ile Gly Gly Ala Pro Pro Glu Ile Leu
   1140              1145              1150 caa tcc agg gcc ctc aga gca cac ctt ccc cta gat atc aac ttc aga    3504
Gln Ser Arg Ala Leu Arg Ala His Leu Pro Leu Asp Ile Asn Phe Arg
      1155              1160              1165 gga tgc atg aag ggc ttc cag ttc caa aag aag gac ttc aat tta ctg    3552
Gly Cys Met Lys Gly Phe Gln Phe Gln Lys Lys Asp Phe Asn Leu Leu
1170              1175              1180 gag cag aca gaa acc ctg gga gtt ggt tat gga tgc cca gaa gac tca    3600
Glu Gln Thr Glu Thr Leu Gly Val Gly Tyr Gly Cys Pro Glu Asp Ser
1185              1190              1195              1200 ctt ata tct cgc aga gca tat ttc aat gga cag agc ttc att gct tca    3648
Leu Ile Ser Arg Arg Ala Tyr Phe Asn Gly Gln Ser Phe Ile Ala Ser
            1205              1210              1215 att cag aaa ata tct ttc ttt gat ggc ttt gaa gga ggt ttt aat ttc    3696
Ile Gln Lys Ile Ser Phe Phe Asp Gly Phe Glu Gly Gly Phe Asn Phe
         1220              1225              1230 cga aca tta caa cca aat ggg tta cta ttc tat tat gct tca ggg tca    3744
Arg Thr Leu Gln Pro Asn Gly Leu Leu Phe Tyr Tyr Ala Ser Gly Ser
   1235              1240              1245 gac gtg ttc tcc atc tca ctg gat aat ggt act gtc atc atg gat gta    3792
Asp Val Phe Ser Ile Ser Leu Asp Asn Gly Thr Val Ile Met Asp Val
   1250              1255              1260 aag gga atc aaa gtt cag tca gta gat aag cag tac aat gat ggg ctg    3840
Lys Gly Ile Lys Val Gln Ser Val Asp Lys Gln Tyr Asn Asp Gly Leu
1265              1270              1275              1280 tcc cac ttc gtc att agc tct gtc tca ccc aca aga tat gaa ctg ata    3888
Ser His Phe Val Ile Ser Ser Val Ser Pro Thr Arg Tyr Glu Leu Ile
            1285              1290              1295 gta gat aaa agc aga gtt ggg agt aag aat cct acc aaa ggg aaa ata    3936
Val Asp Lys Ser Arg Val Gly Ser Lys Asn Pro Thr Lys Gly Lys Ile
         1300              1305              1310 gaa cag aca caa gca agt gaa aag aag ttt tac ttc ggt ggc tca cca    3984
Glu Gln Thr Gln Ala Ser Glu Lys Lys Phe Tyr Phe Gly Gly Ser Pro
   1315              1320              1325 atc agt gct cag tat gct aat ttc act ggc tgc ata agt aat gcc tac    4032
Ile Ser Ala Gln Tyr Ala Asn Phe Thr Gly Cys Ile Ser Asn Ala Tyr
   1330              1335              1340 ttt acc agg gtg gat aga gat gtg gag gtt gaa gat ttc caa cgg tat    4080
Phe Thr Arg Val Asp Arg Asp Val Glu Val Glu Asp Phe Gln Arg Tyr
1345              1350              1355              1360 act gaa aag gtc cac act tct ctt tat gag tgt ccc att gag tct tca    4128
Thr Glu Lys Val His Thr Ser Leu Tyr Glu Cys Pro Ile Glu Ser Ser
            1365              1370              1375 cca ttg ttt ctc ctc cat aaa aaa gga aaa aat tta tcc aag cct aaa    4176
Pro Leu Phe Leu Leu His Lys Lys Gly Lys Asn Leu Ser Lys Pro Lys
         1380              1385              1390 gca agt cag aat aaa aag gga ggg aaa agt aaa gat gca cct tca tgg    4224
```

```
                                                                    -continued Ala Ser Gln Asn Lys Lys Gly Gly Lys Ser Lys Asp Ala Pro Ser Trp
    1395                1400                1405 gat cct gtt gct ctg aaa ctc cca gag cgg aat act cca aga aac tct         4272
Asp Pro Val Ala Leu Lys Leu Pro Glu Arg Asn Thr Pro Arg Asn Ser
1410                1415                1420 cat tgc cac ctt tcc aac agc cct aga gca ata gag cac gcc tat caa         4320
His Cys His Leu Ser Asn Ser Pro Arg Ala Ile Glu His Ala Tyr Gln
1425                1430                1435                1440 tat gga gga aca gcc aac agc cgc caa gag ttt gaa cac tta aaa gga         4368
Tyr Gly Gly Thr Ala Asn Ser Arg Gln Glu Phe Glu His Leu Lys Gly
                1445                1450                1455 gat ttt ggt gcc aaa tct cag ttt tcc att cgt ctg aga act cgt tcc         4416
Asp Phe Gly Ala Lys Ser Gln Phe Ser Ile Arg Leu Arg Thr Arg Ser
        1460                1465                1470 tcc cat ggc atg atc ttc tat gtc tca gat caa gaa gag aat gac ttc         4464
Ser His Gly Met Ile Phe Tyr Val Ser Asp Gln Glu Glu Asn Asp Phe
    1475                1480                1485 atg act cta ttt ttg gcc cat ggc cgc ttg gtt tac atg ttt aat gtt         4512
Met Thr Leu Phe Leu Ala His Gly Arg Leu Val Tyr Met Phe Asn Val
1490                1495                1500 ggt cac aaa aaa ctg aag att aga agc cag gag aaa tac aat gat ggc         4560
Gly His Lys Lys Leu Lys Ile Arg Ser Gln Glu Lys Tyr Asn Asp Gly
1505                1510                1515                1520 ctg tgg cat gat gtg ata ttt att cga gaa agg agc agt ggc cga ctg         4608
Leu Trp His Asp Val Ile Phe Ile Arg Glu Arg Ser Ser Gly Arg Leu
                1525                1530                1535 gta att gat ggt ctc cga gtc cta gaa gaa agt ctt cct cct act gaa         4656
Val Ile Asp Gly Leu Arg Val Leu Glu Glu Ser Leu Pro Pro Thr Glu
        1540                1545                1550 gct acc tgg aaa atc aag ggt ccc att tat ttg gga ggt gtg gct cct         4704
Ala Thr Trp Lys Ile Lys Gly Pro Ile Tyr Leu Gly Gly Val Ala Pro
    1555                1560                1565 gga aag gct gtg aaa aat gtt cag att aac tcc atc tac agt ttt agt         4752
Gly Lys Ala Val Lys Asn Val Gln Ile Asn Ser Ile Tyr Ser Phe Ser
1570                1575                1580 ggc tgt ctc agc aat ctc cag ctc aat ggg gcc tcc atc acc tct gct         4800
Gly Cys Leu Ser Asn Leu Gln Leu Asn Gly Ala Ser Ile Thr Ser Ala
1585                1590                1595                1600 tct cag aca ttc agt gtg acc cct tgc ttt gaa ggc ccc atg gaa aca         4848
Ser Gln Thr Phe Ser Val Thr Pro Cys Phe Glu Gly Pro Met Glu Thr
                1605                1610                1615 gga act tac ttt tca aca gaa gga gga tac gtg gtt cta gat gaa tct         4896
Gly Thr Tyr Phe Ser Thr Glu Gly Gly Tyr Val Val Leu Asp Glu Ser
        1620                1625                1630 ttc aat att gga ttg aag ttt gaa att gca ttt gaa gtc cgt ccc aga         4944
Phe Asn Ile Gly Leu Lys Phe Glu Ile Ala Phe Glu Val Arg Pro Arg
    1635                1640                1645 agc agt tcc gga acc ctg gtc cac ggc cac agt gtc aat ggg gag tac         4992
Ser Ser Ser Gly Thr Leu Val His Gly His Ser Val Asn Gly Glu Tyr
1650                1655                1660 cta aat gtt cac atg aaa aat gga cag gtc ata gtg aaa gtc aat aat         5040
Leu Asn Val His Met Lys Asn Gly Gln Val Ile Val Lys Val Asn Asn
1665                1670                1675                1680 ggc atc aga gat ttt tcc acc tca gta aca ccc aag cag agt ctc tgt         5088
Gly Ile Arg Asp Phe Ser Thr Ser Val Thr Pro Lys Gln Ser Leu Cys
                1685                1690                1695 gat ggc aga tgg cac aga att aca gtt att aga gat tct aat gtg gtt         5136
Asp Gly Arg Trp His Arg Ile Thr Val Ile Arg Asp Ser Asn Val Val
        1700                1705                1710
```

-continued

| | |
|---|---|
| cag ttg gat gtg gac tct gaa gtg aac cat gtg gtt gga ccc ctg aat<br>Gln Leu Asp Val Asp Ser Glu Val Asn His Val Val Gly Pro Leu Asn<br>       1715                    1720                     1725 | 5184 |
| cca aaa cca att gat cac agg gag cct gtg ttt gtt gga ggt gtt cca<br>Pro Lys Pro Ile Asp His Arg Glu Pro Val Phe Val Gly Gly Val Pro<br>1730                     1735                     1740 | 5232 |
| gaa tct cta ctg aca cca cgc ttg gcc ccc agc aaa ccc ttc aca ggc<br>Glu Ser Leu Leu Thr Pro Arg Leu Ala Pro Ser Lys Pro Phe Thr Gly<br>1745                     1750                     1755                     1760 | 5280 |
| tgc ata cgc cac ttt gtg att gat gga cac cca gtg agc ttc agt aaa<br>Cys Ile Arg His Phe Val Ile Asp Gly His Pro Val Ser Phe Ser Lys<br>                1765                     1770                     1775 | 5328 |
| gca gcc ctg gtc agc ggc gcc gta agc atc aac tcc tgt cca gca gcc<br>Ala Ala Leu Val Ser Gly Ala Val Ser Ile Asn Ser Cys Pro Ala Ala<br>1780                     1785                     1790 | 5376 |
| tgacatgaca gagcacagct gcccaaatac aaagttcttt agagcactga aagaaacaca | 5436 |
| aagccagcca ggaggaacag taactcttcc ttcgggtgga agctttcatc gagttgaaca | 5496 |
| ggacttaaac gaatcatcag ggaccggata tttcttattt ctcatttgga ttcttaacct | 5556 |
| tgaatccaaa gtgtctgcaa tggacaacaa ttgaaggaga ggcaaactta cttgtattga | 5616 |
| gagcacacgc aattcctact ggtgaaatta ctgtttctgt ttctaataaa atagaaggga | 5676 |
| ttccaaataa acacttgcac acattttga agtgcggcta gattctcaga ttcacctttc | 5736 |
| ttccagggaa gataactttc aatctatata aaaatctctg tcctaaaact acctttcttt | 5796 |
| attttgaaga gacttactaa cttacatata atctaaatta gatgatagat ttcttttag | 5856 |
| cccttttgtt tggtctatca gtataagaag aatattttag gtttatagct gaagttatca | 5916 |
| aggtttaata aagtaaattt ctaaca | 5942 |

<210> SEQ ID NO 4
<211> LENGTH: 1792
<212> TYPE: PRT
<213> ORGANISM: Homo sapiens

<400> SEQUENCE: 4

Ala Ser Gly Asp Asp Asn Ala Phe Pro Phe Asp Ile Glu Gly Ser Ser
  1               5                  10                  15

Ala Val Gly Arg Gln Asp Pro Pro Glu Thr Ser Glu Pro Arg Val Ala
             20                  25                  30

Leu Gly Arg Leu Pro Pro Ala Ala Glu Lys Cys Asn Ala Gly Phe Phe
         35                  40                  45

His Thr Leu Ser Gly Glu Cys Val Pro Cys Asp Cys Asn Gly Asn Ser
     50                  55                  60

Asn Glu Cys Leu Asp Gly Ser Gly Tyr Cys Val His Cys Gln Arg Asn
 65                  70                  75                  80

Thr Thr Gly Glu His Cys Glu Lys Cys Leu Asp Gly Tyr Ile Gly Asp
                 85                  90                  95

Ser Ile Arg Gly Ala Pro Gln Phe Cys Gln Pro Cys Pro Cys Pro Leu
            100                 105                 110

Pro His Leu Ala Asn Phe Pro Glu Ser Cys Tyr Arg Lys Asn Gly Ala
        115                 120                 125

Val Arg Cys Ile Cys Asn Glu Asn Tyr Ala Gly Pro Asn Cys Glu Arg
    130                 135                 140

Cys Ala Pro Gly Tyr Tyr Gly Asn Pro Phe Leu Ile Gly Ser Thr Cys
145                 150                 155                 160

Lys Lys Cys Asp Cys Ser Gly Asn Ser Asp Pro Asn Leu Ile Phe Glu

-continued

```
                       165                 170                 175

Asp Cys Asp Glu Val Thr Gly Gln Cys Arg Asn Cys Leu Arg Asn Thr
                        180                 185                 190

Thr Gly Phe Lys Cys Glu Arg Cys Ala Pro Gly Tyr Tyr Gly Asp Ala
                        195                 200                 205

Arg Ile Ala Lys Asn Cys Ala Val Cys Asn Cys Gly Gly Pro Cys
                        210                 215                 220

Asp Ser Val Thr Gly Glu Cys Leu Glu Glu Gly Phe Glu Pro Pro Thr
        225                 230                 235                 240

Gly Cys Asp Lys Cys Val Trp Asp Leu Thr Asp Asp Leu Arg Leu Ala
                        245                 250                 255

Ala Leu Ser Ile Glu Glu Gly Lys Ser Gly Val Leu Ser Val Ser Ser
                        260                 265                 270

Gly Ala Ala His Arg His Val Asn Glu Ile Asn Ala Thr Ile Tyr
                        275                 280                 285

Leu Leu Lys Thr Lys Leu Ser Glu Arg Glu Asn Gln Tyr Ala Leu Arg
                        290                 295                 300

Lys Ile Gln Ile Asn Asn Ala Glu Asn Thr Met Lys Ser Leu Leu Ser
        305                 310                 315                 320

Asp Val Glu Glu Leu Val Glu Lys Glu Asn Gln Ala Ser Arg Lys Gly
                        325                 330                 335

Gln Leu Val Gln Lys Glu Ser Met Asp Thr Ile Asn His Ala Ser Gln
                        340                 345                 350

Leu Val Glu Gln Ala His Asp Met Arg Asp Lys Ile Gln Glu Ile Asn
                        355                 360                 365

Asn Lys Met Leu Tyr Tyr Gly Glu Glu His Glu Leu Ser Pro Lys Glu
                        370                 375                 380

Ile Ser Glu Lys Leu Val Leu Ala Gln Lys Met Leu Glu Glu Ile Arg
        385                 390                 395                 400

Ser Arg Gln Pro Phe Phe Thr Gln Arg Glu Leu Val Asp Glu Glu Ala
                        405                 410                 415

Asp Glu Ala Tyr Glu Leu Leu Ser Gln Ala Glu Ser Trp Gln Arg Leu
                        420                 425                 430

His Asn Glu Thr Arg Thr Leu Phe Pro Val Val Leu Glu Gln Leu Asp
                        435                 440                 445

Asp Tyr Asn Ala Lys Leu Ser Asp Leu Gln Glu Ala Leu Asp Gln Ala
                        450                 455                 460

Leu Asn Tyr Val Arg Asp Ala Glu Asp Met Asn Arg Ala Thr Ala Ala
        465                 470                 475                 480

Arg Gln Arg Asp His Glu Lys Gln Gln Glu Arg Val Arg Glu Gln Met
                        485                 490                 495

Glu Val Val Asn Met Ser Leu Ser Thr Ser Ala Asp Ser Leu Thr Thr
                        500                 505                 510

Pro Arg Leu Thr Leu Ser Glu Leu Asp Asp Ile Ile Lys Asn Ala Ser
                        515                 520                 525

Gly Ile Tyr Ala Glu Ile Asp Gly Ala Lys Ser Glu Leu Gln Val Lys
                        530                 535                 540

Leu Ser Asn Leu Ser Asn Leu Ser His Asp Leu Val Gln Glu Ala Ile
        545                 550                 555                 560

Asp His Ala Gln Asp Leu Gln Gln Glu Ala Asn Glu Leu Ser Arg Lys
                        565                 570                 575

Leu His Ser Ser Asp Met Asn Gly Leu Val Gln Lys Ala Leu Asp Ala
                        580                 585                 590
```

-continued

```
Ser Asn Val Tyr Glu Asn Ile Val Asn Tyr Val Ser Glu Ala Asn Glu
            595                 600                 605
Thr Ala Glu Phe Ala Leu Asn Thr Thr Asp Arg Ile Tyr Asp Ala Val
            610                 615                 620
Ser Gly Ile Asp Thr Gln Ile Ile Tyr His Lys Asp Glu Ser Glu Asn
625                 630                 635                 640
Leu Leu Asn Gln Ala Arg Glu Leu Gln Ala Lys Ala Glu Ser Ser Ser
                645                 650                 655
Asp Glu Ala Val Ala Asp Thr Ser Arg Arg Val Gly Gly Ala Leu Ala
            660                 665                 670
Arg Lys Ser Ala Leu Lys Thr Arg Leu Ser Asp Ala Val Lys Gln Leu
            675                 680                 685
Gln Ala Ala Glu Arg Gly Asp Ala Gln Gln Arg Leu Gly Gln Ser Arg
            690                 695                 700
Leu Ile Thr Glu Glu Ala Asn Arg Thr Thr Met Glu Val Gln Gln Ala
705                 710                 715                 720
Thr Ala Pro Met Ala Asn Asn Leu Thr Asn Trp Ser Gln Asn Leu Gln
                725                 730                 735
His Phe Asp Ser Ser Ala Tyr Asn Thr Ala Val Asn Ser Ala Arg Asp
            740                 745                 750
Ala Val Arg Asn Leu Thr Glu Val Val Pro Gln Leu Leu Asp Gln Leu
            755                 760                 765
Arg Thr Val Glu Gln Lys Arg Pro Ala Ser Asn Val Ser Ala Ser Ile
            770                 775                 780
Gln Arg Ile Arg Glu Leu Ile Ala Gln Thr Arg Ser Val Ala Ser Lys
785                 790                 795                 800
Ile Gln Val Ser Met Met Phe Asp Gly Gln Ser Ala Val Glu Val His
                805                 810                 815
Ser Arg Thr Ser Met Asp Asp Leu Lys Ala Phe Thr Ser Leu Ser Leu
            820                 825                 830
Tyr Met Lys Pro Pro Val Lys Arg Pro Glu Leu Thr Glu Thr Ala Asp
            835                 840                 845
Gln Phe Ile Leu Tyr Leu Gly Ser Lys Asn Ala Lys Lys Glu Tyr Met
850                 855                 860
Gly Leu Ala Ile Lys Asn Asp Asn Leu Val Tyr Val Tyr Asn Leu Gly
865                 870                 875                 880
Thr Lys Asp Val Glu Ile Pro Leu Asp Ser Lys Pro Val Ser Ser Trp
                885                 890                 895
Pro Ala Tyr Phe Ser Ile Val Lys Ile Glu Arg Val Gly Lys His Gly
            900                 905                 910
Lys Val Phe Leu Thr Val Pro Ser Leu Ser Ser Thr Ala Glu Glu Lys
            915                 920                 925
Phe Ile Lys Lys Gly Glu Phe Ser Gly Asp Asp Ser Leu Leu Asp Leu
930                 935                 940
Asp Pro Glu Asp Thr Val Phe Tyr Val Gly Gly Val Pro Ser Asn Phe
945                 950                 955                 960
Lys Leu Pro Thr Ser Leu Asn Leu Pro Gly Phe Val Gly Cys Leu Glu
                965                 970                 975
Leu Ala Thr Leu Asn Asn Asp Val Ile Ser Leu Tyr Asn Phe Lys His
            980                 985                 990
Ile Tyr Asn Met Asp Pro Ser Thr Ser Val Pro Cys Ala Arg Asp Lys
            995                 1000                1005
```

-continued

```
Leu Ala Phe Thr Gln Ser Arg Ala Ala Ser Tyr Phe Asp Gly Ser
    1010                1015                1020

Gly Tyr Ala Val Val Arg Asp Ile Pro Arg Arg Gly Lys Phe Gly Gln
1025                1030                1035                1040

Val Thr Arg Phe Asp Ile Glu Val Arg Thr Pro Ala Asp Asn Gly Leu
            1045                1050                1055

Ile Leu Leu Met Val Asn Gly Ser Met Phe Phe Arg Leu Glu Met Arg
            1060                1065                1070

Asn Gly Tyr Leu His Val Phe Tyr Asp Phe Gly Phe Ser Ser Gly Arg
        1075                1080                1085

Val His Leu Glu Asp Thr Leu Lys Lys Ala Gln Ile Asn Asp Ala Lys
    1090                1095                1100

Tyr His Glu Ile Ser Ile Ile Tyr His Asn Lys Lys Met Ile Leu
1105                1110                1115                1120

Val Val Asp Arg Arg His Val Lys Ser Met Asp Asn Glu Lys Met Lys
            1125                1130                1135

Ile Pro Phe Thr Asp Ile Tyr Ile Gly Gly Ala Pro Pro Glu Ile Leu
            1140                1145                1150

Gln Ser Arg Ala Leu Arg Ala His Leu Pro Leu Asp Ile Asn Phe Arg
        1155                1160                1165

Gly Cys Met Lys Gly Phe Gln Phe Gln Lys Lys Asp Phe Asn Leu Leu
    1170                1175                1180

Glu Gln Thr Glu Thr Leu Gly Val Gly Tyr Gly Cys Pro Glu Asp Ser
1185                1190                1195                1200

Leu Ile Ser Arg Arg Ala Tyr Phe Asn Gly Gln Ser Phe Ile Ala Ser
            1205                1210                1215

Ile Gln Lys Ile Ser Phe Phe Asp Gly Phe Glu Gly Gly Phe Asn Phe
        1220                1225                1230

Arg Thr Leu Gln Pro Asn Gly Leu Leu Phe Tyr Tyr Ala Ser Gly Ser
        1235                1240                1245

Asp Val Phe Ser Ile Ser Leu Asp Asn Gly Thr Val Ile Met Asp Val
    1250                1255                1260

Lys Gly Ile Lys Val Gln Ser Val Asp Lys Gln Tyr Asn Asp Gly Leu
1265                1270                1275                1280

Ser His Phe Val Ile Ser Ser Val Ser Pro Thr Arg Tyr Glu Leu Ile
            1285                1290                1295

Val Asp Lys Ser Arg Val Gly Ser Lys Asn Pro Thr Lys Gly Lys Ile
        1300                1305                1310

Glu Gln Thr Gln Ala Ser Glu Lys Lys Phe Tyr Phe Gly Gly Ser Pro
    1315                1320                1325

Ile Ser Ala Gln Tyr Ala Asn Phe Thr Gly Cys Ile Ser Asn Ala Tyr
    1330                1335                1340

Phe Thr Arg Val Asp Arg Asp Val Glu Val Glu Asp Phe Gln Arg Tyr
1345                1350                1355                1360

Thr Glu Lys Val His Thr Ser Leu Tyr Glu Cys Pro Ile Glu Ser Ser
            1365                1370                1375

Pro Leu Phe Leu Leu His Lys Lys Gly Lys Asn Leu Ser Lys Pro Lys
        1380                1385                1390

Ala Ser Gln Asn Lys Lys Gly Gly Lys Ser Lys Asp Ala Pro Ser Trp
    1395                1400                1405

Asp Pro Val Ala Leu Lys Leu Pro Glu Arg Asn Thr Pro Arg Asn Ser
    1410                1415                1420

His Cys His Leu Ser Asn Ser Pro Arg Ala Ile Glu His Ala Tyr Gln
```

-continued

```
1425                1430                1435                1440

Tyr Gly Gly Thr Ala Asn Ser Arg Gln Glu Phe Glu His Leu Lys Gly
                1445                1450                1455

Asp Phe Gly Ala Lys Ser Gln Phe Ser Ile Arg Leu Arg Thr Arg Ser
            1460                1465                1470

Ser His Gly Met Ile Phe Tyr Val Ser Asp Gln Glu Glu Asn Asp Phe
        1475                1480                1485

Met Thr Leu Phe Leu Ala His Gly Arg Leu Val Tyr Met Phe Asn Val
    1490                1495                1500

Gly His Lys Lys Leu Lys Ile Arg Ser Gln Glu Lys Tyr Asn Asp Gly
1505                1510                1515                1520

Leu Trp His Asp Val Ile Phe Ile Arg Glu Arg Ser Ser Gly Arg Leu
            1525                1530                1535

Val Ile Asp Gly Leu Arg Val Leu Glu Glu Ser Leu Pro Pro Thr Glu
        1540                1545                1550

Ala Thr Trp Lys Ile Lys Gly Pro Ile Tyr Leu Gly Gly Val Ala Pro
    1555                1560                1565

Gly Lys Ala Val Lys Asn Val Gln Ile Asn Ser Ile Tyr Ser Phe Ser
1570                1575                1580

Gly Cys Leu Ser Asn Leu Gln Leu Asn Gly Ala Ser Ile Thr Ser Ala
1585                1590                1595                1600

Ser Gln Thr Phe Ser Val Thr Pro Cys Phe Glu Gly Pro Met Glu Thr
            1605                1610                1615

Gly Thr Tyr Phe Ser Thr Glu Gly Gly Tyr Val Val Leu Asp Glu Ser
        1620                1625                1630

Phe Asn Ile Gly Leu Lys Phe Glu Ile Ala Phe Glu Val Arg Pro Arg
    1635                1640                1645

Ser Ser Ser Gly Thr Leu Val His Gly His Ser Val Asn Gly Glu Tyr
1650                1655                1660

Leu Asn Val His Met Lys Asn Gly Gln Val Ile Val Lys Val Asn Asn
1665                1670                1675                1680

Gly Ile Arg Asp Phe Ser Thr Ser Val Thr Pro Lys Gln Ser Leu Cys
            1685                1690                1695

Asp Gly Arg Trp His Arg Ile Thr Val Ile Arg Asp Ser Asn Val Val
        1700                1705                1710

Gln Leu Asp Val Asp Ser Glu Val Asn His Val Val Gly Pro Leu Asn
    1715                1720                1725

Pro Lys Pro Ile Asp His Arg Glu Pro Val Phe Val Gly Gly Val Pro
1730                1735                1740

Glu Ser Leu Leu Thr Pro Arg Leu Ala Pro Ser Lys Pro Phe Thr Gly
1745                1750                1755                1760

Cys Ile Arg His Phe Val Ile Asp Gly His Pro Val Ser Phe Ser Lys
            1765                1770                1775

Ala Ala Leu Val Ser Gly Ala Val Ser Ile Asn Ser Cys Pro Ala Ala
        1780                1785                1790

<210> SEQ ID NO 5
<211> LENGTH: 5498
<212> TYPE: DNA
<213> ORGANISM: Homo sapiens
<220> FEATURE:
<221> NAME/KEY: CDS
<222> LOCATION: (17)..(5488)
<221> NAME/KEY: sig_peptide
<222> LOCATION: (17)..(88)
<221> NAME/KEY: misc_feature
```

<222> LOCATION: (5465)..(5488)

<400> SEQUENCE: 5

| | | |
|---|---|---|
| ggatcaattc gccacc atg gct ttg agc tca gcc tgg cgc tcg gtt ctg cct<br>                      Met Ala Leu Ser Ser Ala Trp Arg Ser Val Leu Pro<br>                       1               5               10 | 52 |
| ctg tgg ctc ctc tgg agc gct gcc tgc tcc cgc gcc gcg tcc ggg gac<br>Leu Trp Leu Leu Trp Ser Ala Ala Cys Ser Arg Ala Ala Ser Gly Asp<br>         15                   20                 25 | 100 |
| gac aac gct ttt cct ttt gac att gaa ggg agc tca gcg gtt ggc agg<br>Asp Asn Ala Phe Pro Phe Asp Ile Glu Gly Ser Ser Ala Val Gly Arg<br>30                 35                 40 | 148 |
| caa gac ccg cct gag acg agc gaa ccc cgc gtg gct ctg gga cgc ctg<br>Gln Asp Pro Pro Glu Thr Ser Glu Pro Arg Val Ala Leu Gly Arg Leu<br>45                 50                55                60 | 196 |
| ccg cct gcg gcc gag aaa tgc aat gct gga ttc ttt cac acc ctg tcg<br>Pro Pro Ala Ala Glu Lys Cys Asn Ala Gly Phe Phe His Thr Leu Ser<br>                 65                 70                 75 | 244 |
| gga gaa tgt gtg ccc tgc gac tgt aat ggc aat tcc aac gag tgt ttg<br>Gly Glu Cys Val Pro Cys Asp Cys Asn Gly Asn Ser Asn Glu Cys Leu<br>                    80                 85                 90 | 292 |
| gac ggc tca gga tac tgt gtg cac tgc cag cgg aac aca aca gga gag<br>Asp Gly Ser Gly Tyr Cys Val His Cys Gln Arg Asn Thr Thr Gly Glu<br>                    95               100             105 | 340 |
| cac tgt gaa aag tgt ctg gat ggt tat atc gga gat tcc atc agg gga<br>His Cys Glu Lys Cys Leu Asp Gly Tyr Ile Gly Asp Ser Ile Arg Gly<br>110                115               120 | 388 |
| gca ccc caa ttc tgc cag ccg tgc ccc tgt ccc ctg ccc cac ttg gcc<br>Ala Pro Gln Phe Cys Gln Pro Cys Pro Cys Pro Leu Pro His Leu Ala<br>125                130               135              140 | 436 |
| aat ttt cca gaa tcc tgc tat agg aaa aat gga gct gtt cgg tgc att<br>Asn Phe Pro Glu Ser Cys Tyr Arg Lys Asn Gly Ala Val Arg Cys Ile<br>                   145                 150              155 | 484 |
| tgt aac gaa aat tat gct gga cct aac tgt gaa aga tgt gct ccc ggt<br>Cys Asn Glu Asn Tyr Ala Gly Pro Asn Cys Glu Arg Cys Ala Pro Gly<br>                    160               165              170 | 532 |
| tac tat gga aac ccc ttc ctc att gga agc acc tgt aag aaa tgt gac<br>Tyr Tyr Gly Asn Pro Phe Leu Ile Gly Ser Thr Cys Lys Lys Cys Asp<br>175                180               185 | 580 |
| tgc agt gga aat tca gat ccc aac ctg atc ttt gaa gat tgt gat gaa<br>Cys Ser Gly Asn Ser Asp Pro Asn Leu Ile Phe Glu Asp Cys Asp Glu<br>190                195               200 | 628 |
| gtc act ggc cag tgt agg aat tgc tta cgc aac acc acc gga ttc aag<br>Val Thr Gly Gln Cys Arg Asn Cys Leu Arg Asn Thr Thr Gly Phe Lys<br>205                210               215              220 | 676 |
| tgt gaa cgt tgc gct cct ggc tac tat ggg gac gcc agg ata gcc aag<br>Cys Glu Arg Cys Ala Pro Gly Tyr Tyr Gly Asp Ala Arg Ile Ala Lys<br>                   225                 230              235 | 724 |
| aac tgt gca gtg tgc aac tgc ggg gga ggc cca tgt gac agt gta acc<br>Asn Cys Ala Val Cys Asn Cys Gly Gly Gly Pro Cys Asp Ser Val Thr<br>                    240               245              250 | 772 |
| gga gaa tgc ttg gaa gaa ggt ttt gaa ccc cct aca ggc tgt gat aag<br>Gly Glu Cys Leu Glu Glu Gly Phe Glu Pro Pro Thr Gly Cys Asp Lys<br>255                260               265 | 820 |
| tgc gtc tgg gac ctg act gat gac ctg cgg tta gca gcg ctc tcc atc<br>Cys Val Trp Asp Leu Thr Asp Asp Leu Arg Leu Ala Ala Leu Ser Ile<br>270                275               280 | 868 |
| gag gaa ggc aaa tcc ggg gtg ctg agc gta tcc tct ggg gcc gcc gct<br>Glu Glu Gly Lys Ser Gly Val Leu Ser Val Ser Ser Gly Ala Ala Ala<br>285                290               295              300 | 916 |

```
cat agg cac gtg aat gaa atc aac gcc acc atc tac ctc ctc aaa aca        964
His Arg His Val Asn Glu Ile Asn Ala Thr Ile Tyr Leu Leu Lys Thr
                    305                 310                 315 aaa ttg tca gaa aga gaa aac caa tac gcc cta aga aag ata caa atc       1012
Lys Leu Ser Glu Arg Glu Asn Gln Tyr Ala Leu Arg Lys Ile Gln Ile
                320                 325                 330 aac aat gct gag aac acg atg aaa agc ctt ctg tct gac gta gag gaa       1060
Asn Asn Ala Glu Asn Thr Met Lys Ser Leu Leu Ser Asp Val Glu Glu
                335                 340                 345 tta gtt gaa aag gaa aat caa gcc tcc aga aaa gga caa ctt gtt cag       1108
Leu Val Glu Lys Glu Asn Gln Ala Ser Arg Lys Gly Gln Leu Val Gln
            350                 355                 360 aag gaa agc atg gac acc att aac cac gca agt cag ctg gta gag caa       1156
Lys Glu Ser Met Asp Thr Ile Asn His Ala Ser Gln Leu Val Glu Gln
365                 370                 375                 380 gcc cat gat atg agg gat aaa atc caa gag atc aac aac aag atg ctc       1204
Ala His Asp Met Arg Asp Lys Ile Gln Glu Ile Asn Asn Lys Met Leu
                385                 390                 395 tat tat ggg gaa gag cat gaa ctt agc ccc aag gaa atc tct gag aag       1252
Tyr Tyr Gly Glu Glu His Glu Leu Ser Pro Lys Glu Ile Ser Glu Lys
                400                 405                 410 ctg gtg ttg gcc cag aag atg ctt gaa gag att aga agc cgt caa cca       1300
Leu Val Leu Ala Gln Lys Met Leu Glu Glu Ile Arg Ser Arg Gln Pro
                415                 420                 425 ttt ttc acc caa cgg gag ctc gtg gat gag gag gca gat gag gct tac       1348
Phe Phe Thr Gln Arg Glu Leu Val Asp Glu Glu Ala Asp Glu Ala Tyr
            430                 435                 440 gaa cta ctg agc cag gct gag agc tgg cag cgg ctg cac aat gag acc       1396
Glu Leu Leu Ser Gln Ala Glu Ser Trp Gln Arg Leu His Asn Glu Thr
445                 450                 455                 460 cgc act ctg ttt cct gtc gtc ctg gag cag ctg gat gac tac aat gct       1444
Arg Thr Leu Phe Pro Val Val Leu Glu Gln Leu Asp Asp Tyr Asn Ala
                465                 470                 475 aag ttg tca gat ctc cag gaa gca ctt gac cag gcc ctt aac tat gtc       1492
Lys Leu Ser Asp Leu Gln Glu Ala Leu Asp Gln Ala Leu Asn Tyr Val
                480                 485                 490 agg gat gcc gaa gac atg aac agg gcc aca gca gcc agg cag cgg gac       1540
Arg Asp Ala Glu Asp Met Asn Arg Ala Thr Ala Ala Arg Gln Arg Asp
                495                 500                 505 cat gag aaa caa cag gaa aga gtg agg gaa caa atg gaa gtg gtg aac       1588
His Glu Lys Gln Gln Glu Arg Val Arg Glu Gln Met Glu Val Val Asn
510                 515                 520 atg tct ctg agc aca tct gcg gac tct ctg aca aca cct cgt cta act       1636
Met Ser Leu Ser Thr Ser Ala Asp Ser Leu Thr Thr Pro Arg Leu Thr
525                 530                 535                 540 ctt tca gaa ctt gat gat ata ata aag aat gcg tca ggg att tat gca       1684
Leu Ser Glu Leu Asp Asp Ile Ile Lys Asn Ala Ser Gly Ile Tyr Ala
                545                 550                 555 gaa ata gat gga gcc aaa agt gaa cta caa gta aaa cta tct aac cta       1732
Glu Ile Asp Gly Ala Lys Ser Glu Leu Gln Val Lys Leu Ser Asn Leu
                560                 565                 570 agt aac ctc agc cat gat tta gtc caa gaa gct att gac cat gca cag       1780
Ser Asn Leu Ser His Asp Leu Val Gln Glu Ala Ile Asp His Ala Gln
                575                 580                 585 gac ctt caa caa gaa gct aat gaa ttg agc agg aag ttg cac agt tca       1828
Asp Leu Gln Gln Glu Ala Asn Glu Leu Ser Arg Lys Leu His Ser Ser
                590                 595                 600 gat atg aac ggg ctg gta cag aag gct ttg gat gca tca aat gtc tat       1876
Asp Met Asn Gly Leu Val Gln Lys Ala Leu Asp Ala Ser Asn Val Tyr
```

```
                605                  610                  615                  620
gaa  aat  att  gtt  aat  tat  gtt  agt  gaa  gcc  aat  gaa  aca  gca  gaa  ttt    1924
Glu  Asn  Ile  Val  Asn  Tyr  Val  Ser  Glu  Ala  Asn  Glu  Thr  Ala  Glu  Phe
                         625                  630                  635 gct  ttg  aac  acc  act  gac  cga  att  tat  gat  gcg  gtg  agt  ggg  att  gat    1972
Ala  Leu  Asn  Thr  Thr  Asp  Arg  Ile  Tyr  Asp  Ala  Val  Ser  Gly  Ile  Asp
                    640                  645                  650 act  caa  atc  att  tac  cat  aaa  gat  gaa  agt  gag  aac  ctc  ctc  aat  caa    2020
Thr  Gln  Ile  Ile  Tyr  His  Lys  Asp  Glu  Ser  Glu  Asn  Leu  Leu  Asn  Gln
               655                  660                  665 gcc  aga  gaa  ctg  caa  gca  aag  gca  gag  tct  agc  agt  gat  gaa  gca  gtg    2068
Ala  Arg  Glu  Leu  Gln  Ala  Lys  Ala  Glu  Ser  Ser  Ser  Asp  Glu  Ala  Val
          670                  675                  680 gct  gac  act  agc  agg  cgt  gtg  ggt  gga  gcc  cta  gca  agg  aaa  agt  gcc    2116
Ala  Asp  Thr  Ser  Arg  Arg  Val  Gly  Gly  Ala  Leu  Ala  Arg  Lys  Ser  Ala
685                  690                  695                  700 ctt  aaa  acc  aga  ctc  agt  gat  gcc  gtt  aag  caa  cta  caa  gca  gca  gag    2164
Leu  Lys  Thr  Arg  Leu  Ser  Asp  Ala  Val  Lys  Gln  Leu  Gln  Ala  Ala  Glu
                    705                  710                  715 aga  ggg  gat  gcc  cag  cag  cgc  ctg  ggg  cag  tct  aga  ctg  atc  acc  gag    2212
Arg  Gly  Asp  Ala  Gln  Gln  Arg  Leu  Gly  Gln  Ser  Arg  Leu  Ile  Thr  Glu
               720                  725                  730 gaa  gcc  aac  agg  acg  acg  atg  gag  gtg  cag  cag  gcc  act  gcc  ccc  atg    2260
Glu  Ala  Asn  Arg  Thr  Thr  Met  Glu  Val  Gln  Gln  Ala  Thr  Ala  Pro  Met
          735                  740                  745 gcc  aac  aat  cta  acc  aac  tgg  tca  cag  aat  ctt  caa  cat  ttt  gac  tct    2308
Ala  Asn  Asn  Leu  Thr  Asn  Trp  Ser  Gln  Asn  Leu  Gln  His  Phe  Asp  Ser
750                  755                  760 tct  gct  tac  aac  act  gca  gtg  aac  tct  gct  agg  gat  gca  gta  aga  aat    2356
Ser  Ala  Tyr  Asn  Thr  Ala  Val  Asn  Ser  Ala  Arg  Asp  Ala  Val  Arg  Asn
765                  770                  775                  780 ctg  acc  gag  gtt  gtc  cct  cag  ctc  ctg  gat  cag  ctt  cgt  acg  gtt  gag    2404
Leu  Thr  Glu  Val  Val  Pro  Gln  Leu  Leu  Asp  Gln  Leu  Arg  Thr  Val  Glu
                    785                  790                  795 cag  aag  cga  cct  gca  agc  aac  gtt  tct  gcc  agc  atc  cag  agg  atc  cga    2452
Gln  Lys  Arg  Pro  Ala  Ser  Asn  Val  Ser  Ala  Ser  Ile  Gln  Arg  Ile  Arg
          800                  805                  810 gag  ctc  att  gct  cag  acc  aga  agt  gtt  gcc  agc  aag  atc  caa  gtc  tcc    2500
Glu  Leu  Ile  Ala  Gln  Thr  Arg  Ser  Val  Ala  Ser  Lys  Ile  Gln  Val  Ser
               815                  820                  825 atg  atg  ttt  gat  ggc  cag  tca  gct  gtg  gaa  gtg  cac  tcg  aga  acc  agt    2548
Met  Met  Phe  Asp  Gly  Gln  Ser  Ala  Val  Glu  Val  His  Ser  Arg  Thr  Ser
          830                  835                  840 atg  gat  gac  tta  aag  gcc  ttc  acg  tct  ctg  agc  ctg  tac  atg  aaa  ccc    2596
Met  Asp  Asp  Leu  Lys  Ala  Phe  Thr  Ser  Leu  Ser  Leu  Tyr  Met  Lys  Pro
845                  850                  855                  860 cct  gtg  aag  cgg  ccg  gaa  ctg  acc  gag  act  gca  gat  cag  ttt  atc  ctg    2644
Pro  Val  Lys  Arg  Pro  Glu  Leu  Thr  Glu  Thr  Ala  Asp  Gln  Phe  Ile  Leu
               865                  870                  875 tac  ctc  gga  agc  aaa  aac  gcc  aaa  aaa  gag  tat  atg  ggt  ctt  gca  atc    2692
Tyr  Leu  Gly  Ser  Lys  Asn  Ala  Lys  Lys  Glu  Tyr  Met  Gly  Leu  Ala  Ile
          880                  885                  890 aaa  aat  gat  aat  ctg  gta  tac  gtc  tat  aat  ttg  gga  act  aaa  gat  gtg    2740
Lys  Asn  Asp  Asn  Leu  Val  Tyr  Val  Tyr  Asn  Leu  Gly  Thr  Lys  Asp  Val
               895                  900                  905 gag  att  ccc  ctg  gac  tcc  aag  ccc  gtc  agt  tcc  tgg  cct  gct  tac  ttc    2788
Glu  Ile  Pro  Leu  Asp  Ser  Lys  Pro  Val  Ser  Ser  Trp  Pro  Ala  Tyr  Phe
          910                  915                  920 agc  att  gtc  aag  att  gaa  agg  gtg  gga  aaa  cat  gga  aag  gtg  ttt  tta    2836
```

```
Ser Ile Val Lys Ile Glu Arg Val Gly Lys His Gly Lys Val Phe Leu
925                 930                 935                 940 aca gtc ccg agt cta agt agc aca gca gag gaa aag ttc att aaa aag      2884
Thr Val Pro Ser Leu Ser Ser Thr Ala Glu Glu Lys Phe Ile Lys Lys
                945                 950                 955 ggg gaa ttt tcg gga gat gac tct ctg ctg gac ctg gac cct gag gac      2932
Gly Glu Phe Ser Gly Asp Asp Ser Leu Leu Asp Leu Asp Pro Glu Asp
                960                 965                 970 aca gtg ttt tat gtt ggt gga gtg cct tcc aac ttc aag ctc cct acc      2980
Thr Val Phe Tyr Val Gly Gly Val Pro Ser Asn Phe Lys Leu Pro Thr
            975                 980                 985 agc tta aac ctg cct ggc ttt gtt ggc tgc ctg gaa ctg gcc act ttg      3028
Ser Leu Asn Leu Pro Gly Phe Val Gly Cys Leu Glu Leu Ala Thr Leu
        990                 995                 1000 aat aat gat gtg atc agc ttg tac aac ttt aag cac atc tat aat atg      3076
Asn Asn Asp Val Ile Ser Leu Tyr Asn Phe Lys His Ile Tyr Asn Met
1005                1010                1015                1020 gac ccc tcc aca tca gtg cca tgt gcc cga gat aag ctg gcc ttc act      3124
Asp Pro Ser Thr Ser Val Pro Cys Ala Arg Asp Lys Leu Ala Phe Thr
                1025                1030                1035 cag agt cgg gct gcc agt tac ttc ttc gat ggc tcc ggt tat gcc gtg      3172
Gln Ser Arg Ala Ala Ser Tyr Phe Phe Asp Gly Ser Gly Tyr Ala Val
                1040                1045                1050 gtg aga gac ata cca agg aga ggg aaa ttt ggt cag gtg act cgc ttt      3220
Val Arg Asp Ile Pro Arg Arg Gly Lys Phe Gly Gln Val Thr Arg Phe
            1055                1060                1065 gac ata gaa gtt cga aca cca gct gac aac ggc ctt att ctc ctg atg      3268
Asp Ile Glu Val Arg Thr Pro Ala Asp Asn Gly Leu Ile Leu Leu Met
    1070                1075                1080 gtc aat gga agt atg ttt ttc aga ctg gaa atg cgc aat ggt tac cta      3316
Val Asn Gly Ser Met Phe Phe Arg Leu Glu Met Arg Asn Gly Tyr Leu
1085                1090                1095                1100 cat gtg ttc tat gat ttt gga ttc agc agt ggc cgt gtg cat ctt gaa      3364
His Val Phe Tyr Asp Phe Gly Phe Ser Ser Gly Arg Val His Leu Glu
                1105                1110                1115 gat acg tta aag aaa gct caa att aat gat gca aaa tac cat gag atc      3412
Asp Thr Leu Lys Lys Ala Gln Ile Asn Asp Ala Lys Tyr His Glu Ile
                1120                1125                1130 tca atc att tac cac aat gat aag aaa atg atc ttg gta gtt gac aga      3460
Ser Ile Ile Tyr His Asn Asp Lys Lys Met Ile Leu Val Val Asp Arg
            1135                1140                1145 agg cat gtc aag agc atg gat aat gaa aag atg aaa ata cct ttt aca      3508
Arg His Val Lys Ser Met Asp Asn Glu Lys Met Lys Ile Pro Phe Thr
    1150                1155                1160 gat ata tac att gga gga gct cct cca gaa atc tta caa tcc agg gcc      3556
Asp Ile Tyr Ile Gly Gly Ala Pro Pro Glu Ile Leu Gln Ser Arg Ala
1165                1170                1175                1180 ctc aga gca cac ctt ccc cta gat atc aac ttc aga gga tgc atg aag      3604
Leu Arg Ala His Leu Pro Leu Asp Ile Asn Phe Arg Gly Cys Met Lys
                1185                1190                1195 ggc ttc cag ttc caa aag aag gac ttc aat tta ctg gag cag aca gaa      3652
Gly Phe Gln Phe Gln Lys Lys Asp Phe Asn Leu Leu Glu Gln Thr Glu
                1200                1205                1210 acc ctg gga gtt ggt tat gga tgc cca gaa gac tca ctt ata tct cgc      3700
Thr Leu Gly Val Gly Tyr Gly Cys Pro Glu Asp Ser Leu Ile Ser Arg
            1215                1220                1225 aga gca tat ttc aat gga cag agc ttc att gct tca att cag aaa ata      3748
Arg Ala Tyr Phe Asn Gly Gln Ser Phe Ile Ala Ser Ile Gln Lys Ile
        1230                1235                1240
```

```
tct ttc ttt gat ggc ttt gaa gga ggt ttt aat ttc cga aca tta caa      3796
Ser Phe Phe Asp Gly Phe Glu Gly Gly Phe Asn Phe Arg Thr Leu Gln
1245                1250                1255                1260 cca aat ggg tta cta ttc tat tat gct tca ggg tca gac gtg ttc tcc      3844
Pro Asn Gly Leu Leu Phe Tyr Tyr Ala Ser Gly Ser Asp Val Phe Ser
            1265                1270                1275 atc tca ctg gat aat ggt act gtc atc atg gat gta aag gga atc aaa      3892
Ile Ser Leu Asp Asn Gly Thr Val Ile Met Asp Val Lys Gly Ile Lys
        1280                1285                1290 gtt cag tca gta gat aag cag tac aat gat ggg ctg tcc cac ttc gtc      3940
Val Gln Ser Val Asp Lys Gln Tyr Asn Asp Gly Leu Ser His Phe Val
    1295                1300                1305 att agc tct gtc tca ccc aca aga tat gaa ctg ata gta gat aaa agc      3988
Ile Ser Ser Val Ser Pro Thr Arg Tyr Glu Leu Ile Val Asp Lys Ser
  1310                1315                1320 aga gtt ggg agt aag aat cct acc aaa ggg aaa ata gaa cag aca caa      4036
Arg Val Gly Ser Lys Asn Pro Thr Lys Gly Lys Ile Glu Gln Thr Gln
1325                1330                1335                1340 gca agt gaa aag aag ttt tac ttc ggt ggc tca cca atc agt gct cag      4084
Ala Ser Glu Lys Lys Phe Tyr Phe Gly Gly Ser Pro Ile Ser Ala Gln
            1345                1350                1355 tat gct aat ttc act ggc tgc ata agt aat gcc tac ttt acc agg gtg      4132
Tyr Ala Asn Phe Thr Gly Cys Ile Ser Asn Ala Tyr Phe Thr Arg Val
        1360                1365                1370 gat aga gat gtg gag gtt gaa gat ttc caa cgg tat act gaa aag gtc      4180
Asp Arg Asp Val Glu Val Glu Asp Phe Gln Arg Tyr Thr Glu Lys Val
    1375                1380                1385 cac act tct ctt tat gag tgt ccc att gag tct tca cca ttg ttt ctc      4228
His Thr Ser Leu Tyr Glu Cys Pro Ile Glu Ser Ser Pro Leu Phe Leu
  1390                1395                1400 ctc cat aaa aaa gga aaa aat tta tcc aag cct aaa gca agt cag aat      4276
Leu His Lys Lys Gly Lys Asn Leu Ser Lys Pro Lys Ala Ser Gln Asn
1405                1410                1415                1420 aaa aag gga ggg aaa agt aaa gat gca cct tca tgg gat cct gtt gct      4324
Lys Lys Gly Gly Lys Ser Lys Asp Ala Pro Ser Trp Asp Pro Val Ala
            1425                1430                1435 ctg aaa ctc cca gag cgg aat act cca aga aac tct cat tgc cac ctt      4372
Leu Lys Leu Pro Glu Arg Asn Thr Pro Arg Asn Ser His Cys His Leu
        1440                1445                1450 tcc aac agc cct aga gca ata gag cac gcc tat caa tat gga gga aca      4420
Ser Asn Ser Pro Arg Ala Ile Glu His Ala Tyr Gln Tyr Gly Gly Thr
    1455                1460                1465 gcc aac agc cgc caa gag ttt gaa cac tta aaa gga gat ttt ggt gcc      4468
Ala Asn Ser Arg Gln Glu Phe Glu His Leu Lys Gly Asp Phe Gly Ala
  1470                1475                1480 aaa tct cag ttt tcc att cgt ctg aga act cgt tcc tcc cat ggc atg      4516
Lys Ser Gln Phe Ser Ile Arg Leu Arg Thr Arg Ser Ser His Gly Met
1485                1490                1495                1500 atc ttc tat gtc tca gat caa gaa gag aat gac ttc atg act cta ttt      4564
Ile Phe Tyr Val Ser Asp Gln Glu Glu Asn Asp Phe Met Thr Leu Phe
            1505                1510                1515 ttg gcc cat ggc cgc ttg gtt tac atg ttt aat gtt ggt cac aaa aaa      4612
Leu Ala His Gly Arg Leu Val Tyr Met Phe Asn Val Gly His Lys Lys
        1520                1525                1530 ctg aag att aga agc cag gag aaa tac aat gat ggc ctg tgg cat gat      4660
Leu Lys Ile Arg Ser Gln Glu Lys Tyr Asn Asp Gly Leu Trp His Asp
    1535                1540                1545 gtg ata ttt att cga gaa agg agc agt ggc cga ctg gta att gat ggt      4708
Val Ile Phe Ile Arg Glu Arg Ser Ser Gly Arg Leu Val Ile Asp Gly
  1550                1555                1560
```

```
ctc cga gtc cta gaa gaa agt ctt cct cct act gaa gct acc tgg aaa    4756
Leu Arg Val Leu Glu Glu Ser Leu Pro Pro Thr Glu Ala Thr Trp Lys
1565                1570                1575                1580 atc aag ggt ccc att tat ttg gga ggt gtg gct cct gga aag gct gtg    4804
Ile Lys Gly Pro Ile Tyr Leu Gly Gly Val Ala Pro Gly Lys Ala Val
            1585                1590                1595 aaa aat gtt cag att aac tcc atc tac agt ttt agt ggc tgt ctc agc    4852
Lys Asn Val Gln Ile Asn Ser Ile Tyr Ser Phe Ser Gly Cys Leu Ser
        1600                1605                1610 aat ctc cag ctc aat ggg gcc tcc atc acc tct gct tct cag aca ttc    4900
Asn Leu Gln Leu Asn Gly Ala Ser Ile Thr Ser Ala Ser Gln Thr Phe
    1615                1620                1625 agt gtg acc cct tgc ttt gaa ggc ccc atg gaa aca gga act tac ttt    4948
Ser Val Thr Pro Cys Phe Glu Gly Pro Met Glu Thr Gly Thr Tyr Phe
1630                1635                1640 tca aca gaa gga gga tac gtg gtt cta gat gaa tct ttc aat att gga    4996
Ser Thr Glu Gly Gly Tyr Val Val Leu Asp Glu Ser Phe Asn Ile Gly
1645                1650                1655                1660 ttg aag ttt gaa att gca ttt gaa gtc cgt ccc aga agc agt tcc gga    5044
Leu Lys Phe Glu Ile Ala Phe Glu Val Arg Pro Arg Ser Ser Ser Gly
            1665                1670                1675 acc ctg gtc cac ggc cac agt gtc aat ggg gag tac cta aat gtt cac    5092
Thr Leu Val His Gly His Ser Val Asn Gly Glu Tyr Leu Asn Val His
        1680                1685                1690 atg aaa aat gga cag gtc ata gtg aaa gtc aat aat ggc atc aga gat    5140
Met Lys Asn Gly Gln Val Ile Val Lys Val Asn Asn Gly Ile Arg Asp
    1695                1700                1705 ttt tcc acc tca gta aca ccc aag cag agt ctc tgt gat ggc aga tgg    5188
Phe Ser Thr Ser Val Thr Pro Lys Gln Ser Leu Cys Asp Gly Arg Trp
1710                1715                1720 cac aga att aca gtt att aga gat tct aat gtg gtt cag ttg gat gtg    5236
His Arg Ile Thr Val Ile Arg Asp Ser Asn Val Val Gln Leu Asp Val
1725                1730                1735                1740 gac tct gaa gtg aac cat gtg gtt gga ccc ctg aat cca aaa cca att    5284
Asp Ser Glu Val Asn His Val Val Gly Pro Leu Asn Pro Lys Pro Ile
            1745                1750                1755 gat cac agg gag cct gtg ttt gtt gga ggt gtt cca gaa tct cta ctg    5332
Asp His Arg Glu Pro Val Phe Val Gly Gly Val Pro Glu Ser Leu Leu
        1760                1765                1770 aca cca cgc ttg gcc ccc agc aaa ccc ttc aca ggc tgc ata cgc cac    5380
Thr Pro Arg Leu Ala Pro Ser Lys Pro Phe Thr Gly Cys Ile Arg His
    1775                1780                1785 ttt gtg att gat gga cac cca gtg agc ttc agt aaa gca gcc ctg gtc    5428
Phe Val Ile Asp Gly His Pro Val Ser Phe Ser Lys Ala Ala Leu Val
1790                1795                1800 agc ggc gcc gta agc atc aac tcc tgt cca gca gcc gac tac aag gac    5476
Ser Gly Ala Val Ser Ile Asn Ser Cys Pro Ala Ala Asp Tyr Lys Asp
1805                1810                1815                1820 gac gat gac aag taagcttggc                                          5498
Asp Asp Asp Lys <210> SEQ ID NO 6
<211> LENGTH: 1824
<212> TYPE: PRT
<213> ORGANISM: Homo sapiens

<400> SEQUENCE: 6

Met Ala Leu Ser Ser Ala Trp Arg Ser Val Leu Pro Leu Trp Leu Leu
1               5                   10                  15
```

-continued

```
Trp Ser Ala Ala Cys Ser Arg Ala Ala Ser Gly Asp Asp Asn Ala Phe
         20                  25                  30
Pro Phe Asp Ile Glu Gly Ser Ser Ala Val Gly Arg Gln Asp Pro Pro
         35                  40                  45
Glu Thr Ser Glu Pro Arg Val Ala Leu Gly Arg Leu Pro Pro Ala Ala
 50                  55                  60
Glu Lys Cys Asn Ala Gly Phe Phe His Thr Leu Ser Gly Glu Cys Val
 65                  70                  75                  80
Pro Cys Asp Cys Asn Gly Asn Ser Asn Glu Cys Leu Asp Gly Ser Gly
                 85                  90                  95
Tyr Cys Val His Cys Gln Arg Asn Thr Thr Gly Glu His Cys Glu Lys
             100                 105                 110
Cys Leu Asp Gly Tyr Ile Gly Asp Ser Ile Arg Gly Ala Pro Gln Phe
         115                 120                 125
Cys Gln Pro Cys Pro Cys Pro Leu Pro His Leu Ala Asn Phe Pro Glu
     130                 135                 140
Ser Cys Tyr Arg Lys Asn Gly Ala Val Arg Cys Ile Cys Asn Glu Asn
145                 150                 155                 160
Tyr Ala Gly Pro Asn Cys Glu Arg Cys Ala Pro Gly Tyr Tyr Gly Asn
                 165                 170                 175
Pro Phe Leu Ile Gly Ser Thr Cys Lys Lys Cys Asp Cys Ser Gly Asn
             180                 185                 190
Ser Asp Pro Asn Leu Ile Phe Glu Asp Cys Asp Glu Val Thr Gly Gln
         195                 200                 205
Cys Arg Asn Cys Leu Arg Asn Thr Thr Gly Phe Lys Cys Glu Arg Cys
     210                 215                 220
Ala Pro Gly Tyr Tyr Gly Asp Ala Arg Ile Ala Lys Asn Cys Ala Val
225                 230                 235                 240
Cys Asn Cys Gly Gly Gly Pro Cys Asp Ser Val Thr Gly Glu Cys Leu
                 245                 250                 255
Glu Glu Gly Phe Glu Pro Pro Thr Gly Cys Asp Lys Cys Val Trp Asp
             260                 265                 270
Leu Thr Asp Asp Leu Arg Leu Ala Ala Leu Ser Ile Glu Glu Gly Lys
         275                 280                 285
Ser Gly Val Leu Ser Val Ser Ser Gly Ala Ala His Arg His Val
     290                 295                 300
Asn Glu Ile Asn Ala Thr Ile Tyr Leu Leu Lys Thr Lys Leu Ser Glu
305                 310                 315                 320
Arg Glu Asn Gln Tyr Ala Leu Arg Lys Ile Gln Ile Asn Asn Ala Glu
                 325                 330                 335
Asn Thr Met Lys Ser Leu Leu Ser Asp Val Glu Glu Leu Val Glu Lys
             340                 345                 350
Glu Asn Gln Ala Ser Arg Lys Gly Gln Leu Val Gln Lys Glu Ser Met
         355                 360                 365
Asp Thr Ile Asn His Ala Ser Gln Leu Val Glu Gln Ala His Asp Met
     370                 375                 380
Arg Asp Lys Ile Gln Glu Ile Asn Asn Lys Met Leu Tyr Tyr Gly Glu
385                 390                 395                 400
Glu His Glu Leu Ser Pro Lys Glu Ile Ser Glu Lys Leu Val Leu Ala
                 405                 410                 415
Gln Lys Met Leu Glu Glu Ile Arg Ser Arg Gln Pro Phe Phe Thr Gln
             420                 425                 430
Arg Glu Leu Val Asp Glu Glu Ala Asp Glu Ala Tyr Glu Leu Leu Ser
```

-continued

```
              435                 440                 445
Gln Ala Glu Ser Trp Gln Arg Leu His Asn Glu Thr Arg Thr Leu Phe
    450                 455                 460
Pro Val Val Leu Glu Gln Leu Asp Asp Tyr Asn Ala Lys Leu Ser Asp
465                 470                 475                 480
Leu Gln Glu Ala Leu Asp Gln Ala Leu Asn Tyr Val Arg Asp Ala Glu
                485                 490                 495
Asp Met Asn Arg Ala Thr Ala Ala Arg Gln Arg Asp His Glu Lys Gln
            500                 505                 510
Gln Glu Arg Val Arg Glu Gln Met Glu Val Val Asn Met Ser Leu Ser
        515                 520                 525
Thr Ser Ala Asp Ser Leu Thr Thr Pro Arg Leu Thr Leu Ser Glu Leu
530                 535                 540
Asp Asp Ile Ile Lys Asn Ala Ser Gly Ile Tyr Ala Glu Ile Asp Gly
545                 550                 555                 560
Ala Lys Ser Glu Leu Gln Val Lys Leu Ser Asn Leu Ser Asn Leu Ser
                565                 570                 575
His Asp Leu Val Gln Glu Ala Ile Asp His Ala Gln Asp Leu Gln Gln
            580                 585                 590
Glu Ala Asn Glu Leu Ser Arg Lys Leu His Ser Ser Asp Met Asn Gly
        595                 600                 605
Leu Val Gln Lys Ala Leu Asp Ala Ser Asn Val Tyr Glu Asn Ile Val
    610                 615                 620
Asn Tyr Val Ser Glu Ala Asn Glu Thr Ala Glu Phe Ala Leu Asn Thr
625                 630                 635                 640
Thr Asp Arg Ile Tyr Asp Ala Val Ser Gly Ile Asp Thr Gln Ile Ile
                645                 650                 655
Tyr His Lys Asp Glu Ser Glu Asn Leu Leu Asn Gln Ala Arg Glu Leu
            660                 665                 670
Gln Ala Lys Ala Glu Ser Ser Asp Glu Ala Val Ala Asp Thr Ser
        675                 680                 685
Arg Arg Val Gly Gly Ala Leu Ala Arg Lys Ser Ala Leu Lys Thr Arg
    690                 695                 700
Leu Ser Asp Ala Val Lys Gln Leu Gln Ala Ala Glu Arg Gly Asp Ala
705                 710                 715                 720
Gln Gln Arg Leu Gly Gln Ser Arg Leu Ile Thr Glu Glu Ala Asn Arg
                725                 730                 735
Thr Thr Met Glu Val Gln Gln Ala Thr Ala Pro Met Ala Asn Asn Leu
            740                 745                 750
Thr Asn Trp Ser Gln Asn Leu Gln His Phe Asp Ser Ser Ala Tyr Asn
        755                 760                 765
Thr Ala Val Asn Ser Ala Arg Asp Ala Val Arg Asn Leu Thr Glu Val
    770                 775                 780
Val Pro Gln Leu Leu Asp Gln Leu Arg Thr Val Glu Gln Lys Arg Pro
785                 790                 795                 800
Ala Ser Asn Val Ser Ala Ser Ile Gln Arg Ile Arg Glu Leu Ile Ala
                805                 810                 815
Gln Thr Arg Ser Val Ala Ser Lys Ile Gln Val Ser Met Met Phe Asp
            820                 825                 830
Gly Gln Ser Ala Val Glu Val His Ser Arg Thr Ser Met Asp Asp Leu
        835                 840                 845
Lys Ala Phe Thr Ser Leu Ser Leu Tyr Met Lys Pro Pro Val Lys Arg
    850                 855                 860
```

-continued

Pro Glu Leu Thr Glu Thr Ala Asp Gln Phe Ile Leu Tyr Leu Gly Ser
865                 870                 875                 880

Lys Asn Ala Lys Lys Glu Tyr Met Gly Leu Ala Ile Lys Asn Asp Asn
            885                 890                 895

Leu Val Tyr Val Tyr Asn Leu Gly Thr Lys Asp Val Glu Ile Pro Leu
        900                 905                 910

Asp Ser Lys Pro Val Ser Ser Trp Pro Ala Tyr Phe Ser Ile Val Lys
        915                 920                 925

Ile Glu Arg Val Gly Lys His Gly Lys Val Phe Leu Thr Val Pro Ser
    930                 935                 940

Leu Ser Ser Thr Ala Glu Glu Lys Phe Ile Lys Lys Gly Glu Phe Ser
945                 950                 955                 960

Gly Asp Asp Ser Leu Leu Asp Leu Asp Pro Glu Asp Thr Val Phe Tyr
            965                 970                 975

Val Gly Gly Val Pro Ser Asn Phe Lys Leu Pro Thr Ser Leu Asn Leu
        980                 985                 990

Pro Gly Phe Val Gly Cys Leu Glu Leu Ala Thr Leu Asn Asn Asp Val
        995                 1000                1005

Ile Ser Leu Tyr Asn Phe Lys His Ile Tyr Asn Met Asp Pro Ser Thr
    1010                1015                1020

Ser Val Pro Cys Ala Arg Asp Lys Leu Ala Phe Thr Gln Ser Arg Ala
1025                1030                1035                1040

Ala Ser Tyr Phe Phe Asp Gly Ser Gly Tyr Ala Val Val Arg Asp Ile
                1045                1050                1055

Pro Arg Arg Gly Lys Phe Gly Gln Val Thr Arg Phe Asp Ile Glu Val
            1060                1065                1070

Arg Thr Pro Ala Asp Asn Gly Leu Ile Leu Leu Met Val Asn Gly Ser
            1075                1080                1085

Met Phe Phe Arg Leu Glu Met Arg Asn Gly Tyr Leu His Val Phe Tyr
    1090                1095                1100

Asp Phe Gly Phe Ser Ser Gly Arg Val His Leu Glu Asp Thr Leu Lys
1105                1110                1115                1120

Lys Ala Gln Ile Asn Asp Ala Lys Tyr His Glu Ile Ser Ile Ile Tyr
            1125                1130                1135

His Asn Asp Lys Lys Met Ile Leu Val Val Asp Arg Arg His Val Lys
            1140                1145                1150

Ser Met Asp Asn Glu Lys Met Lys Ile Pro Phe Thr Asp Ile Tyr Ile
            1155                1160                1165

Gly Gly Ala Pro Pro Glu Ile Leu Gln Ser Arg Ala Leu Arg Ala His
    1170                1175                1180

Leu Pro Leu Asp Ile Asn Phe Arg Gly Cys Met Lys Gly Phe Gln Phe
1185                1190                1195                1200

Gln Lys Lys Asp Phe Asn Leu Leu Glu Gln Thr Glu Thr Leu Gly Val
            1205                1210                1215

Gly Tyr Gly Cys Pro Glu Asp Ser Leu Ile Ser Arg Arg Ala Tyr Phe
            1220                1225                1230

Asn Gly Gln Ser Phe Ile Ala Ser Ile Gln Lys Ile Ser Phe Phe Asp
        1235                1240                1245

Gly Phe Glu Gly Gly Phe Asn Phe Arg Thr Leu Gln Pro Asn Gly Leu
    1250                1255                1260

Leu Phe Tyr Tyr Ala Ser Gly Ser Asp Val Phe Ser Ile Ser Leu Asp
1265                1270                1275                1280

```
Asn Gly Thr Val Ile Met Asp Val Lys Gly Ile Lys Val Gln Ser Val
            1285                1290                1295

Asp Lys Gln Tyr Asn Asp Gly Leu Ser His Phe Val Ile Ser Ser Val
        1300                1305                1310

Ser Pro Thr Arg Tyr Glu Leu Ile Val Asp Lys Ser Arg Val Gly Ser
        1315                1320                1325

Lys Asn Pro Thr Lys Gly Lys Ile Glu Gln Thr Gln Ala Ser Glu Lys
    1330                1335                1340

Lys Phe Tyr Phe Gly Gly Ser Pro Ile Ser Ala Gln Tyr Ala Asn Phe
1345                1350                1355                1360

Thr Gly Cys Ile Ser Asn Ala Tyr Phe Thr Arg Val Asp Arg Asp Val
            1365                1370                1375

Glu Val Glu Asp Phe Gln Arg Tyr Thr Glu Lys Val His Thr Ser Leu
        1380                1385                1390

Tyr Glu Cys Pro Ile Glu Ser Ser Pro Leu Phe Leu Leu His Lys Lys
        1395                1400                1405

Gly Lys Asn Leu Ser Lys Pro Lys Ala Ser Gln Asn Lys Lys Gly Gly
    1410                1415                1420

Lys Ser Lys Asp Ala Pro Ser Trp Asp Pro Val Ala Leu Lys Leu Pro
1425                1430                1435                1440

Glu Arg Asn Thr Pro Arg Asn Ser His Cys His Leu Ser Asn Ser Pro
            1445                1450                1455

Arg Ala Ile Glu His Ala Tyr Gln Tyr Gly Gly Thr Ala Asn Ser Arg
        1460                1465                1470

Gln Glu Phe Glu His Leu Lys Gly Asp Phe Gly Ala Lys Ser Gln Phe
        1475                1480                1485

Ser Ile Arg Leu Arg Thr Arg Ser Ser His Gly Met Ile Phe Tyr Val
    1490                1495                1500

Ser Asp Gln Glu Glu Asn Asp Phe Met Thr Leu Phe Leu Ala His Gly
1505                1510                1515                1520

Arg Leu Val Tyr Met Phe Asn Val Gly His Lys Lys Leu Lys Ile Arg
            1525                1530                1535

Ser Gln Glu Lys Tyr Asn Asp Gly Leu Trp His Asp Val Ile Phe Ile
        1540                1545                1550

Arg Glu Arg Ser Ser Gly Arg Leu Val Ile Asp Gly Leu Arg Val Leu
    1555                1560                1565

Glu Glu Ser Leu Pro Pro Thr Glu Ala Thr Trp Lys Ile Lys Gly Pro
    1570                1575                1580

Ile Tyr Leu Gly Gly Val Ala Pro Gly Lys Ala Val Lys Asn Val Gln
1585                1590                1595                1600

Ile Asn Ser Ile Tyr Ser Phe Ser Gly Cys Leu Ser Asn Leu Gln Leu
            1605                1610                1615

Asn Gly Ala Ser Ile Thr Ser Ala Ser Gln Thr Phe Ser Val Thr Pro
        1620                1625                1630

Cys Phe Glu Gly Pro Met Glu Thr Gly Thr Tyr Phe Ser Thr Glu Gly
        1635                1640                1645

Gly Tyr Val Val Leu Asp Glu Ser Phe Asn Ile Gly Leu Lys Phe Glu
    1650                1655                1660

Ile Ala Phe Glu Val Arg Pro Arg Ser Ser Ser Gly Thr Leu Val His
1665                1670                1675                1680

Gly His Ser Val Asn Gly Glu Tyr Leu Asn Val His Met Lys Asn Gly
            1685                1690                1695

Gln Val Ile Val Lys Val Asn Asn Gly Ile Arg Asp Phe Ser Thr Ser
```

```
                     1700                1705                1710
     Val Thr Pro Lys Gln Ser Leu Cys Asp Gly Arg Trp His Arg Ile Thr
             1715                1720                1725

Val Ile Arg Asp Ser Asn Val Val Gln Leu Asp Val Asp Ser Glu Val
         1730                1735                1740

Asn His Val Val Gly Pro Leu Asn Pro Lys Pro Ile Asp His Arg Glu
     1745                1750                1755                1760

Pro Val Phe Val Gly Val Pro Glu Ser Leu Leu Thr Pro Arg Leu
                 1765                1770                1775

Ala Pro Ser Lys Pro Phe Thr Gly Cys Ile Arg His Phe Val Ile Asp
                 1780                1785                1790

Gly His Pro Val Ser Phe Ser Lys Ala Ala Leu Val Ser Gly Ala Val
             1795                1800                1805

Ser Ile Asn Ser Cys Pro Ala Ala Asp Tyr Lys Asp Asp Asp Lys
         1810                1815                1820

<210> SEQ ID NO 7
<211> LENGTH: 5410
<212> TYPE: DNA
<213> ORGANISM: Homo sapiens
<220> FEATURE:
<221> NAME/KEY: CDS
<222> LOCATION: (1)..(5400)
<221> NAME/KEY: misc_feature
<222> LOCATION: (5377)..(5400)

<400> SEQUENCE: 7 gcg tcc ggg gac gac aac gct ttt cct ttt gac att gaa ggg agc tca     48
Ala Ser Gly Asp Asp Asn Ala Phe Pro Phe Asp Ile Glu Gly Ser Ser
  1               5                  10                  15 gcg gtt ggc agg caa gac ccg cct gag acg agc gaa ccc cgc gtg gct     96
Ala Val Gly Arg Gln Asp Pro Pro Glu Thr Ser Glu Pro Arg Val Ala
             20                  25                  30 ctg gga cgc ctg ccg cct gcg gcc gag aaa tgc aat gct gga ttc ttt    144
Leu Gly Arg Leu Pro Pro Ala Ala Glu Lys Cys Asn Ala Gly Phe Phe
         35                  40                  45 cac acc ctg tcg gga gaa tgt gtg ccc tgc gac tgt aat ggc aat tcc    192
His Thr Leu Ser Gly Glu Cys Val Pro Cys Asp Cys Asn Gly Asn Ser
     50                  55                  60 aac gag tgt ttg gac ggc tca gga tac tgt gtg cac tgc cag cgg aac    240
Asn Glu Cys Leu Asp Gly Ser Gly Tyr Cys Val His Cys Gln Arg Asn
 65                  70                  75                  80 aca aca gga gag cac tgt gaa aag tgt ctg gat ggt tat atc gga gat    288
Thr Thr Gly Glu His Cys Glu Lys Cys Leu Asp Gly Tyr Ile Gly Asp
                 85                  90                  95 tcc atc agg gga gca ccc caa ttc tgc cag ccg tgc ccc tgt ccc ctg    336
Ser Ile Arg Gly Ala Pro Gln Phe Cys Gln Pro Cys Pro Cys Pro Leu
            100                 105                 110 ccc cac ttg gcc aat ttt cca gaa tcc tgc tat agg aaa aat gga gct    384
Pro His Leu Ala Asn Phe Pro Glu Ser Cys Tyr Arg Lys Asn Gly Ala
        115                 120                 125 gtt cgg tgc att tgt aac gaa aat tat gct gga cct aac tgt gaa aga    432
Val Arg Cys Ile Cys Asn Glu Asn Tyr Ala Gly Pro Asn Cys Glu Arg
    130                 135                 140 tgt gct ccc ggt tac tat gga aac ccc ttc ctc att gga agc acc tgt    480
Cys Ala Pro Gly Tyr Tyr Gly Asn Pro Phe Leu Ile Gly Ser Thr Cys
145                 150                 155                 160 aag aaa tgt gac tgc agt gga aat tca gat ccc aac ctg atc ttt gaa    528
Lys Lys Cys Asp Cys Ser Gly Asn Ser Asp Pro Asn Leu Ile Phe Glu
                165                 170                 175
```

```
gat tgt gat gaa gtc act ggc cag tgt agg aat tgc tta cgc aac acc     576
Asp Cys Asp Glu Val Thr Gly Gln Cys Arg Asn Cys Leu Arg Asn Thr
            180                 185                 190 acc gga ttc aag tgt gaa cgt tgc gct cct ggc tac tat ggg gac gcc     624
Thr Gly Phe Lys Cys Glu Arg Cys Ala Pro Gly Tyr Tyr Gly Asp Ala
        195                 200                 205 agg ata gcc aag aac tgt gca gtg tgc aac tgc ggg gga ggc cca tgt     672
Arg Ile Ala Lys Asn Cys Ala Val Cys Asn Cys Gly Gly Gly Pro Cys
210                 215                 220 gac agt gta acc gga gaa tgc ttg gaa gaa ggt ttt gaa ccc cct aca     720
Asp Ser Val Thr Gly Glu Cys Leu Glu Glu Gly Phe Glu Pro Pro Thr
225                 230                 235                 240 ggc tgt gat aag tgc gtc tgg gac ctg act gat gac ctg cgg tta gca     768
Gly Cys Asp Lys Cys Val Trp Asp Leu Thr Asp Asp Leu Arg Leu Ala
            245                 250                 255 gcg ctc tcc atc gag gaa ggc aaa tcc ggg gtg ctg agc gta tcc tct     816
Ala Leu Ser Ile Glu Glu Gly Lys Ser Gly Val Leu Ser Val Ser Ser
            260                 265                 270 ggg gcc gcc gct cat agg cac gtg aat gaa atc aac gcc acc atc tac     864
Gly Ala Ala Ala His Arg His Val Asn Glu Ile Asn Ala Thr Ile Tyr
        275                 280                 285 ctc ctc aaa aca aaa ttg tca gaa aga gaa aac caa tac gcc cta aga     912
Leu Leu Lys Thr Lys Leu Ser Glu Arg Glu Asn Gln Tyr Ala Leu Arg
290                 295                 300 aag ata caa atc aac aat gct gag aac acg atg aaa agc ctt ctg tct     960
Lys Ile Gln Ile Asn Asn Ala Glu Asn Thr Met Lys Ser Leu Leu Ser
305                 310                 315                 320 gac gta gag gaa tta gtt gaa aag gaa aat caa gcc tcc aga aaa gga    1008
Asp Val Glu Glu Leu Val Glu Lys Glu Asn Gln Ala Ser Arg Lys Gly
            325                 330                 335 caa ctt gtt cag aag gaa agc atg gac acc att aac cac gca agt cag    1056
Gln Leu Val Gln Lys Glu Ser Met Asp Thr Ile Asn His Ala Ser Gln
        340                 345                 350 ctg gta gag caa gcc cat gat atg agg gat aaa atc caa gag atc aac    1104
Leu Val Glu Gln Ala His Asp Met Arg Asp Lys Ile Gln Glu Ile Asn
        355                 360                 365 aac aag atg ctc tat tat ggg gaa gag cat gaa ctt agc ccc aag gaa    1152
Asn Lys Met Leu Tyr Tyr Gly Glu Glu His Glu Leu Ser Pro Lys Glu
370                 375                 380 atc tct gag aag ctg gtg ttg gcc cag aag atg ctt gaa gag att aga    1200
Ile Ser Glu Lys Leu Val Leu Ala Gln Lys Met Leu Glu Glu Ile Arg
385                 390                 395                 400 agc cgt caa cca ttt ttc acc caa cgg gag ctc gtg gat gag gag gca    1248
Ser Arg Gln Pro Phe Phe Thr Gln Arg Glu Leu Val Asp Glu Glu Ala
            405                 410                 415 gat gag gct tac gaa cta ctg agc cag gct gag agc tgg cag cgg ctg    1296
Asp Glu Ala Tyr Glu Leu Leu Ser Gln Ala Glu Ser Trp Gln Arg Leu
            420                 425                 430 cac aat gag acc cgc act ctg ttt cct gtc gtc ctg gag cag ctg gat    1344
His Asn Glu Thr Arg Thr Leu Phe Pro Val Val Leu Glu Gln Leu Asp
        435                 440                 445 gac tac aat gct aag ttg tca gat ctc cag gaa gca ctt gac cag gcc    1392
Asp Tyr Asn Ala Lys Leu Ser Asp Leu Gln Glu Ala Leu Asp Gln Ala
450                 455                 460 ctt aac tat gtc agg gat gcc gaa gac atg aac agg gcc aca gca gcc    1440
Leu Asn Tyr Val Arg Asp Ala Glu Asp Met Asn Arg Ala Thr Ala Ala
465                 470                 475                 480 agg cag cgg gac cat gag aaa caa cag gaa aga gtg agg gaa caa atg    1488
Arg Gln Arg Asp His Glu Lys Gln Gln Glu Arg Val Arg Glu Gln Met
```

-continued

|  |  |  |  |  |  |  |  |  |  |  |  |  |  |  |  |
|---|---|---|---|---|---|---|---|---|---|---|---|---|---|---|---|
|  |  |  | 485 |  |  |  | 490 |  |  |  | 495 |  |  |  |  |
| gaa | gtg | gtg | aac | atg | tct | ctg | agc | aca | tct | gcg | gac | tct | ctg | aca | aca | 1536 |
| Glu | Val | Val | Asn | Met | Ser | Leu | Ser | Thr | Ser | Ala | Asp | Ser | Leu | Thr | Thr |  |
|  |  |  | 500 |  |  |  | 505 |  |  |  | 510 |  |  |  |  |
| cct | cgt | cta | act | ctt | tca | gaa | ctt | gat | gat | ata | ata | aag | aat | gcg | tca | 1584 |
| Pro | Arg | Leu | Thr | Leu | Ser | Glu | Leu | Asp | Asp | Ile | Ile | Lys | Asn | Ala | Ser |  |
|  |  | 515 |  |  |  |  | 520 |  |  |  |  | 525 |  |  |  |
| ggg | att | tat | gca | gaa | ata | gat | gga | gcc | aaa | agt | gaa | cta | caa | gta | aaa | 1632 |
| Gly | Ile | Tyr | Ala | Glu | Ile | Asp | Gly | Ala | Lys | Ser | Glu | Leu | Gln | Val | Lys |  |
|  | 530 |  |  |  |  | 535 |  |  |  |  | 540 |  |  |  |  |
| cta | tct | aac | cta | agt | aac | ctc | agc | cat | gat | tta | gtc | caa | gaa | gct | att | 1680 |
| Leu | Ser | Asn | Leu | Ser | Asn | Leu | Ser | His | Asp | Leu | Val | Gln | Glu | Ala | Ile |  |
| 545 |  |  |  |  | 550 |  |  |  |  | 555 |  |  |  |  | 560 |
| gac | cat | gca | cag | gac | ctt | caa | caa | gaa | gct | aat | gaa | ttg | agc | agg | aag | 1728 |
| Asp | His | Ala | Gln | Asp | Leu | Gln | Gln | Glu | Ala | Asn | Glu | Leu | Ser | Arg | Lys |  |
|  |  |  |  | 565 |  |  |  |  | 570 |  |  |  |  | 575 |  |
| ttg | cac | agt | tca | gat | atg | aac | ggg | ctg | gta | cag | aag | gct | ttg | gat | gca | 1776 |
| Leu | His | Ser | Ser | Asp | Met | Asn | Gly | Leu | Val | Gln | Lys | Ala | Leu | Asp | Ala |  |
|  |  |  | 580 |  |  |  | 585 |  |  |  | 590 |  |  |  |  |
| tca | aat | gtc | tat | gaa | aat | att | gtt | aat | tat | gtt | agt | gaa | gcc | aat | gaa | 1824 |
| Ser | Asn | Val | Tyr | Glu | Asn | Ile | Val | Asn | Tyr | Val | Ser | Glu | Ala | Asn | Glu |  |
|  |  | 595 |  |  |  |  | 600 |  |  |  |  | 605 |  |  |  |
| aca | gca | gaa | ttt | gct | ttg | aac | acc | act | gac | cga | att | tat | gat | gcg | gtg | 1872 |
| Thr | Ala | Glu | Phe | Ala | Leu | Asn | Thr | Thr | Asp | Arg | Ile | Tyr | Asp | Ala | Val |  |
|  | 610 |  |  |  |  | 615 |  |  |  |  | 620 |  |  |  |  |
| agt | ggg | att | gat | act | caa | atc | att | tac | cat | aaa | gat | gaa | agt | gag | aac | 1920 |
| Ser | Gly | Ile | Asp | Thr | Gln | Ile | Ile | Tyr | His | Lys | Asp | Glu | Ser | Glu | Asn |  |
| 625 |  |  |  |  | 630 |  |  |  |  | 635 |  |  |  |  | 640 |
| ctc | ctc | aat | caa | gcc | aga | gaa | ctg | caa | gca | aag | gca | gag | tct | agc | agt | 1968 |
| Leu | Leu | Asn | Gln | Ala | Arg | Glu | Leu | Gln | Ala | Lys | Ala | Glu | Ser | Ser | Ser |  |
|  |  |  |  | 645 |  |  |  |  | 650 |  |  |  |  | 655 |  |
| gat | gaa | gca | gtg | gct | gac | act | agc | agg | cgt | gtg | ggt | gga | gcc | cta | gca | 2016 |
| Asp | Glu | Ala | Val | Ala | Asp | Thr | Ser | Arg | Arg | Val | Gly | Gly | Ala | Leu | Ala |  |
|  |  |  | 660 |  |  |  | 665 |  |  |  | 670 |  |  |  |  |
| agg | aaa | agt | gcc | ctt | aaa | acc | aga | ctc | agt | gat | gcc | gtt | aag | caa | cta | 2064 |
| Arg | Lys | Ser | Ala | Leu | Lys | Thr | Arg | Leu | Ser | Asp | Ala | Val | Lys | Gln | Leu |  |
|  |  | 675 |  |  |  |  | 680 |  |  |  |  | 685 |  |  |  |
| caa | gca | gca | gag | aga | ggg | gat | gcc | cag | cag | cgc | ctg | ggg | cag | tct | aga | 2112 |
| Gln | Ala | Ala | Glu | Arg | Gly | Asp | Ala | Gln | Gln | Arg | Leu | Gly | Gln | Ser | Arg |  |
|  | 690 |  |  |  |  | 695 |  |  |  |  | 700 |  |  |  |  |
| ctg | atc | acc | gag | gaa | gcc | aac | agg | acg | acg | atg | gag | gtg | cag | cag | gcc | 2160 |
| Leu | Ile | Thr | Glu | Glu | Ala | Asn | Arg | Thr | Thr | Met | Glu | Val | Gln | Gln | Ala |  |
| 705 |  |  |  |  | 710 |  |  |  |  | 715 |  |  |  |  | 720 |
| act | gcc | ccc | atg | gcc | aac | aat | cta | acc | aac | tgg | tca | cag | aat | ctt | caa | 2208 |
| Thr | Ala | Pro | Met | Ala | Asn | Asn | Leu | Thr | Asn | Trp | Ser | Gln | Asn | Leu | Gln |  |
|  |  |  |  | 725 |  |  |  |  | 730 |  |  |  |  | 735 |  |
| cat | ttt | gac | tct | tct | gct | tac | aac | act | gca | gtg | aac | tct | gct | agg | gat | 2256 |
| His | Phe | Asp | Ser | Ser | Ala | Tyr | Asn | Thr | Ala | Val | Asn | Ser | Ala | Arg | Asp |  |
|  |  |  | 740 |  |  |  | 745 |  |  |  | 750 |  |  |  |  |
| gca | gta | aga | aat | ctg | acc | gag | gtt | gtc | cct | cag | ctc | ctg | gat | cag | ctt | 2304 |
| Ala | Val | Arg | Asn | Leu | Thr | Glu | Val | Val | Pro | Gln | Leu | Leu | Asp | Gln | Leu |  |
|  |  | 755 |  |  |  |  | 760 |  |  |  |  | 765 |  |  |  |
| cgt | acg | gtt | gag | cag | aag | cga | cct | gca | agc | aac | gtt | tct | gcc | agc | atc | 2352 |
| Arg | Thr | Val | Glu | Gln | Lys | Arg | Pro | Ala | Ser | Asn | Val | Ser | Ala | Ser | Ile |  |
|  | 770 |  |  |  |  | 775 |  |  |  |  | 780 |  |  |  |  |
| cag | agg | atc | cga | gag | ctc | att | gct | cag | acc | aga | agt | gtt | gcc | agc | aag | 2400 |
| Gln | Arg | Ile | Arg | Glu | Leu | Ile | Ala | Gln | Thr | Arg | Ser | Val | Ala | Ser | Lys |  |
| 785 |  |  |  |  | 790 |  |  |  |  | 795 |  |  |  |  | 800 |
| atc | caa | gtc | tcc | atg | atg | ttt | gat | ggc | cag | tca | gct | gtg | gaa | gtg | cac | 2448 |

```
Ile Gln Val Ser Met Met Phe Asp Gly Gln Ser Ala Val Glu Val His
                805                 810                 815 tcg aga acc agt atg gat gac tta aag gcc ttc acg tct ctg agc ctg      2496
Ser Arg Thr Ser Met Asp Asp Leu Lys Ala Phe Thr Ser Leu Ser Leu
            820                 825                 830 tac atg aaa ccc cct gtg aag cgg ccg gaa ctg acc gag act gca gat      2544
Tyr Met Lys Pro Pro Val Lys Arg Pro Glu Leu Thr Glu Thr Ala Asp
        835                 840                 845 cag ttt atc ctg tac ctc gga agc aaa aac gcc aaa aaa gag tat atg      2592
Gln Phe Ile Leu Tyr Leu Gly Ser Lys Asn Ala Lys Lys Glu Tyr Met
850                 855                 860 ggt ctt gca atc aaa aat gat aat ctg gta tac gtc tat aat ttg gga      2640
Gly Leu Ala Ile Lys Asn Asp Asn Leu Val Tyr Val Tyr Asn Leu Gly
865                 870                 875                 880 act aaa gat gtg gag att ccc ctg gac tcc aag ccc gtc agt tcc tgg      2688
Thr Lys Asp Val Glu Ile Pro Leu Asp Ser Lys Pro Val Ser Ser Trp
                885                 890                 895 cct gct tac ttc agc att gtc aag att gaa agg gtg gga aaa cat gga      2736
Pro Ala Tyr Phe Ser Ile Val Lys Ile Glu Arg Val Gly Lys His Gly
            900                 905                 910 aag gtg ttt tta aca gtc ccg agt cta agt agc aca gca gag gaa aag      2784
Lys Val Phe Leu Thr Val Pro Ser Leu Ser Ser Thr Ala Glu Glu Lys
        915                 920                 925 ttc att aaa aag ggg gaa ttt tcg gga gat gac tct ctg ctg gac ctg      2832
Phe Ile Lys Lys Gly Glu Phe Ser Gly Asp Asp Ser Leu Leu Asp Leu
930                 935                 940 gac cct gag gac aca gtg ttt tat gtt ggt gga gtg cct tcc aac ttc      2880
Asp Pro Glu Asp Thr Val Phe Tyr Val Gly Gly Val Pro Ser Asn Phe
945                 950                 955                 960 aag ctc cct acc agc tta aac ctg cct ggc ttt gtt ggc tgc ctg gaa      2928
Lys Leu Pro Thr Ser Leu Asn Leu Pro Gly Phe Val Gly Cys Leu Glu
                965                 970                 975 ctg gcc act ttg aat aat gat gtg atc agc ttg tac aac ttt aag cac      2976
Leu Ala Thr Leu Asn Asn Asp Val Ile Ser Leu Tyr Asn Phe Lys His
            980                 985                 990 atc tat aat atg gac ccc tcc aca tca gtg cca tgt gcc cga gat aag      3024
Ile Tyr Asn Met Asp Pro Ser Thr Ser Val Pro Cys Ala Arg Asp Lys
        995                 1000                1005 ctg gcc ttc act cag agt cgg gct gcc agt tac ttc ttc gat ggc tcc      3072
Leu Ala Phe Thr Gln Ser Arg Ala Ala Ser Tyr Phe Phe Asp Gly Ser
1010                1015                1020 ggt tat gcc gtg gtg aga gac ata cca agg aga ggg aaa ttt ggt cag      3120
Gly Tyr Ala Val Val Arg Asp Ile Pro Arg Arg Gly Lys Phe Gly Gln
1025                1030                1035                1040 gtg act cgc ttt gac ata gaa gtt cga aca cca gct gac aac ggc ctt      3168
Val Thr Arg Phe Asp Ile Glu Val Arg Thr Pro Ala Asp Asn Gly Leu
                1045                1050                1055 att ctc ctg atg gtc aat gga agt atg ttt ttc aga ctg gaa atg cgc      3216
Ile Leu Leu Met Val Asn Gly Ser Met Phe Phe Arg Leu Glu Met Arg
            1060                1065                1070 aat ggt tac cta cat gtg ttc tat gat ttt gga ttc agc agt ggc cgt      3264
Asn Gly Tyr Leu His Val Phe Tyr Asp Phe Gly Phe Ser Ser Gly Arg
        1075                1080                1085 gtg cat ctt gaa gat acg tta aag aaa gct caa att aat gat gca aaa      3312
Val His Leu Glu Asp Thr Leu Lys Lys Ala Gln Ile Asn Asp Ala Lys
1090                1095                1100 tac cat gag atc tca atc att tac cac aat gat aag aaa atg atc ttg      3360
Tyr His Glu Ile Ser Ile Ile Tyr His Asn Asp Lys Lys Met Ile Leu
1105                1110                1115                1120
```

```
gta gtt gac aga agg cat gtc aag agc atg gat aat gaa aag atg aaa    3408
Val Val Asp Arg Arg His Val Lys Ser Met Asp Asn Glu Lys Met Lys
            1125                1130                1135 ata cct ttt aca gat ata tac att gga gga gct cct cca gaa atc tta    3456
Ile Pro Phe Thr Asp Ile Tyr Ile Gly Gly Ala Pro Pro Glu Ile Leu
        1140                1145                1150 caa tcc agg gcc ctc aga gca cac ctt ccc cta gat atc aac ttc aga    3504
Gln Ser Arg Ala Leu Arg Ala His Leu Pro Leu Asp Ile Asn Phe Arg
    1155                1160                1165 gga tgc atg aag ggc ttc cag ttc caa aag aag gac ttc aat tta ctg    3552
Gly Cys Met Lys Gly Phe Gln Phe Gln Lys Lys Asp Phe Asn Leu Leu
1170                1175                1180 gag cag aca gaa acc ctg gga gtt ggt tat gga tgc cca gaa gac tca    3600
Glu Gln Thr Glu Thr Leu Gly Val Gly Tyr Gly Cys Pro Glu Asp Ser
1185                1190                1195                1200 ctt ata tct cgc aga gca tat ttc aat gga cag agc ttc att gct tca    3648
Leu Ile Ser Arg Arg Ala Tyr Phe Asn Gly Gln Ser Phe Ile Ala Ser
            1205                1210                1215 att cag aaa ata tct ttc ttt gat ggc ttt gaa gga ggt ttt aat ttc    3696
Ile Gln Lys Ile Ser Phe Phe Asp Gly Phe Glu Gly Gly Phe Asn Phe
        1220                1225                1230 cga aca tta caa cca aat ggg tta cta ttc tat tat gct tca ggg tca    3744
Arg Thr Leu Gln Pro Asn Gly Leu Leu Phe Tyr Tyr Ala Ser Gly Ser
    1235                1240                1245 gac gtg ttc tcc atc tca ctg gat aat ggt act gtc atc atg gat gta    3792
Asp Val Phe Ser Ile Ser Leu Asp Asn Gly Thr Val Ile Met Asp Val
1250                1255                1260 aag gga atc aaa gtt cag tca gta gat aag cag tac aat gat ggg ctg    3840
Lys Gly Ile Lys Val Gln Ser Val Asp Lys Gln Tyr Asn Asp Gly Leu
1265                1270                1275                1280 tcc cac ttc gtc att agc tct gtc tca ccc aca aga tat gaa ctg ata    3888
Ser His Phe Val Ile Ser Ser Val Ser Pro Thr Arg Tyr Glu Leu Ile
            1285                1290                1295 gta gat aaa agc aga gtt ggg agt aag aat cct acc aaa ggg aaa ata    3936
Val Asp Lys Ser Arg Val Gly Ser Lys Asn Pro Thr Lys Gly Lys Ile
        1300                1305                1310 gaa cag aca caa gca agt gaa aag aag ttt tac ttc ggt ggc tca cca    3984
Glu Gln Thr Gln Ala Ser Glu Lys Lys Phe Tyr Phe Gly Gly Ser Pro
    1315                1320                1325 atc agt gct cag tat gct aat ttc act ggc tgc ata agt aat gcc tac    4032
Ile Ser Ala Gln Tyr Ala Asn Phe Thr Gly Cys Ile Ser Asn Ala Tyr
1330                1335                1340 ttt acc agg gtg gat aga gat gtg gag gtt gaa gat ttc caa cgg tat    4080
Phe Thr Arg Val Asp Arg Asp Val Glu Val Glu Asp Phe Gln Arg Tyr
1345                1350                1355                1360 act gaa aag gtc cac act tct ctt tat gag tgt ccc att gag tct tca    4128
Thr Glu Lys Val His Thr Ser Leu Tyr Glu Cys Pro Ile Glu Ser Ser
            1365                1370                1375 cca ttg ttt ctc ctc cat aaa aaa gga aaa aat tta tcc aag cct aaa    4176
Pro Leu Phe Leu Leu His Lys Lys Gly Lys Asn Leu Ser Lys Pro Lys
        1380                1385                1390 gca agt cag aat aaa aag gga ggg aaa agt aaa gat gca cct tca tgg    4224
Ala Ser Gln Asn Lys Lys Gly Gly Lys Ser Lys Asp Ala Pro Ser Trp
    1395                1400                1405 gat cct gtt gct ctg aaa ctc cca gag cgg aat act cca aga aac tct    4272
Asp Pro Val Ala Leu Lys Leu Pro Glu Arg Asn Thr Pro Arg Asn Ser
1410                1415                1420 cat tgc cac ctt tcc aac agc cct aga gca ata gag cac gcc tat caa    4320
His Cys His Leu Ser Asn Ser Pro Arg Ala Ile Glu His Ala Tyr Gln
1425                1430                1435                1440
```

-continued

```
tat gga gga aca gcc aac agc cgc caa gag ttt gaa cac tta aaa gga      4368
Tyr Gly Gly Thr Ala Asn Ser Arg Gln Glu Phe Glu His Leu Lys Gly
            1445                1450                1455 gat ttt ggt gcc aaa tct cag ttt tcc att cgt ctg aga act cgt tcc      4416
Asp Phe Gly Ala Lys Ser Gln Phe Ser Ile Arg Leu Arg Thr Arg Ser
        1460                1465                1470 tcc cat ggc atg atc ttc tat gtc tca gat caa gaa gag aat gac ttc      4464
Ser His Gly Met Ile Phe Tyr Val Ser Asp Gln Glu Glu Asn Asp Phe
    1475                1480                1485 atg act cta ttt ttg gcc cat ggc cgc ttg gtt tac atg ttt aat gtt      4512
Met Thr Leu Phe Leu Ala His Gly Arg Leu Val Tyr Met Phe Asn Val
1490                1495                1500 ggt cac aaa aaa ctg aag att aga agc cag gag aaa tac aat gat ggc      4560
Gly His Lys Lys Leu Lys Ile Arg Ser Gln Glu Lys Tyr Asn Asp Gly
1505                1510                1515                1520 ctg tgg cat gat gtg ata ttt att cga gaa agg agc agt ggc cga ctg      4608
Leu Trp His Asp Val Ile Phe Ile Arg Glu Arg Ser Ser Gly Arg Leu
            1525                1530                1535 gta att gat ggt ctc cga gtc cta gaa gaa agt ctt cct cct act gaa      4656
Val Ile Asp Gly Leu Arg Val Leu Glu Glu Ser Leu Pro Pro Thr Glu
        1540                1545                1550 gct acc tgg aaa atc aag ggt ccc att tat ttg gga ggt gtg gct cct      4704
Ala Thr Trp Lys Ile Lys Gly Pro Ile Tyr Leu Gly Gly Val Ala Pro
    1555                1560                1565 gga aag gct gtg aaa aat gtt cag att aac tcc atc tac agt ttt agt      4752
Gly Lys Ala Val Lys Asn Val Gln Ile Asn Ser Ile Tyr Ser Phe Ser
1570                1575                1580 ggc tgt ctc agc aat ctc cag ctc aat ggg gcc tcc atc acc tct gct      4800
Gly Cys Leu Ser Asn Leu Gln Leu Asn Gly Ala Ser Ile Thr Ser Ala
1585                1590                1595                1600 tct cag aca ttc agt gtg acc cct tgc ttt gaa ggc ccc atg gaa aca      4848
Ser Gln Thr Phe Ser Val Thr Pro Cys Phe Glu Gly Pro Met Glu Thr
            1605                1610                1615 gga act tac ttt tca aca gaa gga gga tac gtg gtt cta gat gaa tct      4896
Gly Thr Tyr Phe Ser Thr Glu Gly Gly Tyr Val Val Leu Asp Glu Ser
        1620                1625                1630 ttc aat att gga ttg aag ttt gaa att gca ttt gaa gtc cgt ccc aga      4944
Phe Asn Ile Gly Leu Lys Phe Glu Ile Ala Phe Glu Val Arg Pro Arg
    1635                1640                1645 agc agt tcc gga acc ctg gtc cac ggc cac agt gtc aat ggg gag tac      4992
Ser Ser Ser Gly Thr Leu Val His Gly His Ser Val Asn Gly Glu Tyr
1650                1655                1660 cta aat gtt cac atg aaa aat gga cag gtc ata gtg aaa gtc aat aat      5040
Leu Asn Val His Met Lys Asn Gly Gln Val Ile Val Lys Val Asn Asn
1665                1670                1675                1680 ggc atc aga gat ttt tcc acc tca gta aca ccc aag cag agt ctc tgt      5088
Gly Ile Arg Asp Phe Ser Thr Ser Val Thr Pro Lys Gln Ser Leu Cys
            1685                1690                1695 gat ggc aga tgg cac aga att aca gtt att aga gat tct aat gtg gtt      5136
Asp Gly Arg Trp His Arg Ile Thr Val Ile Arg Asp Ser Asn Val Val
        1700                1705                1710 cag ttg gat gtg gac tct gaa gtg aac cat gtg gtt gga ccc ctg aat      5184
Gln Leu Asp Val Asp Ser Glu Val Asn His Val Val Gly Pro Leu Asn
    1715                1720                1725 cca aaa cca att gat cac agg gag cct gtg ttt gtt gga ggt gtt cca      5232
Pro Lys Pro Ile Asp His Arg Glu Pro Val Phe Val Gly Gly Val Pro
1730                1735                1740 gaa tct cta ctg aca cca cgc ttg gcc ccc agc aaa ccc ttc aca ggc      5280
Glu Ser Leu Leu Thr Pro Arg Leu Ala Pro Ser Lys Pro Phe Thr Gly
```

```
                  1745                1750                1755                1760
tgc ata cgc cac ttt gtg att gat gga cac cca gtg agc ttc agt aaa              5328
Cys Ile Arg His Phe Val Ile Asp Gly His Pro Val Ser Phe Ser Lys
            1765                1770                1775 gca gcc ctg gtc agc ggc gcc gta agc atc aac tcc tgt cca gca gcc              5376
Ala Ala Leu Val Ser Gly Ala Val Ser Ile Asn Ser Cys Pro Ala Ala
        1780                1785                1790 gac tac aag gac gac gat gac aag taagcttggc                                   5410
Asp Tyr Lys Asp Asp Asp Asp Lys
        1795                1800

<210> SEQ ID NO 8
<211> LENGTH: 1800
<212> TYPE: PRT
<213> ORGANISM: Homo sapiens

<400> SEQUENCE: 8

Ala Ser Gly Asp Asp Asn Ala Phe Pro Phe Asp Ile Glu Gly Ser Ser
 1               5                  10                  15

Ala Val Gly Arg Gln Asp Pro Pro Glu Thr Ser Glu Pro Arg Val Ala
            20                  25                  30

Leu Gly Arg Leu Pro Pro Ala Ala Glu Lys Cys Asn Ala Gly Phe Phe
        35                  40                  45

His Thr Leu Ser Gly Glu Cys Val Pro Cys Asp Cys Asn Gly Asn Ser
    50                  55                  60

Asn Glu Cys Leu Asp Gly Ser Gly Tyr Cys Val His Cys Gln Arg Asn
65                  70                  75                  80

Thr Thr Gly Glu His Cys Glu Lys Cys Leu Asp Gly Tyr Ile Gly Asp
                85                  90                  95

Ser Ile Arg Gly Ala Pro Gln Phe Cys Gln Pro Cys Pro Cys Pro Leu
            100                 105                 110

Pro His Leu Ala Asn Phe Pro Glu Ser Cys Tyr Arg Lys Asn Gly Ala
        115                 120                 125

Val Arg Cys Ile Cys Asn Glu Asn Tyr Ala Gly Pro Asn Cys Glu Arg
    130                 135                 140

Cys Ala Pro Gly Tyr Tyr Gly Asn Pro Phe Leu Ile Gly Ser Thr Cys
145                 150                 155                 160

Lys Lys Cys Asp Cys Ser Gly Asn Ser Asp Pro Asn Leu Ile Phe Glu
                165                 170                 175

Asp Cys Asp Glu Val Thr Gly Gln Cys Arg Asn Cys Leu Arg Asn Thr
            180                 185                 190

Thr Gly Phe Lys Cys Glu Arg Cys Ala Pro Gly Tyr Tyr Gly Asp Ala
        195                 200                 205

Arg Ile Ala Lys Asn Cys Ala Val Cys Asn Cys Gly Gly Pro Cys
    210                 215                 220

Asp Ser Val Thr Gly Glu Cys Leu Glu Glu Gly Phe Glu Pro Pro Thr
225                 230                 235                 240

Gly Cys Asp Lys Cys Val Trp Asp Leu Thr Asp Asp Leu Arg Leu Ala
                245                 250                 255

Ala Leu Ser Ile Glu Glu Gly Lys Ser Gly Val Leu Ser Val Ser Ser
            260                 265                 270

Gly Ala Ala Ala His Arg His Val Asn Glu Ile Asn Ala Thr Ile Tyr
        275                 280                 285

Leu Leu Lys Thr Lys Leu Ser Glu Arg Glu Asn Gln Tyr Ala Leu Arg
    290                 295                 300
```

-continued

```
Lys Ile Gln Ile Asn Asn Ala Glu Asn Thr Met Lys Ser Leu Leu Ser
305                 310                 315                 320

Asp Val Glu Glu Leu Val Glu Lys Glu Asn Gln Ala Ser Arg Lys Gly
            325                 330                 335

Gln Leu Val Gln Lys Glu Ser Met Asp Thr Ile Asn His Ala Ser Gln
            340                 345                 350

Leu Val Glu Gln Ala His Asp Met Arg Asp Lys Ile Gln Glu Ile Asn
            355                 360                 365

Asn Lys Met Leu Tyr Tyr Gly Glu His Glu Leu Ser Pro Lys Glu
    370                 375                 380

Ile Ser Glu Lys Leu Val Leu Ala Gln Lys Met Leu Glu Glu Ile Arg
385                 390                 395                 400

Ser Arg Gln Pro Phe Phe Thr Gln Arg Glu Leu Val Asp Glu Glu Ala
            405                 410                 415

Asp Glu Ala Tyr Glu Leu Leu Ser Gln Ala Glu Ser Trp Gln Arg Leu
            420                 425                 430

His Asn Glu Thr Arg Thr Leu Phe Pro Val Val Leu Glu Gln Leu Asp
            435                 440                 445

Asp Tyr Asn Ala Lys Leu Ser Asp Leu Gln Glu Ala Leu Asp Gln Ala
    450                 455                 460

Leu Asn Tyr Val Arg Asp Ala Glu Asp Met Asn Arg Ala Thr Ala Ala
465                 470                 475                 480

Arg Gln Arg Asp His Glu Lys Gln Gln Glu Arg Val Arg Glu Gln Met
            485                 490                 495

Glu Val Val Asn Met Ser Leu Ser Thr Ser Ala Asp Ser Leu Thr Thr
            500                 505                 510

Pro Arg Leu Thr Leu Ser Glu Leu Asp Asp Ile Ile Lys Asn Ala Ser
            515                 520                 525

Gly Ile Tyr Ala Glu Ile Asp Gly Ala Lys Ser Glu Leu Gln Val Lys
            530                 535                 540

Leu Ser Asn Leu Ser Asn Leu Ser His Asp Leu Val Gln Glu Ala Ile
545                 550                 555                 560

Asp His Ala Gln Asp Leu Gln Gln Glu Ala Asn Glu Leu Ser Arg Lys
            565                 570                 575

Leu His Ser Ser Asp Met Asn Gly Leu Val Gln Lys Ala Leu Asp Ala
            580                 585                 590

Ser Asn Val Tyr Glu Asn Ile Val Asn Tyr Val Ser Glu Ala Asn Glu
            595                 600                 605

Thr Ala Glu Phe Ala Leu Asn Thr Thr Asp Arg Ile Tyr Asp Ala Val
            610                 615                 620

Ser Gly Ile Asp Thr Gln Ile Ile Tyr His Lys Asp Glu Ser Glu Asn
625                 630                 635                 640

Leu Leu Asn Gln Ala Arg Glu Leu Gln Ala Lys Ala Glu Ser Ser Ser
            645                 650                 655

Asp Glu Ala Val Ala Asp Thr Ser Arg Arg Val Gly Ala Leu Ala
            660                 665                 670

Arg Lys Ser Ala Leu Lys Thr Arg Leu Ser Asp Ala Val Lys Gln Leu
            675                 680                 685

Gln Ala Ala Glu Arg Gly Asp Ala Gln Gln Arg Leu Gly Gln Ser Arg
            690                 695                 700

Leu Ile Thr Glu Glu Ala Asn Arg Thr Thr Met Glu Val Gln Gln Ala
705                 710                 715                 720

Thr Ala Pro Met Ala Asn Asn Leu Thr Asn Trp Ser Gln Asn Leu Gln
```

```
                725                 730                 735
His Phe Asp Ser Ser Ala Tyr Asn Thr Ala Val Asn Ser Ala Arg Asp
            740                 745                 750

Ala Val Arg Asn Leu Thr Glu Val Val Pro Gln Leu Leu Asp Gln Leu
        755                 760                 765

Arg Thr Val Glu Gln Lys Arg Pro Ala Ser Asn Val Ser Ala Ser Ile
    770                 775                 780

Gln Arg Ile Arg Glu Leu Ile Ala Gln Thr Arg Ser Val Ala Ser Lys
785                 790                 795                 800

Ile Gln Val Ser Met Met Phe Asp Gly Gln Ser Ala Val Glu Val His
                805                 810                 815

Ser Arg Thr Ser Met Asp Asp Leu Lys Ala Phe Thr Ser Leu Ser Leu
            820                 825                 830

Tyr Met Lys Pro Pro Val Lys Arg Pro Glu Leu Thr Glu Thr Ala Asp
        835                 840                 845

Gln Phe Ile Leu Tyr Leu Gly Ser Lys Asn Ala Lys Lys Glu Tyr Met
    850                 855                 860

Gly Leu Ala Ile Lys Asn Asp Asn Leu Val Tyr Val Tyr Asn Leu Gly
865                 870                 875                 880

Thr Lys Asp Val Glu Ile Pro Leu Asp Ser Lys Pro Val Ser Ser Trp
                885                 890                 895

Pro Ala Tyr Phe Ser Ile Val Lys Ile Glu Arg Val Gly Lys His Gly
            900                 905                 910

Lys Val Phe Leu Thr Val Pro Ser Leu Ser Ser Thr Ala Glu Glu Lys
        915                 920                 925

Phe Ile Lys Lys Gly Glu Phe Ser Gly Asp Asp Ser Leu Leu Asp Leu
    930                 935                 940

Asp Pro Glu Asp Thr Val Phe Tyr Val Gly Gly Val Pro Ser Asn Phe
945                 950                 955                 960

Lys Leu Pro Thr Ser Leu Asn Leu Pro Gly Phe Val Gly Cys Leu Glu
                965                 970                 975

Leu Ala Thr Leu Asn Asn Asp Val Ile Ser Leu Tyr Asn Phe Lys His
            980                 985                 990

Ile Tyr Asn Met Asp Pro Ser Thr Ser Val Pro Cys Ala Arg Asp Lys
        995                 1000                1005

Leu Ala Phe Thr Gln Ser Arg Ala Ala Ser Tyr Phe Phe Asp Gly Ser
    1010                1015                1020

Gly Tyr Ala Val Val Arg Asp Ile Pro Arg Arg Gly Lys Phe Gly Gln
1025                1030                1035                1040

Val Thr Arg Phe Asp Ile Glu Val Arg Thr Pro Ala Asp Asn Gly Leu
                1045                1050                1055

Ile Leu Leu Met Val Asn Gly Ser Met Phe Phe Arg Leu Glu Met Arg
            1060                1065                1070

Asn Gly Tyr Leu His Val Phe Tyr Asp Phe Gly Phe Ser Ser Gly Arg
        1075                1080                1085

Val His Leu Glu Asp Thr Leu Lys Lys Ala Gln Ile Asn Asp Ala Lys
    1090                1095                1100

Tyr His Glu Ile Ser Ile Ile Tyr His Asn Asp Lys Lys Met Ile Leu
1105                1110                1115                1120

Val Val Asp Arg Arg His Val Lys Ser Met Asp Asn Glu Lys Met Lys
                1125                1130                1135

Ile Pro Phe Thr Asp Ile Tyr Ile Gly Gly Ala Pro Pro Glu Ile Leu
            1140                1145                1150
```

-continued

```
Gln Ser Arg Ala Leu Arg Ala His Leu Pro Leu Asp Ile Asn Phe Arg
        1155                1160                1165
Gly Cys Met Lys Gly Phe Gln Phe Gln Lys Lys Asp Phe Asn Leu Leu
    1170                1175                1180
Glu Gln Thr Glu Thr Leu Gly Val Gly Tyr Gly Cys Pro Glu Asp Ser
1185                1190                1195                1200
Leu Ile Ser Arg Arg Ala Tyr Phe Asn Gly Gln Ser Phe Ile Ala Ser
            1205                1210                1215
Ile Gln Lys Ile Ser Phe Phe Asp Gly Phe Glu Gly Gly Phe Asn Phe
        1220                1225                1230
Arg Thr Leu Gln Pro Asn Gly Leu Leu Phe Tyr Tyr Ala Ser Gly Ser
        1235                1240                1245
Asp Val Phe Ser Ile Ser Leu Asp Asn Gly Thr Val Ile Met Asp Val
    1250                1255                1260
Lys Gly Ile Lys Val Gln Ser Val Asp Lys Gln Tyr Asn Asp Gly Leu
1265                1270                1275                1280
Ser His Phe Val Ile Ser Ser Val Ser Pro Thr Arg Tyr Glu Leu Ile
            1285                1290                1295
Val Asp Lys Ser Arg Val Gly Ser Lys Asn Pro Thr Lys Gly Lys Ile
        1300                1305                1310
Glu Gln Thr Gln Ala Ser Glu Lys Lys Phe Tyr Phe Gly Gly Ser Pro
        1315                1320                1325
Ile Ser Ala Gln Tyr Ala Asn Phe Thr Gly Cys Ile Ser Asn Ala Tyr
    1330                1335                1340
Phe Thr Arg Val Asp Arg Asp Val Glu Val Glu Asp Phe Gln Arg Tyr
1345                1350                1355                1360
Thr Glu Lys Val His Thr Ser Leu Tyr Glu Cys Pro Ile Glu Ser Ser
            1365                1370                1375
Pro Leu Phe Leu Leu His Lys Lys Gly Lys Asn Leu Ser Lys Pro Lys
        1380                1385                1390
Ala Ser Gln Asn Lys Lys Gly Gly Lys Ser Lys Asp Ala Pro Ser Trp
        1395                1400                1405
Asp Pro Val Ala Leu Lys Leu Pro Glu Arg Asn Thr Pro Arg Asn Ser
    1410                1415                1420
His Cys His Leu Ser Asn Ser Pro Arg Ala Ile Glu His Ala Tyr Gln
1425                1430                1435                1440
Tyr Gly Gly Thr Ala Asn Ser Arg Gln Glu Phe Glu His Leu Lys Gly
            1445                1450                1455
Asp Phe Gly Ala Lys Ser Gln Phe Ser Ile Arg Leu Arg Thr Arg Ser
        1460                1465                1470
Ser His Gly Met Ile Phe Tyr Val Ser Asp Gln Glu Glu Asn Asp Phe
        1475                1480                1485
Met Thr Leu Phe Leu Ala His Gly Arg Leu Val Tyr Met Phe Asn Val
    1490                1495                1500
Gly His Lys Lys Leu Lys Ile Arg Ser Gln Glu Lys Tyr Asn Asp Gly
1505                1510                1515                1520
Leu Trp His Asp Val Ile Phe Ile Arg Glu Arg Ser Ser Gly Arg Leu
            1525                1530                1535
Val Ile Asp Gly Leu Arg Val Leu Glu Glu Ser Leu Pro Pro Thr Glu
        1540                1545                1550
Ala Thr Trp Lys Ile Lys Gly Pro Ile Tyr Leu Gly Gly Val Ala Pro
        1555                1560                1565
```

```
Gly Lys Ala Val Lys Asn Val Gln Ile Asn Ser Ile Tyr Ser Phe Ser
    1570                1575                1580

Gly Cys Leu Ser Asn Leu Gln Leu Asn Gly Ala Ser Ile Thr Ser Ala
1585                1590                1595                1600

Ser Gln Thr Phe Ser Val Thr Pro Cys Phe Glu Gly Pro Met Glu Thr
                1605                1610                1615

Gly Thr Tyr Phe Ser Thr Glu Gly Gly Tyr Val Val Leu Asp Glu Ser
            1620                1625                1630

Phe Asn Ile Gly Leu Lys Phe Glu Ile Ala Phe Glu Val Arg Pro Arg
        1635                1640                1645

Ser Ser Ser Gly Thr Leu Val His Gly His Ser Val Asn Gly Glu Tyr
    1650                1655                1660

Leu Asn Val His Met Lys Asn Gly Gln Val Ile Val Lys Val Asn Asn
1665                1670                1675                1680

Gly Ile Arg Asp Phe Ser Thr Ser Val Thr Pro Lys Gln Ser Leu Cys
                1685                1690                1695

Asp Gly Arg Trp His Arg Ile Thr Val Ile Arg Asp Ser Asn Val Val
            1700                1705                1710

Gln Leu Asp Val Asp Ser Glu Val Asn His Val Gly Pro Leu Asn
        1715                1720                1725

Pro Lys Pro Ile Asp His Arg Glu Pro Val Phe Val Gly Gly Val Pro
    1730                1735                1740

Glu Ser Leu Leu Thr Pro Arg Leu Ala Pro Ser Lys Pro Phe Thr Gly
1745                1750                1755                1760

Cys Ile Arg His Phe Val Ile Asp Gly His Pro Val Ser Phe Ser Lys
                1765                1770                1775

Ala Ala Leu Val Ser Gly Ala Val Ser Ile Asn Ser Cys Pro Ala Ala
            1780                1785                1790

Asp Tyr Lys Asp Asp Asp Asp Lys
        1795                1800

<210> SEQ ID NO 9
<211> LENGTH: 5824
<212> TYPE: DNA
<213> ORGANISM: Mus musculus
<220> FEATURE:
<221> NAME/KEY: CDS
<222> LOCATION: (209)..(5656)
<221> NAME/KEY: sig_peptide
<222> LOCATION: (209)..(281)

<400> SEQUENCE: 9
gggaccagca ggagagagag aagagaccac gctgactctc actccctctt ctttaataca      60
acaaagttgc aacttgggct cctggatcta ataccgcag gtccagagaa gacaaaacac      120
caggcatcac tgcatctctt aggggtacc caccaagacc tccaggtcct tcactccagg      180
aagggccctg ttgaatatct gcagagag atg ggt tgg agc aca gct tgg tgc       232
                                Met Gly Trp Ser Thr Ala Trp Cys
                                  1               5 tca gtc ctg gcc ctg tgg ctc ctc tgg tgt gct gtc tgc tcc aac gca      280
Ser Val Leu Ala Leu Trp Leu Leu Trp Cys Ala Val Cys Ser Asn Ala
     10                  15                  20 gcg tca ggg gac ggc aat gcg ttt cct ttt gac atc gag ggg agc gca      328
Ala Ser Gly Asp Gly Asn Ala Phe Pro Phe Asp Ile Glu Gly Ser Ala
 25                  30                  35                  40 gtg gtc ggc agg caa gac cca tcg gag act agc gac tca ggc gtg aca      376
Val Val Gly Arg Gln Asp Pro Ser Glu Thr Ser Asp Ser Gly Val Thr
             45                  50                  55
```

```
ctg gga cgc ctg ccg cct gct gct gag aga tgt gac gct gga ttc ttc     424
Leu Gly Arg Leu Pro Pro Ala Ala Glu Arg Cys Asp Ala Gly Phe Phe
            60                  65                  70 cgc aca ctg tca gga gaa tgt gca ccc tgt gac tgt aat ggc aat tcc     472
Arg Thr Leu Ser Gly Glu Cys Ala Pro Cys Asp Cys Asn Gly Asn Ser
        75                  80                  85 cat gag tgc ttg gat ggc tcc gga ttc tgt ctg cac tgc cag cgg aac     520
His Glu Cys Leu Asp Gly Ser Gly Phe Cys Leu His Cys Gln Arg Asn
        90                  95                 100 aca aca gga gag cac tgt gaa aaa tgt ctg gat ggc tat att gga gac     568
Thr Thr Gly Glu His Cys Glu Lys Cys Leu Asp Gly Tyr Ile Gly Asp
105                 110                 115                 120 tcc atc aga ggc aca ccc cgg ttc tgc cag ccg tgc ccc tgt ccc ttg     616
Ser Ile Arg Gly Thr Pro Arg Phe Cys Gln Pro Cys Pro Cys Pro Leu
                125                 130                 135 ccc cac ctg gcc aac ttt gca gaa tcc tgc tac agg aaa aat gga gct     664
Pro His Leu Ala Asn Phe Ala Glu Ser Cys Tyr Arg Lys Asn Gly Ala
            140                 145                 150 gtt cgg tgt att tgt aaa gaa aac tat gtt gga cct aac tgt gaa aga     712
Val Arg Cys Ile Cys Lys Glu Asn Tyr Val Gly Pro Asn Cys Glu Arg
        155                 160                 165 tgt gct cct ggt tac tat gga aac ccc tta ctc att gga agc acc tgt     760
Cys Ala Pro Gly Tyr Tyr Gly Asn Pro Leu Leu Ile Gly Ser Thr Cys
170                 175                 180 aag aaa tgt gac tgc agt gga aat tcg gat ccc aac ctg atc ttt gaa     808
Lys Lys Cys Asp Cys Ser Gly Asn Ser Asp Pro Asn Leu Ile Phe Glu
185                 190                 195                 200 gac tgt gat gaa atc act ggc cag tgc agg aac tgc tta cga aat acc     856
Asp Cys Asp Glu Ile Thr Gly Gln Cys Arg Asn Cys Leu Arg Asn Thr
                205                 210                 215 acc gga ttc aag tgt gaa cgc tgt gca cct ggt tac tat gga gac gcc     904
Thr Gly Phe Lys Cys Glu Arg Cys Ala Pro Gly Tyr Tyr Gly Asp Ala
            220                 225                 230 agg aca gcc aag aac tgt gca gtg tgc aac tgt ggg ggc ggc ccg cgt     952
Arg Thr Ala Lys Asn Cys Ala Val Cys Asn Cys Gly Gly Gly Pro Arg
        235                 240                 245 gac agt gta acc gga gag tgc ttg gaa gaa gga ttt gaa gtc cct aca    1000
Asp Ser Val Thr Gly Glu Cys Leu Glu Glu Gly Phe Glu Val Pro Thr
250                 255                 260 ggc tgt gat aag tgc gtc tgg gac ttg acc gat gac ctg cga tta gca    1048
Gly Cys Asp Lys Cys Val Trp Asp Leu Thr Asp Asp Leu Arg Leu Ala
265                 270                 275                 280 gcg ctc tcc atc gaa gag agc aaa tcc ggg ctg ctg agc gtg tcc tct    1096
Ala Leu Ser Ile Glu Glu Ser Lys Ser Gly Leu Leu Ser Val Ser Ser
                285                 290                 295 gcg gct gcg gcg cat aga cac gtg acc gac atg aac tct acc atc cac    1144
Ala Ala Ala Ala His Arg His Val Thr Asp Met Asn Ser Thr Ile His
            300                 305                 310 ctc ctc aga aca agg ctg tca gaa aga gaa aac cag tat acc cta aga    1192
Leu Leu Arg Thr Arg Leu Ser Glu Arg Glu Asn Gln Tyr Thr Leu Arg
        315                 320                 325 aag ata cag ata aac aac tcg gag aac aca ctg aga agc ctc ctg cct    1240
Lys Ile Gln Ile Asn Asn Ser Glu Asn Thr Leu Arg Ser Leu Leu Pro
330                 335                 340 gat gta gag gga ctc cat gag aag gga agt caa gcc tca aga aag ggt    1288
Asp Val Glu Gly Leu His Glu Lys Gly Ser Gln Ala Ser Arg Lys Gly
345                 350                 355                 360 atg ctg gtt gag aag gaa agc atg gat aca att gac caa gca acc cat    1336
Met Leu Val Glu Lys Glu Ser Met Asp Thr Ile Asp Gln Ala Thr His
```

-continued

```
                   365                 370                 375
ctt gtc gag caa gcc cac aac atg agg gac aaa atc caa gag atc aac    1384
Leu Val Glu Gln Ala His Asn Met Arg Asp Lys Ile Gln Glu Ile Asn
            380                 385                 390 agc aag atg ctc tac tat gga gag aat cag gaa ctt ggc ccc gag gaa    1432
Ser Lys Met Leu Tyr Tyr Gly Glu Asn Gln Glu Leu Gly Pro Glu Glu
        395                 400                 405 ata gct gag aag ctg gtg ttg gcc cag aaa atg ctg gaa gag atc cga    1480
Ile Ala Glu Lys Leu Val Leu Ala Gln Lys Met Leu Glu Glu Ile Arg
    410                 415                 420 agc cgg cag cca ttc ctc acc cat cgg gag ctg gtg gat gag gag gca    1528
Ser Arg Gln Pro Phe Leu Thr His Arg Glu Leu Val Asp Glu Glu Ala
425                 430                 435                 440 gat gag gcc cag gaa ttg ctg agc caa gct gag aac tgg cag cgg ctg    1576
Asp Glu Ala Gln Glu Leu Leu Ser Gln Ala Glu Asn Trp Gln Arg Leu
                445                 450                 455 cac aat gac acc cgc tct tta ttc ccc gtg gtg ctg gag cag ctg gac    1624
His Asn Asp Thr Arg Ser Leu Phe Pro Val Val Leu Glu Gln Leu Asp
            460                 465                 470 gac tac aac gct aag ctg tcc gac ctc cag gaa tcc att aac cag gcc    1672
Asp Tyr Asn Ala Lys Leu Ser Asp Leu Gln Glu Ser Ile Asn Gln Ala
        475                 480                 485 ctc gac cat gtc agg gat gca gaa gac atg aat aga gcc atc act ttc    1720
Leu Asp His Val Arg Asp Ala Glu Asp Met Asn Arg Ala Ile Thr Phe
    490                 495                 500 aag cag cgg gac cat gag aaa caa cat gag aga gtg aag gaa cag atg    1768
Lys Gln Arg Asp His Glu Lys Gln His Glu Arg Val Lys Glu Gln Met
505                 510                 515                 520 gaa gtt gtg ggt gcc tct ctg agt atg tct gca gac tct ctt acc ata    1816
Glu Val Val Gly Ala Ser Leu Ser Met Ser Ala Asp Ser Leu Thr Ile
                525                 530                 535 cct cag ctc act ctt gag gaa ctt gat gag ata ata aag aat gca tct    1864
Pro Gln Leu Thr Leu Glu Glu Leu Asp Glu Ile Ile Lys Asn Ala Ser
            540                 545                 550 gga att tat gca gaa ata gat gga gcc aaa aat gag ctg caa gga aaa    1912
Gly Ile Tyr Ala Glu Ile Asp Gly Ala Lys Asn Glu Leu Gln Gly Lys
        555                 560                 565 cta tcc aac ctg agt aac ctc agt cat gac ttg gtt cag gaa gct acg    1960
Leu Ser Asn Leu Ser Asn Leu Ser His Asp Leu Val Gln Glu Ala Thr
    570                 575                 580 gac cat gca tac aat ctt caa cag gaa gcc gat gag cta agc aga aat    2008
Asp His Ala Tyr Asn Leu Gln Gln Glu Ala Asp Glu Leu Ser Arg Asn
585                 590                 595                 600 ttg cac agt tca gac atg aac ggg ctg gta cag aag gct ttg gat gca    2056
Leu His Ser Ser Asp Met Asn Gly Leu Val Gln Lys Ala Leu Asp Ala
                605                 610                 615 tca aac gtc tat gaa aat atc gcc aat tat gtc agt gaa gcc aac gaa    2104
Ser Asn Val Tyr Glu Asn Ile Ala Asn Tyr Val Ser Glu Ala Asn Glu
            620                 625                 630 aca gca gaa ctt gct ctg aat atc act gat cga att tat gat gct gtg    2152
Thr Ala Glu Leu Ala Leu Asn Ile Thr Asp Arg Ile Tyr Asp Ala Val
        635                 640                 645 agt ggg att gac acg cag atc att tac cat aag gat gaa agt gac aac    2200
Ser Gly Ile Asp Thr Gln Ile Ile Tyr His Lys Asp Glu Ser Asp Asn
    650                 655                 660 ctt ctc aat caa gcc aga gag ctg cag gcc aag gca gat tca tgc aat    2248
Leu Leu Asn Gln Ala Arg Glu Leu Gln Ala Lys Ala Asp Ser Cys Asn
665                 670                 675                 680 gat gaa gca gtg gct gac acc agc agg cgt gtg ggt gga gcc ctg tgg    2296
```

```
                    Asp Glu Ala Val Ala Asp Thr Ser Arg Arg Val Gly Gly Ala Leu Trp
                                    685                 690                 695 agg aag ggc gcc ctc aga gac aga ctg aat gat gct gtt aag caa cta            2344
Arg Lys Gly Ala Leu Arg Asp Arg Leu Asn Asp Ala Val Lys Gln Leu
            700                 705                 710 cag gca gca gag aga ggg gac gcc cac cag cgc ctg ggc cag tcc aag            2392
Gln Ala Ala Glu Arg Gly Asp Ala His Gln Arg Leu Gly Gln Ser Lys
            715                 720                 725 ctc ttc att gag gaa gct aac aag acg aca gcg gct gtc caa cag gtt            2440
Leu Phe Ile Glu Glu Ala Asn Lys Thr Thr Ala Ala Val Gln Gln Val
        730                 735                 740 acc aca cca atg gct aac aac ctc agc aac tgg tcc cag aac ctg cag            2488
Thr Thr Pro Met Ala Asn Asn Leu Ser Asn Trp Ser Gln Asn Leu Gln
745                 750                 755                 760 acc ttt gac tca tct gca tat aac act gca gtg gac tct gct cgg gac            2536
Thr Phe Asp Ser Ser Ala Tyr Asn Thr Ala Val Asp Ser Ala Arg Asp
                765                 770                 775 gca gtg aga aac ctc acc gag gtt gtc ccc cag ctt ctg gat cag ctt            2584
Ala Val Arg Asn Leu Thr Glu Val Val Pro Gln Leu Leu Asp Gln Leu
            780                 785                 790 cgt act gtg gag cag aag cgg cct gca agc aac att tct gcc agc atc            2632
Arg Thr Val Glu Gln Lys Arg Pro Ala Ser Asn Ile Ser Ala Ser Ile
        795                 800                 805 cag agc atc cga gag ctc att gct caa acc agg agt gtc gca agc aag            2680
Gln Ser Ile Arg Glu Leu Ile Ala Gln Thr Arg Ser Val Ala Ser Lys
    810                 815                 820 atc caa gtc tcc atg atg ttt gat ggc cag tca gct gtc gaa gtg cac            2728
Ile Gln Val Ser Met Met Phe Asp Gly Gln Ser Ala Val Glu Val His
825                 830                 835                 840 ccc aaa gtc agt gtg gat gac ctg aag gcc ttc aca tcc atc agc ttg            2776
Pro Lys Val Ser Val Asp Asp Leu Lys Ala Phe Thr Ser Ile Ser Leu
                845                 850                 855 tac atg aag cct cct cca aag ccg gca gag ccc act ggg gcc tgg gta            2824
Tyr Met Lys Pro Pro Pro Lys Pro Ala Glu Pro Thr Gly Ala Trp Val
            860                 865                 870 gca gat cag ttt gtc ctc tac ctc gga agc aaa aac gcc aaa aaa gaa            2872
Ala Asp Gln Phe Val Leu Tyr Leu Gly Ser Lys Asn Ala Lys Lys Glu
        875                 880                 885 tac atg ggt ctg gca atc aaa aat gat aac ctg gta tac gtt tac aat            2920
Tyr Met Gly Leu Ala Ile Lys Asn Asp Asn Leu Val Tyr Val Tyr Asn
    890                 895                 900 ttg ggg atg aaa gat gtg gaa att ctc ctg gat tcc aag cct gtg agc            2968
Leu Gly Met Lys Asp Val Glu Ile Leu Leu Asp Ser Lys Pro Val Ser
905                 910                 915                 920 tcc tgg ccc gct tac ttt agt att gtc aag att gaa agg gta ggg gaa            3016
Ser Trp Pro Ala Tyr Phe Ser Ile Val Lys Ile Glu Arg Val Gly Glu
                925                 930                 935 cac gga aag gtg ttc ttg aca gtc ccc agt ctc agt agc aca gca gaa            3064
His Gly Lys Val Phe Leu Thr Val Pro Ser Leu Ser Ser Thr Ala Glu
            940                 945                 950 gaa aag ttt att aag aag ggg gag ttt gca gga gat gac tcc ttg ctg            3112
Glu Lys Phe Ile Lys Lys Gly Glu Phe Ala Gly Asp Asp Ser Leu Leu
        955                 960                 965 gat gtg acc cct gag gac act gtg ttt tac gtt ggt ggg gtg cct gcg            3160
Asp Val Thr Pro Glu Asp Thr Val Phe Tyr Val Gly Gly Val Pro Ala
    970                 975                 980 aac ttc aag ctc cct gcc agc tta aac ctg ccc agc tac tca ggc tgc            3208
Asn Phe Lys Leu Pro Ala Ser Leu Asn Leu Pro Ser Tyr Ser Gly Cys
985                 990                 995                 1000
```

-continued

| | |
|---|---|
| cta gag ctg gcc act ctg aat aat gat gtg atc agc ttg tac aac ttc<br>Leu Glu Leu Ala Thr Leu Asn Asn Asp Val Ile Ser Leu Tyr Asn Phe<br>            1005                    1010                    1015 | 3256 |
| aag cac atc tat aat atg gat cca tca aag tca gtg ccc tgt gcc agg<br>Lys His Ile Tyr Asn Met Asp Pro Ser Lys Ser Val Pro Cys Ala Arg<br>            1020                    1025                    1030 | 3304 |
| gat aaa ctg gct ttc act cag agt agg gct gcc agc tac ttc ttc gat<br>Asp Lys Leu Ala Phe Thr Gln Ser Arg Ala Ala Ser Tyr Phe Phe Asp<br>            1035                    1040                    1045 | 3352 |
| ggc tcc agt tat gca gtg gtg agg gac atc acg agg aga ggg aag ttt<br>Gly Ser Ser Tyr Ala Val Val Arg Asp Ile Thr Arg Arg Gly Lys Phe<br>    1050                    1055                    1060 | 3400 |
| ggt cag gtg act cgc ttt gac ata gaa atc cga aca cca gct gac aat<br>Gly Gln Val Thr Arg Phe Asp Ile Glu Ile Arg Thr Pro Ala Asp Asn<br>1065                    1070                    1075                    1080 | 3448 |
| ggc ctt gtg ctc ctg atg gtc aat ggc agt atg ttt ttc agc ctc gaa<br>Gly Leu Val Leu Leu Met Val Asn Gly Ser Met Phe Phe Ser Leu Glu<br>                  1085                    1090                    1095 | 3496 |
| atg cgc aat ggc tac cta cat gtg ttc tat gac ttt gga ttc agc aat<br>Met Arg Asn Gly Tyr Leu His Val Phe Tyr Asp Phe Gly Phe Ser Asn<br>    1100                    1105                    1110 | 3544 |
| ggc ccc gtg cat ctt gaa gac acg ttg aaa aaa gcc cag att aat gat<br>Gly Pro Val His Leu Glu Asp Thr Leu Lys Lys Ala Gln Ile Asn Asp<br>            1115                    1120                    1125 | 3592 |
| gcg aaa tat cat gag atc tca atc att tat cac aac gac aaa aaa atg<br>Ala Lys Tyr His Glu Ile Ser Ile Ile Tyr His Asn Asp Lys Lys Met<br>    1130                    1135                    1140 | 3640 |
| att ttg gtg gtg gac aga cgg cac gtt aag agc aca gac aat gag aag<br>Ile Leu Val Val Asp Arg Arg His Val Lys Ser Thr Asp Asn Glu Lys<br>1145                    1150                    1155                    1160 | 3688 |
| aaa aag att cct ttc acg gac atc tac atc gga ggt gcg ccc caa gaa<br>Lys Lys Ile Pro Phe Thr Asp Ile Tyr Ile Gly Gly Ala Pro Gln Glu<br>            1165                    1170                    1175 | 3736 |
| gtc tta cag tcc agg acc cta aga gca cac ctt ccc cta gat atc aac<br>Val Leu Gln Ser Arg Thr Leu Arg Ala His Leu Pro Leu Asp Ile Asn<br>    1180                    1185                    1190 | 3784 |
| ttt agg ggg tgc atg aag ggg ttc cag ttc caa aag aaa gat ttc aat<br>Phe Arg Gly Cys Met Lys Gly Phe Gln Phe Gln Lys Lys Asp Phe Asn<br>            1195                    1200                    1205 | 3832 |
| tta ctg gag cag aca gaa acc cta gga gtt ggt tat gga tgc cca gag<br>Leu Leu Glu Gln Thr Glu Thr Leu Gly Val Gly Tyr Gly Cys Pro Glu<br>1210                    1215                    1220 | 3880 |
| gac tct ctg ata tct cgc aga gca tat ttc aat ggg caa agt ttt att<br>Asp Ser Leu Ile Ser Arg Arg Ala Tyr Phe Asn Gly Gln Ser Phe Ile<br>1225                    1230                    1235                    1240 | 3928 |
| gct tca att cag aaa ata tct ttc ttt gat ggc ttt gaa gga ggc ttc<br>Ala Ser Ile Gln Lys Ile Ser Phe Phe Asp Gly Phe Glu Gly Gly Phe<br>            1245                    1250                    1255 | 3976 |
| aat ttc cga aca tta cag cca aat ggg tta cta ttc tac tac aca tca<br>Asn Phe Arg Thr Leu Gln Pro Asn Gly Leu Leu Phe Tyr Tyr Thr Ser<br>    1260                    1265                    1270 | 4024 |
| ggg tcg gac gtg ttt tcc att tca ctg gac aac ggc act gtt gtc atg<br>Gly Ser Asp Val Phe Ser Ile Ser Leu Asp Asn Gly Thr Val Val Met<br>            1275                    1280                    1285 | 4072 |
| gac gta aag ggc atc aag gtc atg tca aca gac aag cag tac cac gat<br>Asp Val Lys Gly Ile Lys Val Met Ser Thr Asp Lys Gln Tyr His Asp<br>    1290                    1295                    1300 | 4120 |
| ggg ctg ccc cac ttc gtg gtc acc tcc atc tca gac aca aga tat gaa<br>Gly Leu Pro His Phe Val Val Thr Ser Ile Ser Asp Thr Arg Tyr Glu<br>1305                    1310                    1315                    1320 | 4168 |

```
ctg gta gta gac aaa agc cga ctt cga ggg aag aat cca aca aaa ggg      4216
Leu Val Val Asp Lys Ser Arg Leu Arg Gly Lys Asn Pro Thr Lys Gly
            1325                1330                1335 aag gca gag cag act caa aca act gag aag aag ttc tac ttt ggt ggc      4264
Lys Ala Glu Gln Thr Gln Thr Thr Glu Lys Lys Phe Tyr Phe Gly Gly
            1340                1345                1350 tca ccc atc agt cct cag tat gct aat ttc act gga tgt ata agc aat      4312
Ser Pro Ile Ser Pro Gln Tyr Ala Asn Phe Thr Gly Cys Ile Ser Asn
            1355                1360                1365 gcc tac ttt acc agg ttg gat aga gat gtg gaa gtc gaa gac ttc cag      4360
Ala Tyr Phe Thr Arg Leu Asp Arg Asp Val Glu Val Glu Asp Phe Gln
            1370                1375                1380 cgc tat tct gaa aag gtc cac act tca ctc tat gag tgt ccg att gag      4408
Arg Tyr Ser Glu Lys Val His Thr Ser Leu Tyr Glu Cys Pro Ile Glu
1385                1390                1395                1400 tcg tca cct ctg ttt ctc ctt cac aaa aaa gga aag aat tcc tca aag      4456
Ser Ser Pro Leu Phe Leu Leu His Lys Lys Gly Lys Asn Ser Ser Lys
            1405                1410                1415 cct aaa aca aac aaa cag gga gag aag agt aag gat gcg cct tca tgg      4504
Pro Lys Thr Asn Lys Gln Gly Glu Lys Ser Lys Asp Ala Pro Ser Trp
            1420                1425                1430 gat cct att ggc ctg aag ttt ctg gaa cag aaa gct cca aga gat tcc      4552
Asp Pro Ile Gly Leu Lys Phe Leu Glu Gln Lys Ala Pro Arg Asp Ser
            1435                1440                1445 cac tgc cac ctc tcc agc agc ccc agg gca ata gaa cat gcc tat caa      4600
His Cys His Leu Ser Ser Ser Pro Arg Ala Ile Glu His Ala Tyr Gln
            1450                1455                1460 tat ggc ggc acg gcc aac agt cgc cag gag ttt gaa cac gaa caa gga      4648
Tyr Gly Gly Thr Ala Asn Ser Arg Gln Glu Phe Glu His Glu Gln Gly
1465                1470                1475                1480 gat ttt ggt gaa aaa tcc cag ttt gcc att cgt ctg aag acc cgt tcc      4696
Asp Phe Gly Glu Lys Ser Gln Phe Ala Ile Arg Leu Lys Thr Arg Ser
            1485                1490                1495 tca cat ggg atg att ttc tat gtc tca gac caa gaa gag aat gat ttc      4744
Ser His Gly Met Ile Phe Tyr Val Ser Asp Gln Glu Glu Asn Asp Phe
            1500                1505                1510 atg acc ctg ttc ttg gcc cat ggt cgc ttg gtc ttt atg ttt aat gtt      4792
Met Thr Leu Phe Leu Ala His Gly Arg Leu Val Phe Met Phe Asn Val
            1515                1520                1525 ggc cat aag aaa ctg aag att aga agc cag gag aaa tac aat gat gga      4840
Gly His Lys Lys Leu Lys Ile Arg Ser Gln Glu Lys Tyr Asn Asp Gly
            1530                1535                1540 ttg tgg cat gat gtg ata ttt att cgg gaa aag agc agt ggt cga ctg      4888
Leu Trp His Asp Val Ile Phe Ile Arg Glu Lys Ser Ser Gly Arg Leu
1545                1550                1555                1560 gtc att gat ggt cta cga gtc cta gaa gaa agg ctt ccc cct agt ggc      4936
Val Ile Asp Gly Leu Arg Val Leu Glu Glu Arg Leu Pro Pro Ser Gly
            1565                1570                1575 gct gcc tgg aaa atc aag ggt ccc att tat ctg gga gga gtg gct ccc      4984
Ala Ala Trp Lys Ile Lys Gly Pro Ile Tyr Leu Gly Gly Val Ala Pro
            1580                1585                1590 gga aga gcc gtg aaa aat gtc cag att acc tcc gtc tac agc ttc agt      5032
Gly Arg Ala Val Lys Asn Val Gln Ile Thr Ser Val Tyr Ser Phe Ser
            1595                1600                1605 ggc tgc ctt ggc aat ctc cag ctc aat ggt gcc tcc atc acc tcc gct      5080
Gly Cys Leu Gly Asn Leu Gln Leu Asn Gly Ala Ser Ile Thr Ser Ala
            1610                1615                1620 tct caa acg ttt agc gtg acc cct tgc ttt gaa ggg cca atg gaa aca      5128
Ser Gln Thr Phe Ser Val Thr Pro Cys Phe Glu Gly Pro Met Glu Thr
```

-continued

```
                1625                1630                1635                1640
gga act tat ttt tcc aca gaa ggc ggc tat gtg gtt cta gat gag tct        5176
Gly Thr Tyr Phe Ser Thr Glu Gly Gly Tyr Val Val Leu Asp Glu Ser
                    1645                1650                1655 ttc aat att ggg tta aaa ttt gaa att gcc ttt gaa gtc cgc ccc cgg        5224
Phe Asn Ile Gly Leu Lys Phe Glu Ile Ala Phe Glu Val Arg Pro Arg
            1660                1665                1670 agc agt tct gga acc ctt gtc cat ggc cac agc gtc aac ggg gaa tac        5272
Ser Ser Ser Gly Thr Leu Val His Gly His Ser Val Asn Gly Glu Tyr
        1675                1680                1685 ctg aac gtg cac atg aga aac gga cag gtc ata gtg aag gtc aac aac        5320
Leu Asn Val His Met Arg Asn Gly Gln Val Ile Val Lys Val Asn Asn
    1690                1695                1700 ggt gtc aga gac ttt tct acc tca gta act ccc aag cag aat ctc tgt        5368
Gly Val Arg Asp Phe Ser Thr Ser Val Thr Pro Lys Gln Asn Leu Cys
1705                1710                1715                1720 gat ggc aga tgg cac aga att aca gtt att aga gat tca aac gtg gtt        5416
Asp Gly Arg Trp His Arg Ile Thr Val Ile Arg Asp Ser Asn Val Val
                1725                1730                1735 cag ttg gat gta gac tca gaa gtg aac cat gta gtt ggg ccg ttg aat        5464
Gln Leu Asp Val Asp Ser Glu Val Asn His Val Val Gly Pro Leu Asn
            1740                1745                1750 cca aag cca gtt gat cac agg gag cct gtg ttt gtt gga ggt gtt cca        5512
Pro Lys Pro Val Asp His Arg Glu Pro Val Phe Val Gly Gly Val Pro
        1755                1760                1765 gag tct tta ctg aca cca cgt ttg gct ccc agc aaa ccc ttc acc ggc        5560
Glu Ser Leu Leu Thr Pro Arg Leu Ala Pro Ser Lys Pro Phe Thr Gly
    1770                1775                1780 tgc atc cgc cac ttt gta att gac agc cgc cct gtg agc ttc agt aaa        5608
Cys Ile Arg His Phe Val Ile Asp Ser Arg Pro Val Ser Phe Ser Lys
1785                1790                1795                1800 gct gcc ctg gtc agt ggt gct gtg agc atc aac tcc tgt ccc aca gcc        5656
Ala Ala Leu Val Ser Gly Ala Val Ser Ile Asn Ser Cys Pro Thr Ala
                1805                1810                1815 tgacacagct gcaaggctgc tgaagacagc tcttcctaac actgaaataa acatagtagt     5716 gggggtcgg gagggtcaga ggcctggaac tcccctccct actgaagctc tcacctggtt      5776 gaagggatt tcaataaatc agagaccagc cgcaaaaaaa aaaaaaaa                   5824
```

<210> SEQ ID NO 10
<211> LENGTH: 1816
<212> TYPE: PRT
<213> ORGANISM: Mus musculus

<400> SEQUENCE: 10

```
Met Gly Trp Ser Thr Ala Trp Cys Ser Val Leu Ala Leu Trp Leu Leu
1               5                   10                  15

Trp Cys Ala Val Cys Ser Asn Ala Ala Ser Gly Asp Gly Asn Ala Phe
            20                  25                  30

Pro Phe Asp Ile Glu Gly Ser Ala Val Val Gly Arg Gln Asp Pro Ser
        35                  40                  45

Glu Thr Ser Asp Ser Gly Val Thr Leu Gly Arg Leu Pro Pro Ala Ala
    50                  55                  60

Glu Arg Cys Asp Ala Gly Phe Phe Arg Thr Leu Ser Gly Glu Cys Ala
65                  70                  75                  80

Pro Cys Asp Cys Asn Gly Asn Ser His Glu Cys Leu Asp Gly Ser Gly
                85                  90                  95

Phe Cys Leu His Cys Gln Arg Asn Thr Thr Gly Glu His Cys Glu Lys
```

-continued

```
                 100                 105                 110
Cys Leu Asp Gly Tyr Ile Gly Asp Ser Ile Arg Gly Thr Pro Arg Phe
            115                 120                 125

Cys Gln Pro Cys Pro Cys Pro Leu Pro His Leu Ala Asn Phe Ala Glu
            130                 135                 140

Ser Cys Tyr Arg Lys Asn Gly Ala Val Arg Cys Ile Cys Lys Glu Asn
145                 150                 155                 160

Tyr Val Gly Pro Asn Cys Glu Arg Cys Ala Pro Gly Tyr Tyr Gly Asn
                165                 170                 175

Pro Leu Leu Ile Gly Ser Thr Cys Lys Cys Asp Cys Ser Gly Asn
            180                 185                 190

Ser Asp Pro Asn Leu Ile Phe Glu Asp Cys Asp Glu Ile Thr Gly Gln
            195                 200                 205

Cys Arg Asn Cys Leu Arg Asn Thr Thr Gly Phe Lys Cys Glu Arg Cys
            210                 215                 220

Ala Pro Gly Tyr Tyr Gly Asp Ala Arg Thr Ala Lys Asn Cys Ala Val
225                 230                 235                 240

Cys Asn Cys Gly Gly Pro Arg Asp Ser Val Thr Gly Glu Cys Leu
            245                 250                 255

Glu Glu Gly Phe Glu Val Pro Thr Gly Cys Asp Lys Cys Val Trp Asp
            260                 265                 270

Leu Thr Asp Asp Leu Arg Leu Ala Ala Leu Ser Ile Glu Glu Ser Lys
            275                 280                 285

Ser Gly Leu Leu Ser Val Ser Ser Ala Ala Ala His Arg His Val
            290                 295                 300

Thr Asp Met Asn Ser Thr Ile His Leu Leu Arg Thr Arg Leu Ser Glu
305                 310                 315                 320

Arg Glu Asn Gln Tyr Thr Leu Arg Lys Ile Gln Ile Asn Asn Ser Glu
                325                 330                 335

Asn Thr Leu Arg Ser Leu Leu Pro Asp Val Glu Gly Leu His Glu Lys
            340                 345                 350

Gly Ser Gln Ala Ser Arg Lys Gly Met Leu Val Glu Lys Glu Ser Met
            355                 360                 365

Asp Thr Ile Asp Gln Ala Thr His Leu Val Glu Gln Ala His Asn Met
370                 375                 380

Arg Asp Lys Ile Gln Glu Ile Asn Ser Lys Met Leu Tyr Tyr Gly Glu
385                 390                 395                 400

Asn Gln Glu Leu Gly Pro Glu Glu Ile Ala Glu Lys Leu Val Leu Ala
                405                 410                 415

Gln Lys Met Leu Glu Glu Ile Arg Ser Arg Gln Pro Phe Leu Thr His
            420                 425                 430

Arg Glu Leu Val Asp Glu Glu Ala Asp Glu Ala Gln Glu Leu Leu Ser
435                 440                 445

Gln Ala Glu Asn Trp Gln Arg Leu His Asn Asp Thr Arg Ser Leu Phe
450                 455                 460

Pro Val Val Leu Glu Gln Leu Asp Asp Tyr Asn Ala Lys Leu Ser Asp
465                 470                 475                 480

Leu Gln Glu Ser Ile Asn Gln Ala Leu Asp His Val Arg Asp Ala Glu
                485                 490                 495

Asp Met Asn Arg Ala Ile Thr Phe Lys Gln Arg Asp His Glu Lys Gln
            500                 505                 510

His Glu Arg Val Lys Glu Gln Met Glu Val Val Gly Ala Ser Leu Ser
            515                 520                 525
```

-continued

```
Met Ser Ala Asp Ser Leu Thr Ile Pro Gln Leu Thr Leu Glu Glu Leu
    530                 535                 540
Asp Glu Ile Ile Lys Asn Ala Ser Gly Ile Tyr Ala Glu Ile Asp Gly
545                 550                 555                 560
Ala Lys Asn Glu Leu Gln Gly Lys Leu Ser Asn Leu Ser Asn Leu Ser
                565                 570                 575
His Asp Leu Val Gln Glu Ala Thr Asp His Ala Tyr Asn Leu Gln Gln
                580                 585                 590
Glu Ala Asp Glu Leu Ser Arg Asn Leu His Ser Ser Asp Met Asn Gly
            595                 600                 605
Leu Val Gln Lys Ala Leu Asp Ala Ser Asn Val Tyr Glu Asn Ile Ala
610                 615                 620
Asn Tyr Val Ser Glu Ala Asn Glu Thr Ala Glu Leu Ala Leu Asn Ile
625                 630                 635                 640
Thr Asp Arg Ile Tyr Asp Ala Val Ser Gly Ile Asp Thr Gln Ile Ile
                645                 650                 655
Tyr His Lys Asp Glu Ser Asp Asn Leu Leu Asn Gln Ala Arg Glu Leu
                660                 665                 670
Gln Ala Lys Ala Asp Ser Cys Asn Asp Glu Ala Val Ala Asp Thr Ser
            675                 680                 685
Arg Arg Val Gly Gly Ala Leu Trp Arg Lys Gly Ala Leu Arg Asp Arg
690                 695                 700
Leu Asn Asp Ala Val Lys Gln Leu Gln Ala Ala Glu Arg Gly Asp Ala
705                 710                 715                 720
His Gln Arg Leu Gly Gln Ser Lys Leu Phe Ile Glu Glu Ala Asn Lys
                725                 730                 735
Thr Thr Ala Ala Val Gln Gln Val Thr Thr Pro Met Ala Asn Asn Leu
                740                 745                 750
Ser Asn Trp Ser Gln Asn Leu Gln Thr Phe Asp Ser Ser Ala Tyr Asn
            755                 760                 765
Thr Ala Val Asp Ser Ala Arg Asp Ala Val Arg Asn Leu Thr Glu Val
770                 775                 780
Val Pro Gln Leu Leu Asp Gln Leu Arg Thr Val Glu Gln Lys Arg Pro
785                 790                 795                 800
Ala Ser Asn Ile Ser Ala Ser Ile Gln Ser Ile Arg Glu Leu Ile Ala
                805                 810                 815
Gln Thr Arg Ser Val Ala Ser Lys Ile Gln Val Ser Met Met Phe Asp
                820                 825                 830
Gly Gln Ser Ala Val Glu Val His Pro Lys Val Ser Val Asp Asp Leu
            835                 840                 845
Lys Ala Phe Thr Ser Ile Ser Leu Tyr Met Lys Pro Pro Lys Pro
850                 855                 860
Ala Glu Pro Thr Gly Ala Trp Val Ala Asp Gln Phe Val Leu Tyr Leu
865                 870                 875                 880
Gly Ser Lys Asn Ala Lys Lys Glu Tyr Met Gly Leu Ala Ile Lys Asn
                885                 890                 895
Asp Asn Leu Val Tyr Val Tyr Asn Leu Gly Met Lys Asp Val Glu Ile
                900                 905                 910
Leu Leu Asp Ser Lys Pro Val Ser Ser Trp Pro Ala Tyr Phe Ser Ile
            915                 920                 925
Val Lys Ile Glu Arg Val Gly Glu His Gly Lys Val Phe Leu Thr Val
930                 935                 940
```

-continued

```
Pro Ser Leu Ser Ser Thr Ala Glu Glu Lys Phe Ile Lys Lys Gly Glu
945                 950                 955                 960

Phe Ala Gly Asp Asp Ser Leu Leu Asp Val Thr Pro Glu Asp Thr Val
            965                 970                 975

Phe Tyr Val Gly Gly Val Pro Ala Asn Phe Lys Leu Pro Ala Ser Leu
        980                 985                 990

Asn Leu Pro Ser Tyr Ser Gly Cys Leu Glu Leu Ala Thr Leu Asn Asn
    995                 1000                1005

Asp Val Ile Ser Leu Tyr Asn Phe Lys His Ile Tyr Asn Met Asp Pro
1010                1015                1020

Ser Lys Ser Val Pro Cys Ala Arg Asp Lys Leu Ala Phe Thr Gln Ser
1025                1030                1035                1040

Arg Ala Ala Ser Tyr Phe Phe Asp Gly Ser Ser Tyr Ala Val Val Arg
                1045                1050                1055

Asp Ile Thr Arg Arg Gly Lys Phe Gly Gln Val Thr Arg Phe Asp Ile
                1060                1065                1070

Glu Ile Arg Thr Pro Ala Asp Asn Gly Leu Val Leu Leu Met Val Asn
            1075                1080                1085

Gly Ser Met Phe Phe Ser Leu Glu Met Arg Asn Gly Tyr Leu His Val
1090                1095                1100

Phe Tyr Asp Phe Gly Phe Ser Asn Gly Pro Val His Leu Glu Asp Thr
1105                1110                1115                1120

Leu Lys Lys Ala Gln Ile Asn Asp Ala Lys Tyr His Glu Ile Ser Ile
                1125                1130                1135

Ile Tyr His Asn Asp Lys Lys Met Ile Leu Val Val Asp Arg Arg His
            1140                1145                1150

Val Lys Ser Thr Asp Asn Glu Lys Lys Lys Ile Pro Phe Thr Asp Ile
            1155                1160                1165

Tyr Ile Gly Gly Ala Pro Gln Glu Val Leu Gln Ser Arg Thr Leu Arg
1170                1175                1180

Ala His Leu Pro Leu Asp Ile Asn Phe Arg Gly Cys Met Lys Gly Phe
1185                1190                1195                1200

Gln Phe Gln Lys Lys Asp Phe Asn Leu Leu Glu Gln Thr Glu Thr Leu
                1205                1210                1215

Gly Val Gly Tyr Gly Cys Pro Glu Asp Ser Leu Ile Ser Arg Arg Ala
            1220                1225                1230

Tyr Phe Asn Gly Gln Ser Phe Ile Ala Ser Ile Gln Lys Ile Ser Phe
    1235                1240                1245

Phe Asp Gly Phe Glu Gly Gly Phe Asn Phe Arg Thr Leu Gln Pro Asn
1250                1255                1260

Gly Leu Leu Phe Tyr Tyr Thr Ser Gly Ser Asp Val Phe Ser Ile Ser
1265                1270                1275                1280

Leu Asp Asn Gly Thr Val Val Met Asp Val Lys Gly Ile Lys Val Met
            1285                1290                1295

Ser Thr Asp Lys Gln Tyr His Asp Gly Leu Pro His Phe Val Val Thr
            1300                1305                1310

Ser Ile Ser Asp Thr Arg Tyr Glu Leu Val Val Asp Lys Ser Arg Leu
    1315                1320                1325

Arg Gly Lys Asn Pro Thr Lys Gly Lys Ala Glu Gln Thr Gln Thr Thr
    1330                1335                1340

Glu Lys Lys Phe Tyr Phe Gly Gly Ser Pro Ile Ser Pro Gln Tyr Ala
1345                1350                1355                1360

Asn Phe Thr Gly Cys Ile Ser Asn Ala Tyr Phe Thr Arg Leu Asp Arg
```

-continued

```
            1365                1370                1375
Asp Val Glu Val Glu Asp Phe Gln Arg Tyr Ser Glu Lys Val His Thr
        1380                1385                1390
Ser Leu Tyr Glu Cys Pro Ile Glu Ser Ser Pro Leu Phe Leu Leu His
    1395                1400                1405
Lys Lys Gly Lys Asn Ser Ser Lys Pro Lys Thr Asn Lys Gln Gly Glu
1410                1415                1420
Lys Ser Lys Asp Ala Pro Ser Trp Asp Pro Ile Gly Leu Lys Phe Leu
1425                1430                1435                1440
Glu Gln Lys Ala Pro Arg Asp Ser His Cys His Leu Ser Ser Ser Pro
        1445                1450                1455
Arg Ala Ile Glu His Ala Tyr Gln Tyr Gly Gly Thr Ala Asn Ser Arg
        1460                1465                1470
Gln Glu Phe Glu His Glu Gln Gly Asp Phe Gly Glu Lys Ser Gln Phe
    1475                1480                1485
Ala Ile Arg Leu Lys Thr Arg Ser Ser His Gly Met Ile Phe Tyr Val
        1490                1495                1500
Ser Asp Gln Glu Glu Asn Asp Phe Met Thr Leu Phe Leu Ala His Gly
1505                1510                1515                1520
Arg Leu Val Phe Met Phe Asn Val Gly His Lys Lys Leu Lys Ile Arg
            1525                1530                1535
Ser Gln Glu Lys Tyr Asn Asp Gly Leu Trp His Asp Val Ile Phe Ile
        1540                1545                1550
Arg Glu Lys Ser Ser Gly Arg Leu Val Ile Asp Gly Leu Arg Val Leu
        1555                1560                1565
Glu Glu Arg Leu Pro Pro Ser Gly Ala Ala Trp Lys Ile Lys Gly Pro
    1570                1575                1580
Ile Tyr Leu Gly Gly Val Ala Pro Gly Arg Ala Val Lys Asn Val Gln
1585                1590                1595                1600
Ile Thr Ser Val Tyr Ser Phe Ser Gly Cys Leu Gly Asn Leu Gln Leu
            1605                1610                1615
Asn Gly Ala Ser Ile Thr Ser Ala Ser Gln Thr Phe Ser Val Thr Pro
        1620                1625                1630
Cys Phe Glu Gly Pro Met Glu Thr Gly Thr Tyr Phe Ser Thr Glu Gly
        1635                1640                1645
Gly Tyr Val Val Leu Asp Glu Ser Phe Asn Ile Gly Leu Lys Phe Glu
    1650                1655                1660
Ile Ala Phe Glu Val Arg Pro Arg Ser Ser Ser Gly Thr Leu Val His
1665                1670                1675                1680
Gly His Ser Val Asn Gly Glu Tyr Leu Asn Val His Met Arg Asn Gly
            1685                1690                1695
Gln Val Ile Val Lys Val Asn Asn Gly Val Arg Asp Phe Ser Thr Ser
        1700                1705                1710
Val Thr Pro Lys Gln Asn Leu Cys Asp Gly Arg Trp His Arg Ile Thr
    1715                1720                1725
Val Ile Arg Asp Ser Asn Val Val Gln Leu Asp Val Asp Ser Glu Val
    1730                1735                1740
Asn His Val Val Gly Pro Leu Asn Pro Lys Pro Val Asp His Arg Glu
1745                1750                1755                1760
Pro Val Phe Val Gly Gly Val Pro Glu Ser Leu Leu Thr Pro Arg Leu
        1765                1770                1775
Ala Pro Ser Lys Pro Phe Thr Gly Cys Ile Arg His Phe Val Ile Asp
        1780                1785                1790
```

```
Ser Arg Pro Val Ser Phe Ser Lys Ala Ala Leu Val Ser Gly Ala Val
    1795            1800            1805

Ser Ile Asn Ser Cys Pro Thr Ala
    1810            1815

<210> SEQ ID NO 11
<211> LENGTH: 5544
<212> TYPE: DNA
<213> ORGANISM: Mus musculus
<220> FEATURE:
<221> NAME/KEY: CDS
<222> LOCATION: (1)..(5376)

<400> SEQUENCE: 11 gcg tca ggg gac ggc aat gcg ttt cct ttt gac atc gag ggg agc gca      48
Ala Ser Gly Asp Gly Asn Ala Phe Pro Phe Asp Ile Glu Gly Ser Ala
 1               5                  10                  15 gtg gtc ggc agg caa gac cca tcg gag act agc gac tca ggc gtg aca      96
Val Val Gly Arg Gln Asp Pro Ser Glu Thr Ser Asp Ser Gly Val Thr
             20                  25                  30 ctg gga cgc ctg ccg cct gct gct gag aga tgt gac gct gga ttc ttc     144
Leu Gly Arg Leu Pro Pro Ala Ala Glu Arg Cys Asp Ala Gly Phe Phe
         35                  40                  45 cgc aca ctg tca gga gaa tgt gca ccc tgt gac tgt aat ggc aat tcc     192
Arg Thr Leu Ser Gly Glu Cys Ala Pro Cys Asp Cys Asn Gly Asn Ser
     50                  55                  60 cat gag tgc ttg gat ggc tcc gga ttc tgt ctg cac tgc cag cgg aac     240
His Glu Cys Leu Asp Gly Ser Gly Phe Cys Leu His Cys Gln Arg Asn
 65                  70                  75                  80 aca aca gga gag cac tgt gaa aaa tgt ctg gat ggc tat att gga gac     288
Thr Thr Gly Glu His Cys Glu Lys Cys Leu Asp Gly Tyr Ile Gly Asp
                 85                  90                  95 tcc atc aga ggc aca ccc cgg ttc tgc cag ccg tgc ccc tgt ccc ttg     336
Ser Ile Arg Gly Thr Pro Arg Phe Cys Gln Pro Cys Pro Cys Pro Leu
            100                 105                 110 ccc cac ctg gcc aac ttt gca gaa tcc tgc tac agg aaa aat gga gct     384
Pro His Leu Ala Asn Phe Ala Glu Ser Cys Tyr Arg Lys Asn Gly Ala
        115                 120                 125 gtt cgg tgt att tgt aaa gaa aac tat gtt gga cct aac tgt gaa aga     432
Val Arg Cys Ile Cys Lys Glu Asn Tyr Val Gly Pro Asn Cys Glu Arg
    130                 135                 140 tgt gct cct ggt tac tat gga aac ccc tta ctc att gga agc acc tgt     480
Cys Ala Pro Gly Tyr Tyr Gly Asn Pro Leu Leu Ile Gly Ser Thr Cys
145                 150                 155                 160 aag aaa tgt gac tgc agt gga aat tcg gat ccc aac ctg atc ttt gaa     528
Lys Lys Cys Asp Cys Ser Gly Asn Ser Asp Pro Asn Leu Ile Phe Glu
                165                 170                 175 gac tgt gat gaa atc act ggc cag tgc agg aac tgc tta cga aat acc     576
Asp Cys Asp Glu Ile Thr Gly Gln Cys Arg Asn Cys Leu Arg Asn Thr
            180                 185                 190 acc gga ttc aag tgt gaa cgc tgt gca cct ggt tac tat gga gac gcc     624
Thr Gly Phe Lys Cys Glu Arg Cys Ala Pro Gly Tyr Tyr Gly Asp Ala
        195                 200                 205 agg aca gcc aag aac tgt gca gtg tgc aac tgt ggg ggc ggc ccg cgt     672
Arg Thr Ala Lys Asn Cys Ala Val Cys Asn Cys Gly Gly Gly Pro Arg
    210                 215                 220 gac agt gta acc gga gag tgc ttg gaa gaa gga ttt gaa gtc cct aca     720
Asp Ser Val Thr Gly Glu Cys Leu Glu Glu Gly Phe Glu Val Pro Thr
225                 230                 235                 240 ggc tgt gat aag tgc gtc tgg gac ttg acc gat gac ctg cga tta gca     768
```

```
                                                    -continued

Gly Cys Asp Lys Cys Val Trp Asp Leu Thr Asp Asp Leu Arg Leu Ala
                245                 250                 255 gcg ctc tcc atc gaa gag agc aaa tcc ggg ctg ctg agc gtg tcc tct      816
Ala Leu Ser Ile Glu Glu Ser Lys Ser Gly Leu Leu Ser Val Ser Ser
                260                 265                 270 gcg gct gcg gcg cat aga cac gtg acc gac atg aac tct acc atc cac      864
Ala Ala Ala Ala His Arg His Val Thr Asp Met Asn Ser Thr Ile His
                275                 280                 285 ctc ctc aga aca agg ctg tca gaa aga gaa aac cag tat acc cta aga      912
Leu Leu Arg Thr Arg Leu Ser Glu Arg Glu Asn Gln Tyr Thr Leu Arg
            290                 295                 300 aag ata cag ata aac aac tcg gag aac aca ctg aga agc ctc ctg cct      960
Lys Ile Gln Ile Asn Asn Ser Glu Asn Thr Leu Arg Ser Leu Leu Pro
305                 310                 315                 320 gat gta gag gga ctc cat gag aag gga agt caa gcc tca aga aag ggt     1008
Asp Val Glu Gly Leu His Glu Lys Gly Ser Gln Ala Ser Arg Lys Gly
                325                 330                 335 atg ctg gtt gag aag gaa agc atg gat aca att gac caa gca acc cat     1056
Met Leu Val Glu Lys Glu Ser Met Asp Thr Ile Asp Gln Ala Thr His
                340                 345                 350 ctt gtc gag caa gcc cac aac atg agg gac aaa atc caa gag atc aac     1104
Leu Val Glu Gln Ala His Asn Met Arg Asp Lys Ile Gln Glu Ile Asn
                355                 360                 365 agc aag atg ctc tac tat gga gag aat cag gaa ctt ggc ccc gag gaa     1152
Ser Lys Met Leu Tyr Tyr Gly Glu Asn Gln Glu Leu Gly Pro Glu Glu
            370                 375                 380 ata gct gag aag ctg gtg ttg gcc cag aaa atg ctg gaa gag atc cga     1200
Ile Ala Glu Lys Leu Val Leu Ala Gln Lys Met Leu Glu Glu Ile Arg
385                 390                 395                 400 agc cgg cag cca ttc ctc acc cat cgg gag ctg gtg gat gag gag gca     1248
Ser Arg Gln Pro Phe Leu Thr His Arg Glu Leu Val Asp Glu Glu Ala
                405                 410                 415 gat gag gcc cag gaa ttg ctg agc caa gct gag aac tgg cag cgg ctg     1296
Asp Glu Ala Gln Glu Leu Leu Ser Gln Ala Glu Asn Trp Gln Arg Leu
                420                 425                 430 cac aat gac acc cgc tct tta ttc ccc gtg gtg ctg gag cag ctg gac     1344
His Asn Asp Thr Arg Ser Leu Phe Pro Val Val Leu Glu Gln Leu Asp
            435                 440                 445 gac tac aac gct aag ctg tcc gac ctc cag gaa tcc att aac cag gcc     1392
Asp Tyr Asn Ala Lys Leu Ser Asp Leu Gln Glu Ser Ile Asn Gln Ala
450                 455                 460 ctc gac cat gtc agg gat gca gaa gac atg aat aga gcc atc act ttc     1440
Leu Asp His Val Arg Asp Ala Glu Asp Met Asn Arg Ala Ile Thr Phe
465                 470                 475                 480 aag cag cgg gac cat gag aaa caa cat gag aga gtg aag gaa cag atg     1488
Lys Gln Arg Asp His Glu Lys Gln His Glu Arg Val Lys Glu Gln Met
                485                 490                 495 gaa gtt gtg ggt gcc tct ctg agt atg tct gca gac tct ctt acc ata     1536
Glu Val Val Gly Ala Ser Leu Ser Met Ser Ala Asp Ser Leu Thr Ile
                500                 505                 510 cct cag ctc act ctt gag gaa ctt gat gag ata ata aag aat gca tct     1584
Pro Gln Leu Thr Leu Glu Glu Leu Asp Glu Ile Ile Lys Asn Ala Ser
            515                 520                 525 gga att tat gca gaa ata gat gga gcc aaa aat gag ctg caa gga aaa     1632
Gly Ile Tyr Ala Glu Ile Asp Gly Ala Lys Asn Glu Leu Gln Gly Lys
        530                 535                 540 cta tcc aac ctg agt aac ctc agt cat gac ttg gtt cag gaa gct acg     1680
Leu Ser Asn Leu Ser Asn Leu Ser His Asp Leu Val Gln Glu Ala Thr
545                 550                 555                 560
```

```
gac cat gca tac aat ctt caa cag gaa gcc gat gag cta agc aga aat    1728
Asp His Ala Tyr Asn Leu Gln Gln Glu Ala Asp Glu Leu Ser Arg Asn
            565                 570                 575 ttg cac agt tca gac atg aac ggg ctg gta cag aag gct ttg gat gca    1776
Leu His Ser Ser Asp Met Asn Gly Leu Val Gln Lys Ala Leu Asp Ala
        580                 585                 590 tca aac gtc tat gaa aat atc gcc aat tat gtc agt gaa gcc aac gaa    1824
Ser Asn Val Tyr Glu Asn Ile Ala Asn Tyr Val Ser Glu Ala Asn Glu
            595                 600                 605 aca gca gaa ctt gct ctg aat atc act gat cga att tat gat gct gtg    1872
Thr Ala Glu Leu Ala Leu Asn Ile Thr Asp Arg Ile Tyr Asp Ala Val
        610                 615                 620 agt ggg att gac acg cag atc att tac cat aag gat gaa agt gac aac    1920
Ser Gly Ile Asp Thr Gln Ile Ile Tyr His Lys Asp Glu Ser Asp Asn
625                 630                 635                 640 ctt ctc aat caa gcc aga gag ctg cag gcc aag gca gat tca tgc aat    1968
Leu Leu Asn Gln Ala Arg Glu Leu Gln Ala Lys Ala Asp Ser Cys Asn
            645                 650                 655 gat gaa gca gtg gct gac acc agc agg cgt gtg ggt gga gcc ctg tgg    2016
Asp Glu Ala Val Ala Asp Thr Ser Arg Arg Val Gly Gly Ala Leu Trp
        660                 665                 670 agg aag ggc gcc ctc aga gac aga ctg aat gat gct gtt aag caa cta    2064
Arg Lys Gly Ala Leu Arg Asp Arg Leu Asn Asp Ala Val Lys Gln Leu
            675                 680                 685 cag gca gca gag aga ggg gac gcc cac cag cgc ctg ggc cag tcc aag    2112
Gln Ala Ala Glu Arg Gly Asp Ala His Gln Arg Leu Gly Gln Ser Lys
        690                 695                 700 ctc ttc att gag gaa gct aac aag acg aca gcg gct gtc caa cag gtt    2160
Leu Phe Ile Glu Glu Ala Asn Lys Thr Thr Ala Ala Val Gln Gln Val
705                 710                 715                 720 acc aca cca atg gct aac aac ctc agc aac tgg tcc cag aac ctg cag    2208
Thr Thr Pro Met Ala Asn Asn Leu Ser Asn Trp Ser Gln Asn Leu Gln
            725                 730                 735 acc ttt gac tca tct gca tat aac act gca gtg gac tct gct cgg gac    2256
Thr Phe Asp Ser Ser Ala Tyr Asn Thr Ala Val Asp Ser Ala Arg Asp
        740                 745                 750 gca gtg aga aac ctc acc gag gtt gtc ccc cag ctt ctg gat cag ctt    2304
Ala Val Arg Asn Leu Thr Glu Val Val Pro Gln Leu Leu Asp Gln Leu
            755                 760                 765 cgt act gtg gag cag aag cgg cct gca agc aac att tct gcc agc atc    2352
Arg Thr Val Glu Gln Lys Arg Pro Ala Ser Asn Ile Ser Ala Ser Ile
        770                 775                 780 cag agc atc cga gag ctc att gct caa acc agg agt gtc gca agc aag    2400
Gln Ser Ile Arg Glu Leu Ile Ala Gln Thr Arg Ser Val Ala Ser Lys
785                 790                 795                 800 atc caa gtc tcc atg atg ttt gat ggc cag tca gct gtc gaa gtg cac    2448
Ile Gln Val Ser Met Met Phe Asp Gly Gln Ser Ala Val Glu Val His
            805                 810                 815 ccc aaa gtc agt gtg gat gac ctg aag gcc ttc aca tcc atc agc ttg    2496
Pro Lys Val Ser Val Asp Asp Leu Lys Ala Phe Thr Ser Ile Ser Leu
        820                 825                 830 tac atg aag cct cct cca aag ccg gca gag ccc act ggg gcc tgg gta    2544
Tyr Met Lys Pro Pro Pro Lys Pro Ala Glu Pro Thr Gly Ala Trp Val
            835                 840                 845 gca gat cag ttt gtc ctc tac ctc gga agc aaa aac gcc aaa aaa gaa    2592
Ala Asp Gln Phe Val Leu Tyr Leu Gly Ser Lys Asn Ala Lys Lys Glu
        850                 855                 860 tac atg ggt ctg gca atc aaa aat gat aac ctg gta tac gtt tac aat    2640
Tyr Met Gly Leu Ala Ile Lys Asn Asp Asn Leu Val Tyr Val Tyr Asn
865                 870                 875                 880
```

```
ttg ggg atg aaa gat gtg gaa att ctc ctg gat tcc aag cct gtg agc    2688
Leu Gly Met Lys Asp Val Glu Ile Leu Leu Asp Ser Lys Pro Val Ser
                885                 890                 895 tcc tgg ccc gct tac ttt agt att gtc aag att gaa agg gta ggg gaa    2736
Ser Trp Pro Ala Tyr Phe Ser Ile Val Lys Ile Glu Arg Val Gly Glu
            900                 905                 910 cac gga aag gtg ttc ttg aca gtc ccc agt ctc agt agc aca gca gaa    2784
His Gly Lys Val Phe Leu Thr Val Pro Ser Leu Ser Ser Thr Ala Glu
        915                 920                 925 gaa aag ttt att aag aag ggg gag ttt gca gga gat gac tcc ttg ctg    2832
Glu Lys Phe Ile Lys Lys Gly Glu Phe Ala Gly Asp Asp Ser Leu Leu
    930                 935                 940 gat gtg acc cct gag gac act gtg ttt tac gtt ggt ggg gtg cct gcg    2880
Asp Val Thr Pro Glu Asp Thr Val Phe Tyr Val Gly Gly Val Pro Ala
945                 950                 955                 960 aac ttc aag ctc cct gcc agc tta aac ctg ccc agc tac tca ggc tgc    2928
Asn Phe Lys Leu Pro Ala Ser Leu Asn Leu Pro Ser Tyr Ser Gly Cys
                965                 970                 975 cta gag ctg gcc act ctg aat aat gat gtg atc agc ttg tac aac ttc    2976
Leu Glu Leu Ala Thr Leu Asn Asn Asp Val Ile Ser Leu Tyr Asn Phe
            980                 985                 990 aag cac atc tat aat atg gat cca tca aag tca gtg ccc tgt gcc agg    3024
Lys His Ile Tyr Asn Met Asp Pro Ser Lys Ser Val Pro Cys Ala Arg
        995                 1000                1005 gat aaa ctg gct ttc act cag agt agg gct gcc agc tac ttc ttc gat    3072
Asp Lys Leu Ala Phe Thr Gln Ser Arg Ala Ala Ser Tyr Phe Phe Asp
    1010                1015                1020 ggc tcc agt tat gca gtg gtg agg gac atc acg agg aga ggg aag ttt    3120
Gly Ser Ser Tyr Ala Val Val Arg Asp Ile Thr Arg Arg Gly Lys Phe
1025                1030                1035                1040 ggt cag gtg act cgc ttt gac ata gaa atc cga aca cca gct gac aat    3168
Gly Gln Val Thr Arg Phe Asp Ile Glu Ile Arg Thr Pro Ala Asp Asn
                1045                1050                1055 ggc ctt gtg ctc ctg atg gtc aat ggc agt atg ttt ttc agc ctc gaa    3216
Gly Leu Val Leu Leu Met Val Asn Gly Ser Met Phe Phe Ser Leu Glu
            1060                1065                1070 atg cgc aat ggc tac cta cat gtg ttc tat gac ttt gga ttc agc aat    3264
Met Arg Asn Gly Tyr Leu His Val Phe Tyr Asp Phe Gly Phe Ser Asn
        1075                1080                1085 ggc ccc gtg cat ctt gaa gac acg ttg aaa aaa gcc cag att aat gat    3312
Gly Pro Val His Leu Glu Asp Thr Leu Lys Lys Ala Gln Ile Asn Asp
    1090                1095                1100 gcg aaa tat cat gag atc tca atc att tat cac aac gac aaa aaa atg    3360
Ala Lys Tyr His Glu Ile Ser Ile Ile Tyr His Asn Asp Lys Lys Met
1105                1110                1115                1120 att ttg gtg gtg gac aga cgg cac gtt aag agc aca gac aat gag aag    3408
Ile Leu Val Val Asp Arg Arg His Val Lys Ser Thr Asp Asn Glu Lys
                1125                1130                1135 aaa aag att cct ttc acg gac atc tac atc gga ggt gcg ccc caa gaa    3456
Lys Lys Ile Pro Phe Thr Asp Ile Tyr Ile Gly Gly Ala Pro Gln Glu
            1140                1145                1150 gtc tta cag tcc agg acc cta aga gca cac ctt ccc cta gat atc aac    3504
Val Leu Gln Ser Arg Thr Leu Arg Ala His Leu Pro Leu Asp Ile Asn
        1155                1160                1165 ttt agg ggg tgc atg aag ggg ttc cag ttc caa aag aaa gat ttc aat    3552
Phe Arg Gly Cys Met Lys Gly Phe Gln Phe Gln Lys Lys Asp Phe Asn
    1170                1175                1180 tta ctg gag cag aca gaa acc cta gga gtt ggt tat gga tgc cca gag    3600
Leu Leu Glu Gln Thr Glu Thr Leu Gly Val Gly Tyr Gly Cys Pro Glu
```

```
                                                -continued
1185                  1190                  1195                  1200 gac tct ctg ata tct cgc aga gca tat ttc aat ggg caa agt ttt att         3648
Asp Ser Leu Ile Ser Arg Arg Ala Tyr Phe Asn Gly Gln Ser Phe Ile
                1205                  1210                  1215 gct tca att cag aaa ata tct ttc ttt gat ggc ttt gaa gga ggc ttc         3696
Ala Ser Ile Gln Lys Ile Ser Phe Phe Asp Gly Phe Glu Gly Gly Phe
                1220                  1225                  1230 aat ttc cga aca tta cag cca aat ggg tta cta ttc tac tac aca tca         3744
Asn Phe Arg Thr Leu Gln Pro Asn Gly Leu Leu Phe Tyr Tyr Thr Ser
                1235                  1240                  1245 ggg tcg gac gtg ttt tcc att tca ctg gac aac ggc act gtt gtc atg         3792
Gly Ser Asp Val Phe Ser Ile Ser Leu Asp Asn Gly Thr Val Val Met
       1250                  1255                  1260 gac gta aag ggc atc aag gtc atg tca aca gac aag cag tac cac gat         3840
Asp Val Lys Gly Ile Lys Val Met Ser Thr Asp Lys Gln Tyr His Asp
1265                  1270                  1275                  1280 ggg ctg ccc cac ttc gtg gtc acc tcc atc tca gac aca aga tat gaa         3888
Gly Leu Pro His Phe Val Val Thr Ser Ile Ser Asp Thr Arg Tyr Glu
                1285                  1290                  1295 ctg gta gta gac aaa agc cga ctt cga ggg aag aat cca aca aaa ggg         3936
Leu Val Val Asp Lys Ser Arg Leu Arg Gly Lys Asn Pro Thr Lys Gly
                1300                  1305                  1310 aag gca gag cag act caa aca act gag aag aag ttc tac ttt ggt ggc         3984
Lys Ala Glu Gln Thr Gln Thr Thr Glu Lys Lys Phe Tyr Phe Gly Gly
                1315                  1320                  1325 tca ccc atc agt cct cag tat gct aat ttc act gga tgt ata agc aat         4032
Ser Pro Ile Ser Pro Gln Tyr Ala Asn Phe Thr Gly Cys Ile Ser Asn
       1330                  1335                  1340 gcc tac ttt acc agg ttg gat aga gat gtg gaa gtc gaa gac ttc cag         4080
Ala Tyr Phe Thr Arg Leu Asp Arg Asp Val Glu Val Glu Asp Phe Gln
1345                  1350                  1355                  1360 cgc tat tct gaa aag gtc cac act tca ctc tat gag tgt ccg att gag         4128
Arg Tyr Ser Glu Lys Val His Thr Ser Leu Tyr Glu Cys Pro Ile Glu
                1365                  1370                  1375 tcg tca cct ctg ttt ctc ctt cac aaa aaa gga aag aat tcc tca aag         4176
Ser Ser Pro Leu Phe Leu Leu His Lys Lys Gly Lys Asn Ser Ser Lys
                1380                  1385                  1390 cct aaa aca aac aaa cag gga gag aag agt aag gat gcg cct tca tgg         4224
Pro Lys Thr Asn Lys Gln Gly Glu Lys Ser Lys Asp Ala Pro Ser Trp
                1395                  1400                  1405 gat cct att ggc ctg aag ttt ctg gaa cag aaa gct cca aga gat tcc         4272
Asp Pro Ile Gly Leu Lys Phe Leu Glu Gln Lys Ala Pro Arg Asp Ser
       1410                  1415                  1420 cac tgc cac ctc tcc agc agc ccc agg gca ata gaa cat gcc tat caa         4320
His Cys His Leu Ser Ser Ser Pro Arg Ala Ile Glu His Ala Tyr Gln
1425                  1430                  1435                  1440 tat ggc ggc acg gcc aac agt cgc cag gag ttt gaa cac gaa caa gga         4368
Tyr Gly Gly Thr Ala Asn Ser Arg Gln Glu Phe Glu His Glu Gln Gly
                1445                  1450                  1455 gat ttt ggt gaa aaa tcc cag ttt gcc att cgt ctg aag acc cgt tcc         4416
Asp Phe Gly Glu Lys Ser Gln Phe Ala Ile Arg Leu Lys Thr Arg Ser
                1460                  1465                  1470 tca cat ggg atg att ttc tat gtc tca gac caa gaa gag aat gat ttc         4464
Ser His Gly Met Ile Phe Tyr Val Ser Asp Gln Glu Glu Asn Asp Phe
       1475                  1480                  1485 atg acc ctg ttc ttg gcc cat ggt cgc ttg gtc ttt atg ttt aat gtt         4512
Met Thr Leu Phe Leu Ala His Gly Arg Leu Val Phe Met Phe Asn Val
1490                  1495                  1500 ggc cat aag aaa ctg aag att aga agc cag gag aaa tac aat gat gga         4560
```

```
Gly His Lys Lys Leu Lys Ile Arg Ser Gln Glu Lys Tyr Asn Asp Gly
1505                1510                1515                1520 ttg tgg cat gat gtg ata ttt att cgg gaa aag agc agt ggt cga ctg        4608
Leu Trp His Asp Val Ile Phe Ile Arg Glu Lys Ser Ser Gly Arg Leu
            1525                1530                1535 gtc att gat ggt cta cga gtc cta gaa gaa agg ctt ccc cct agt ggc        4656
Val Ile Asp Gly Leu Arg Val Leu Glu Glu Arg Leu Pro Pro Ser Gly
        1540                1545                1550 gct gcc tgg aaa atc aag ggt ccc att tat ctg gga gga gtg gct ccc        4704
Ala Ala Trp Lys Ile Lys Gly Pro Ile Tyr Leu Gly Gly Val Ala Pro
    1555                1560                1565 gga aga gcc gtg aaa aat gtc cag att acc tcc gtc tac agc ttc agt        4752
Gly Arg Ala Val Lys Asn Val Gln Ile Thr Ser Val Tyr Ser Phe Ser
 1570                1575                1580 ggc tgc ctt ggc aat ctc cag ctc aat ggt gcc tcc atc acc tcc gct        4800
Gly Cys Leu Gly Asn Leu Gln Leu Asn Gly Ala Ser Ile Thr Ser Ala
1585                1590                1595                1600 tct caa acg ttt agc gtg acc cct tgc ttt gaa ggg cca atg gaa aca        4848
Ser Gln Thr Phe Ser Val Thr Pro Cys Phe Glu Gly Pro Met Glu Thr
                1605                1610                1615 gga act tat ttt tcc aca gaa ggc ggc tat gtg gtt cta gat gag tct        4896
Gly Thr Tyr Phe Ser Thr Glu Gly Gly Tyr Val Val Leu Asp Glu Ser
            1620                1625                1630 ttc aat att ggg tta aaa ttt gaa att gcc ttt gaa gtc cgc ccc cgg        4944
Phe Asn Ile Gly Leu Lys Phe Glu Ile Ala Phe Glu Val Arg Pro Arg
        1635                1640                1645 agc agt tct gga acc ctt gtc cat ggc cac agc gtc aac ggg gaa tac        4992
Ser Ser Ser Gly Thr Leu Val His Gly His Ser Val Asn Gly Glu Tyr
    1650                1655                1660 ctg aac gtg cac atg aga aac gga cag gtc ata gtg aag gtc aac aac        5040
Leu Asn Val His Met Arg Asn Gly Gln Val Ile Val Lys Val Asn Asn
1665                1670                1675                1680 ggt gtc aga gac ttt tct acc tca gta act ccc aag cag aat ctc tgt        5088
Gly Val Arg Asp Phe Ser Thr Ser Val Thr Pro Lys Gln Asn Leu Cys
                1685                1690                1695 gat ggc aga tgg cac aga att aca gtt att aga gat tca aac gtg gtt        5136
Asp Gly Arg Trp His Arg Ile Thr Val Ile Arg Asp Ser Asn Val Val
            1700                1705                1710 cag ttg gat gta gac tca gaa gtg aac cat gta gtt ggg ccg ttg aat        5184
Gln Leu Asp Val Asp Ser Glu Val Asn His Val Val Gly Pro Leu Asn
        1715                1720                1725 cca aag cca gtt gat cac agg gag cct gtg ttt gtt gga ggt gtt cca        5232
Pro Lys Pro Val Asp His Arg Glu Pro Val Phe Val Gly Gly Val Pro
    1730                1735                1740 gag tct tta ctg aca cca cgt ttg gct ccc agc aaa ccc ttc acc ggc        5280
Glu Ser Leu Leu Thr Pro Arg Leu Ala Pro Ser Lys Pro Phe Thr Gly
1745                1750                1755                1760 tgc atc cgc cac ttt gta att gac agc cgc cct gtg agc ttc agt aaa        5328
Cys Ile Arg His Phe Val Ile Asp Ser Arg Pro Val Ser Phe Ser Lys
                1765                1770                1775 gct gcc ctg gtc agt ggt gct gtg agc atc aac tcc tgt ccc aca gcc        5376
Ala Ala Leu Val Ser Gly Ala Val Ser Ile Asn Ser Cys Pro Thr Ala
            1780                1785                1790 tgacacagct gcaaggctgc tgaagacagc tcttcctaac actgaaataa acatagtagt     5436 gggggtcgg gagggtcaga ggcctggaac tcccctccct actgaagctc tcacctggtt      5496
gaaggggatt tcaataaatc agagaccagc cgcaaaaaaa aaaaaaaa                  5544

<210> SEQ ID NO 12
```

-continued

```
<211> LENGTH: 1792
<212> TYPE: PRT
<213> ORGANISM: Mus musculus

<400> SEQUENCE: 12

Ala Ser Gly Asp Gly Asn Ala Phe Pro Phe Asp Ile Glu Gly Ser Ala
 1               5                  10                  15

Val Val Gly Arg Gln Asp Pro Ser Glu Thr Ser Asp Ser Gly Val Thr
            20                  25                  30

Leu Gly Arg Leu Pro Pro Ala Ala Glu Arg Cys Asp Ala Gly Phe Phe
        35                  40                  45

Arg Thr Leu Ser Gly Glu Cys Ala Pro Cys Asp Cys Asn Gly Asn Ser
 50                  55                  60

His Glu Cys Leu Asp Gly Ser Gly Phe Cys Leu His Cys Gln Arg Asn
 65                  70                  75                  80

Thr Thr Gly Glu His Cys Glu Lys Cys Leu Asp Gly Tyr Ile Gly Asp
                85                  90                  95

Ser Ile Arg Gly Thr Pro Arg Phe Cys Gln Pro Cys Pro Cys Pro Leu
            100                 105                 110

Pro His Leu Ala Asn Phe Ala Glu Ser Cys Tyr Arg Lys Asn Gly Ala
        115                 120                 125

Val Arg Cys Ile Cys Lys Glu Asn Tyr Val Gly Pro Asn Cys Glu Arg
130                 135                 140

Cys Ala Pro Gly Tyr Tyr Gly Asn Pro Leu Leu Ile Gly Ser Thr Cys
145                 150                 155                 160

Lys Lys Cys Asp Cys Ser Gly Asn Ser Asp Pro Asn Leu Ile Phe Glu
                165                 170                 175

Asp Cys Asp Glu Ile Thr Gly Gln Cys Arg Asn Cys Leu Arg Asn Thr
            180                 185                 190

Thr Gly Phe Lys Cys Glu Arg Cys Ala Pro Gly Tyr Tyr Gly Asp Ala
        195                 200                 205

Arg Thr Ala Lys Asn Cys Ala Val Cys Asn Cys Gly Gly Gly Pro Arg
210                 215                 220

Asp Ser Val Thr Gly Glu Cys Leu Glu Glu Gly Phe Glu Val Pro Thr
225                 230                 235                 240

Gly Cys Asp Lys Cys Val Trp Asp Leu Thr Asp Asp Leu Arg Leu Ala
                245                 250                 255

Ala Leu Ser Ile Glu Glu Ser Lys Ser Gly Leu Leu Ser Val Ser Ser
            260                 265                 270

Ala Ala Ala His Arg His Val Thr Asp Met Asn Ser Thr Ile His
        275                 280                 285

Leu Leu Arg Thr Arg Leu Ser Glu Arg Glu Asn Gln Tyr Thr Leu Arg
290                 295                 300

Lys Ile Gln Ile Asn Asn Ser Glu Asn Thr Leu Arg Ser Leu Leu Pro
305                 310                 315                 320

Asp Val Glu Gly Leu His Glu Lys Gly Ser Gln Ala Ser Arg Lys Gly
                325                 330                 335

Met Leu Val Glu Lys Glu Ser Met Asp Thr Ile Asp Gln Ala Thr His
            340                 345                 350

Leu Val Glu Gln Ala His Asn Met Arg Asp Lys Ile Gln Glu Ile Asn
        355                 360                 365

Ser Lys Met Leu Tyr Tyr Gly Glu Asn Gln Glu Leu Gly Pro Glu Glu
370                 375                 380

Ile Ala Glu Lys Leu Val Leu Ala Gln Lys Met Leu Glu Glu Ile Arg
```

```
385                390                395                400

Ser Arg Gln Pro Phe Leu Thr His Arg Glu Leu Val Asp Glu Glu Ala
                    405                410                415

Asp Glu Ala Gln Glu Leu Leu Ser Gln Ala Glu Asn Trp Gln Arg Leu
                420                425                430

His Asn Asp Thr Arg Ser Leu Phe Pro Val Val Leu Glu Gln Leu Asp
            435                440                445

Asp Tyr Asn Ala Lys Leu Ser Asp Leu Gln Glu Ser Ile Asn Gln Ala
        450                455                460

Leu Asp His Val Arg Asp Ala Glu Asp Met Asn Arg Ala Ile Thr Phe
465                470                475                480

Lys Gln Arg Asp His Glu Lys Gln His Glu Arg Val Lys Glu Gln Met
                485                490                495

Glu Val Val Gly Ala Ser Leu Ser Met Ser Ala Asp Ser Leu Thr Ile
                500                505                510

Pro Gln Leu Thr Leu Glu Glu Leu Asp Glu Ile Ile Lys Asn Ala Ser
            515                520                525

Gly Ile Tyr Ala Glu Ile Asp Gly Ala Lys Asn Glu Leu Gln Gly Lys
        530                535                540

Leu Ser Asn Leu Ser Asn Leu Ser His Asp Leu Val Gln Glu Ala Thr
545                550                555                560

Asp His Ala Tyr Asn Leu Gln Gln Glu Ala Asp Glu Leu Ser Arg Asn
                565                570                575

Leu His Ser Ser Asp Met Asn Gly Leu Val Gln Lys Ala Leu Asp Ala
                580                585                590

Ser Asn Val Tyr Glu Asn Ile Ala Asn Tyr Val Ser Glu Ala Asn Glu
            595                600                605

Thr Ala Glu Leu Ala Leu Asn Ile Thr Asp Arg Ile Tyr Asp Ala Val
        610                615                620

Ser Gly Ile Asp Thr Gln Ile Ile Tyr His Lys Asp Glu Ser Asp Asn
625                630                635                640

Leu Leu Asn Gln Ala Arg Glu Leu Gln Ala Lys Ala Asp Ser Cys Asn
                645                650                655

Asp Glu Ala Val Ala Asp Thr Ser Arg Arg Val Gly Gly Ala Leu Trp
                660                665                670

Arg Lys Gly Ala Leu Arg Asp Arg Leu Asn Asp Ala Val Lys Gln Leu
            675                680                685

Gln Ala Ala Glu Arg Gly Asp Ala His Gln Arg Leu Gly Gln Ser Lys
        690                695                700

Leu Phe Ile Glu Glu Ala Asn Lys Thr Thr Ala Ala Val Gln Gln Val
705                710                715                720

Thr Thr Pro Met Ala Asn Asn Leu Ser Asn Trp Ser Gln Asn Leu Gln
                725                730                735

Thr Phe Asp Ser Ser Ala Tyr Asn Thr Ala Val Asp Ser Ala Arg Asp
                740                745                750

Ala Val Arg Asn Leu Thr Glu Val Pro Gln Leu Leu Asp Gln Leu
            755                760                765

Arg Thr Val Glu Gln Lys Arg Pro Ala Ser Asn Ile Ser Ala Ser Ile
        770                775                780

Gln Ser Ile Arg Glu Leu Ile Ala Gln Thr Arg Ser Val Ala Ser Lys
785                790                795                800

Ile Gln Val Ser Met Met Phe Asp Gly Gln Ser Ala Val Glu Val His
                805                810                815
```

```
Pro Lys Val Ser Val Asp Asp Leu Lys Ala Phe Thr Ser Ile Ser Leu
        820                 825                 830

Tyr Met Lys Pro Pro Lys Pro Ala Glu Pro Thr Gly Ala Trp Val
        835                 840                 845

Ala Asp Gln Phe Val Leu Tyr Leu Gly Ser Lys Asn Ala Lys Lys Glu
    850                 855                 860

Tyr Met Gly Leu Ala Ile Lys Asn Asp Asn Leu Val Tyr Val Tyr Asn
865                 870                 875                 880

Leu Gly Met Lys Asp Val Glu Ile Leu Leu Asp Ser Lys Pro Val Ser
                885                 890                 895

Ser Trp Pro Ala Tyr Phe Ser Ile Val Lys Ile Glu Arg Val Gly Glu
            900                 905                 910

His Gly Lys Val Phe Leu Thr Val Pro Ser Leu Ser Ser Thr Ala Glu
        915                 920                 925

Glu Lys Phe Ile Lys Lys Gly Glu Phe Ala Gly Asp Asp Ser Leu Leu
    930                 935                 940

Asp Val Thr Pro Glu Asp Thr Val Phe Tyr Val Gly Val Pro Ala
945                 950                 955                 960

Asn Phe Lys Leu Pro Ala Ser Leu Asn Leu Pro Ser Tyr Ser Gly Cys
                965                 970                 975

Leu Glu Leu Ala Thr Leu Asn Asn Asp Val Ile Ser Leu Tyr Asn Phe
            980                 985                 990

Lys His Ile Tyr Asn Met Asp Pro Ser Lys Ser Val Pro Cys Ala Arg
        995                 1000                1005

Asp Lys Leu Ala Phe Thr Gln Ser Arg Ala Ala Ser Tyr Phe Phe Asp
    1010                1015                1020

Gly Ser Ser Tyr Ala Val Val Arg Asp Ile Thr Arg Arg Gly Lys Phe
1025                1030                1035                1040

Gly Gln Val Thr Arg Phe Asp Ile Glu Ile Arg Thr Pro Ala Asp Asn
                1045                1050                1055

Gly Leu Val Leu Leu Met Val Asn Gly Ser Met Phe Phe Ser Leu Glu
            1060                1065                1070

Met Arg Asn Gly Tyr Leu His Val Phe Tyr Asp Phe Gly Phe Ser Asn
        1075                1080                1085

Gly Pro Val His Leu Glu Asp Thr Leu Lys Lys Ala Gln Ile Asn Asp
    1090                1095                1100

Ala Lys Tyr His Glu Ile Ser Ile Ile Tyr His Asn Asp Lys Lys Met
1105                1110                1115                1120

Ile Leu Val Val Asp Arg Arg His Val Lys Ser Thr Asp Asn Glu Lys
                1125                1130                1135

Lys Lys Ile Pro Phe Thr Asp Ile Tyr Ile Gly Gly Ala Pro Gln Glu
            1140                1145                1150

Val Leu Gln Ser Arg Thr Leu Arg Ala His Leu Pro Leu Asp Ile Asn
        1155                1160                1165

Phe Arg Gly Cys Met Lys Gly Phe Gln Phe Gln Lys Lys Asp Phe Asn
    1170                1175                1180

Leu Leu Glu Gln Thr Glu Thr Leu Gly Val Gly Tyr Gly Cys Pro Glu
1185                1190                1195                1200

Asp Ser Leu Ile Ser Arg Arg Ala Tyr Phe Asn Gly Gln Ser Phe Ile
                1205                1210                1215

Ala Ser Ile Gln Lys Ile Ser Phe Phe Asp Gly Phe Glu Gly Gly Phe
            1220                1225                1230
```

```
Asn Phe Arg Thr Leu Gln Pro Asn Gly Leu Leu Phe Tyr Tyr Thr Ser
    1235                1240                1245

Gly Ser Asp Val Phe Ser Ile Ser Leu Asp Asn Gly Thr Val Val Met
1250                1255                1260

Asp Val Lys Gly Ile Lys Val Met Ser Thr Asp Lys Gln Tyr His Asp
1265                1270                1275                1280

Gly Leu Pro His Phe Val Val Ser Ile Ser Asp Thr Arg Tyr Glu
        1285                1290                1295

Leu Val Val Asp Lys Ser Arg Leu Arg Gly Lys Asn Pro Thr Lys Gly
        1300                1305                1310

Lys Ala Glu Gln Thr Gln Thr Thr Glu Lys Lys Phe Tyr Phe Gly Gly
        1315                1320                1325

Ser Pro Ile Ser Pro Gln Tyr Ala Asn Phe Thr Gly Cys Ile Ser Asn
    1330                1335                1340

Ala Tyr Phe Thr Arg Leu Asp Arg Asp Val Glu Val Glu Asp Phe Gln
1345                1350                1355                1360

Arg Tyr Ser Glu Lys Val His Thr Ser Leu Tyr Glu Cys Pro Ile Glu
        1365                1370                1375

Ser Ser Pro Leu Phe Leu Leu His Lys Lys Gly Lys Asn Ser Ser Lys
        1380                1385                1390

Pro Lys Thr Asn Lys Gln Gly Glu Lys Ser Lys Asp Ala Pro Ser Trp
        1395                1400                1405

Asp Pro Ile Gly Leu Lys Phe Leu Glu Gln Lys Ala Pro Arg Asp Ser
    1410                1415                1420

His Cys His Leu Ser Ser Ser Pro Arg Ala Ile Glu His Ala Tyr Gln
1425                1430                1435                1440

Tyr Gly Gly Thr Ala Asn Ser Arg Gln Glu Phe Glu His Glu Gln Gly
        1445                1450                1455

Asp Phe Gly Glu Lys Ser Gln Phe Ala Ile Arg Leu Lys Thr Arg Ser
        1460                1465                1470

Ser His Gly Met Ile Phe Tyr Val Ser Asp Gln Glu Glu Asn Asp Phe
        1475                1480                1485

Met Thr Leu Phe Leu Ala His Gly Arg Leu Val Phe Met Phe Asn Val
    1490                1495                1500

Gly His Lys Lys Leu Lys Ile Arg Ser Gln Glu Lys Tyr Asn Asp Gly
1505                1510                1515                1520

Leu Trp His Asp Val Ile Phe Ile Arg Glu Lys Ser Ser Gly Arg Leu
        1525                1530                1535

Val Ile Asp Gly Leu Arg Val Leu Glu Glu Arg Leu Pro Pro Ser Gly
        1540                1545                1550

Ala Ala Trp Lys Ile Lys Gly Pro Ile Tyr Leu Gly Gly Val Ala Pro
    1555                1560                1565

Gly Arg Ala Val Lys Asn Val Gln Ile Thr Ser Val Tyr Ser Phe Ser
    1570                1575                1580

Gly Cys Leu Gly Asn Leu Gln Leu Asn Gly Ala Ser Ile Thr Ser Ala
1585                1590                1595                1600

Ser Gln Thr Phe Ser Val Thr Pro Cys Phe Glu Gly Pro Met Glu Thr
        1605                1610                1615

Gly Thr Tyr Phe Ser Thr Glu Gly Gly Tyr Val Val Leu Asp Glu Ser
        1620                1625                1630

Phe Asn Ile Gly Leu Lys Phe Glu Ile Ala Phe Glu Val Arg Pro Arg
    1635                1640                1645

Ser Ser Ser Gly Thr Leu Val His Gly His Ser Val Asn Gly Glu Tyr
```

-continued

```
              1650                1655                1660

Leu Asn Val His Met Arg Asn Gly Gln Val Ile Val Lys Val Asn Asn
1665                1670                1675                1680

Gly Val Arg Asp Phe Ser Thr Ser Val Thr Pro Lys Gln Asn Leu Cys
                1685                1690                1695

Asp Gly Arg Trp His Arg Ile Thr Val Ile Arg Asp Ser Asn Val Val
                    1700                1705                1710

Gln Leu Asp Val Asp Ser Glu Val Asn His Val Gly Pro Leu Asn
        1715                1720                1725

Pro Lys Pro Val Asp His Arg Glu Pro Val Phe Val Gly Val Pro
    1730                1735                1740

Glu Ser Leu Leu Thr Pro Arg Leu Ala Pro Ser Lys Pro Phe Thr Gly
1745                1750                1755                1760

Cys Ile Arg His Phe Val Ile Asp Ser Arg Pro Val Ser Phe Ser Lys
                1765                1770                1775

Ala Ala Leu Val Ser Gly Ala Val Ser Ile Asn Ser Cys Pro Thr Ala
                    1780                1785                1790

<210> SEQ ID NO 13
<211> LENGTH: 5613
<212> TYPE: DNA
<213> ORGANISM: Homo sapiens
<220> FEATURE:
<221> NAME/KEY: CDS
<222> LOCATION: (118)..(5475)
<221> NAME/KEY: sig_peptide
<222> LOCATION: (118)..(180)

<400> SEQUENCE: 13
cccggagcag ggcgagagct cgcgtcgccg gaaaggaaga cgggaagaaa gggcaggcgg      60
ctcggcgggc gtcttctcca ctcctctgcc gcgtccccgt ggctgcaggg agccggc        117 atg ggg ctt ctc cag ttg cta gct ttc agt ttc tta gcc ctg tgc aga      165
Met Gly Leu Leu Gln Leu Leu Ala Phe Ser Phe Leu Ala Leu Cys Arg
 1               5                  10                  15 gcc cga gtg cgc gct cag gaa ccc gag ttc agc tac ggc tgc gca gaa      213
Ala Arg Val Arg Ala Gln Glu Pro Glu Phe Ser Tyr Gly Cys Ala Glu
            20                  25                  30 ggc agc tgc tat ccc gcc acg ggc gac ctt ctc atc ggc cga gca cag      261
Gly Ser Cys Tyr Pro Ala Thr Gly Asp Leu Leu Ile Gly Arg Ala Gln
        35                  40                  45 aag ctt tcg gtg acc tcg acg tgc ggg ctg cac aag ccc gaa ccc tac      309
Lys Leu Ser Val Thr Ser Thr Cys Gly Leu His Lys Pro Glu Pro Tyr
    50                  55                  60 tgt atc gtc agc cac ttg cag gag gac aaa aaa tgc ttc ata tgc aat      357
Cys Ile Val Ser His Leu Gln Glu Asp Lys Lys Cys Phe Ile Cys Asn
65                  70                  75                  80 tcc caa gat cct tat cat gag acc ctg aat cct gac agc cat ctc att      405
Ser Gln Asp Pro Tyr His Glu Thr Leu Asn Pro Asp Ser His Leu Ile
                85                  90                  95 gaa aat gtg gtc act aca ttt gct cca aac cgc ctt aag att tgg tgg      453
Glu Asn Val Val Thr Thr Phe Ala Pro Asn Arg Leu Lys Ile Trp Trp
            100                 105                 110 caa tct gaa aat ggt gtg gaa aat gta act atc caa ctg gat ttg gaa      501
Gln Ser Glu Asn Gly Val Glu Asn Val Thr Ile Gln Leu Asp Leu Glu
        115                 120                 125 gca gaa ttc cat ttt act cat ctc ata atg act ttc aag aca ttc cgt      549
Ala Glu Phe His Phe Thr His Leu Ile Met Thr Phe Lys Thr Phe Arg
    130                 135                 140
```

```
cca gct gct atg ctg ata gaa cga tcg tcc gac ttt ggg aaa acc tgg      597
Pro Ala Ala Met Leu Ile Glu Arg Ser Ser Asp Phe Gly Lys Thr Trp
145                 150                 155                 160 ggt gtg tat aga tac ttc gcc tat gac tgt gag gcc tcg ttt cca ggc      645
Gly Val Tyr Arg Tyr Phe Ala Tyr Asp Cys Glu Ala Ser Phe Pro Gly
                165                 170                 175 att tca act ggc ccc atg aaa aaa gtc gat gac ata att tgt gat tct      693
Ile Ser Thr Gly Pro Met Lys Lys Val Asp Asp Ile Ile Cys Asp Ser
            180                 185                 190 cga tat tct gac att gaa ccc tca act gaa gga gag gtg ata ttt cgt      741
Arg Tyr Ser Asp Ile Glu Pro Ser Thr Glu Gly Glu Val Ile Phe Arg
        195                 200                 205 gct tta gat cct gct ttc aaa ata gaa gat cct tat agc cca agg ata      789
Ala Leu Asp Pro Ala Phe Lys Ile Glu Asp Pro Tyr Ser Pro Arg Ile
    210                 215                 220 cag aat tta tta aaa att acc aac ttg aga atc aag ttt gtg aaa ctg      837
Gln Asn Leu Leu Lys Ile Thr Asn Leu Arg Ile Lys Phe Val Lys Leu
225                 230                 235                 240 cat act ttg gga gat aac ctt ctg gat tcc agg atg gaa atc aga gaa      885
His Thr Leu Gly Asp Asn Leu Leu Asp Ser Arg Met Glu Ile Arg Glu
                245                 250                 255 aag tat tat tat gca gtt tat gat atg gtg gtt cga gga aat tgc ttc      933
Lys Tyr Tyr Tyr Ala Val Tyr Asp Met Val Val Arg Gly Asn Cys Phe
                260                 265                 270 tgc tat ggt cat gcc agc gaa tgt gcc cct gtg gat gga ttc aat gaa      981
Cys Tyr Gly His Ala Ser Glu Cys Ala Pro Val Asp Gly Phe Asn Glu
            275                 280                 285 gaa gtg gaa gga atg gtt cac gga cac tgc atg tgc agg cat aac acc     1029
Glu Val Glu Gly Met Val His Gly His Cys Met Cys Arg His Asn Thr
        290                 295                 300 aag ggc tta aac tgt gaa ctc tgc atg gat ttc tac cat gat tta cct     1077
Lys Gly Leu Asn Cys Glu Leu Cys Met Asp Phe Tyr His Asp Leu Pro
305                 310                 315                 320 tgg aga cct gct gaa ggc cga aac agc aac gcc tgt aaa aaa tgt aac     1125
Trp Arg Pro Ala Glu Gly Arg Asn Ser Asn Ala Cys Lys Lys Cys Asn
                325                 330                 335 tgc aat gaa cat tcc atc tct tgt cac ttt gac atg gct gtt tac ctg     1173
Cys Asn Glu His Ser Ile Ser Cys His Phe Asp Met Ala Val Tyr Leu
            340                 345                 350 gcc acg ggg aac gtc agc gga ggc gtg tgt gat gac tgt cag cac aac     1221
Ala Thr Gly Asn Val Ser Gly Gly Val Cys Asp Asp Cys Gln His Asn
        355                 360                 365 acc atg ggg cgc aac tgt gag cag tgc aag ccg ttt tac tac cag cac     1269
Thr Met Gly Arg Asn Cys Glu Gln Cys Lys Pro Phe Tyr Tyr Gln His
370                 375                 380 cca gag agg gac atc cga gat cct aat ttc tgt gaa cga tgt acg tgt     1317
Pro Glu Arg Asp Ile Arg Asp Pro Asn Phe Cys Glu Arg Cys Thr Cys
385                 390                 395                 400 gac cca gct ggc tct caa aat gag gga att tgt gac agc tat act gat     1365
Asp Pro Ala Gly Ser Gln Asn Glu Gly Ile Cys Asp Ser Tyr Thr Asp
                405                 410                 415 ttt tct act ggt ctc att gct ggc cag tgt cgg tgt aaa tta aat gtg     1413
Phe Ser Thr Gly Leu Ile Ala Gly Gln Cys Arg Cys Lys Leu Asn Val
            420                 425                 430 gaa gga gaa cat tgt gat gtt tgc aaa gaa ggc ttc tat gat tta agc     1461
Glu Gly Glu His Cys Asp Val Cys Lys Glu Gly Phe Tyr Asp Leu Ser
        435                 440                 445 agt gaa gat cca ttt ggt tgt aaa tct tgt gct tgc aat cct ctg gga     1509
Ser Glu Asp Pro Phe Gly Cys Lys Ser Cys Ala Cys Asn Pro Leu Gly
450                 455                 460
```

```
aca att cct gga ggg aat cct tgt gat tcc gag aca ggt cac tgc tac    1557
Thr Ile Pro Gly Gly Asn Pro Cys Asp Ser Glu Thr Gly His Cys Tyr
465                 470                 475                 480 tgc aag cgt ctg gtg aca gga cag cat tgt gac cag tgc ctg cca gag    1605
Cys Lys Arg Leu Val Thr Gly Gln His Cys Asp Gln Cys Leu Pro Glu
                485                 490                 495 cac tgg ggc tta agc aat gat ttg gat gga tgt cga cca tgt gac tgt    1653
His Trp Gly Leu Ser Asn Asp Leu Asp Gly Cys Arg Pro Cys Asp Cys
            500                 505                 510 gac ctt ggg gga gcc tta aac aac agt tgc ttt gcg gag tca ggc cag    1701
Asp Leu Gly Gly Ala Leu Asn Asn Ser Cys Phe Ala Glu Ser Gly Gln
        515                 520                 525 tgc tca tgc cgg cct cac atg att gga cgt cag tgc aac gaa gtg gaa    1749
Cys Ser Cys Arg Pro His Met Ile Gly Arg Gln Cys Asn Glu Val Glu
    530                 535                 540 cct ggt tac tac ttt gcc acc ctg gat cac tac ctc tat gaa gcg gag    1797
Pro Gly Tyr Tyr Phe Ala Thr Leu Asp His Tyr Leu Tyr Glu Ala Glu
545                 550                 555                 560 gaa gcc aac ttg ggg cct ggg gtt agc ata gtg gag cgg caa tat atc    1845
Glu Ala Asn Leu Gly Pro Gly Val Ser Ile Val Glu Arg Gln Tyr Ile
                565                 570                 575 cag gac cgg att ccc tcc tgg act gga gcc ggc ttc gtc cga gtg cct    1893
Gln Asp Arg Ile Pro Ser Trp Thr Gly Ala Gly Phe Val Arg Val Pro
            580                 585                 590 gaa ggg gct tat ttg gag ttt ttc att gac aac ata cca tat tcc atg    1941
Glu Gly Ala Tyr Leu Glu Phe Phe Ile Asp Asn Ile Pro Tyr Ser Met
        595                 600                 605 gag tac gac atc cta att cgc tac gag cca cag cta ccc gac cac tgg    1989
Glu Tyr Asp Ile Leu Ile Arg Tyr Glu Pro Gln Leu Pro Asp His Trp
    610                 615                 620 gaa aaa gct gtc atc aca gtg cag cga cct gga agg att cca acc agc    2037
Glu Lys Ala Val Ile Thr Val Gln Arg Pro Gly Arg Ile Pro Thr Ser
625                 630                 635                 640 agc cga tgt ggt aat acc atc ccc gat gat gac aac cag gtg gtg tca    2085
Ser Arg Cys Gly Asn Thr Ile Pro Asp Asp Asp Asn Gln Val Val Ser
                645                 650                 655 tta tca cca ggc tca aga tat gtc gtc ctt cct cgg ccg gtg tgc ttt    2133
Leu Ser Pro Gly Ser Arg Tyr Val Val Leu Pro Arg Pro Val Cys Phe
            660                 665                 670 gag aag gga aca aac tac acg gtg agg ttg gag ctg cct cag tac acc    2181
Glu Lys Gly Thr Asn Tyr Thr Val Arg Leu Glu Leu Pro Gln Tyr Thr
        675                 680                 685 tcc tct gat agc gac gtg gag agc ccc tac acg ctg atc gat tct ctt    2229
Ser Ser Asp Ser Asp Val Glu Ser Pro Tyr Thr Leu Ile Asp Ser Leu
    690                 695                 700 gtt ctc atg cca tac tgt aaa tca ctg gac atc ttc acc gtg gga ggt    2277
Val Leu Met Pro Tyr Cys Lys Ser Leu Asp Ile Phe Thr Val Gly Gly
705                 710                 715                 720 tca gga gat ggg gtg gtc acc aac agt gcc tgg gaa acc ttt cag aga    2325
Ser Gly Asp Gly Val Val Thr Asn Ser Ala Trp Glu Thr Phe Gln Arg
                725                 730                 735 tac cga tgt cta gag aac agc aga agc gtt gtg aaa aca ccg atg aca    2373
Tyr Arg Cys Leu Glu Asn Ser Arg Ser Val Val Lys Thr Pro Met Thr
            740                 745                 750 gat gtt tgc aga aac atc atc ttt agc att tct gcc ctg tta cac cag    2421
Asp Val Cys Arg Asn Ile Ile Phe Ser Ile Ser Ala Leu Leu His Gln
        755                 760                 765 aca ggc ctg gct tgt gaa tgc gac cct cag ggt tcg tta agt tcc gtg    2469
Thr Gly Leu Ala Cys Glu Cys Asp Pro Gln Gly Ser Leu Ser Ser Val
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 770 |     |     |     | 775 |     |     |     | 780 |     |     |     |     |     |      |
| tgt | gat | ccc | aac | gga | ggc | cag | tgc | cag | tgc | cgg | ccc | aac | gtg | gtt | gga | 2517 |
| Cys | Asp | Pro | Asn | Gly | Gly | Gln | Cys | Gln | Cys | Arg | Pro | Asn | Val | Val | Gly |      |
| 785 |     |     |     | 790 |     |     |     | 795 |     |     |     |     |     |     | 800 |      |
| aga | acc | tgc | aac | aga | tgt | gca | cct | gga | act | ttt | ggc | ttt | ggc | ccc | agt | 2565 |
| Arg | Thr | Cys | Asn | Arg | Cys | Ala | Pro | Gly | Thr | Phe | Gly | Phe | Gly | Pro | Ser |      |
|     |     |     | 805 |     |     |     |     | 810 |     |     |     |     | 815 |     |     |      |
| gga | tgc | aaa | cct | tgt | gag | tgc | cat | ctg | caa | gga | tct | gtc | aat | gcc | ttc | 2613 |
| Gly | Cys | Lys | Pro | Cys | Glu | Cys | His | Leu | Gln | Gly | Ser | Val | Asn | Ala | Phe |      |
|     |     |     | 820 |     |     |     |     | 825 |     |     |     |     | 830 |     |     |      |
| tgc | aat | ccc | gtc | act | ggc | cag | tgc | cac | tgt | ttc | cag | gga | gtg | tat | gct | 2661 |
| Cys | Asn | Pro | Val | Thr | Gly | Gln | Cys | His | Cys | Phe | Gln | Gly | Val | Tyr | Ala |      |
|     |     |     | 835 |     |     |     |     | 840 |     |     |     |     | 845 |     |     |      |
| cgg | cag | tgt | gat | cgg | tgc | tta | cct | ggg | cac | tgg | ggc | ttt | cca | agt | tgc | 2709 |
| Arg | Gln | Cys | Asp | Arg | Cys | Leu | Pro | Gly | His | Trp | Gly | Phe | Pro | Ser | Cys |      |
|     |     |     | 850 |     |     |     |     | 855 |     |     |     |     | 860 |     |     |      |
| cag | ccc | tgc | cag | tgc | aat | ggc | cac | gcc | gat | gac | tgc | gac | cca | gtg | act | 2757 |
| Gln | Pro | Cys | Gln | Cys | Asn | Gly | His | Ala | Asp | Asp | Cys | Asp | Pro | Val | Thr |      |
|     |     | 865 |     |     |     |     | 870 |     |     |     |     | 875 |     |     | 880 |      |
| ggg | gag | tgc | ttg | aac | tgc | cag | gac | tac | acc | atg | ggt | cat | aac | tgt | gaa | 2805 |
| Gly | Glu | Cys | Leu | Asn | Cys | Gln | Asp | Tyr | Thr | Met | Gly | His | Asn | Cys | Glu |      |
|     |     |     |     | 885 |     |     |     |     | 890 |     |     |     |     | 895 |     |      |
| agg | tgc | ttg | gct | ggt | tac | tat | ggc | gac | ccc | atc | att | ggg | tca | ggt | gat | 2853 |
| Arg | Cys | Leu | Ala | Gly | Tyr | Tyr | Gly | Asp | Pro | Ile | Ile | Gly | Ser | Gly | Asp |      |
|     |     |     | 900 |     |     |     |     | 905 |     |     |     |     | 910 |     |     |      |
| cac | tgc | cgc | cct | tgc | cct | tgc | cca | gat | ggt | ccc | gac | agt | gga | cgc | cag | 2901 |
| His | Cys | Arg | Pro | Cys | Pro | Cys | Pro | Asp | Gly | Pro | Asp | Ser | Gly | Arg | Gln |      |
|     |     | 915 |     |     |     |     | 920 |     |     |     |     | 925 |     |     |     |      |
| ttt | gcc | agg | agc | tgc | tac | caa | gat | cct | gtt | act | tta | cag | ctt | gcc | tgt | 2949 |
| Phe | Ala | Arg | Ser | Cys | Tyr | Gln | Asp | Pro | Val | Thr | Leu | Gln | Leu | Ala | Cys |      |
|     | 930 |     |     |     |     | 935 |     |     |     |     | 940 |     |     |     |     |      |
| gtt | tgt | gat | cct | gga | tac | att | ggt | tcc | aga | tgt | gac | gac | tgt | gcc | tca | 2997 |
| Val | Cys | Asp | Pro | Gly | Tyr | Ile | Gly | Ser | Arg | Cys | Asp | Asp | Cys | Ala | Ser |      |
| 945 |     |     |     |     | 950 |     |     |     |     | 955 |     |     |     |     | 960 |      |
| gga | tac | ttt | ggc | aat | cca | tca | gaa | gtt | ggg | ggg | tcg | tgt | cag | cct | tgc | 3045 |
| Gly | Tyr | Phe | Gly | Asn | Pro | Ser | Glu | Val | Gly | Gly | Ser | Cys | Gln | Pro | Cys |      |
|     |     |     |     | 965 |     |     |     |     | 970 |     |     |     |     | 975 |     |      |
| cag | tgt | cac | aac | aac | att | gac | acg | aca | gac | cca | gaa | gcc | tgt | gac | aag | 3093 |
| Gln | Cys | His | Asn | Asn | Ile | Asp | Thr | Thr | Asp | Pro | Glu | Ala | Cys | Asp | Lys |      |
|     |     |     | 980 |     |     |     |     | 985 |     |     |     |     | 990 |     |     |      |
| gag | act | ggg | agg | tgt | ctc | aag | tgc | ctg | tac | cac | acg | gaa | ggg | gaa | cac | 3141 |
| Glu | Thr | Gly | Arg | Cys | Leu | Lys | Cys | Leu | Tyr | His | Thr | Glu | Gly | Glu | His |      |
|     |     |     | 995 |     |     |     |     | 1000|     |     |     |     | 1005|     |     |      |
| tgt | cag | ttc | tgc | cgg | ttt | gga | tac | tat | ggt | gat | gcc | ctc | cgg | cag | gac | 3189 |
| Cys | Gln | Phe | Cys | Arg | Phe | Gly | Tyr | Tyr | Gly | Asp | Ala | Leu | Arg | Gln | Asp |      |
|     | 1010|     |     |     |     | 1015|     |     |     |     | 1020|     |     |     |     |      |
| tgt | cga | aag | tgt | gtc | tgt | aat | tac | ctg | ggc | acc | gtg | caa | gag | cac | tgt | 3237 |
| Cys | Arg | Lys | Cys | Val | Cys | Asn | Tyr | Leu | Gly | Thr | Val | Gln | Glu | His | Cys |      |
| 1025|     |     |     | 1030|     |     |     |     | 1035|     |     |     |     | 1040|     |      |
| aac | ggc | tct | gac | tgc | cag | tgc | gac | aaa | gcc | act | ggt | cag | tgc | ttg | tgt | 3285 |
| Asn | Gly | Ser | Asp | Cys | Gln | Cys | Asp | Lys | Ala | Thr | Gly | Gln | Cys | Leu | Cys |      |
|     |     |     | 1045|     |     |     |     | 1050|     |     |     |     | 1055|     |     |      |
| ctt | cct | aat | gtg | atc | ggg | cag | aac | tgt | gac | cgc | tgt | gcg | ccc | aat | acc | 3333 |
| Leu | Pro | Asn | Val | Ile | Gly | Gln | Asn | Cys | Asp | Arg | Cys | Ala | Pro | Asn | Thr |      |
|     |     |     | 1060|     |     |     |     | 1065|     |     |     |     | 1070|     |     |      |
| tgg | cag | ctg | gcc | agt | ggc | act | ggc | tgt | gac | cca | tgc | aac | tgc | aat | gct | 3381 |
| Trp | Gln | Leu | Ala | Ser | Gly | Thr | Gly | Cys | Asp | Pro | Cys | Asn | Cys | Asn | Ala |      |
|     |     |     | 1075|     |     |     |     | 1080|     |     |     |     | 1085|     |     |      |
| gct | cat | tcc | ttc | ggg | cca | tct | tgc | aat | gag | ttc | acg | ggg | cag | tgc | cag | 3429 |

```
Ala His Ser Phe Gly Pro Ser Cys Asn Glu Phe Thr Gly Gln Cys Gln
    1090                1095                1100 tgc atg cct ggg ttt gga ggc cgc acc tgc agc gag tgc cag gaa ctc      3477
Cys Met Pro Gly Phe Gly Gly Arg Thr Cys Ser Glu Cys Gln Glu Leu
1105                1110                1115                1120 ttc tgg gga gac ccc gac gtg gag tgc cga gcc tgt gac tgt gac ccc      3525
Phe Trp Gly Asp Pro Asp Val Glu Cys Arg Ala Cys Asp Cys Asp Pro
                1125                1130                1135 agg ggc att gag acg cca cag tgt gac cag tcc acg ggc cag tgt gtc      3573
Arg Gly Ile Glu Thr Pro Gln Cys Asp Gln Ser Thr Gly Gln Cys Val
            1140                1145                1150 tgc gtt gag ggt gtt gag ggt cca cgc tgt gac aag tgc acg cga ggg      3621
Cys Val Glu Gly Val Glu Gly Pro Arg Cys Asp Lys Cys Thr Arg Gly
        1155                1160                1165 tac tcg ggg gtc ttc cct gac tgc aca ccc tgc cac cag tgc ttt gct      3669
Tyr Ser Gly Val Phe Pro Asp Cys Thr Pro Cys His Gln Cys Phe Ala
    1170                1175                1180 ctc tgg gat gtg atc att gcc gag ctg acc aac agg aca cac aga ttc      3717
Leu Trp Asp Val Ile Ile Ala Glu Leu Thr Asn Arg Thr His Arg Phe
1185                1190                1195                1200 ctg gag aaa gcc aag gcc ttg aag atc agt ggt gtg atc ggg cct tac      3765
Leu Glu Lys Ala Lys Ala Leu Lys Ile Ser Gly Val Ile Gly Pro Tyr
                1205                1210                1215 cgt gag act gtg gac tcg gtg gag agg aaa gtc agc gag ata aaa gac      3813
Arg Glu Thr Val Asp Ser Val Glu Arg Lys Val Ser Glu Ile Lys Asp
            1220                1225                1230 atc ctg gcg cag agc ccc gca gca gag cca ctg aaa aac att ggg aat      3861
Ile Leu Ala Gln Ser Pro Ala Ala Glu Pro Leu Lys Asn Ile Gly Asn
        1235                1240                1245 ctc ttt gag gaa gca gag aaa ctg att aaa gat gtt aca gaa atg atg      3909
Leu Phe Glu Glu Ala Glu Lys Leu Ile Lys Asp Val Thr Glu Met Met
    1250                1255                1260 gct caa gta gaa gtg aaa tta tct gac aca act tcc caa agc aac agc      3957
Ala Gln Val Glu Val Lys Leu Ser Asp Thr Thr Ser Gln Ser Asn Ser
1265                1270                1275                1280 aca gcc aaa gaa ctg gat tct cta cag aca gaa gcc gaa agc cta gac      4005
Thr Ala Lys Glu Leu Asp Ser Leu Gln Thr Glu Ala Glu Ser Leu Asp
                1285                1290                1295 aac act gtg aaa gaa ctt gct gaa caa ctg gaa ttt atc aaa aac tca      4053
Asn Thr Val Lys Glu Leu Ala Glu Gln Leu Glu Phe Ile Lys Asn Ser
            1300                1305                1310 gat att cgg ggt gcc ttg gat agc att acc aag tat ttc cag atg tct      4101
Asp Ile Arg Gly Ala Leu Asp Ser Ile Thr Lys Tyr Phe Gln Met Ser
        1315                1320                1325 ctt gag gca gag gag agg gtg aat gcc tcc acc aca gaa ccc aac agc      4149
Leu Glu Ala Glu Glu Arg Val Asn Ala Ser Thr Thr Glu Pro Asn Ser
    1330                1335                1340 act gtg gag cag tca gcc ctc atg aga gac aga gta gaa gac gtg atg      4197
Thr Val Glu Gln Ser Ala Leu Met Arg Asp Arg Val Glu Asp Val Met
1345                1350                1355                1360 atg gag cga gaa tcc cag ttc aag gaa aaa caa gag gag cag gct cgc      4245
Met Glu Arg Glu Ser Gln Phe Lys Glu Lys Gln Glu Glu Gln Ala Arg
                1365                1370                1375 ctc ctt gat gaa ctg gca ggc aag cta caa agc cta gac ctt tca gcc      4293
Leu Leu Asp Glu Leu Ala Gly Lys Leu Gln Ser Leu Asp Leu Ser Ala
            1380                1385                1390 gct gcc gaa atg acc tgt gga aca ccc cca ggg gcc tcc tgt tcc gag      4341
Ala Ala Glu Met Thr Cys Gly Thr Pro Pro Gly Ala Ser Cys Ser Glu
        1395                1400                1405
```

-continued

| | |
|---|---|
| act gaa tgt ggc ggg cca aac tgc aga act gac gaa gga gag agg aag<br>Thr Glu Cys Gly Gly Pro Asn Cys Arg Thr Asp Glu Gly Glu Arg Lys<br>    1410                       1415                       1420 | 4389 |
| tgt ggg ggg cct ggc tgt ggt ggt ctg gtt act gtt gca cac aac gcc<br>Cys Gly Gly Pro Gly Cys Gly Gly Leu Val Thr Val Ala His Asn Ala<br>1425                       1430                       1435                       1440 | 4437 |
| tgg cag aaa gcc atg gac ttg gac caa gat gtc ctg agt gcc ctg gct<br>Trp Gln Lys Ala Met Asp Leu Asp Gln Asp Val Leu Ser Ala Leu Ala<br>    1445                       1450                       1455 | 4485 |
| gaa gtg gaa cag ctc tcc aag atg gtc tct gaa gca aaa ctg agg gca<br>Glu Val Glu Gln Leu Ser Lys Met Val Ser Glu Ala Lys Leu Arg Ala<br>        1460                       1465                       1470 | 4533 |
| gat gag gca aaa caa agt gct gaa gac att ctg ttg aag aca aat gct<br>Asp Glu Ala Lys Gln Ser Ala Glu Asp Ile Leu Leu Lys Thr Asn Ala<br>            1475                       1480                       1485 | 4581 |
| acc aaa gaa aaa atg gac aag agc aat gag gag ctg aga aat cta atc<br>Thr Lys Glu Lys Met Asp Lys Ser Asn Glu Glu Leu Arg Asn Leu Ile<br>                1490                       1495                       1500 | 4629 |
| aag caa atc aga aac ttt ttg acc cag gat agt gct gat ttg gac agc<br>Lys Gln Ile Arg Asn Phe Leu Thr Gln Asp Ser Ala Asp Leu Asp Ser<br>1505                       1510                       1515                       1520 | 4677 |
| att gaa gca gtt gct aat gaa gta ttg aaa atg gag atg cct agc acc<br>Ile Glu Ala Val Ala Asn Glu Val Leu Lys Met Glu Met Pro Ser Thr<br>                    1525                       1530                       1535 | 4725 |
| cca cag cag tta cag aac ttg aca gaa gat ata cgt gaa cga gtt gaa<br>Pro Gln Gln Leu Gln Asn Leu Thr Glu Asp Ile Arg Glu Arg Val Glu<br>    1540                       1545                       1550 | 4773 |
| agc ctt tct caa gta gag gtt att ctt cag cat agt gct gct gac att<br>Ser Leu Ser Gln Val Glu Val Ile Leu Gln His Ser Ala Ala Asp Ile<br>        1555                       1560                       1565 | 4821 |
| gcc aga gct gag atg ttg tta gaa gaa gct aaa aga gca agc aaa agt<br>Ala Arg Ala Glu Met Leu Leu Glu Glu Ala Lys Arg Ala Ser Lys Ser<br>            1570                       1575                       1580 | 4869 |
| gca aca gat gtt aaa gtc act gca gat atg gta aag gaa gct ctg gaa<br>Ala Thr Asp Val Lys Val Thr Ala Asp Met Val Lys Glu Ala Leu Glu<br>1585                       1590                       1595                       1600 | 4917 |
| gaa gca gaa aag gcc cag gtc gca gca gag aag gca att aaa caa gca<br>Glu Ala Glu Lys Ala Gln Val Ala Ala Glu Lys Ala Ile Lys Gln Ala<br>                    1605                       1610                       1615 | 4965 |
| gat gaa gac att caa gga acc cag aac ctg tta act tcg att gag tct<br>Asp Glu Asp Ile Gln Gly Thr Gln Asn Leu Leu Thr Ser Ile Glu Ser<br>    1620                       1625                       1630 | 5013 |
| gaa aca gca gct tct gag gaa acc ttg ttc aac gcg tcc cag cgc atc<br>Glu Thr Ala Ala Ser Glu Glu Thr Leu Phe Asn Ala Ser Gln Arg Ile<br>        1635                       1640                       1645 | 5061 |
| agc gag tta gag agg aat gtg gaa gaa ctt aag cgg aaa gct gcc caa<br>Ser Glu Leu Glu Arg Asn Val Glu Glu Leu Lys Arg Lys Ala Ala Gln<br>            1650                       1655                       1660 | 5109 |
| aac tcc ggg gag gca gaa tat att gaa aaa gta gta tat act gtg aag<br>Asn Ser Gly Glu Ala Glu Tyr Ile Glu Lys Val Val Tyr Thr Val Lys<br>1665                       1670                       1675                       1680 | 5157 |
| caa agt gca gaa gat gtt aag aag act tta gat ggt gaa ctt gat gaa<br>Gln Ser Ala Glu Asp Val Lys Lys Thr Leu Asp Gly Glu Leu Asp Glu<br>                    1685                       1690                       1695 | 5205 |
| aag tat aaa aaa gta gaa aat tta att gcc aaa aaa act gaa gag tca<br>Lys Tyr Lys Lys Val Glu Asn Leu Ile Ala Lys Lys Thr Glu Glu Ser<br>    1700                       1705                       1710 | 5253 |
| gct gat gcc aga agg aaa gcc gaa atg cta caa aat gaa gca aaa act<br>Ala Asp Ala Arg Arg Lys Ala Glu Met Leu Gln Asn Glu Ala Lys Thr<br>        1715                       1720                       1725 | 5301 |

-continued

```
ctt tta gct caa gca aat agc aag ctg caa ctg ctc aaa gat tta gaa      5349
Leu Leu Ala Gln Ala Asn Ser Lys Leu Gln Leu Leu Lys Asp Leu Glu
    1730                1735                1740 aga aaa tat gaa gac aat caa aga tac tta gaa gat aaa gct caa gaa      5397
Arg Lys Tyr Glu Asp Asn Gln Arg Tyr Leu Glu Asp Lys Ala Gln Glu
1745                1750                1755                1760 tta gca aga ctg gaa gga gaa gtc cgt tca ctc cta aag gat ata agc      5445
Leu Ala Arg Leu Glu Gly Glu Val Arg Ser Leu Leu Lys Asp Ile Ser
                1765                1770                1775 cag aaa gtt gct gtg tat agc aca tgc ttg taacagagga gaataaaaaa        5495
Gln Lys Val Ala Val Tyr Ser Thr Cys Leu
            1780                1785 tggctgaggt gaacaaggta aaacaactac attttaaaaa ctgacttaat gctcttcaaa    5555
ataaaacatc acctatttaa tgtttttaat cacattttgt atgagttaaa taaagccc     5613
```

<210> SEQ ID NO 14
<211> LENGTH: 1786
<212> TYPE: PRT
<213> ORGANISM: Homo sapiens

<400> SEQUENCE: 14

```
Met Gly Leu Leu Gln Leu Leu Ala Phe Ser Phe Leu Ala Leu Cys Arg
  1               5                  10                  15

Ala Arg Val Arg Ala Gln Glu Pro Glu Phe Ser Tyr Gly Cys Ala Glu
             20                  25                  30

Gly Ser Cys Tyr Pro Ala Thr Gly Asp Leu Leu Ile Gly Arg Ala Gln
         35                  40                  45

Lys Leu Ser Val Thr Ser Thr Cys Gly Leu His Lys Pro Glu Pro Tyr
 50                  55                  60

Cys Ile Val Ser His Leu Gln Glu Asp Lys Lys Cys Phe Ile Cys Asn
 65                  70                  75                  80

Ser Gln Asp Pro Tyr His Glu Thr Leu Asn Pro Asp Ser His Leu Ile
                 85                  90                  95

Glu Asn Val Val Thr Thr Phe Ala Pro Asn Arg Leu Lys Ile Trp Trp
            100                 105                 110

Gln Ser Glu Asn Gly Val Glu Asn Val Thr Ile Gln Leu Asp Leu Glu
        115                 120                 125

Ala Glu Phe His Phe Thr His Leu Ile Met Thr Phe Lys Thr Phe Arg
    130                 135                 140

Pro Ala Ala Met Leu Ile Glu Arg Ser Ser Asp Phe Gly Lys Thr Trp
145                 150                 155                 160

Gly Val Tyr Arg Tyr Phe Ala Tyr Asp Cys Glu Ala Ser Phe Pro Gly
                165                 170                 175

Ile Ser Thr Gly Pro Met Lys Lys Val Asp Asp Ile Ile Cys Asp Ser
            180                 185                 190

Arg Tyr Ser Asp Ile Glu Pro Ser Thr Glu Gly Glu Val Ile Phe Arg
        195                 200                 205

Ala Leu Asp Pro Ala Phe Lys Ile Glu Asp Pro Tyr Ser Pro Arg Ile
    210                 215                 220

Gln Asn Leu Leu Lys Ile Thr Asn Leu Arg Ile Lys Phe Val Lys Leu
225                 230                 235                 240

His Thr Leu Gly Asp Asn Leu Leu Asp Ser Arg Met Glu Ile Arg Glu
                245                 250                 255

Lys Tyr Tyr Tyr Ala Val Tyr Asp Met Val Val Arg Gly Asn Cys Phe
            260                 265                 270
```

```
Cys Tyr Gly His Ala Ser Glu Cys Ala Pro Val Asp Gly Phe Asn Glu
        275                 280                 285

Glu Val Glu Gly Met Val His Gly His Cys Met Cys Arg His Asn Thr
    290                 295                 300

Lys Gly Leu Asn Cys Glu Leu Cys Met Asp Phe Tyr His Asp Leu Pro
305                 310                 315                 320

Trp Arg Pro Ala Glu Gly Arg Asn Ser Asn Ala Cys Lys Lys Cys Asn
                325                 330                 335

Cys Asn Glu His Ser Ile Ser His Phe Asp Met Ala Val Tyr Leu
            340                 345                 350

Ala Thr Gly Asn Val Ser Gly Gly Val Cys Asp Asp Cys Gln His Asn
            355                 360                 365

Thr Met Gly Arg Asn Cys Glu Gln Cys Lys Pro Phe Tyr Tyr Gln His
    370                 375                 380

Pro Glu Arg Asp Ile Arg Asp Pro Asn Phe Cys Glu Arg Cys Thr Cys
385                 390                 395                 400

Asp Pro Ala Gly Ser Gln Asn Glu Gly Ile Cys Asp Ser Tyr Thr Asp
                405                 410                 415

Phe Ser Thr Gly Leu Ile Ala Gly Gln Cys Arg Cys Lys Leu Asn Val
            420                 425                 430

Glu Gly Glu His Cys Asp Val Cys Lys Glu Gly Phe Tyr Asp Leu Ser
            435                 440                 445

Ser Glu Asp Pro Phe Gly Cys Lys Ser Cys Ala Cys Asn Pro Leu Gly
        450                 455                 460

Thr Ile Pro Gly Gly Asn Pro Cys Asp Ser Glu Thr Gly His Cys Tyr
465                 470                 475                 480

Cys Lys Arg Leu Val Thr Gly Gln His Cys Asp Gln Cys Leu Pro Glu
                485                 490                 495

His Trp Gly Leu Ser Asn Asp Leu Asp Gly Cys Arg Pro Cys Asp Cys
            500                 505                 510

Asp Leu Gly Gly Ala Leu Asn Asn Ser Cys Phe Ala Glu Ser Gly Gln
            515                 520                 525

Cys Ser Cys Arg Pro His Met Ile Gly Arg Gln Cys Asn Glu Val Glu
        530                 535                 540

Pro Gly Tyr Tyr Phe Ala Thr Leu Asp His Tyr Leu Tyr Glu Ala Glu
545                 550                 555                 560

Glu Ala Asn Leu Gly Pro Gly Val Ser Ile Val Glu Arg Gln Tyr Ile
                565                 570                 575

Gln Asp Arg Ile Pro Ser Trp Thr Gly Ala Gly Phe Val Arg Val Pro
            580                 585                 590

Glu Gly Ala Tyr Leu Glu Phe Phe Ile Asp Asn Ile Pro Tyr Ser Met
            595                 600                 605

Glu Tyr Asp Ile Leu Ile Arg Tyr Glu Pro Gln Leu Pro Asp His Trp
        610                 615                 620

Glu Lys Ala Val Ile Thr Val Gln Arg Pro Gly Arg Ile Pro Thr Ser
625                 630                 635                 640

Ser Arg Cys Gly Asn Thr Ile Pro Asp Asp Asn Gln Val Val Ser
                645                 650                 655

Leu Ser Pro Gly Ser Arg Tyr Val Val Leu Pro Arg Pro Val Cys Phe
            660                 665                 670

Glu Lys Gly Thr Asn Tyr Thr Val Arg Leu Glu Leu Pro Gln Tyr Thr
            675                 680                 685
```

-continued

```
Ser Ser Asp Ser Asp Val Glu Ser Pro Tyr Thr Leu Ile Asp Ser Leu
        690                 695                 700
Val Leu Met Pro Tyr Cys Lys Ser Leu Asp Ile Phe Thr Val Gly Gly
705                 710                 715                 720
Ser Gly Asp Gly Val Val Thr Asn Ser Ala Trp Glu Thr Phe Gln Arg
                725                 730                 735
Tyr Arg Cys Leu Glu Asn Ser Arg Ser Val Val Lys Thr Pro Met Thr
            740                 745                 750
Asp Val Cys Arg Asn Ile Ile Phe Ser Ile Ser Ala Leu Leu His Gln
            755                 760                 765
Thr Gly Leu Ala Cys Glu Cys Asp Pro Gln Gly Ser Leu Ser Ser Val
770                 775                 780
Cys Asp Pro Asn Gly Gln Cys Gln Cys Arg Pro Asn Val Val Gly
785                 790                 795                 800
Arg Thr Cys Asn Arg Cys Ala Pro Gly Thr Phe Gly Phe Gly Pro Ser
                805                 810                 815
Gly Cys Lys Pro Cys Glu Cys His Leu Gln Gly Ser Val Asn Ala Phe
            820                 825                 830
Cys Asn Pro Val Thr Gly Gln Cys His Cys Phe Gln Gly Val Tyr Ala
            835                 840                 845
Arg Gln Cys Asp Arg Cys Leu Pro Gly His Trp Gly Phe Pro Ser Cys
    850                 855                 860
Gln Pro Cys Gln Cys Asn Gly His Ala Asp Asp Cys Asp Pro Val Thr
865                 870                 875                 880
Gly Glu Cys Leu Asn Cys Gln Asp Tyr Thr Met Gly His Asn Cys Glu
                885                 890                 895
Arg Cys Leu Ala Gly Tyr Tyr Gly Asp Pro Ile Ile Gly Ser Gly Asp
            900                 905                 910
His Cys Arg Pro Cys Pro Cys Pro Asp Gly Pro Asp Ser Gly Arg Gln
            915                 920                 925
Phe Ala Arg Ser Cys Tyr Gln Asp Pro Val Thr Leu Gln Leu Ala Cys
    930                 935                 940
Val Cys Asp Pro Gly Tyr Ile Gly Ser Arg Cys Asp Asp Cys Ala Ser
945                 950                 955                 960
Gly Tyr Phe Gly Asn Pro Ser Glu Val Gly Gly Ser Cys Gln Pro Cys
                965                 970                 975
Gln Cys His Asn Asn Ile Asp Thr Thr Asp Pro Glu Ala Cys Asp Lys
            980                 985                 990
Glu Thr Gly Arg Cys Leu Lys Cys Leu Tyr His Thr Glu Gly Glu His
            995                 1000                1005
Cys Gln Phe Cys Arg Phe Gly Tyr Tyr Gly Asp Ala Leu Arg Gln Asp
    1010                1015                1020
Cys Arg Lys Cys Val Cys Asn Tyr Leu Gly Thr Val Gln Glu His Cys
1025                1030                1035                1040
Asn Gly Ser Asp Cys Gln Cys Asp Lys Ala Thr Gly Gln Cys Leu Cys
                1045                1050                1055
Leu Pro Asn Val Ile Gly Gln Asn Cys Asp Arg Cys Ala Pro Asn Thr
            1060                1065                1070
Trp Gln Leu Ala Ser Gly Thr Gly Cys Asp Pro Cys Asn Cys Asn Ala
            1075                1080                1085
Ala His Ser Phe Gly Pro Ser Cys Asn Glu Phe Thr Gly Gln Cys Gln
    1090                1095                1100
Cys Met Pro Gly Phe Gly Gly Arg Thr Cys Ser Glu Cys Gln Glu Leu
```

-continued

```
                1105                1110                1115                1120

Phe Trp Gly Asp Pro Asp Val Glu Cys Arg Ala Cys Asp Cys Asp Pro
                        1125                1130                1135

Arg Gly Ile Glu Thr Pro Gln Cys Asp Gln Ser Thr Gly Gln Cys Val
                1140                1145                1150

Cys Val Glu Gly Val Glu Gly Pro Arg Cys Asp Lys Cys Thr Arg Gly
                1155                1160                1165

Tyr Ser Gly Val Phe Pro Asp Cys Thr Pro Cys His Gln Cys Phe Ala
            1170                1175                1180

Leu Trp Asp Val Ile Ile Ala Glu Leu Thr Asn Arg Thr His Arg Phe
        1185                1190                1195                1200

Leu Glu Lys Ala Lys Ala Leu Lys Ile Ser Gly Val Ile Gly Pro Tyr
                    1205                1210                1215

Arg Glu Thr Val Asp Ser Val Glu Arg Lys Val Ser Glu Ile Lys Asp
                        1220                1225                1230

Ile Leu Ala Gln Ser Pro Ala Ala Glu Pro Leu Lys Asn Ile Gly Asn
                    1235                1240                1245

Leu Phe Glu Glu Ala Glu Lys Leu Ile Lys Asp Val Thr Glu Met Met
                1250                1255                1260

Ala Gln Val Glu Val Lys Leu Ser Asp Thr Thr Ser Gln Ser Asn Ser
        1265                1270                1275                1280

Thr Ala Lys Glu Leu Asp Ser Leu Gln Thr Glu Ala Glu Ser Leu Asp
                    1285                1290                1295

Asn Thr Val Lys Glu Leu Ala Glu Gln Leu Glu Phe Ile Lys Asn Ser
                        1300                1305                1310

Asp Ile Arg Gly Ala Leu Asp Ser Ile Thr Lys Tyr Phe Gln Met Ser
                    1315                1320                1325

Leu Glu Ala Glu Glu Arg Val Asn Ala Ser Thr Thr Glu Pro Asn Ser
                1330                1335                1340

Thr Val Glu Gln Ser Ala Leu Met Arg Asp Arg Val Glu Asp Val Met
        1345                1350                1355                1360

Met Glu Arg Glu Ser Gln Phe Lys Glu Lys Gln Glu Glu Gln Ala Arg
                    1365                1370                1375

Leu Leu Asp Glu Leu Ala Gly Lys Leu Gln Ser Leu Asp Leu Ser Ala
                1380                1385                1390

Ala Ala Glu Met Thr Cys Gly Thr Pro Pro Gly Ala Ser Cys Ser Glu
                    1395                1400                1405

Thr Glu Cys Gly Gly Pro Asn Cys Arg Thr Asp Glu Gly Glu Arg Lys
            1410                1415                1420

Cys Gly Gly Pro Gly Cys Gly Gly Leu Val Thr Val Ala His Asn Ala
        1425                1430                1435                1440

Trp Gln Lys Ala Met Asp Leu Asp Gln Asp Val Leu Ser Ala Leu Ala
                        1445                1450                1455

Glu Val Glu Gln Leu Ser Lys Met Val Ser Glu Ala Lys Leu Arg Ala
                    1460                1465                1470

Asp Glu Ala Lys Gln Ser Ala Glu Asp Ile Leu Leu Lys Thr Asn Ala
                    1475                1480                1485

Thr Lys Glu Lys Met Asp Lys Ser Asn Glu Glu Leu Arg Asn Leu Ile
            1490                1495                1500

Lys Gln Ile Arg Asn Phe Leu Thr Gln Asp Ser Ala Asp Leu Asp Ser
        1505                1510                1515                1520

Ile Glu Ala Val Ala Asn Glu Val Leu Lys Met Glu Met Pro Ser Thr
                    1525                1530                1535
```

```
Pro Gln Gln Leu Gln Asn Leu Thr Glu Asp Ile Arg Glu Arg Val Glu
        1540                1545                1550

Ser Leu Ser Gln Val Glu Val Ile Leu Gln His Ser Ala Ala Asp Ile
    1555                1560                1565

Ala Arg Ala Glu Met Leu Leu Glu Glu Ala Lys Arg Ala Ser Lys Ser
    1570                1575                1580

Ala Thr Asp Val Lys Val Thr Ala Asp Met Val Lys Glu Ala Leu Glu
1585                1590                1595                1600

Glu Ala Glu Lys Ala Gln Val Ala Glu Lys Ala Ile Lys Gln Ala
            1605                1610                1615

Asp Glu Asp Ile Gln Gly Thr Gln Asn Leu Leu Thr Ser Ile Glu Ser
        1620                1625                1630

Glu Thr Ala Ala Ser Glu Glu Thr Leu Phe Asn Ala Ser Gln Arg Ile
    1635                1640                1645

Ser Glu Leu Glu Arg Asn Val Glu Glu Leu Lys Arg Lys Ala Ala Gln
    1650                1655                1660

Asn Ser Gly Glu Ala Glu Tyr Ile Glu Lys Val Val Tyr Thr Val Lys
1665                1670                1675                1680

Gln Ser Ala Glu Asp Val Lys Lys Thr Leu Asp Gly Glu Leu Asp Glu
            1685                1690                1695

Lys Tyr Lys Lys Val Glu Asn Leu Ile Ala Lys Lys Thr Glu Glu Ser
        1700                1705                1710

Ala Asp Ala Arg Arg Lys Ala Glu Met Leu Gln Asn Glu Ala Lys Thr
    1715                1720                1725

Leu Leu Ala Gln Ala Asn Ser Lys Leu Gln Leu Leu Lys Asp Leu Glu
    1730                1735                1740

Arg Lys Tyr Glu Asp Asn Gln Arg Tyr Leu Glu Asp Lys Ala Gln Glu
1745                1750                1755                1760

Leu Ala Arg Leu Glu Gly Glu Val Arg Ser Leu Leu Lys Asp Ile Ser
            1765                1770                1775

Gln Lys Val Ala Val Tyr Ser Thr Cys Leu
        1780                1785

<210> SEQ ID NO 15
<211> LENGTH: 5433
<212> TYPE: DNA
<213> ORGANISM: Homo sapiens
<220> FEATURE:
<221> NAME/KEY: CDS
<222> LOCATION: (1)..(5295)

<400> SEQUENCE: 15 cag gaa ccc gag ttc agc tac ggc tgc gca gaa ggc agc tgc tat ccc      48
Gln Glu Pro Glu Phe Ser Tyr Gly Cys Ala Glu Gly Ser Cys Tyr Pro
  1               5                   10                  15 gcc acg ggc gac ctt ctc atc ggc cga gca cag aag ctt tcg gtg acc      96
Ala Thr Gly Asp Leu Leu Ile Gly Arg Ala Gln Lys Leu Ser Val Thr
             20                  25                  30 tcg acg tgc ggg ctg cac aag ccc gaa ccc tac tgt atc gtc agc cac     144
Ser Thr Cys Gly Leu His Lys Pro Glu Pro Tyr Cys Ile Val Ser His
         35                  40                  45 ttg cag gag gac aaa aaa tgc ttc ata tgc aat tcc caa gat cct tat     192
Leu Gln Glu Asp Lys Lys Cys Phe Ile Cys Asn Ser Gln Asp Pro Tyr
     50                  55                  60 cat gag acc ctg aat cct gac agc cat ctc att gaa aat gtg gtc act     240
His Glu Thr Leu Asn Pro Asp Ser His Leu Ile Glu Asn Val Val Thr
 65                  70                  75                  80
```

```
aca ttt gct cca aac cgc ctt aag att tgg tgg caa tct gaa aat ggt    288
Thr Phe Ala Pro Asn Arg Leu Lys Ile Trp Trp Gln Ser Glu Asn Gly
             85                  90                  95 gtg gaa aat gta act atc caa ctg gat ttg gaa gca gaa ttc cat ttt    336
Val Glu Asn Val Thr Ile Gln Leu Asp Leu Glu Ala Glu Phe His Phe
            100                 105                 110 act cat ctc ata atg act ttc aag aca ttc cgt cca gct gct atg ctg    384
Thr His Leu Ile Met Thr Phe Lys Thr Phe Arg Pro Ala Ala Met Leu
            115                 120                 125 ata gaa cga tcg tcc gac ttt ggg aaa acc tgg ggt gtg tat aga tac    432
Ile Glu Arg Ser Ser Asp Phe Gly Lys Thr Trp Gly Val Tyr Arg Tyr
        130                 135                 140 ttc gcc tat gac tgt gag gcc tcg ttt cca ggc att tca act ggc ccc    480
Phe Ala Tyr Asp Cys Glu Ala Ser Phe Pro Gly Ile Ser Thr Gly Pro
145                 150                 155                 160 atg aaa aaa gtc gat gac ata att tgt gat tct cga tat tct gac att    528
Met Lys Lys Val Asp Asp Ile Ile Cys Asp Ser Arg Tyr Ser Asp Ile
                165                 170                 175 gaa ccc tca act gaa gga gag gtg ata ttt cgt gct tta gat cct gct    576
Glu Pro Ser Thr Glu Gly Glu Val Ile Phe Arg Ala Leu Asp Pro Ala
            180                 185                 190 ttc aaa ata gaa gat cct tat agc cca agg ata cag aat tta tta aaa    624
Phe Lys Ile Glu Asp Pro Tyr Ser Pro Arg Ile Gln Asn Leu Leu Lys
            195                 200                 205 att acc aac ttg aga atc aag ttt gtg aaa ctg cat act ttg gga gat    672
Ile Thr Asn Leu Arg Ile Lys Phe Val Lys Leu His Thr Leu Gly Asp
        210                 215                 220 aac ctt ctg gat tcc agg atg gaa atc aga gaa aag tat tat tat gca    720
Asn Leu Leu Asp Ser Arg Met Glu Ile Arg Glu Lys Tyr Tyr Tyr Ala
225                 230                 235                 240 gtt tat gat atg gtg gtt cga gga aat tgc ttc tgc tat ggt cat gcc    768
Val Tyr Asp Met Val Val Arg Gly Asn Cys Phe Cys Tyr Gly His Ala
                245                 250                 255 agc gaa tgt gcc cct gtg gat gga ttc aat gaa gaa gtg gaa gga atg    816
Ser Glu Cys Ala Pro Val Asp Gly Phe Asn Glu Glu Val Glu Gly Met
            260                 265                 270 gtt cac gga cac tgc atg tgc agg cat aac acc aag ggc tta aac tgt    864
Val His Gly His Cys Met Cys Arg His Asn Thr Lys Gly Leu Asn Cys
            275                 280                 285 gaa ctc tgc atg gat ttc tac cat gat tta cct tgg aga cct gct gaa    912
Glu Leu Cys Met Asp Phe Tyr His Asp Leu Pro Trp Arg Pro Ala Glu
        290                 295                 300 ggc cga aac agc aac gcc tgt aaa aaa tgt aac tgc aat gaa cat tcc    960
Gly Arg Asn Ser Asn Ala Cys Lys Lys Cys Asn Cys Asn Glu His Ser
305                 310                 315                 320 atc tct tgt cac ttt gac atg gct gtt tac ctg gcc acg ggg aac gtc    1008
Ile Ser Cys His Phe Asp Met Ala Val Tyr Leu Ala Thr Gly Asn Val
                325                 330                 335 agc gga ggc gtg tgt gat gac tgt cag cac aac acc atg ggg cgc aac    1056
Ser Gly Gly Val Cys Asp Asp Cys Gln His Asn Thr Met Gly Arg Asn
            340                 345                 350 tgt gag cag tgc aag ccg ttt tac tac cag cac cca gag agg gac atc    1104
Cys Glu Gln Cys Lys Pro Phe Tyr Tyr Gln His Pro Glu Arg Asp Ile
            355                 360                 365 cga gat cct aat ttc tgt gaa cga tgt acg tgt gac cca gct ggc tct    1152
Arg Asp Pro Asn Phe Cys Glu Arg Cys Thr Cys Asp Pro Ala Gly Ser
        370                 375                 380 caa aat gag gga att tgt gac agc tat act gat ttt tct act ggt ctc    1200
Gln Asn Glu Gly Ile Cys Asp Ser Tyr Thr Asp Phe Ser Thr Gly Leu
```

-continued

| | | | | |
|---|---|---|---|---|
| 385 | 390 | 395 | 400 | |
| att gct ggc cag tgt cgg tgt aaa tta aat gtg gaa gga gaa cat tgt<br>Ile Ala Gly Gln Cys Arg Cys Lys Leu Asn Val Glu Gly Glu His Cys<br>405 410 415 | | | | 1248 |
| gat gtt tgc aaa gaa ggc ttc tat gat tta agc agt gaa gat cca ttt<br>Asp Val Cys Lys Glu Gly Phe Tyr Asp Leu Ser Ser Glu Asp Pro Phe<br>420 425 430 | | | | 1296 |
| ggt tgt aaa tct tgt gct tgc aat cct ctg gga aca att cct gga ggg<br>Gly Cys Lys Ser Cys Ala Cys Asn Pro Leu Gly Thr Ile Pro Gly Gly<br>435 440 445 | | | | 1344 |
| aat cct tgt gat tcc gag aca ggt cac tgc tac tgc aag cgt ctg gtg<br>Asn Pro Cys Asp Ser Glu Thr Gly His Cys Tyr Cys Lys Arg Leu Val<br>450 455 460 | | | | 1392 |
| aca gga cag cat tgt gac cag tgc ctg cca gag cac tgg ggc tta agc<br>Thr Gly Gln His Cys Asp Gln Cys Leu Pro Glu His Trp Gly Leu Ser<br>465 470 475 480 | | | | 1440 |
| aat gat ttg gat gga tgt cga cca tgt gac tgt gac ctt ggg gga gcc<br>Asn Asp Leu Asp Gly Cys Arg Pro Cys Asp Cys Asp Leu Gly Gly Ala<br>485 490 495 | | | | 1488 |
| tta aac aac agt tgc ttt gcg gag tca ggc cag tgc tca tgc cgg cct<br>Leu Asn Asn Ser Cys Phe Ala Glu Ser Gly Gln Cys Ser Cys Arg Pro<br>500 505 510 | | | | 1536 |
| cac atg att gga cgt cag tgc aac gaa gtg gaa cct ggt tac tac ttt<br>His Met Ile Gly Arg Gln Cys Asn Glu Val Glu Pro Gly Tyr Tyr Phe<br>515 520 525 | | | | 1584 |
| gcc acc ctg gat cac tac ctc tat gaa gcg gag gaa gcc aac ttg ggg<br>Ala Thr Leu Asp His Tyr Leu Tyr Glu Ala Glu Glu Ala Asn Leu Gly<br>530 535 540 | | | | 1632 |
| cct ggg gtt agc ata gtg gag cgg caa tat atc cag gac cgg att ccc<br>Pro Gly Val Ser Ile Val Glu Arg Gln Tyr Ile Gln Asp Arg Ile Pro<br>545 550 555 560 | | | | 1680 |
| tcc tgg act gga gcc ggc ttc gtc cga gtg cct gaa ggg gct tat ttg<br>Ser Trp Thr Gly Ala Gly Phe Val Arg Val Pro Glu Gly Ala Tyr Leu<br>565 570 575 | | | | 1728 |
| gag ttt ttc att gac aac ata cca tat tcc atg gag tac gac atc cta<br>Glu Phe Phe Ile Asp Asn Ile Pro Tyr Ser Met Glu Tyr Asp Ile Leu<br>580 585 590 | | | | 1776 |
| att cgc tac gag cca cag cta ccc gac cac tgg gaa aaa gct gtc atc<br>Ile Arg Tyr Glu Pro Gln Leu Pro Asp His Trp Glu Lys Ala Val Ile<br>595 600 605 | | | | 1824 |
| aca gtg cag cga cct gga agg att cca acc agc agc cga tgt ggt aat<br>Thr Val Gln Arg Pro Gly Arg Ile Pro Thr Ser Ser Arg Cys Gly Asn<br>610 615 620 | | | | 1872 |
| acc atc ccc gat gat gac aac cag gtg gtg tca tta tca cca ggc tca<br>Thr Ile Pro Asp Asp Asp Asn Gln Val Val Ser Leu Ser Pro Gly Ser<br>625 630 635 640 | | | | 1920 |
| aga tat gtc gtc ctt cct cgg ccg gtg tgc ttt gag aag gga aca aac<br>Arg Tyr Val Val Leu Pro Arg Pro Val Cys Phe Glu Lys Gly Thr Asn<br>645 650 655 | | | | 1968 |
| tac acg gtg agg ttg gag ctg cct cag tac acc tcc tct gat agc gac<br>Tyr Thr Val Arg Leu Glu Leu Pro Gln Tyr Thr Ser Ser Asp Ser Asp<br>660 665 670 | | | | 2016 |
| gtg gag agc ccc tac acg ctg atc gat tct ctt gtt ctc atg cca tac<br>Val Glu Ser Pro Tyr Thr Leu Ile Asp Ser Leu Val Leu Met Pro Tyr<br>675 680 685 | | | | 2064 |
| tgt aaa tca ctg gac atc ttc acc gtg gga ggt tca gga gat ggg gtg<br>Cys Lys Ser Leu Asp Ile Phe Thr Val Gly Gly Ser Gly Asp Gly Val<br>690 695 700 | | | | 2112 |
| gtc acc aac agt gcc tgg gaa acc ttt cag aga tac cga tgt cta gag | | | | 2160 |

-continued

| | | |
|---|---|---|
| Val Thr Asn Ser Ala Trp Glu Thr Phe Gln Arg Tyr Arg Cys Leu Glu<br>705                    710                      715                    720 | | |
| aac agc aga agc gtt gtg aaa aca ccg atg aca gat gtt tgc aga aac<br>Asn Ser Arg Ser Val Val Lys Thr Pro Met Thr Asp Val Cys Arg Asn<br>                    725                      730                    735 | 2208 | |
| atc atc ttt agc att tct gcc ctg tta cac cag aca ggc ctg gct tgt<br>Ile Ile Phe Ser Ile Ser Ala Leu Leu His Gln Thr Gly Leu Ala Cys<br>                740                      745                    750 | 2256 | |
| gaa tgc gac cct cag ggt tcg tta agt tcc gtg tgt gat ccc aac gga<br>Glu Cys Asp Pro Gln Gly Ser Leu Ser Ser Val Cys Asp Pro Asn Gly<br>        755                      760                    765 | 2304 | |
| ggc cag tgc cag tgc cgg ccc aac gtg gtt gga aga acc tgc aac aga<br>Gly Gln Cys Gln Cys Arg Pro Asn Val Val Gly Arg Thr Cys Asn Arg<br>770                    775                      780 | 2352 | |
| tgt gca cct gga act ttt ggc ttt ggc ccc agt gga tgc aaa cct tgt<br>Cys Ala Pro Gly Thr Phe Gly Phe Gly Pro Ser Gly Cys Lys Pro Cys<br>785                    790                    795                    800 | 2400 | |
| gag tgc cat ctg caa gga tct gtc aat gcc ttc tgc aat ccc gtc act<br>Glu Cys His Leu Gln Gly Ser Val Asn Ala Phe Cys Asn Pro Val Thr<br>                805                      810                    815 | 2448 | |
| ggc cag tgc cac tgt ttc cag gga gtg tat gct cgg cag tgt gat cgg<br>Gly Gln Cys His Cys Phe Gln Gly Val Tyr Ala Arg Gln Cys Asp Arg<br>        820                      825                    830 | 2496 | |
| tgc tta cct ggg cac tgg ggc ttt cca agt tgc cag ccc tgc cag tgc<br>Cys Leu Pro Gly His Trp Gly Phe Pro Ser Cys Gln Pro Cys Gln Cys<br>                835                      840                    845 | 2544 | |
| aat ggc cac gcc gat gac tgc gac cca gtg act ggg gag tgc ttg aac<br>Asn Gly His Ala Asp Asp Cys Asp Pro Val Thr Gly Glu Cys Leu Asn<br>850                      855                      860 | 2592 | |
| tgc cag gac tac acc atg ggt cat aac tgt gaa agg tgc ttg gct ggt<br>Cys Gln Asp Tyr Thr Met Gly His Asn Cys Glu Arg Cys Leu Ala Gly<br>865                    870                    875                    880 | 2640 | |
| tac tat ggc gac ccc atc att ggg tca ggt gat cac tgc cgc cct tgc<br>Tyr Tyr Gly Asp Pro Ile Ile Gly Ser Gly Asp His Cys Arg Pro Cys<br>                    885                      890                    895 | 2688 | |
| cct tgc cca gat ggt ccc gac agt gga cgc cag ttt gcc agg agc tgc<br>Pro Cys Pro Asp Gly Pro Asp Ser Gly Arg Gln Phe Ala Arg Ser Cys<br>        900                      905                    910 | 2736 | |
| tac caa gat cct gtt act tta cag ctt gcc tgt gtt tgt gat cct gga<br>Tyr Gln Asp Pro Val Thr Leu Gln Leu Ala Cys Val Cys Asp Pro Gly<br>                915                      920                    925 | 2784 | |
| tac att ggt tcc aga tgt gac gac tgt gcc tca gga tac ttt ggc aat<br>Tyr Ile Gly Ser Arg Cys Asp Asp Cys Ala Ser Gly Tyr Phe Gly Asn<br>930                      935                      940 | 2832 | |
| cca tca gaa gtt ggg ggg tcg tgt cag cct tgc cag tgt cac aac aac<br>Pro Ser Glu Val Gly Gly Ser Cys Gln Pro Cys Gln Cys His Asn Asn<br>945                      950                      955                    960 | 2880 | |
| att gac acg aca gac cca gaa gcc tgt gac aag gag act ggg agg tgt<br>Ile Asp Thr Thr Asp Pro Glu Ala Cys Asp Lys Glu Thr Gly Arg Cys<br>                    965                      970                    975 | 2928 | |
| ctc aag tgc ctg tac cac acg gaa ggg gaa cac tgt cag ttc tgc cgg<br>Leu Lys Cys Leu Tyr His Thr Glu Gly Glu His Cys Gln Phe Cys Arg<br>        980                      985                    990 | 2976 | |
| ttt gga tac tat ggt gat gcc ctc cgg cag gac tgt cga aag tgt gtc<br>Phe Gly Tyr Tyr Gly Asp Ala Leu Arg Gln Asp Cys Arg Lys Cys Val<br>                995                    1000                   1005 | 3024 | |
| tgt aat tac ctg ggc acc gtg caa gag cac tgt aac ggc tct gac tgc<br>Cys Asn Tyr Leu Gly Thr Val Gln Glu His Cys Asn Gly Ser Asp Cys<br>        1010                      1015                    1020 | 3072 | |

```
cag tgc gac aaa gcc act ggt cag tgc ttg tgt ctt cct aat gtg atc      3120
Gln Cys Asp Lys Ala Thr Gly Gln Cys Leu Cys Leu Pro Asn Val Ile
1025                1030                1035                1040 ggg cag aac tgt gac cgc tgt gcg ccc aat acc tgg cag ctg gcc agt      3168
Gly Gln Asn Cys Asp Arg Cys Ala Pro Asn Thr Trp Gln Leu Ala Ser
            1045                1050                1055 ggc act ggc tgt gac cca tgc aac tgc aat gct gct cat tcc ttc ggg      3216
Gly Thr Gly Cys Asp Pro Cys Asn Cys Asn Ala Ala His Ser Phe Gly
        1060                1065                1070 cca tct tgc aat gag ttc acg ggg cag tgc cag tgc atg cct ggg ttt      3264
Pro Ser Cys Asn Glu Phe Thr Gly Gln Cys Gln Cys Met Pro Gly Phe
    1075                1080                1085 gga ggc cgc acc tgc agc gag tgc cag gaa ctc ttc tgg gga gac ccc      3312
Gly Gly Arg Thr Cys Ser Glu Cys Gln Glu Leu Phe Trp Gly Asp Pro
1090                1095                1100 gac gtg gag tgc cga gcc tgt gac tgt gac ccc agg ggc att gag acg      3360
Asp Val Glu Cys Arg Ala Cys Asp Cys Asp Pro Arg Gly Ile Glu Thr
1105                1110                1115                1120 cca cag tgt gac cag tcc acg ggc cag tgt gtc tgc gtt gag ggt gtt      3408
Pro Gln Cys Asp Gln Ser Thr Gly Gln Cys Val Cys Val Glu Gly Val
            1125                1130                1135 gag ggt cca cgc tgt gac aag tgc acg cga ggg tac tcg ggg gtc ttc      3456
Glu Gly Pro Arg Cys Asp Lys Cys Thr Arg Gly Tyr Ser Gly Val Phe
        1140                1145                1150 cct gac tgc aca ccc tgc cac cag tgc ttt gct ctc tgg gat gtg atc      3504
Pro Asp Cys Thr Pro Cys His Gln Cys Phe Ala Leu Trp Asp Val Ile
    1155                1160                1165 att gcc gag ctg acc aac agg aca cac aga ttc ctg gag aaa gcc aag      3552
Ile Ala Glu Leu Thr Asn Arg Thr His Arg Phe Leu Glu Lys Ala Lys
1170                1175                1180 gcc ttg aag atc agt ggt gtg atc ggg cct tac cgt gag act gtg gac      3600
Ala Leu Lys Ile Ser Gly Val Ile Gly Pro Tyr Arg Glu Thr Val Asp
1185                1190                1195                1200 tcg gtg gag agg aaa gtc agc gag ata aaa gac atc ctg gcg cag agc      3648
Ser Val Glu Arg Lys Val Ser Glu Ile Lys Asp Ile Leu Ala Gln Ser
            1205                1210                1215 ccc gca gca gag cca ctg aaa aac att ggg aat ctc ttt gag gaa gca      3696
Pro Ala Ala Glu Pro Leu Lys Asn Ile Gly Asn Leu Phe Glu Glu Ala
        1220                1225                1230 gag aaa ctg att aaa gat gtt aca gaa atg atg gct caa gta gaa gtg      3744
Glu Lys Leu Ile Lys Asp Val Thr Glu Met Met Ala Gln Val Glu Val
    1235                1240                1245 aaa tta tct gac aca act tcc caa agc aac agc aca gcc aaa gaa ctg      3792
Lys Leu Ser Asp Thr Thr Ser Gln Ser Asn Ser Thr Ala Lys Glu Leu
1250                1255                1260 gat tct cta cag aca gaa gcc gaa agc cta gac aac act gtg aaa gaa      3840
Asp Ser Leu Gln Thr Glu Ala Glu Ser Leu Asp Asn Thr Val Lys Glu
1265                1270                1275                1280 ctt gct gaa caa ctg gaa ttt atc aaa aac tca gat att cgg ggt gcc      3888
Leu Ala Glu Gln Leu Glu Phe Ile Lys Asn Ser Asp Ile Arg Gly Ala
            1285                1290                1295 ttg gat agc att acc aag tat ttc cag atg tct ctt gag gca gag gag      3936
Leu Asp Ser Ile Thr Lys Tyr Phe Gln Met Ser Leu Glu Ala Glu Glu
        1300                1305                1310 agg gtg aat gcc tcc acc aca gaa ccc aac agc act gtg gag cag tca      3984
Arg Val Asn Ala Ser Thr Thr Glu Pro Asn Ser Thr Val Glu Gln Ser
    1315                1320                1325 gcc ctc atg aga gac aga gta gaa gac gtg atg atg gag cga gaa tcc      4032
Ala Leu Met Arg Asp Arg Val Glu Asp Val Met Met Glu Arg Glu Ser
1330                1335                1340
```

```
cag ttc aag gaa aaa caa gag gag cag gct cgc ctc ctt gat gaa ctg      4080
Gln Phe Lys Glu Lys Gln Glu Glu Gln Ala Arg Leu Leu Asp Glu Leu
1345                1350                1355                1360 gca ggc aag cta caa agc cta gac ctt tca gcc gct gcc gaa atg acc      4128
Ala Gly Lys Leu Gln Ser Leu Asp Leu Ser Ala Ala Ala Glu Met Thr
                1365                1370                1375 tgt gga aca ccc cca ggg gcc tcc tgt tcc gag act gaa tgt ggc ggg      4176
Cys Gly Thr Pro Pro Gly Ala Ser Cys Ser Glu Thr Glu Cys Gly Gly
        1380                1385                1390 cca aac tgc aga act gac gaa gga gag agg aag tgt ggg ggc cct ggc      4224
Pro Asn Cys Arg Thr Asp Glu Gly Glu Arg Lys Cys Gly Gly Pro Gly
    1395                1400                1405 tgt ggt ggt ctg gtt act gtt gca cac aac gcc tgg cag aaa gcc atg      4272
Cys Gly Gly Leu Val Thr Val Ala His Asn Ala Trp Gln Lys Ala Met
 1410                1415                1420 gac ttg gac caa gat gtc ctg agt gcc ctg gct gaa gtg gaa cag ctc      4320
Asp Leu Asp Gln Asp Val Leu Ser Ala Leu Ala Glu Val Glu Gln Leu
1425                1430                1435                1440 tcc aag atg gtc tct gaa gca aaa ctg agg gca gat gag gca aaa caa      4368
Ser Lys Met Val Ser Glu Ala Lys Leu Arg Ala Asp Glu Ala Lys Gln
                1445                1450                1455 agt gct gaa gac att ctg ttg aag aca aat gct acc aaa gaa aaa atg      4416
Ser Ala Glu Asp Ile Leu Leu Lys Thr Asn Ala Thr Lys Glu Lys Met
        1460                1465                1470 gac aag agc aat gag gag ctg aga aat cta atc aag caa atc aga aac      4464
Asp Lys Ser Asn Glu Glu Leu Arg Asn Leu Ile Lys Gln Ile Arg Asn
    1475                1480                1485 ttt ttg acc cag gat agt gct gat ttg gac agc att gaa gca gtt gct      4512
Phe Leu Thr Gln Asp Ser Ala Asp Leu Asp Ser Ile Glu Ala Val Ala
 1490                1495                1500 aat gaa gta ttg aaa atg gag atg cct agc acc cca cag cag tta cag      4560
Asn Glu Val Leu Lys Met Glu Met Pro Ser Thr Pro Gln Gln Leu Gln
1505                1510                1515                1520 aac ttg aca gaa gat ata cgt gaa cga gtt gaa agc ctt tct caa gta      4608
Asn Leu Thr Glu Asp Ile Arg Glu Arg Val Glu Ser Leu Ser Gln Val
                1525                1530                1535 gag gtt att ctt cag cat agt gct gct gac att gcc aga gct gag atg      4656
Glu Val Ile Leu Gln His Ser Ala Ala Asp Ile Ala Arg Ala Glu Met
        1540                1545                1550 ttg tta gaa gaa gct aaa aga gca agc aaa agt gca aca gat gtt aaa      4704
Leu Leu Glu Glu Ala Lys Arg Ala Ser Lys Ser Ala Thr Asp Val Lys
    1555                1560                1565 gtc act gca gat atg gta aag gaa gct ctg gaa gaa gca gaa aag gcc      4752
Val Thr Ala Asp Met Val Lys Glu Ala Leu Glu Glu Ala Glu Lys Ala
 1570                1575                1580 cag gtc gca gca gag aag gca att aaa caa gca gat gaa gac att caa      4800
Gln Val Ala Ala Glu Lys Ala Ile Lys Gln Ala Asp Glu Asp Ile Gln
1585                1590                1595                1600 gga acc cag aac ctg tta act tcg att gag tct gaa aca gca gct tct      4848
Gly Thr Gln Asn Leu Leu Thr Ser Ile Glu Ser Glu Thr Ala Ala Ser
                1605                1610                1615 gag gaa acc ttg ttc aac gcg tcc cag cgc atc agc gag tta gag agg      4896
Glu Glu Thr Leu Phe Asn Ala Ser Gln Arg Ile Ser Glu Leu Glu Arg
        1620                1625                1630 aat gtg gaa gaa ctt aag cgg aaa gct gcc caa aac tcc ggg gag gca      4944
Asn Val Glu Glu Leu Lys Arg Lys Ala Ala Gln Asn Ser Gly Glu Ala
    1635                1640                1645 gaa tat att gaa aaa gta gta tat act gtg aag caa agt gca gaa gat      4992
Glu Tyr Ile Glu Lys Val Val Tyr Thr Val Lys Gln Ser Ala Glu Asp
```

```
                                                             1650                      1655                      1660
gtt aag aag act tta gat ggt gaa ctt gat gaa aag tat aaa aaa gta    5040
Val Lys Lys Thr Leu Asp Gly Glu Leu Asp Glu Lys Tyr Lys Lys Val
1665                1670                1675                1680 gaa aat tta att gcc aaa aaa act gaa gag tca gct gat gcc aga agg    5088
Glu Asn Leu Ile Ala Lys Lys Thr Glu Glu Ser Ala Asp Ala Arg Arg
           1685                1690                1695 aaa gcc gaa atg cta caa aat gaa gca aaa act ctt tta gct caa gca    5136
Lys Ala Glu Met Leu Gln Asn Glu Ala Lys Thr Leu Leu Ala Gln Ala
       1700                1705                1710 aat agc aag ctg caa ctg ctc aaa gat tta gaa aga aaa tat gaa gac    5184
Asn Ser Lys Leu Gln Leu Leu Lys Asp Leu Glu Arg Lys Tyr Glu Asp
   1715                1720                1725 aat caa aga tac tta gaa gat aaa gct caa gaa tta gca aga ctg gaa    5232
Asn Gln Arg Tyr Leu Glu Asp Lys Ala Gln Glu Leu Ala Arg Leu Glu
1730                1735                1740 gga gaa gtc cgt tca ctc cta aag gat ata agc cag aaa gtt gct gtg    5280
Gly Glu Val Arg Ser Leu Leu Lys Asp Ile Ser Gln Lys Val Ala Val
1745                1750                1755                1760 tat agc aca tgc ttg taacagagga gaataaaaaa tggctgaggt gaacaaggta    5335
Tyr Ser Thr Cys Leu
           1765 aaacaactac attttaaaaa ctgacttaat gctcttcaaa ataaaacatc acctatttaa   5395 tgtttttaat cacattttgt atgagttaaa taaagccc                          5433

<210> SEQ ID NO 16
<211> LENGTH: 1765
<212> TYPE: PRT
<213> ORGANISM: Homo sapiens

<400> SEQUENCE: 16

Gln Glu Pro Glu Phe Ser Tyr Gly Cys Ala Glu Gly Ser Cys Tyr Pro
 1               5                  10                  15

Ala Thr Gly Asp Leu Leu Ile Gly Arg Ala Gln Lys Leu Ser Val Thr
            20                  25                  30

Ser Thr Cys Gly Leu His Lys Pro Glu Pro Tyr Cys Ile Val Ser His
        35                  40                  45

Leu Gln Glu Asp Lys Lys Cys Phe Ile Cys Asn Ser Gln Asp Pro Tyr
    50                  55                  60

His Glu Thr Leu Asn Pro Asp Ser His Leu Ile Glu Asn Val Val Thr
65                  70                  75                  80

Thr Phe Ala Pro Asn Arg Leu Lys Ile Trp Trp Gln Ser Glu Asn Gly
                85                  90                  95

Val Glu Asn Val Thr Ile Gln Leu Asp Leu Glu Ala Glu Phe His Phe
            100                 105                 110

Thr His Leu Ile Met Thr Phe Lys Thr Phe Arg Pro Ala Ala Met Leu
        115                 120                 125

Ile Glu Arg Ser Ser Asp Phe Gly Lys Thr Trp Gly Val Tyr Arg Tyr
    130                 135                 140

Phe Ala Tyr Asp Cys Glu Ala Ser Phe Pro Gly Ile Ser Thr Gly Pro
145                 150                 155                 160

Met Lys Lys Val Asp Asp Ile Ile Cys Asp Ser Arg Tyr Ser Asp Ile
                165                 170                 175

Glu Pro Ser Thr Glu Gly Glu Val Ile Phe Arg Ala Leu Asp Pro Ala
            180                 185                 190

Phe Lys Ile Glu Asp Pro Tyr Ser Pro Arg Ile Gln Asn Leu Leu Lys
```

-continued

```
            195                 200                 205
Ile Thr Asn Leu Arg Ile Lys Phe Val Lys Leu His Thr Leu Gly Asp
            210                 215                 220

Asn Leu Leu Asp Ser Arg Met Glu Ile Arg Glu Lys Tyr Tyr Tyr Ala
225                 230                 235                 240

Val Tyr Asp Met Val Val Arg Gly Asn Cys Phe Cys Tyr Gly His Ala
                245                 250                 255

Ser Glu Cys Ala Pro Val Asp Gly Phe Asn Glu Glu Val Glu Gly Met
                260                 265                 270

Val His Gly His Cys Met Cys Arg His Asn Thr Lys Gly Leu Asn Cys
                275                 280                 285

Glu Leu Cys Met Asp Phe Tyr His Asp Leu Pro Trp Arg Pro Ala Glu
            290                 295                 300

Gly Arg Asn Ser Asn Ala Cys Lys Lys Cys Asn Cys Asn Glu His Ser
305                 310                 315                 320

Ile Ser Cys His Phe Asp Met Ala Val Tyr Leu Ala Thr Gly Asn Val
                325                 330                 335

Ser Gly Gly Val Cys Asp Asp Cys Gln His Asn Thr Met Gly Arg Asn
                340                 345                 350

Cys Glu Gln Cys Lys Pro Phe Tyr Tyr Gln His Pro Glu Arg Asp Ile
            355                 360                 365

Arg Asp Pro Asn Phe Cys Glu Arg Cys Thr Cys Asp Pro Ala Gly Ser
370                 375                 380

Gln Asn Glu Gly Ile Cys Asp Ser Tyr Thr Asp Phe Ser Thr Gly Leu
385                 390                 395                 400

Ile Ala Gly Gln Cys Arg Cys Lys Leu Asn Val Glu Gly Glu His Cys
                405                 410                 415

Asp Val Cys Lys Glu Gly Phe Tyr Asp Leu Ser Ser Glu Asp Pro Phe
                420                 425                 430

Gly Cys Lys Ser Cys Ala Cys Asn Pro Leu Gly Thr Ile Pro Gly Gly
            435                 440                 445

Asn Pro Cys Asp Ser Glu Thr Gly His Cys Tyr Cys Lys Arg Leu Val
            450                 455                 460

Thr Gly Gln His Cys Asp Gln Cys Leu Pro Glu His Trp Gly Leu Ser
465                 470                 475                 480

Asn Asp Leu Asp Gly Cys Arg Pro Cys Asp Cys Asp Leu Gly Gly Ala
                485                 490                 495

Leu Asn Asn Ser Cys Phe Ala Glu Ser Gly Gln Cys Ser Cys Arg Pro
                500                 505                 510

His Met Ile Gly Arg Gln Cys Asn Glu Val Glu Pro Gly Tyr Tyr Phe
            515                 520                 525

Ala Thr Leu Asp His Tyr Leu Tyr Glu Ala Glu Ala Asn Leu Gly
            530                 535                 540

Pro Gly Val Ser Ile Val Glu Arg Gln Tyr Ile Gln Asp Arg Ile Pro
545                 550                 555                 560

Ser Trp Thr Gly Ala Gly Phe Val Arg Val Pro Glu Gly Ala Tyr Leu
                565                 570                 575

Glu Phe Phe Ile Asp Asn Ile Pro Tyr Ser Met Glu Tyr Asp Ile Leu
                580                 585                 590

Ile Arg Tyr Glu Pro Gln Leu Pro Asp His Trp Glu Lys Ala Val Ile
            595                 600                 605

Thr Val Gln Arg Pro Gly Arg Ile Pro Thr Ser Ser Arg Cys Gly Asn
            610                 615                 620
```

-continued

```
Thr Ile Pro Asp Asp Asp Asn Gln Val Val Ser Leu Ser Pro Gly Ser
625                 630                 635                 640

Arg Tyr Val Val Leu Pro Arg Pro Val Cys Phe Glu Lys Gly Thr Asn
            645                 650                 655

Tyr Thr Val Arg Leu Glu Leu Pro Gln Tyr Thr Ser Ser Asp Ser Asp
            660                 665                 670

Val Glu Ser Pro Tyr Thr Leu Ile Asp Ser Leu Val Leu Met Pro Tyr
            675                 680                 685

Cys Lys Ser Leu Asp Ile Phe Thr Val Gly Ser Gly Asp Gly Val
            690                 695                 700

Val Thr Asn Ser Ala Trp Glu Thr Phe Gln Arg Tyr Arg Cys Leu Glu
705                 710                 715                 720

Asn Ser Arg Ser Val Val Lys Thr Pro Met Thr Asp Val Cys Arg Asn
            725                 730                 735

Ile Ile Phe Ser Ile Ser Ala Leu Leu His Gln Thr Gly Leu Ala Cys
            740                 745                 750

Glu Cys Asp Pro Gln Gly Ser Leu Ser Ser Val Cys Asp Pro Asn Gly
            755                 760                 765

Gly Gln Cys Gln Cys Arg Pro Asn Val Val Gly Arg Thr Cys Asn Arg
770                 775                 780

Cys Ala Pro Gly Thr Phe Gly Phe Gly Pro Ser Gly Cys Lys Pro Cys
785                 790                 795                 800

Glu Cys His Leu Gln Gly Ser Val Asn Ala Phe Cys Asn Pro Val Thr
            805                 810                 815

Gly Gln Cys His Cys Phe Gln Gly Val Tyr Ala Arg Gln Cys Asp Arg
            820                 825                 830

Cys Leu Pro Gly His Trp Gly Phe Pro Ser Cys Gln Pro Cys Gln Cys
            835                 840                 845

Asn Gly His Ala Asp Asp Cys Asp Pro Val Thr Gly Glu Cys Leu Asn
850                 855                 860

Cys Gln Asp Tyr Thr Met Gly His Asn Cys Glu Arg Cys Leu Ala Gly
865                 870                 875                 880

Tyr Tyr Gly Asp Pro Ile Ile Gly Ser Gly Asp His Cys Arg Pro Cys
            885                 890                 895

Pro Cys Pro Asp Gly Pro Asp Ser Gly Arg Gln Phe Ala Arg Ser Cys
            900                 905                 910

Tyr Gln Asp Pro Val Thr Leu Gln Leu Ala Cys Val Cys Asp Pro Gly
            915                 920                 925

Tyr Ile Gly Ser Arg Cys Asp Asp Cys Ala Ser Gly Tyr Phe Gly Asn
            930                 935                 940

Pro Ser Glu Val Gly Gly Ser Cys Gln Pro Cys Gln Cys His Asn Asn
945                 950                 955                 960

Ile Asp Thr Thr Asp Pro Glu Ala Cys Asp Lys Glu Thr Gly Arg Cys
            965                 970                 975

Leu Lys Cys Leu Tyr His Thr Glu Gly Glu His Cys Gln Phe Cys Arg
            980                 985                 990

Phe Gly Tyr Tyr Gly Asp Ala Leu Arg Gln Asp Cys Arg Lys Cys Val
            995                 1000                1005

Cys Asn Tyr Leu Gly Thr Val Gln Glu His Cys Asn Gly Ser Asp Cys
    1010                1015                1020

Gln Cys Asp Lys Ala Thr Gly Gln Cys Leu Cys Leu Pro Asn Val Ile
1025                1030                1035                1040
```

```
Gly Gln Asn Cys Asp Arg Cys Ala Pro Asn Thr Trp Gln Leu Ala Ser
                1045                1050                1055

Gly Thr Gly Cys Asp Pro Cys Asn Cys Asn Ala Ala His Ser Phe Gly
                1060                1065                1070

Pro Ser Cys Asn Glu Phe Thr Gly Gln Cys Gln Cys Met Pro Gly Phe
                1075                1080                1085

Gly Gly Arg Thr Cys Ser Glu Cys Gln Glu Leu Phe Trp Gly Asp Pro
    1090                1095                1100

Asp Val Glu Cys Arg Ala Cys Asp Cys Asp Pro Arg Gly Ile Glu Thr
1105                1110                1115                1120

Pro Gln Cys Asp Gln Ser Thr Gly Gln Cys Val Cys Val Glu Gly Val
                1125                1130                1135

Glu Gly Pro Arg Cys Asp Lys Cys Thr Arg Gly Tyr Ser Gly Val Phe
                1140                1145                1150

Pro Asp Cys Thr Pro Cys His Gln Cys Phe Ala Leu Trp Asp Val Ile
                1155                1160                1165

Ile Ala Glu Leu Thr Asn Arg Thr His Arg Phe Leu Glu Lys Ala Lys
    1170                1175                1180

Ala Leu Lys Ile Ser Gly Val Ile Gly Pro Tyr Arg Glu Thr Val Asp
1185                1190                1195                1200

Ser Val Glu Arg Lys Val Ser Glu Ile Lys Asp Ile Leu Ala Gln Ser
                1205                1210                1215

Pro Ala Ala Glu Pro Leu Lys Asn Ile Gly Asn Leu Phe Glu Glu Ala
                1220                1225                1230

Glu Lys Leu Ile Lys Asp Val Thr Glu Met Met Ala Gln Val Glu Val
                1235                1240                1245

Lys Leu Ser Asp Thr Thr Ser Gln Ser Asn Ser Thr Ala Lys Glu Leu
    1250                1255                1260

Asp Ser Leu Gln Thr Glu Ala Glu Ser Leu Asp Asn Thr Val Lys Glu
1265                1270                1275                1280

Leu Ala Glu Gln Leu Glu Phe Ile Lys Asn Ser Asp Ile Arg Gly Ala
                1285                1290                1295

Leu Asp Ser Ile Thr Lys Tyr Phe Gln Met Ser Leu Glu Ala Glu Glu
                1300                1305                1310

Arg Val Asn Ala Ser Thr Thr Glu Pro Asn Ser Thr Val Glu Gln Ser
                1315                1320                1325

Ala Leu Met Arg Asp Arg Val Glu Asp Val Met Met Glu Arg Glu Ser
    1330                1335                1340

Gln Phe Lys Glu Lys Gln Glu Glu Gln Ala Arg Leu Leu Asp Glu Leu
1345                1350                1355                1360

Ala Gly Lys Leu Gln Ser Leu Asp Leu Ser Ala Ala Ala Glu Met Thr
                1365                1370                1375

Cys Gly Thr Pro Pro Gly Ala Ser Cys Ser Glu Thr Glu Cys Gly Gly
                1380                1385                1390

Pro Asn Cys Arg Thr Asp Glu Gly Glu Arg Lys Cys Gly Gly Pro Gly
                1395                1400                1405

Cys Gly Gly Leu Val Thr Val Ala His Asn Ala Trp Gln Lys Ala Met
    1410                1415                1420

Asp Leu Asp Gln Asp Val Leu Ser Ala Leu Ala Glu Val Glu Gln Leu
1425                1430                1435                1440

Ser Lys Met Val Ser Glu Ala Lys Leu Arg Ala Asp Glu Ala Lys Gln
                1445                1450                1455

Ser Ala Glu Asp Ile Leu Leu Lys Thr Asn Ala Thr Lys Glu Lys Met
```

-continued

```
                    1460                1465                1470
Asp Lys Ser Asn Glu Glu Leu Arg Asn Leu Ile Lys Gln Ile Arg Asn
            1475                1480                1485
Phe Leu Thr Gln Asp Ser Ala Asp Leu Asp Ser Ile Glu Ala Val Ala
    1490                1495                1500
Asn Glu Val Leu Lys Met Glu Met Pro Ser Thr Pro Gln Gln Leu Gln
1505                1510                1515                1520
Asn Leu Thr Glu Asp Ile Arg Glu Arg Val Glu Ser Leu Ser Gln Val
            1525                1530                1535
Glu Val Ile Leu Gln His Ser Ala Ala Asp Ile Ala Arg Ala Glu Met
    1540                1545                1550
Leu Leu Glu Glu Ala Lys Arg Ala Ser Lys Ser Ala Thr Asp Val Lys
1555                1560                1565
Val Thr Ala Asp Met Val Lys Glu Ala Leu Glu Glu Ala Glu Lys Ala
    1570                1575                1580
Gln Val Ala Ala Glu Lys Ala Ile Lys Gln Ala Asp Glu Asp Ile Gln
1585                1590                1595                1600
Gly Thr Gln Asn Leu Leu Thr Ser Ile Glu Ser Glu Thr Ala Ala Ser
            1605                1610                1615
Glu Glu Thr Leu Phe Asn Ala Ser Gln Arg Ile Ser Glu Leu Glu Arg
    1620                1625                1630
Asn Val Glu Glu Leu Lys Arg Lys Ala Ala Gln Asn Ser Gly Glu Ala
1635                1640                1645
Glu Tyr Ile Glu Lys Val Val Tyr Thr Val Lys Gln Ser Ala Glu Asp
    1650                1655                1660
Val Lys Lys Thr Leu Asp Gly Glu Leu Asp Glu Lys Tyr Lys Lys Val
1665                1670                1675                1680
Glu Asn Leu Ile Ala Lys Lys Thr Glu Glu Ser Ala Asp Ala Arg Arg
            1685                1690                1695
Lys Ala Glu Met Leu Gln Asn Glu Ala Lys Thr Leu Leu Ala Gln Ala
            1700                1705                1710
Asn Ser Lys Leu Gln Leu Leu Lys Asp Leu Glu Arg Lys Tyr Glu Asp
        1715                1720                1725
Asn Gln Arg Tyr Leu Glu Asp Lys Ala Gln Glu Leu Ala Arg Leu Glu
    1730                1735                1740
Gly Glu Val Arg Ser Leu Leu Lys Asp Ile Ser Gln Lys Val Ala Val
1745                1750                1755                1760
Tyr Ser Thr Cys Leu
            1765
```

<210> SEQ ID NO 17
<211> LENGTH: 5689
<212> TYPE: DNA
<213> ORGANISM: Mus musculus
<220> FEATURE:
<221> NAME/KEY: CDS
<222> LOCATION: (178)..(5535)
<221> NAME/KEY: sig_peptide
<222> LOCATION: (178)..(240)

<400> SEQUENCE: 17

| | | | | | |
|---|---|---|---|---|---|
| gcccagcccc | cgcttccgtg | ggagcggcag | gaaatggaag | ggcccctctc | ctctctccca | 60 |
| acatttgcct | tttctccccg | ctacctctcc | agaaaggaag | acccgaagaa | aagacaggca | 120 |
| gcttgcctgc | tgcgtcctcc | ttcccgtgcc | gcgtcccctc | gtctgcgagg | actggac | 177 |

-continued

```
atg ggg ctg ctc cag gtg ttc gcc ttt ggt gtc cta gcc cta tgg ggc     225
Met Gly Leu Leu Gln Val Phe Ala Phe Gly Val Leu Ala Leu Trp Gly
 1               5                  10                 15 acc cga gtg tgc gct cag gaa ccg gag ttc agc tat ggc tgc gca gaa     273
Thr Arg Val Cys Ala Gln Glu Pro Glu Phe Ser Tyr Gly Cys Ala Glu
             20                  25                  30 ggc agc tgc tac cct gcc act ggc gac ctt ctc atc ggc cga gcg caa     321
Gly Ser Cys Tyr Pro Ala Thr Gly Asp Leu Leu Ile Gly Arg Ala Gln
         35                  40                  45 aag ctc tcc gtg act tcg aca tgt gga ctg cac aaa cca gag ccc tac     369
Lys Leu Ser Val Thr Ser Thr Cys Gly Leu His Lys Pro Glu Pro Tyr
     50                  55                  60 tgt att gtt agc cac ctg cag gag gac aag aaa tgc ttc ata tgt gac     417
Cys Ile Val Ser His Leu Gln Glu Asp Lys Lys Cys Phe Ile Cys Asp
 65                  70                  75                  80 tcc cga gac cct tat cac gag acc ctc aac ccc gac agc cat ctc att     465
Ser Arg Asp Pro Tyr His Glu Thr Leu Asn Pro Asp Ser His Leu Ile
                 85                  90                  95 gag aac gtg gtc acc aca ttt gct cca aac cgc ctt aag atc tgg tgg     513
Glu Asn Val Val Thr Thr Phe Ala Pro Asn Arg Leu Lys Ile Trp Trp
             100                 105                 110 caa tcg gaa aat ggt gtg gag aac gtg acc atc caa ctg gac ctg gaa     561
Gln Ser Glu Asn Gly Val Glu Asn Val Thr Ile Gln Leu Asp Leu Glu
         115                 120                 125 gca gaa ttc cat ttc act cat ctc atc atg acc ttc aag aca ttc cgc     609
Ala Glu Phe His Phe Thr His Leu Ile Met Thr Phe Lys Thr Phe Arg
     130                 135                 140 cca gcc gcc atg ctg atc gag cgg tct tct gac ttt ggg aag act tgg     657
Pro Ala Ala Met Leu Ile Glu Arg Ser Ser Asp Phe Gly Lys Thr Trp
145                 150                 155                 160 ggc gtg tac aga tac ttc gcc tac gac tgt gag agc tcg ttc cca ggc     705
Gly Val Tyr Arg Tyr Phe Ala Tyr Asp Cys Glu Ser Ser Phe Pro Gly
                 165                 170                 175 att tca act gga ccc atg aag aaa gtg gat gac atc atc tgt gac tct     753
Ile Ser Thr Gly Pro Met Lys Lys Val Asp Asp Ile Ile Cys Asp Ser
             180                 185                 190 cga tat tct gac att gag ccc tcg aca gaa gga gag gta ata ttt cgt     801
Arg Tyr Ser Asp Ile Glu Pro Ser Thr Glu Gly Glu Val Ile Phe Arg
         195                 200                 205 gct tta gat cct gct ttc aaa att gaa gac cct tat agt cca agg ata     849
Ala Leu Asp Pro Ala Phe Lys Ile Glu Asp Pro Tyr Ser Pro Arg Ile
     210                 215                 220 cag aat cta tta aaa atc acc aac ttg aga atc aag ttt gtg aaa ctg     897
Gln Asn Leu Leu Lys Ile Thr Asn Leu Arg Ile Lys Phe Val Lys Leu
225                 230                 235                 240 cac acc ttg ggg gat aac ctt ttg gac tcc aga atg gaa atc gag gag     945
His Thr Leu Gly Asp Asn Leu Leu Asp Ser Arg Met Glu Ile Arg Glu
                 245                 250                 255 aag tac tat tac gct gtt tat gat atg gtg gtt cga ggg aac tgc ttc     993
Lys Tyr Tyr Tyr Ala Val Tyr Asp Met Val Val Arg Gly Asn Cys Phe
             260                 265                 270 tgc tat ggc cac gcc agt gaa tgc gcc cct gtg gat gga gtc aat gaa    1041
Cys Tyr Gly His Ala Ser Glu Cys Ala Pro Val Asp Gly Val Asn Glu
         275                 280                 285 gaa gtg gaa gga atg gtt cac ggg cac tgc atg tgc aga cac aac acc    1089
Glu Val Glu Gly Met Val His Gly His Cys Met Cys Arg His Asn Thr
     290                 295                 300 aaa ggc ctg aac tgt gag ctg tgc atg gat ttc tac cac gat ttg ccg    1137
Lys Gly Leu Asn Cys Glu Leu Cys Met Asp Phe Tyr His Asp Leu Pro
305                 310                 315                 320
```

```
tgg aga cct gct gaa ggc cgg aac agc aac gcc tgc aaa aaa tgt aac    1185
Trp Arg Pro Ala Glu Gly Arg Asn Ser Asn Ala Cys Lys Lys Cys Asn
                325                 330                 335 tgc aat gaa cat tcc agc tcg tgt cac ttt gac atg gca gtc ttc ctg    1233
Cys Asn Glu His Ser Ser Ser Cys His Phe Asp Met Ala Val Phe Leu
            340                 345                 350 gct act ggc aac gtc agc ggg gga gtg tgt gat aac tgt cag cac aac    1281
Ala Thr Gly Asn Val Ser Gly Gly Val Cys Asp Asn Cys Gln His Asn
        355                 360                 365 acc atg ggg cgc aac tgt gaa cag tgc aaa ccg ttc tac ttc cag cac    1329
Thr Met Gly Arg Asn Cys Glu Gln Cys Lys Pro Phe Tyr Phe Gln His
    370                 375                 380 cct gag agg gac atc cgg gac ccc aat ctc tgt gaa cca tgt acc tgt    1377
Pro Glu Arg Asp Ile Arg Asp Pro Asn Leu Cys Glu Pro Cys Thr Cys
385                 390                 395                 400 gac cca gct ggt tct gag aat ggc ggg atc tgt gat ggg tac act gat    1425
Asp Pro Ala Gly Ser Glu Asn Gly Gly Ile Cys Asp Gly Tyr Thr Asp
                405                 410                 415 ttt tct gtg ggt ctc att gct ggt cag tgt cgg tgc aaa ttg cac gtg    1473
Phe Ser Val Gly Leu Ile Ala Gly Gln Cys Arg Cys Lys Leu His Val
            420                 425                 430 gag gga gag cgc tgt gat gtt tgt aaa gaa ggc ttc tac gac tta agt    1521
Glu Gly Glu Arg Cys Asp Val Cys Lys Glu Gly Phe Tyr Asp Leu Ser
        435                 440                 445 gct gaa gac ccg tat ggt tgt aaa tca tgt gct tgc aat cct ctg gga    1569
Ala Glu Asp Pro Tyr Gly Cys Lys Ser Cys Ala Cys Asn Pro Leu Gly
    450                 455                 460 aca att cct ggt ggg aat cct tgt gat tct gag act ggc tac tgc tac    1617
Thr Ile Pro Gly Gly Asn Pro Cys Asp Ser Glu Thr Gly Tyr Cys Tyr
465                 470                 475                 480 tgt aag cgc ctg gtg aca gga cag cgc tgt gac cag tgc ctg ccg cag    1665
Cys Lys Arg Leu Val Thr Gly Gln Arg Cys Asp Gln Cys Leu Pro Gln
                485                 490                 495 cac tgg ggt tta agc aat gat ttg gat ggg tgt cga cct tgt gac tgt    1713
His Trp Gly Leu Ser Asn Asp Leu Asp Gly Cys Arg Pro Cys Asp Cys
            500                 505                 510 gac ctt gga ggg gcg ctg aac aat agc tgc tcc gag gac tcc ggc cag    1761
Asp Leu Gly Gly Ala Leu Asn Asn Ser Cys Ser Glu Asp Ser Gly Gln
        515                 520                 525 tgc tcc tgc ctg ccc cac atg att ggg cgg cag tgt aac gag gtg gag    1809
Cys Ser Cys Leu Pro His Met Ile Gly Arg Gln Cys Asn Glu Val Glu
    530                 535                 540 tcc ggt tac tac ttc acc acc ctg gac cac tac atc tac gaa gcc gag    1857
Ser Gly Tyr Tyr Phe Thr Thr Leu Asp His Tyr Ile Tyr Glu Ala Glu
545                 550                 555                 560 gaa gcc aat ctg ggg cct gga gtc gtt gtg gtg gaa agg cag tac att    1905
Glu Ala Asn Leu Gly Pro Gly Val Val Val Val Glu Arg Gln Tyr Ile
                565                 570                 575 cag gac cgc att cct tcc tgg aca gga cct ggc ttc gtc cgg gtg cct    1953
Gln Asp Arg Ile Pro Ser Trp Thr Gly Pro Gly Phe Val Arg Val Pro
            580                 585                 590 gaa ggg gct tat ttg gag ttt ttc att gac aac ata cca tat tcc atg    2001
Glu Gly Ala Tyr Leu Glu Phe Phe Ile Asp Asn Ile Pro Tyr Ser Met
        595                 600                 605 gag tat gaa atc ctg att cgc tat gag cca cag ctg ccg gac cac tgg    2049
Glu Tyr Glu Ile Leu Ile Arg Tyr Glu Pro Gln Leu Pro Asp His Trp
    610                 615                 620 gag aaa gct gtc atc act gta cag cgg ccg ggg aag att cca gcc agc    2097
Glu Lys Ala Val Ile Thr Val Gln Arg Pro Gly Lys Ile Pro Ala Ser
```

-continued

```
         625                 630                 635                 640
agc cga tgt ggt aac acc gtt ccc gat gat gac aac cag gtg gtg tcc      2145
Ser Arg Cys Gly Asn Thr Val Pro Asp Asp Asp Asn Gln Val Val Ser
                645                 650                 655 ttg tca ccg ggc tca aga tac gtt gtc ctc cct cgc ccc gtg tgc ttt      2193
Leu Ser Pro Gly Ser Arg Tyr Val Val Leu Pro Arg Pro Val Cys Phe
            660                 665                 670 gag aag gga atg aac tac acg gtg agg ttg gag ctg ccc cag tat acg      2241
Glu Lys Gly Met Asn Tyr Thr Val Arg Leu Glu Leu Pro Gln Tyr Thr
        675                 680                 685 gca tcg ggc agt gac gtg gag agc cct tac acg ttc atc gac tcg ctt      2289
Ala Ser Gly Ser Asp Val Glu Ser Pro Tyr Thr Phe Ile Asp Ser Leu
    690                 695                 700 gtt ctc atg ccc tac tgt aaa tcg ctg gac atc ttc act gtt ggc ggc      2337
Val Leu Met Pro Tyr Cys Lys Ser Leu Asp Ile Phe Thr Val Gly Gly
705                 710                 715                 720 tca ggc gat ggg gag gtc acc aat agt gcc tgg gaa acc ttc cag cgc      2385
Ser Gly Asp Gly Glu Val Thr Asn Ser Ala Trp Glu Thr Phe Gln Arg
                725                 730                 735 tac agg tgt ctg gag aac agc agg agt gtg gta aaa aca ccc atg aca      2433
Tyr Arg Cys Leu Glu Asn Ser Arg Ser Val Val Lys Thr Pro Met Thr
            740                 745                 750 gat gtc tgc aga aac att atc ttc agc att tct gcc ttg att cac cag      2481
Asp Val Cys Arg Asn Ile Ile Phe Ser Ile Ser Ala Leu Ile His Gln
        755                 760                 765 acg ggc ctt gct tgt gaa tgt gac ccc cag gga tct ctg agt tct gtg      2529
Thr Gly Leu Ala Cys Glu Cys Asp Pro Gln Gly Ser Leu Ser Ser Val
    770                 775                 780 tgt gac ccc aat ggt ggc cag tgc cag tgc cgt cct aat gtg gtt gga      2577
Cys Asp Pro Asn Gly Gly Gln Cys Gln Cys Arg Pro Asn Val Val Gly
785                 790                 795                 800 aga acc tgc aac agg tgt gcc ccg ggc acc ttt ggc ttt ggc ccc aac      2625
Arg Thr Cys Asn Arg Cys Ala Pro Gly Thr Phe Gly Phe Gly Pro Asn
                805                 810                 815 gga tgc aaa cct tgt gac tgc cat ctg caa ggg tct gcc agt gcc ttc      2673
Gly Cys Lys Pro Cys Asp Cys His Leu Gln Gly Ser Ala Ser Ala Phe
            820                 825                 830 tgc gat gcg atc act ggc cag tgc cac tgt ttc cag ggc atc tat gct      2721
Cys Asp Ala Ile Thr Gly Gln Cys His Cys Phe Gln Gly Ile Tyr Ala
        835                 840                 845 cgg cag tgt gac cga tgt ctc cct ggg tat tgg ggc ttt ccc agc tgc      2769
Arg Gln Cys Asp Arg Cys Leu Pro Gly Tyr Trp Gly Phe Pro Ser Cys
    850                 855                 860 cag ccc tgc cag tgt aat ggt cat gct cta gac tgt gac aca gtg aca      2817
Gln Pro Cys Gln Cys Asn Gly His Ala Leu Asp Cys Asp Thr Val Thr
865                 870                 875                 880 ggg gag tgt ctg agc tgt cag gac tac acc acg ggc cac aac tgc gaa      2865
Gly Glu Cys Leu Ser Cys Gln Asp Tyr Thr Thr Gly His Asn Cys Glu
                885                 890                 895 agg tgc ctg gct ggc tac tac ggt gat ccc atc att ggg tca gga gac      2913
Arg Cys Leu Ala Gly Tyr Tyr Gly Asp Pro Ile Ile Gly Ser Gly Asp
            900                 905                 910 cac tgt cgc cct tgc cct tgt cct gat ggt cct gac agt gga cga cag      2961
His Cys Arg Pro Cys Pro Cys Pro Asp Gly Pro Asp Ser Gly Arg Gln
        915                 920                 925 ttt gcc agg agc tgt tat caa gac ccc gtc act ctc cag ctt gcg tgt      3009
Phe Ala Arg Ser Cys Tyr Gln Asp Pro Val Thr Leu Gln Leu Ala Cys
    930                 935                 940 gtt tgt gat cct ggg tac att ggc tcc aga tgt gat gac tgt gcc tct      3057
```

```
                                                         -continued

Val Cys Asp Pro Gly Tyr Ile Gly Ser Arg Cys Asp Asp Cys Ala Ser
945                 950                 955                 960 gga ttt ttt ggc aat ccc tca gac ttt ggg ggt tca tgt caa ccg tgt    3105
Gly Phe Phe Gly Asn Pro Ser Asp Phe Gly Gly Ser Cys Gln Pro Cys
                965                 970                 975 cag tgc cac cac aac att gac act acc gat cca gaa gcc tgt gac aag    3153
Gln Cys His His Asn Ile Asp Thr Thr Asp Pro Glu Ala Cys Asp Lys
    980                 985                 990 gac acg gga cga tgc ctc aag tgc ctg tac cac acg gaa ggg gac cat    3201
Asp Thr Gly Arg Cys Leu Lys Cys Leu Tyr His Thr Glu Gly Asp His
        995                 1000                1005 tgc cag ctc tgc cag tat ggg tac tac ggc gat gct ctt cgg caa gac    3249
Cys Gln Leu Cys Gln Tyr Gly Tyr Tyr Gly Asp Ala Leu Arg Gln Asp
    1010                1015                1020 tgt aga aag tgt gtc tgc aat tac ctg ggc acg gtg aag gaa cat tgt    3297
Cys Arg Lys Cys Val Cys Asn Tyr Leu Gly Thr Val Lys Glu His Cys
1025                1030                1035                1040 aat ggc tct gac tgc cac tgt gac aaa gcc act ggt cag tgc tcg tgc    3345
Asn Gly Ser Asp Cys His Cys Asp Lys Ala Thr Gly Gln Cys Ser Cys
                1045                1050                1055 ctt ccc aat gtg atc ggg cag aac tgt gac cgg tgt gcg ccc aac acc    3393
Leu Pro Asn Val Ile Gly Gln Asn Cys Asp Arg Cys Ala Pro Asn Thr
            1060                1065                1070 tgg cag ctg gct agc ggg act ggc tgc ggg ccc tgc aat tgc aat gct    3441
Trp Gln Leu Ala Ser Gly Thr Gly Cys Gly Pro Cys Asn Cys Asn Ala
    1075                1080                1085 gcg cat tcc ttt ggg cca tcc tgc aac gag ttc aca ggg cag tgc cag    3489
Ala His Ser Phe Gly Pro Ser Cys Asn Glu Phe Thr Gly Gln Cys Gln
1090                1095                1100 tgc atg ccg ggc ttt gga ggc cga acc tgc agc gag tgc cag gag ctc    3537
Cys Met Pro Gly Phe Gly Gly Arg Thr Cys Ser Glu Cys Gln Glu Leu
1105                1110                1115                1120 ttc tgg gga gac cct gat gtg gaa tgc cga gcc tgt gac tgt gat ccc    3585
Phe Trp Gly Asp Pro Asp Val Glu Cys Arg Ala Cys Asp Cys Asp Pro
                1125                1130                1135 agg ggc att gag aca cct cag tgt gac cag tcc acg ggc cag tgt gtc    3633
Arg Gly Ile Glu Thr Pro Gln Cys Asp Gln Ser Thr Gly Gln Cys Val
            1140                1145                1150 tgt gtg gag ggt gta gag ggt cct cgc tgc gac aag tgc acc aga ggt    3681
Cys Val Glu Gly Val Glu Gly Pro Arg Cys Asp Lys Cys Thr Arg Gly
    1155                1160                1165 tac tcg ggg gtc ttt cct gac tgc aca ccc tgc cac cag tgc ttt gct    3729
Tyr Ser Gly Val Phe Pro Asp Cys Thr Pro Cys His Gln Cys Phe Ala
1170                1175                1180 ctc tgg gat gct atc att ggt gag ctg acc aac agg acc cac aaa ttc    3777
Leu Trp Asp Ala Ile Ile Gly Glu Leu Thr Asn Arg Thr His Lys Phe
1185                1190                1195                1200 ctg gag aaa gcc aag gct ctg aaa atc agt ggt gtg att ggt ccc tac    3825
Leu Glu Lys Ala Lys Ala Leu Lys Ile Ser Gly Val Ile Gly Pro Tyr
                1205                1210                1215 cga gag acc gtg gac tct gta gag aag aaa gtc aat gag ata aaa gac    3873
Arg Glu Thr Val Asp Ser Val Glu Lys Lys Val Asn Glu Ile Lys Asp
            1220                1225                1230 atc ctg gcc cag agc cca gca gcg gaa cca ctg aaa aac att ggc att    3921
Ile Leu Ala Gln Ser Pro Ala Ala Glu Pro Leu Lys Asn Ile Gly Ile
    1235                1240                1245 ctc ttc gag gag gca gag aaa cta acc aaa gat gtc aca gaa aag atg    3969
Leu Phe Glu Glu Ala Glu Lys Leu Thr Lys Asp Val Thr Glu Lys Met
1250                1255                1260
```

-continued

| | |
|---|---|
| gcg cag gta gaa gtg aaa tta act gat aca gct tca cag agt aac agc<br>Ala Gln Val Glu Val Lys Leu Thr Asp Thr Ala Ser Gln Ser Asn Ser<br>1265                  1270                  1275                  1280 | 4017 |
| aca gct gga gag ctc ggc gca ctg cag gca gaa gca gag agc ctt gac<br>Thr Ala Gly Glu Leu Gly Ala Leu Gln Ala Glu Ala Glu Ser Leu Asp<br>                  1285                  1290                  1295 | 4065 |
| aag acc gtg aag gag ctg gca gaa cag ctg gag ttt atc aaa aac tcc<br>Lys Thr Val Lys Glu Leu Ala Glu Gln Leu Glu Phe Ile Lys Asn Ser<br>1300                  1305                  1310 | 4113 |
| gat att cag ggc gcc ttg gat agc atc acc aag tat ttc cag atg tct<br>Asp Ile Gln Gly Ala Leu Asp Ser Ile Thr Lys Tyr Phe Gln Met Ser<br>                  1315                  1320                  1325 | 4161 |
| ctt gag gca gag aag cgg gtg aat gcc tcc acc aca gac ccc aac agc<br>Leu Glu Ala Glu Lys Arg Val Asn Ala Ser Thr Thr Asp Pro Asn Ser<br>    1330                  1335                  1340 | 4209 |
| act gtg gag cag tct gcc ctc acg cga gac aga gta gaa gat ctg atg<br>Thr Val Glu Gln Ser Ala Leu Thr Arg Asp Arg Val Glu Asp Leu Met<br>1345                  1350                  1355                  1360 | 4257 |
| ttg gag cga gag tct ccg ttc aag gag cag cag gag gaa cag gca cgc<br>Leu Glu Arg Glu Ser Pro Phe Lys Glu Gln Gln Glu Glu Gln Ala Arg<br>                  1365                  1370                  1375 | 4305 |
| ctc ctg gac gaa ctg gcc ggc aaa ctg caa agt ctc gac ctg tcg gct<br>Leu Leu Asp Glu Leu Ala Gly Lys Leu Gln Ser Leu Asp Leu Ser Ala<br>    1380                  1385                  1390 | 4353 |
| gct gca cag atg acc tgt gga aca cct cca ggg gct gac tgt tct gaa<br>Ala Ala Gln Met Thr Cys Gly Thr Pro Pro Gly Ala Asp Cys Ser Glu<br>1395                  1400                  1405 | 4401 |
| agt gaa tgt ggt ggc ccc aac tgc aga act gac gaa gga gag aag aag<br>Ser Glu Cys Gly Gly Pro Asn Cys Arg Thr Asp Glu Gly Glu Lys Lys<br>                  1410                  1415                  1420 | 4449 |
| tgt ggg ggg cct ggc tgt ggt ggt ctg gtc act gtg gcc cac agt gct<br>Cys Gly Gly Pro Gly Cys Gly Gly Leu Val Thr Val Ala His Ser Ala<br>1425                  1430                  1435                  1440 | 4497 |
| tgg cag aaa gcc atg gat ttt gac cgt gat gtc ctg agt gcc ctg gct<br>Trp Gln Lys Ala Met Asp Phe Asp Arg Asp Val Leu Ser Ala Leu Ala<br>                  1445                  1450                  1455 | 4545 |
| gaa gtc gaa cag ctc tcc aag atg gtc tct gaa gca aaa gtg aga gca<br>Glu Val Glu Gln Leu Ser Lys Met Val Ser Glu Ala Lys Val Arg Ala<br>    1460                  1465                  1470 | 4593 |
| gat gag gcg aag cag aat gcg cag gat gtc ctg tta aaa aca aat gct<br>Asp Glu Ala Lys Gln Asn Ala Gln Asp Val Leu Leu Lys Thr Asn Ala<br>1475                  1480                  1485 | 4641 |
| acc aaa gaa aaa gtg gac aag agc aac gag gac ctg cgg aac ctc atc<br>Thr Lys Glu Lys Val Asp Lys Ser Asn Glu Asp Leu Arg Asn Leu Ile<br>                  1490                  1495                  1500 | 4689 |
| aag cag atc aga aac ttc ctg act gag gat agt gct gat cta gac agt<br>Lys Gln Ile Arg Asn Phe Leu Thr Glu Asp Ser Ala Asp Leu Asp Ser<br>1505                  1510                  1515                  1520 | 4737 |
| att gaa gca gtt gct aat gaa gta ctg aaa agt gga aat gct agc acg<br>Ile Glu Ala Val Ala Asn Glu Val Leu Lys Ser Gly Asn Ala Ser Thr<br>                  1525                  1530                  1535 | 4785 |
| cca cag cag tta cag aac cta aca gaa gac att cgg gag cga gtt gaa<br>Pro Gln Gln Leu Gln Asn Leu Thr Glu Asp Ile Arg Glu Arg Val Glu<br>    1540                  1545                  1550 | 4833 |
| acc ctc tct caa gta gag gtt att ttg cag cag agt gca gct gac att<br>Thr Leu Ser Gln Val Glu Val Ile Leu Gln Gln Ser Ala Ala Asp Ile<br>1555                  1560                  1565 | 4881 |
| gcc aga gct gag ctg ttg ctt gag gaa gct aag aga gca agc aaa agt<br>Ala Arg Ala Glu Leu Leu Leu Glu Glu Ala Lys Arg Ala Ser Lys Ser<br>                  1570                  1575                  1580 | 4929 |

```
gca aca gat gtt aaa gtc act gca gac atg gtg aag gaa gca tta gaa      4977
Ala Thr Asp Val Lys Val Thr Ala Asp Met Val Lys Glu Ala Leu Glu
1585                1590                1595                1600 gaa gca gaa aag gcc cag gtt gca gca gag aag gcg att aaa caa gct      5025
Glu Ala Glu Lys Ala Gln Val Ala Ala Glu Lys Ala Ile Lys Gln Ala
        1605                1610                1615 gat gag gat atc caa gga acc caa aac ctg cta aca tcg att gaa tct      5073
Asp Glu Asp Ile Gln Gly Thr Gln Asn Leu Leu Thr Ser Ile Glu Ser
            1620                1625                1630 gaa acg gca gct tct gag gaa acc ctg acc aac gcc tcc cag cgc atc      5121
Glu Thr Ala Ala Ser Glu Glu Thr Leu Thr Asn Ala Ser Gln Arg Ile
1635                1640                1645 agc aag ctt gag agg aac gtg gaa gag ctt aag cgt aaa gct gcc cag      5169
Ser Lys Leu Glu Arg Asn Val Glu Glu Leu Lys Arg Lys Ala Ala Gln
        1650                1655                1660 aac tct ggg gag gca gaa tat atc gaa aaa gta gta tat tct gta aaa      5217
Asn Ser Gly Glu Ala Glu Tyr Ile Glu Lys Val Val Tyr Ser Val Lys
1665                1670                1675                1680 cag aat gca gac gat gtt aaa aag act cta gat ggc gaa ctt gat gaa      5265
Gln Asn Ala Asp Asp Val Lys Lys Thr Leu Asp Gly Glu Leu Asp Glu
                1685                1690                1695 aag tat aag aag gta gaa agt tta att gcc caa aaa act gaa gag tca      5313
Lys Tyr Lys Lys Val Glu Ser Leu Ile Ala Gln Lys Thr Glu Glu Ser
            1700                1705                1710 gca gat gcc agg agg aaa gct gag ctg cta caa aat gaa gca aaa aca      5361
Ala Asp Ala Arg Arg Lys Ala Glu Leu Leu Gln Asn Glu Ala Lys Thr
        1715                1720                1725 ctc ttg gct caa gct aac agc aag ctc cag ctg ttg gaa gac tta gaa      5409
Leu Leu Ala Gln Ala Asn Ser Lys Leu Gln Leu Leu Glu Asp Leu Glu
1730                1735                1740 aga aaa tat gag gac aat caa aaa tac tta gaa gat aaa gct caa gaa      5457
Arg Lys Tyr Glu Asp Asn Gln Lys Tyr Leu Glu Asp Lys Ala Gln Glu
1745                1750                1755                1760 ttg gtg cga ctg gaa gga gag gtt cgc tcc ctc ctt aag gac ata agt      5505
Leu Val Arg Leu Glu Gly Glu Val Arg Ser Leu Leu Lys Asp Ile Ser
                1765                1770                1775 gag aaa gtt gcg gtt tac agc acc tgc tta taacaggaag gggctgtaga        5555
Glu Lys Val Ala Val Tyr Ser Thr Cys Leu
            1780                1785 ggggctcggt gaccaaggta aaccacacgc gcaaaccgag gcagtcatct acaaataacc    5615
catcatctat ttaatgtttt taaccaccta cttttgtatg gagttaaata aagacattg     5675 gttttgtata aaca                                                      5689

<210> SEQ ID NO 18
<211> LENGTH: 1786
<212> TYPE: PRT
<213> ORGANISM: Mus musculus

<400> SEQUENCE: 18

Met Gly Leu Leu Gln Val Phe Ala Phe Gly Val Leu Ala Leu Trp Gly
1               5                   10                  15

Thr Arg Val Cys Ala Gln Glu Pro Glu Phe Ser Tyr Gly Cys Ala Glu
            20                  25                  30

Gly Ser Cys Tyr Pro Ala Thr Gly Asp Leu Leu Ile Gly Arg Ala Gln
        35                  40                  45

Lys Leu Ser Val Thr Ser Thr Cys Gly Leu His Lys Pro Glu Pro Tyr
    50                  55                  60
```

-continued

```
Cys Ile Val Ser His Leu Gln Glu Asp Lys Lys Cys Phe Ile Cys Asp
 65                  70                  75                  80

Ser Arg Asp Pro Tyr His Glu Thr Leu Asn Pro Asp Ser His Leu Ile
                 85                  90                  95

Glu Asn Val Val Thr Thr Phe Ala Pro Asn Arg Leu Lys Ile Trp Trp
            100                 105                 110

Gln Ser Glu Asn Gly Val Glu Asn Val Thr Ile Gln Leu Asp Leu Glu
            115                 120                 125

Ala Glu Phe His Phe Thr His Leu Ile Met Thr Phe Lys Thr Phe Arg
130                 135                 140

Pro Ala Ala Met Leu Ile Glu Arg Ser Ser Asp Phe Gly Lys Thr Trp
145                 150                 155                 160

Gly Val Tyr Arg Tyr Phe Ala Tyr Asp Cys Glu Ser Ser Phe Pro Gly
                165                 170                 175

Ile Ser Thr Gly Pro Met Lys Lys Val Asp Asp Ile Ile Cys Asp Ser
                180                 185                 190

Arg Tyr Ser Asp Ile Glu Pro Ser Thr Glu Gly Glu Val Ile Phe Arg
            195                 200                 205

Ala Leu Asp Pro Ala Phe Lys Ile Glu Asp Pro Tyr Ser Pro Arg Ile
210                 215                 220

Gln Asn Leu Leu Lys Ile Thr Asn Leu Arg Ile Lys Phe Val Lys Leu
225                 230                 235                 240

His Thr Leu Gly Asp Asn Leu Leu Asp Ser Arg Met Glu Ile Arg Glu
                245                 250                 255

Lys Tyr Tyr Tyr Ala Val Tyr Asp Met Val Val Arg Gly Asn Cys Phe
                260                 265                 270

Cys Tyr Gly His Ala Ser Glu Cys Ala Pro Val Asp Gly Val Asn Glu
            275                 280                 285

Glu Val Glu Gly Met Val His Gly His Cys Met Cys Arg His Asn Thr
290                 295                 300

Lys Gly Leu Asn Cys Glu Leu Cys Met Asp Phe Tyr His Asp Leu Pro
305                 310                 315                 320

Trp Arg Pro Ala Glu Gly Arg Asn Ser Asn Ala Cys Lys Lys Cys Asn
                325                 330                 335

Cys Asn Glu His Ser Ser Ser Cys His Phe Asp Met Ala Val Phe Leu
            340                 345                 350

Ala Thr Gly Asn Val Ser Gly Gly Val Cys Asp Asn Cys Gln His Asn
            355                 360                 365

Thr Met Gly Arg Asn Cys Glu Gln Cys Lys Pro Phe Tyr Phe Gln His
370                 375                 380

Pro Glu Arg Asp Ile Arg Asp Pro Asn Leu Cys Glu Pro Cys Thr Cys
385                 390                 395                 400

Asp Pro Ala Gly Ser Glu Asn Gly Gly Ile Cys Asp Gly Tyr Thr Asp
                405                 410                 415

Phe Ser Val Gly Leu Ile Ala Gly Gln Cys Arg Cys Lys Leu His Val
                420                 425                 430

Glu Gly Glu Arg Cys Asp Val Cys Lys Glu Gly Phe Tyr Asp Leu Ser
            435                 440                 445

Ala Glu Asp Pro Tyr Gly Cys Lys Ser Cys Ala Cys Asn Pro Leu Gly
            450                 455                 460

Thr Ile Pro Gly Gly Asn Pro Cys Asp Ser Glu Thr Gly Tyr Cys Tyr
465                 470                 475                 480

Cys Lys Arg Leu Val Thr Gly Gln Arg Cys Asp Gln Cys Leu Pro Gln
```

-continued

```
                485                 490                 495
His Trp Gly Leu Ser Asn Asp Leu Asp Gly Cys Arg Pro Cys Asp Cys
                500                 505                 510

Asp Leu Gly Gly Ala Leu Asn Asn Ser Cys Ser Glu Asp Ser Gly Gln
                515                 520                 525

Cys Ser Cys Leu Pro His Met Ile Gly Arg Gln Cys Asn Glu Val Glu
                530                 535                 540

Ser Gly Tyr Tyr Phe Thr Thr Leu Asp His Tyr Ile Tyr Glu Ala Glu
545                 550                 555                 560

Glu Ala Asn Leu Gly Pro Gly Val Val Val Glu Arg Gln Tyr Ile
                565                 570                 575

Gln Asp Arg Ile Pro Ser Trp Thr Gly Pro Gly Phe Val Arg Val Pro
                580                 585                 590

Glu Gly Ala Tyr Leu Glu Phe Phe Ile Asp Asn Ile Pro Tyr Ser Met
                595                 600                 605

Glu Tyr Glu Ile Leu Ile Arg Tyr Glu Pro Gln Leu Pro Asp His Trp
                610                 615                 620

Glu Lys Ala Val Ile Thr Val Gln Arg Pro Gly Lys Ile Pro Ala Ser
625                 630                 635                 640

Ser Arg Cys Gly Asn Thr Val Pro Asp Asp Asn Gln Val Val Ser
                645                 650                 655

Leu Ser Pro Gly Ser Arg Tyr Val Val Leu Pro Arg Pro Val Cys Phe
                660                 665                 670

Glu Lys Gly Met Asn Tyr Thr Val Arg Leu Glu Leu Pro Gln Tyr Thr
                675                 680                 685

Ala Ser Gly Ser Asp Val Glu Ser Pro Tyr Thr Phe Ile Asp Ser Leu
                690                 695                 700

Val Leu Met Pro Tyr Cys Lys Ser Leu Asp Ile Phe Thr Val Gly Gly
705                 710                 715                 720

Ser Gly Asp Gly Glu Val Thr Asn Ser Ala Trp Glu Thr Phe Gln Arg
                725                 730                 735

Tyr Arg Cys Leu Glu Asn Ser Arg Ser Val Val Lys Thr Pro Met Thr
                740                 745                 750

Asp Val Cys Arg Asn Ile Ile Phe Ser Ile Ser Ala Leu Ile His Gln
                755                 760                 765

Thr Gly Leu Ala Cys Glu Cys Asp Pro Gln Gly Ser Leu Ser Ser Val
770                 775                 780

Cys Asp Pro Asn Gly Gly Gln Cys Gln Cys Arg Pro Asn Val Val Gly
785                 790                 795                 800

Arg Thr Cys Asn Arg Cys Ala Pro Gly Thr Phe Gly Phe Gly Pro Asn
                805                 810                 815

Gly Cys Lys Pro Cys Asp Cys His Leu Gln Gly Ser Ala Ser Ala Phe
                820                 825                 830

Cys Asp Ala Ile Thr Gly Gln Cys His Cys Phe Gln Gly Ile Tyr Ala
                835                 840                 845

Arg Gln Cys Asp Arg Cys Leu Pro Gly Tyr Trp Gly Phe Pro Ser Cys
                850                 855                 860

Gln Pro Cys Gln Cys Asn Gly His Ala Leu Asp Cys Asp Thr Val Thr
865                 870                 875                 880

Gly Glu Cys Leu Ser Cys Gln Asp Tyr Thr Thr Gly His Asn Cys Glu
                885                 890                 895

Arg Cys Leu Ala Gly Tyr Tyr Gly Asp Pro Ile Ile Gly Ser Gly Asp
                900                 905                 910
```

```
His Cys Arg Pro Cys Pro Cys Pro Asp Gly Pro Asp Ser Gly Arg Gln
            915                 920                 925

Phe Ala Arg Ser Cys Tyr Gln Asp Pro Val Thr Leu Gln Leu Ala Cys
        930                 935                 940

Val Cys Asp Pro Gly Tyr Ile Gly Ser Arg Cys Asp Asp Cys Ala Ser
945                 950                 955                 960

Gly Phe Phe Gly Asn Pro Ser Asp Phe Gly Ser Cys Gln Pro Cys
                965                 970                 975

Gln Cys His His Asn Ile Asp Thr Thr Asp Pro Glu Ala Cys Asp Lys
            980                 985                 990

Asp Thr Gly Arg Cys Leu Lys Cys Leu Tyr His Thr Glu Gly Asp His
            995                 1000                1005

Cys Gln Leu Cys Gln Tyr Gly Tyr Tyr Gly Asp Ala Leu Arg Gln Asp
    1010                1015                1020

Cys Arg Lys Cys Val Cys Asn Tyr Leu Gly Thr Val Lys Glu His Cys
1025                1030                1035                1040

Asn Gly Ser Asp Cys His Cys Asp Lys Ala Thr Gly Gln Cys Ser Cys
            1045                1050                1055

Leu Pro Asn Val Ile Gly Gln Asn Cys Asp Arg Cys Ala Pro Asn Thr
            1060                1065                1070

Trp Gln Leu Ala Ser Gly Thr Gly Cys Gly Pro Cys Asn Cys Asn Ala
        1075                1080                1085

Ala His Ser Phe Gly Pro Ser Cys Asn Glu Phe Thr Gly Gln Cys Gln
        1090                1095                1100

Cys Met Pro Gly Phe Gly Gly Arg Thr Cys Ser Glu Cys Gln Glu Leu
1105                1110                1115                1120

Phe Trp Gly Asp Pro Asp Val Glu Cys Arg Ala Cys Asp Cys Asp Pro
            1125                1130                1135

Arg Gly Ile Glu Thr Pro Gln Cys Asp Gln Ser Thr Gly Gln Cys Val
            1140                1145                1150

Cys Val Glu Gly Val Glu Gly Pro Arg Cys Asp Lys Cys Thr Arg Gly
        1155                1160                1165

Tyr Ser Gly Val Phe Pro Asp Cys Thr Pro Cys His Gln Cys Phe Ala
    1170                1175                1180

Leu Trp Asp Ala Ile Ile Gly Glu Leu Thr Asn Arg Thr His Lys Phe
1185                1190                1195                1200

Leu Glu Lys Ala Lys Ala Leu Lys Ile Ser Gly Val Ile Gly Pro Tyr
            1205                1210                1215

Arg Glu Thr Val Asp Ser Val Glu Lys Lys Val Asn Glu Ile Lys Asp
            1220                1225                1230

Ile Leu Ala Gln Ser Pro Ala Ala Glu Pro Leu Lys Asn Ile Gly Ile
            1235                1240                1245

Leu Phe Glu Glu Ala Glu Lys Leu Thr Lys Asp Val Thr Glu Lys Met
    1250                1255                1260

Ala Gln Val Glu Val Lys Leu Thr Asp Thr Ala Ser Gln Ser Asn Ser
1265                1270                1275                1280

Thr Ala Gly Glu Leu Gly Ala Leu Gln Ala Glu Ala Glu Ser Leu Asp
            1285                1290                1295

Lys Thr Val Lys Glu Leu Ala Glu Gln Leu Glu Phe Ile Lys Asn Ser
            1300                1305                1310

Asp Ile Gln Gly Ala Leu Asp Ser Ile Thr Lys Tyr Phe Gln Met Ser
            1315                1320                1325
```

-continued

```
Leu Glu Ala Glu Lys Arg Val Asn Ala Ser Thr Thr Asp Pro Asn Ser
    1330                1335                1340

Thr Val Glu Gln Ser Ala Leu Thr Arg Asp Arg Val Glu Asp Leu Met
1345                1350                1355                1360

Leu Glu Arg Glu Ser Pro Phe Lys Glu Gln Gln Glu Gln Ala Arg
        1365                1370                1375

Leu Leu Asp Glu Leu Ala Gly Lys Leu Gln Ser Leu Asp Leu Ser Ala
        1380                1385                1390

Ala Ala Gln Met Thr Cys Gly Thr Pro Pro Gly Ala Asp Cys Ser Glu
        1395                1400                1405

Ser Glu Cys Gly Gly Pro Asn Cys Arg Thr Asp Glu Gly Glu Lys Lys
        1410                1415                1420

Cys Gly Gly Pro Gly Cys Gly Gly Leu Val Thr Val Ala His Ser Ala
1425                1430                1435                1440

Trp Gln Lys Ala Met Asp Phe Asp Arg Asp Val Leu Ser Ala Leu Ala
                1445                1450                1455

Glu Val Glu Gln Leu Ser Lys Met Val Ser Glu Ala Lys Val Arg Ala
        1460                1465                1470

Asp Glu Ala Lys Gln Asn Ala Gln Asp Val Leu Leu Lys Thr Asn Ala
        1475                1480                1485

Thr Lys Glu Lys Val Asp Lys Ser Asn Glu Asp Leu Arg Asn Leu Ile
    1490                1495                1500

Lys Gln Ile Arg Asn Phe Leu Thr Glu Asp Ser Ala Asp Leu Asp Ser
1505                1510                1515                1520

Ile Glu Ala Val Ala Asn Glu Val Leu Lys Ser Gly Asn Ala Ser Thr
                1525                1530                1535

Pro Gln Gln Leu Gln Asn Leu Thr Glu Asp Ile Arg Glu Arg Val Glu
        1540                1545                1550

Thr Leu Ser Gln Val Glu Val Ile Leu Gln Gln Ser Ala Ala Asp Ile
        1555                1560                1565

Ala Arg Ala Glu Leu Leu Leu Glu Glu Ala Lys Arg Ala Ser Lys Ser
    1570                1575                1580

Ala Thr Asp Val Lys Val Thr Ala Asp Met Val Lys Glu Ala Leu Glu
1585                1590                1595                1600

Glu Ala Glu Lys Ala Gln Val Ala Ala Glu Lys Ala Ile Lys Gln Ala
        1605                1610                1615

Asp Glu Asp Ile Gln Gly Thr Gln Asn Leu Leu Thr Ser Ile Glu Ser
        1620                1625                1630

Glu Thr Ala Ala Ser Glu Glu Thr Leu Thr Asn Ala Ser Gln Arg Ile
        1635                1640                1645

Ser Lys Leu Glu Arg Asn Val Glu Glu Leu Lys Arg Lys Ala Ala Gln
    1650                1655                1660

Asn Ser Gly Glu Ala Glu Tyr Ile Glu Lys Val Val Tyr Ser Val Lys
1665                1670                1675                1680

Gln Asn Ala Asp Asp Val Lys Lys Thr Leu Asp Gly Glu Leu Asp Glu
        1685                1690                1695

Lys Tyr Lys Lys Val Glu Ser Leu Ile Ala Gln Lys Thr Glu Glu Ser
        1700                1705                1710

Ala Asp Ala Arg Arg Lys Ala Glu Leu Leu Gln Asn Glu Ala Lys Thr
    1715                1720                1725

Leu Leu Ala Gln Ala Asn Ser Lys Leu Gln Leu Leu Glu Asp Leu Glu
    1730                1735                1740

Arg Lys Tyr Glu Asp Asn Gln Lys Tyr Leu Glu Asp Lys Ala Gln Glu
```

```
                1745           1750              1755             1760
            Leu Val Arg Leu Glu Gly Glu Val Arg Ser Leu Leu Lys Asp Ile Ser
                              1765              1770             1775
            Glu Lys Val Ala Val Tyr Ser Thr Cys Leu
                      1780                  1785

<210> SEQ ID NO 19
<211> LENGTH: 5329
<212> TYPE: DNA
<213> ORGANISM: Mus musculus
<220> FEATURE:
<221> NAME/KEY: CDS
<222> LOCATION: (1)..(5175)

<400> SEQUENCE: 19 gag ccc tac tgt att gtt agc cac ctg cag gag gac aag aaa tgc ttc        48
Glu Pro Tyr Cys Ile Val Ser His Leu Gln Glu Asp Lys Lys Cys Phe
 1               5                  10                  15 ata tgt gac tcc cga gac cct tat cac gag acc ctc aac ccc gac agc        96
Ile Cys Asp Ser Arg Asp Pro Tyr His Glu Thr Leu Asn Pro Asp Ser
             20                  25                  30 cat ctc att gag aac gtg gtc acc aca ttt gct cca aac cgc ctt aag       144
His Leu Ile Glu Asn Val Val Thr Thr Phe Ala Pro Asn Arg Leu Lys
         35                  40                  45 atc tgg tgg caa tcg gaa aat ggt gtg gag aac gtg acc atc caa ctg       192
Ile Trp Trp Gln Ser Glu Asn Gly Val Glu Asn Val Thr Ile Gln Leu
     50                  55                  60 gac ctg gaa gca gaa ttc cat ttc act cat ctc atc atg acc ttc aag       240
Asp Leu Glu Ala Glu Phe His Phe Thr His Leu Ile Met Thr Phe Lys
 65                  70                  75                  80 aca ttc cgc cca gcc gcc atg ctg atc gag cgg tct tct gac ttt ggg       288
Thr Phe Arg Pro Ala Ala Met Leu Ile Glu Arg Ser Ser Asp Phe Gly
                 85                  90                  95 aag act tgg ggc gtg tac aga tac ttc gcc tac gac tgt gag agc tcg       336
Lys Thr Trp Gly Val Tyr Arg Tyr Phe Ala Tyr Asp Cys Glu Ser Ser
            100                 105                 110 ttc cca ggc att tca act gga ccc atg aag aaa gtg gat gac atc atc       384
Phe Pro Gly Ile Ser Thr Gly Pro Met Lys Lys Val Asp Asp Ile Ile
        115                 120                 125 tgt gac tct cga tat tct gac att gag ccc tcg aca gaa gga gag gta       432
Cys Asp Ser Arg Tyr Ser Asp Ile Glu Pro Ser Thr Glu Gly Glu Val
    130                 135                 140 ata ttt cgt gct tta gat cct gct ttc aaa att gaa gac cct tat agt       480
Ile Phe Arg Ala Leu Asp Pro Ala Phe Lys Ile Glu Asp Pro Tyr Ser
145                 150                 155                 160 cca agg ata cag aat cta tta aaa atc acc aac ttg aga atc aag ttt       528
Pro Arg Ile Gln Asn Leu Leu Lys Ile Thr Asn Leu Arg Ile Lys Phe
                165                 170                 175 gtg aaa ctg cac acc ttg ggg gat aac ctt ttg gac tcc aga atg gaa       576
Val Lys Leu His Thr Leu Gly Asp Asn Leu Leu Asp Ser Arg Met Glu
            180                 185                 190 atc cga gag aag tac tat tac gct gtt tat gat atg gtg gtt cga ggg       624
Ile Arg Glu Lys Tyr Tyr Tyr Ala Val Tyr Asp Met Val Val Arg Gly
        195                 200                 205 aac tgc ttc tgc tat ggc cac gcc agt gaa tgc gcc cct gtg gat gga       672
Asn Cys Phe Cys Tyr Gly His Ala Ser Glu Cys Ala Pro Val Asp Gly
    210                 215                 220 gtc aat gaa gaa gtg gaa gga atg gtt cac ggg cac tgc atg tgc aga       720
Val Asn Glu Glu Val Glu Gly Met Val His Gly His Cys Met Cys Arg
225                 230                 235                 240
```

```
cac aac acc aaa ggc ctg aac tgt gag ctg tgc atg gat ttc tac cac        768
His Asn Thr Lys Gly Leu Asn Cys Glu Leu Cys Met Asp Phe Tyr His
            245                 250                 255 gat ttg ccg tgg aga cct gct gaa ggc cgg aac agc aac gcc tgc aaa        816
Asp Leu Pro Trp Arg Pro Ala Glu Gly Arg Asn Ser Asn Ala Cys Lys
            260                 265                 270 aaa tgt aac tgc aat gaa cat tcc agc tcg tgt cac ttt gac atg gca        864
Lys Cys Asn Cys Asn Glu His Ser Ser Ser Cys His Phe Asp Met Ala
            275                 280                 285 gtc ttc ctg gct act ggc aac gtc agc ggg gga gtg tgt gat aac tgt        912
Val Phe Leu Ala Thr Gly Asn Val Ser Gly Gly Val Cys Asp Asn Cys
            290                 295                 300 cag cac aac acc atg ggg cgc aac tgt gaa cag tgc aaa ccg ttc tac        960
Gln His Asn Thr Met Gly Arg Asn Cys Glu Gln Cys Lys Pro Phe Tyr
305                 310                 315                 320 ttc cag cac cct gag agg gac atc cgg gac ccc aat ctc tgt gaa cca       1008
Phe Gln His Pro Glu Arg Asp Ile Arg Asp Pro Asn Leu Cys Glu Pro
            325                 330                 335 tgt acc tgt gac cca gct ggt tct gag aat ggc ggg atc tgt gat ggg       1056
Cys Thr Cys Asp Pro Ala Gly Ser Glu Asn Gly Gly Ile Cys Asp Gly
            340                 345                 350 tac act gat ttt tct gtg ggt ctc att gct ggt cag tgt cgg tgc aaa       1104
Tyr Thr Asp Phe Ser Val Gly Leu Ile Ala Gly Gln Cys Arg Cys Lys
            355                 360                 365 ttg cac gtg gag gga gag cgc tgt gat gtt tgt aaa gaa ggc ttc tac       1152
Leu His Val Glu Gly Glu Arg Cys Asp Val Cys Lys Glu Gly Phe Tyr
370                 375                 380 gac tta agt gct gaa gac ccg tat ggt tgt aaa tca tgt gct tgc aat       1200
Asp Leu Ser Ala Glu Asp Pro Tyr Gly Cys Lys Ser Cys Ala Cys Asn
385                 390                 395                 400 cct ctg gga aca att cct ggt ggg aat cct tgt gat tct gag act ggc       1248
Pro Leu Gly Thr Ile Pro Gly Gly Asn Pro Cys Asp Ser Glu Thr Gly
            405                 410                 415 tac tgc tac tgt aag cgc ctg gtg aca gga cag cgc tgt gac cag tgc       1296
Tyr Cys Tyr Cys Lys Arg Leu Val Thr Gly Gln Arg Cys Asp Gln Cys
            420                 425                 430 ctg ccg cag cac tgg ggt tta agc aat gat ttg gat ggg tgt cga cct       1344
Leu Pro Gln His Trp Gly Leu Ser Asn Asp Leu Asp Gly Cys Arg Pro
            435                 440                 445 tgt gac tgt gac ctt gga ggg gcg ctg aac aat agc tgc tcc gag gac       1392
Cys Asp Cys Asp Leu Gly Gly Ala Leu Asn Asn Ser Cys Ser Glu Asp
450                 455                 460 tcc ggc cag tgc tcc tgc ctc ccc cac atg att ggg cgg cag tgt aac       1440
Ser Gly Gln Cys Ser Cys Leu Pro His Met Ile Gly Arg Gln Cys Asn
465                 470                 475                 480 gag gtg gag tcc ggt tac tac ttc acc acc ctg gac cac tac atc tac       1488
Glu Val Glu Ser Gly Tyr Tyr Phe Thr Thr Leu Asp His Tyr Ile Tyr
            485                 490                 495 gaa gcc gag gaa gcc aat ctg ggg cct gga gtc gtt gtg gtg gaa agg       1536
Glu Ala Glu Glu Ala Asn Leu Gly Pro Gly Val Val Val Val Glu Arg
            500                 505                 510 cag tac att cag gac cgc att cct tcc tgg aca gga cct ggc ttc gtc       1584
Gln Tyr Ile Gln Asp Arg Ile Pro Ser Trp Thr Gly Pro Gly Phe Val
            515                 520                 525 cgg gtg cct gaa ggg gct tat ttg gag ttt ttc att gac aac ata cca       1632
Arg Val Pro Glu Gly Ala Tyr Leu Glu Phe Phe Ile Asp Asn Ile Pro
            530                 535                 540 tat tcc atg gag tat gaa atc ctg att cgc tat gag cca cag ctg ccg       1680
Tyr Ser Met Glu Tyr Glu Ile Leu Ile Arg Tyr Glu Pro Gln Leu Pro
545                 550                 555                 560
```

```
gac cac tgg gag aaa gct gtc atc act gta cag cgg ccg ggg aag att       1728
Asp His Trp Glu Lys Ala Val Ile Thr Val Gln Arg Pro Gly Lys Ile
                565                 570                 575 cca gcc agc agc cga tgt ggt aac acc gtt ccc gat gat gac aac cag       1776
Pro Ala Ser Ser Arg Cys Gly Asn Thr Val Pro Asp Asp Asp Asn Gln
            580                 585                 590 gtg gtg tcc ttg tca ccg ggc tca aga tac gtt gtc ctc cct cgc ccc       1824
Val Val Ser Leu Ser Pro Gly Ser Arg Tyr Val Val Leu Pro Arg Pro
        595                 600                 605 gtg tgc ttt gag aag gga atg aac tac acg gtg agg ttg gag ctg ccc       1872
Val Cys Phe Glu Lys Gly Met Asn Tyr Thr Val Arg Leu Glu Leu Pro
    610                 615                 620 cag tat acg gca tcg ggc agt gac gtg gag agc cct tac acg ttc atc       1920
Gln Tyr Thr Ala Ser Gly Ser Asp Val Glu Ser Pro Tyr Thr Phe Ile
625                 630                 635                 640 gac tcg ctt gtt ctc atg ccc tac tgt aaa tcg ctg gac atc ttc act       1968
Asp Ser Leu Val Leu Met Pro Tyr Cys Lys Ser Leu Asp Ile Phe Thr
                645                 650                 655 gtt ggc ggc tca ggc gat ggg gag gtc acc aat agt gcc tgg gaa acc       2016
Val Gly Gly Ser Gly Asp Gly Glu Val Thr Asn Ser Ala Trp Glu Thr
            660                 665                 670 ttc cag cgc tac agg tgt ctg gag aac agc agg agt gtg gta aaa aca       2064
Phe Gln Arg Tyr Arg Cys Leu Glu Asn Ser Arg Ser Val Val Lys Thr
        675                 680                 685 ccc atg aca gat gtc tgc aga aac att atc ttc agc att tct gcc ttg       2112
Pro Met Thr Asp Val Cys Arg Asn Ile Ile Phe Ser Ile Ser Ala Leu
    690                 695                 700 att cac cag acg ggc ctt gct tgt gaa tgt gac ccc cag gga tct ctg       2160
Ile His Gln Thr Gly Leu Ala Cys Glu Cys Asp Pro Gln Gly Ser Leu
705                 710                 715                 720 agt tct gtg tgt gac ccc aat ggt ggc cag tgc cag tgc cgt cct aat       2208
Ser Ser Val Cys Asp Pro Asn Gly Gly Gln Cys Gln Cys Arg Pro Asn
                725                 730                 735 gtg gtt gga aga acc tgc aac agg tgt gcc ccg ggc acc ttt ggc ttt       2256
Val Val Gly Arg Thr Cys Asn Arg Cys Ala Pro Gly Thr Phe Gly Phe
            740                 745                 750 ggc ccc aac gga tgc aaa cct tgt gac tgc cat ctg caa ggg tct gcc       2304
Gly Pro Asn Gly Cys Lys Pro Cys Asp Cys His Leu Gln Gly Ser Ala
        755                 760                 765 agt gcc ttc tgc gat gcg atc act ggc cag tgc cac tgt ttc cag ggc       2352
Ser Ala Phe Cys Asp Ala Ile Thr Gly Gln Cys His Cys Phe Gln Gly
    770                 775                 780 atc tat gct cgg cag tgt gac cga tgt ctc cct ggg tat tgg ggc ttt       2400
Ile Tyr Ala Arg Gln Cys Asp Arg Cys Leu Pro Gly Tyr Trp Gly Phe
785                 790                 795                 800 ccc agc tgc cag ccc tgc cag tgt aat ggt cat gct cta gac tgt gac       2448
Pro Ser Cys Gln Pro Cys Gln Cys Asn Gly His Ala Leu Asp Cys Asp
                805                 810                 815 aca gtg aca ggg gag tgt ctg agc tgt cag gac tac acc acg ggc cac       2496
Thr Val Thr Gly Glu Cys Leu Ser Cys Gln Asp Tyr Thr Thr Gly His
            820                 825                 830 aac tgc gaa agg tgc ctg gct ggc tac tac ggt gat ccc atc att ggg       2544
Asn Cys Glu Arg Cys Leu Ala Gly Tyr Tyr Gly Asp Pro Ile Ile Gly
        835                 840                 845 tca gga gac cac tgt cgc cct tgc cct tgt cct gat ggt cct gac agt       2592
Ser Gly Asp His Cys Arg Pro Cys Pro Cys Pro Asp Gly Pro Asp Ser
    850                 855                 860 gga cga cag ttt gcc agg agc tgt tat caa gac ccc gtc act ctc cag       2640
Gly Arg Gln Phe Ala Arg Ser Cys Tyr Gln Asp Pro Val Thr Leu Gln
```

```
                                          -continued
865                  870                  875                  880 ctt gcg tgt gtt tgt gat cct ggg tac att ggc tcc aga tgt gat gac    2688
Leu Ala Cys Val Cys Asp Pro Gly Tyr Ile Gly Ser Arg Cys Asp Asp
                885                  890                  895 tgt gcc tct gga ttt ttt ggc aat ccc tca gac ttt ggg ggt tca tgt    2736
Cys Ala Ser Gly Phe Phe Gly Asn Pro Ser Asp Phe Gly Gly Ser Cys
            900                  905                  910 caa ccg tgt cag tgc cac cac aac att gac act acc gat cca gaa gcc    2784
Gln Pro Cys Gln Cys His His Asn Ile Asp Thr Thr Asp Pro Glu Ala
        915                  920                  925 tgt gac aag gac acg gga cga tgc ctc aag tgc ctg tac cac acg gaa    2832
Cys Asp Lys Asp Thr Gly Arg Cys Leu Lys Cys Leu Tyr His Thr Glu
    930                  935                  940 ggg gac cat tgc cag ctc tgc cag tat ggg tac tac ggc gat gct ctt    2880
Gly Asp His Cys Gln Leu Cys Gln Tyr Gly Tyr Tyr Gly Asp Ala Leu
945                  950                  955                  960 cgg caa gac tgt aga aag tgt gtc tgc aat tac ctg ggc acg gtg aag    2928
Arg Gln Asp Cys Arg Lys Cys Val Cys Asn Tyr Leu Gly Thr Val Lys
                965                  970                  975 gaa cat tgt aat ggc tct gac tgc cac tgt gac aaa gcc act ggt cag    2976
Glu His Cys Asn Gly Ser Asp Cys His Cys Asp Lys Ala Thr Gly Gln
            980                  985                  990 tgc tcg tgc ctt ccc aat gtg atc ggg cag aac tgt gac cgg tgt gcg    3024
Cys Ser Cys Leu Pro Asn Val Ile Gly Gln Asn Cys Asp Arg Cys Ala
        995                  1000                 1005 ccc aac acc tgg cag ctg gct agc ggg act ggc tgc ggg ccc tgc aat    3072
Pro Asn Thr Trp Gln Leu Ala Ser Gly Thr Gly Cys Gly Pro Cys Asn
    1010                 1015                 1020 tgc aat gct gcg cat tcc ttt ggg cca tcc tgc aac gag ttc aca ggg    3120
Cys Asn Ala Ala His Ser Phe Gly Pro Ser Cys Asn Glu Phe Thr Gly
1025                 1030                 1035                 1040 cag tgc cag tgc atg ccg ggc ttt gga ggc cga acc tgc agc gag tgc    3168
Gln Cys Gln Cys Met Pro Gly Phe Gly Gly Arg Thr Cys Ser Glu Cys
                1045                 1050                 1055 cag gag ctc ttc tgg gga gac cct gat gtg gaa tgc cga gcc tgt gac    3216
Gln Glu Leu Phe Trp Gly Asp Pro Asp Val Glu Cys Arg Ala Cys Asp
            1060                 1065                 1070 tgt gat ccc agg ggc att gag aca cct cag tgt gac cag tcc acg ggc    3264
Cys Asp Pro Arg Gly Ile Glu Thr Pro Gln Cys Asp Gln Ser Thr Gly
        1075                 1080                 1085 cag tgt gtc tgt gtg gag ggt gta gag ggt cct cgc tgc gac aag tgc    3312
Gln Cys Val Cys Val Glu Gly Val Glu Gly Pro Arg Cys Asp Lys Cys
    1090                 1095                 1100 acc aga ggt tac tcg ggg gtc ttt cct gac tgc aca ccc tgc cac cag    3360
Thr Arg Gly Tyr Ser Gly Val Phe Pro Asp Cys Thr Pro Cys His Gln
1105                 1110                 1115                 1120 tgc ttt gct ctc tgg gat gct atc att ggt gag ctg acc aac agg acc    3408
Cys Phe Ala Leu Trp Asp Ala Ile Ile Gly Glu Leu Thr Asn Arg Thr
                1125                 1130                 1135 cac aaa ttc ctg gag aaa gcc aag gct ctg aaa atc agt ggt gtg att    3456
His Lys Phe Leu Glu Lys Ala Lys Ala Leu Lys Ile Ser Gly Val Ile
            1140                 1145                 1150 ggt ccc tac cga gag acc gtg gac tct gta gag aag aaa gtc aat gag    3504
Gly Pro Tyr Arg Glu Thr Val Asp Ser Val Glu Lys Lys Val Asn Glu
        1155                 1160                 1165 ata aaa gac atc ctg gcc cag agc cca gca gcg gaa cca ctg aaa aac    3552
Ile Lys Asp Ile Leu Ala Gln Ser Pro Ala Ala Glu Pro Leu Lys Asn
    1170                 1175                 1180 att ggc att ctc ttc gag gag gca gag aaa cta acc aaa gat gtc aca    3600
```

-continued

```
Ile Gly Ile Leu Phe Glu Glu Ala Glu Lys Leu Thr Lys Asp Val Thr
1185                1190                1195                1200 gaa aag atg gcg cag gta gaa gtg aaa tta act gat aca gct tca cag     3648
Glu Lys Met Ala Gln Val Glu Val Lys Leu Thr Asp Thr Ala Ser Gln
        1205                1210                1215 agt aac agc aca gct gga gag ctc ggc gca ctg cag gca gaa gca gag     3696
Ser Asn Ser Thr Ala Gly Glu Leu Gly Ala Leu Gln Ala Glu Ala Glu
    1220                1225                1230 agc ctt gac aag acc gtg aag gag ctg gca gaa cag ctg gag ttt atc     3744
Ser Leu Asp Lys Thr Val Lys Glu Leu Ala Glu Gln Leu Glu Phe Ile
1235                1240                1245 aaa aac tcc gat att cag ggc gcc ttg gat agc atc acc aag tat ttc     3792
Lys Asn Ser Asp Ile Gln Gly Ala Leu Asp Ser Ile Thr Lys Tyr Phe
    1250                1255                1260 cag atg tct ctt gag gca gag aag cgg gtg aat gcc tcc acc aca gac     3840
Gln Met Ser Leu Glu Ala Glu Lys Arg Val Asn Ala Ser Thr Thr Asp
1265                1270                1275                1280 ccc aac agc act gtg gag cag tct gcc ctc acg cga gac aga gta gaa     3888
Pro Asn Ser Thr Val Glu Gln Ser Ala Leu Thr Arg Asp Arg Val Glu
        1285                1290                1295 gat ctg atg ttg gag cga gag tct ccg ttc aag gag cag cag gag gaa     3936
Asp Leu Met Leu Glu Arg Glu Ser Pro Phe Lys Glu Gln Gln Glu Glu
    1300                1305                1310 cag gca cgc ctc ctg gac gaa ctg gcc ggc aaa ctg caa agt ctc gac     3984
Gln Ala Arg Leu Leu Asp Glu Leu Ala Gly Lys Leu Gln Ser Leu Asp
1315                1320                1325 ctg tcg gct gct gca cag atg acc tgt gga aca cct cca ggg gct gac     4032
Leu Ser Ala Ala Ala Gln Met Thr Cys Gly Thr Pro Pro Gly Ala Asp
    1330                1335                1340 tgt tct gaa agt gaa tgt ggt ggc ccc aac tgc aga act gac gaa gga     4080
Cys Ser Glu Ser Glu Cys Gly Gly Pro Asn Cys Arg Thr Asp Glu Gly
1345                1350                1355                1360 gag aag aag tgt ggg ggg cct ggc tgt ggt ggt ctg gtc act gtg gcc     4128
Glu Lys Lys Cys Gly Gly Pro Gly Cys Gly Gly Leu Val Thr Val Ala
        1365                1370                1375 cac agt gct tgg cag aaa gcc atg gat ttt gac cgt gat gtc ctg agt     4176
His Ser Ala Trp Gln Lys Ala Met Asp Phe Asp Arg Asp Val Leu Ser
    1380                1385                1390 gcc ctg gct gaa gtc gaa cag ctc tcc aag atg gtc tct gaa gca aaa     4224
Ala Leu Ala Glu Val Glu Gln Leu Ser Lys Met Val Ser Glu Ala Lys
1395                1400                1405 gtg aga gca gat gag gcg aag cag aat gcg cag gat gtc ctg tta aaa     4272
Val Arg Ala Asp Glu Ala Lys Gln Asn Ala Gln Asp Val Leu Leu Lys
        1410                1415                1420 aca aat gct acc aaa gaa aaa gtg gac aag agc aac gag gac ctg cgg     4320
Thr Asn Ala Thr Lys Glu Lys Val Asp Lys Ser Asn Glu Asp Leu Arg
1425                1430                1435                1440 aac ctc atc aag cag atc aga aac ttc ctg act gag gat agt gct gat     4368
Asn Leu Ile Lys Gln Ile Arg Asn Phe Leu Thr Glu Asp Ser Ala Asp
        1445                1450                1455 cta gac agt att gaa gca gtt gct aat gaa gta ctg aaa agt gga aat     4416
Leu Asp Ser Ile Glu Ala Val Ala Asn Glu Val Leu Lys Ser Gly Asn
    1460                1465                1470 gct agc acg cca cag cag tta cag aac cta aca gaa gac att cgg gag     4464
Ala Ser Thr Pro Gln Gln Leu Gln Asn Leu Thr Glu Asp Ile Arg Glu
1475                1480                1485 cga gtt gaa acc ctc tct caa gta gag gtt att ttg cag cag agt gca     4512
Arg Val Glu Thr Leu Ser Gln Val Glu Val Ile Leu Gln Gln Ser Ala
        1490                1495                1500
```

```
gct gac att gcc aga gct gag ctg ttg ctt gag gaa gct aag aga gca      4560
Ala Asp Ile Ala Arg Ala Glu Leu Leu Leu Glu Glu Ala Lys Arg Ala
1505                1510                1515                1520 agc aaa agt gca aca gat gtt aaa gtc act gca gac atg gtg aag gaa      4608
Ser Lys Ser Ala Thr Asp Val Lys Val Thr Ala Asp Met Val Lys Glu
            1525                1530                1535 gca tta gaa gaa gca gaa aag gcc cag gtt gca gca gag aag gcg att      4656
Ala Leu Glu Glu Ala Glu Lys Ala Gln Val Ala Ala Glu Lys Ala Ile
        1540                1545                1550 aaa caa gct gat gag gat atc caa gga acc caa aac ctg cta aca tcg      4704
Lys Gln Ala Asp Glu Asp Ile Gln Gly Thr Gln Asn Leu Leu Thr Ser
    1555                1560                1565 att gaa tct gaa acg gca gct tct gag gaa acc ctg acc aac gcc tcc      4752
Ile Glu Ser Glu Thr Ala Ala Ser Glu Glu Thr Leu Thr Asn Ala Ser
1570                1575                1580 cag cgc atc agc aag ctt gag agg aac gtg gaa gag ctt aag cgt aaa      4800
Gln Arg Ile Ser Lys Leu Glu Arg Asn Val Glu Glu Leu Lys Arg Lys
1585                1590                1595                1600 gct gcc cag aac tct ggg gag gca gaa tat atc gaa aaa gta gta tat      4848
Ala Ala Gln Asn Ser Gly Glu Ala Glu Tyr Ile Glu Lys Val Val Tyr
            1605                1610                1615 tct gta aaa cag aat gca gac gat gtt aaa aag act cta gat ggc gaa      4896
Ser Val Lys Gln Asn Ala Asp Asp Val Lys Lys Thr Leu Asp Gly Glu
        1620                1625                1630 ctt gat gaa aag tat aag aag gta gaa agt tta att gcc caa aaa act      4944
Leu Asp Glu Lys Tyr Lys Lys Val Glu Ser Leu Ile Ala Gln Lys Thr
    1635                1640                1645 gaa gag tca gca gat gcc agg agg aaa gct gag ctg cta caa aat gaa      4992
Glu Glu Ser Ala Asp Ala Arg Arg Lys Ala Glu Leu Leu Gln Asn Glu
1650                1655                1660 gca aaa aca ctc ttg gct caa gct aac agc aag ctc cag ctg ttg gaa      5040
Ala Lys Thr Leu Leu Ala Gln Ala Asn Ser Lys Leu Gln Leu Leu Glu
1665                1670                1675                1680 gac tta gaa aga aaa tat gag gac aat caa aaa tac tta gaa gat aaa      5088
Asp Leu Glu Arg Lys Tyr Glu Asp Asn Gln Lys Tyr Leu Glu Asp Lys
            1685                1690                1695 gct caa gaa ttg gtg cga ctg gaa gga gag gtt cgc tcc ctc ctt aag      5136
Ala Gln Glu Leu Val Arg Leu Glu Gly Glu Val Arg Ser Leu Leu Lys
        1700                1705                1710 gac ata agt gag aaa gtt gcg gtt tac agc acc tgc tta taacaggaag       5185
Asp Ile Ser Glu Lys Val Ala Val Tyr Ser Thr Cys Leu
    1715                1720                1725 gggctgtaga ggggctcggt gaccaaggta aaccacacgc gcaaaccgag gcagtcatct    5245
acaaataacc catcatctat ttaatgtttt taaccaccta cttttgtatg gagttaaata   5305
aaagacattg gttttgtata aaca                                          5329

<210> SEQ ID NO 20
<211> LENGTH: 1725
<212> TYPE: PRT
<213> ORGANISM: Mus musculus

<400> SEQUENCE: 20

Glu Pro Tyr Cys Ile Val Ser His Leu Gln Glu Asp Lys Lys Cys Phe
1               5                   10                  15

Ile Cys Asp Ser Arg Asp Pro Tyr His Glu Thr Leu Asn Pro Asp Ser
            20                  25                  30

His Leu Ile Glu Asn Val Val Thr Thr Phe Ala Pro Asn Arg Leu Lys
        35                  40                  45
```

-continued

```
Ile Trp Trp Gln Ser Glu Asn Gly Val Glu Asn Val Thr Ile Gln Leu
 50                  55                  60

Asp Leu Glu Ala Glu Phe His Phe Thr His Leu Ile Met Thr Phe Lys
 65                  70                  75                  80

Thr Phe Arg Pro Ala Ala Met Leu Ile Glu Arg Ser Ser Asp Phe Gly
                 85                  90                  95

Lys Thr Trp Gly Val Tyr Arg Tyr Phe Ala Tyr Asp Cys Glu Ser Ser
                100                 105                 110

Phe Pro Gly Ile Ser Thr Gly Pro Met Lys Lys Val Asp Asp Ile Ile
             115                 120                 125

Cys Asp Ser Arg Tyr Ser Asp Ile Glu Pro Ser Thr Glu Gly Glu Val
130                 135                 140

Ile Phe Arg Ala Leu Asp Pro Ala Phe Lys Ile Glu Asp Pro Tyr Ser
145                 150                 155                 160

Pro Arg Ile Gln Asn Leu Leu Lys Ile Thr Asn Leu Arg Ile Lys Phe
                165                 170                 175

Val Lys Leu His Thr Leu Gly Asp Asn Leu Leu Asp Ser Arg Met Glu
             180                 185                 190

Ile Arg Glu Lys Tyr Tyr Tyr Ala Val Tyr Asp Met Val Val Arg Gly
         195                 200                 205

Asn Cys Phe Cys Tyr Gly His Ala Ser Glu Cys Ala Pro Val Asp Gly
210                 215                 220

Val Asn Glu Glu Val Glu Gly Met Val His Gly His Cys Met Cys Arg
225                 230                 235                 240

His Asn Thr Lys Gly Leu Asn Cys Glu Leu Cys Met Asp Phe Tyr His
                245                 250                 255

Asp Leu Pro Trp Arg Pro Ala Glu Gly Arg Asn Ser Asn Ala Cys Lys
             260                 265                 270

Lys Cys Asn Cys Asn Glu His Ser Ser Ser Cys His Phe Asp Met Ala
         275                 280                 285

Val Phe Leu Ala Thr Gly Asn Val Ser Gly Gly Val Cys Asp Asn Cys
         290                 295                 300

Gln His Asn Thr Met Gly Arg Asn Cys Glu Gln Cys Lys Pro Phe Tyr
305                 310                 315                 320

Phe Gln His Pro Glu Arg Asp Ile Arg Asp Pro Asn Leu Cys Glu Pro
                325                 330                 335

Cys Thr Cys Asp Pro Ala Gly Ser Glu Asn Gly Gly Ile Cys Asp Gly
             340                 345                 350

Tyr Thr Asp Phe Ser Val Gly Leu Ile Ala Gly Gln Cys Arg Cys Lys
         355                 360                 365

Leu His Val Glu Gly Glu Arg Cys Asp Val Cys Lys Glu Gly Phe Tyr
     370                 375                 380

Asp Leu Ser Ala Glu Asp Pro Tyr Gly Cys Lys Ser Cys Ala Cys Asn
385                 390                 395                 400

Pro Leu Gly Thr Ile Pro Gly Gly Asn Pro Cys Asp Ser Glu Thr Gly
                405                 410                 415

Tyr Cys Tyr Cys Lys Arg Leu Val Thr Gly Gln Arg Cys Asp Gln Cys
             420                 425                 430

Leu Pro Gln His Trp Gly Leu Ser Asn Asp Leu Asp Gly Cys Arg Pro
         435                 440                 445

Cys Asp Cys Asp Leu Gly Gly Ala Leu Asn Asn Ser Cys Ser Glu Asp
450                 455                 460

Ser Gly Gln Cys Ser Cys Leu Pro His Met Ile Gly Arg Gln Cys Asn
```

```
465                 470                 475                 480
Glu Val Glu Ser Gly Tyr Tyr Phe Thr Thr Leu Asp His Tyr Ile Tyr
                485                 490                 495
Glu Ala Glu Ala Asn Leu Gly Pro Gly Val Val Val Glu Arg
            500                 505                 510
Gln Tyr Ile Gln Asp Arg Ile Pro Ser Trp Thr Gly Pro Gly Phe Val
            515                 520                 525
Arg Val Pro Glu Gly Ala Tyr Leu Glu Phe Phe Ile Asp Asn Ile Pro
        530                 535                 540
Tyr Ser Met Glu Tyr Glu Ile Leu Ile Arg Tyr Glu Pro Gln Leu Pro
545                 550                 555                 560
Asp His Trp Glu Lys Ala Val Ile Thr Val Gln Arg Pro Gly Lys Ile
                565                 570                 575
Pro Ala Ser Ser Arg Cys Gly Asn Thr Val Pro Asp Asp Asn Gln
            580                 585                 590
Val Val Ser Leu Ser Pro Gly Ser Arg Tyr Val Val Leu Pro Arg Pro
            595                 600                 605
Val Cys Phe Glu Lys Gly Met Asn Tyr Thr Val Arg Leu Glu Leu Pro
610                 615                 620
Gln Tyr Thr Ala Ser Gly Ser Asp Val Glu Ser Pro Tyr Thr Phe Ile
625                 630                 635                 640
Asp Ser Leu Val Leu Met Pro Tyr Cys Lys Ser Leu Asp Ile Phe Thr
                645                 650                 655
Val Gly Gly Ser Gly Asp Gly Glu Val Thr Asn Ser Ala Trp Glu Thr
                660                 665                 670
Phe Gln Arg Tyr Arg Cys Leu Glu Asn Ser Arg Ser Val Val Lys Thr
            675                 680                 685
Pro Met Thr Asp Val Cys Arg Asn Ile Ile Phe Ser Ile Ser Ala Leu
        690                 695                 700
Ile His Gln Thr Gly Leu Ala Cys Glu Cys Asp Pro Gln Gly Ser Leu
705                 710                 715                 720
Ser Ser Val Cys Asp Pro Asn Gly Gly Gln Cys Gln Cys Arg Pro Asn
                725                 730                 735
Val Val Gly Arg Thr Cys Asn Arg Cys Ala Pro Gly Thr Phe Gly Phe
            740                 745                 750
Gly Pro Asn Gly Cys Lys Pro Cys Asp Cys His Leu Gln Gly Ser Ala
            755                 760                 765
Ser Ala Phe Cys Asp Ala Ile Thr Gly Gln Cys His Cys Phe Gln Gly
        770                 775                 780
Ile Tyr Ala Arg Gln Cys Asp Arg Cys Leu Pro Gly Tyr Trp Gly Phe
785                 790                 795                 800
Pro Ser Cys Gln Pro Cys Gln Cys Asn Gly His Ala Leu Asp Cys Asp
                805                 810                 815
Thr Val Thr Gly Glu Cys Leu Ser Cys Gln Asp Tyr Thr Thr Gly His
                820                 825                 830
Asn Cys Glu Arg Cys Leu Ala Gly Tyr Tyr Gly Asp Pro Ile Ile Gly
            835                 840                 845
Ser Gly Asp His Cys Arg Pro Cys Pro Cys Pro Asp Gly Pro Asp Ser
        850                 855                 860
Gly Arg Gln Phe Ala Arg Ser Cys Tyr Gln Asp Pro Val Thr Leu Gln
865                 870                 875                 880
Leu Ala Cys Val Cys Asp Pro Gly Tyr Ile Gly Ser Arg Cys Asp Asp
                885                 890                 895
```

-continued

```
Cys Ala Ser Gly Phe Phe Gly Asn Pro Ser Asp Phe Gly Gly Ser Cys
            900                 905                 910
Gln Pro Cys Gln Cys His His Asn Ile Asp Thr Thr Asp Pro Glu Ala
        915                 920                 925
Cys Asp Lys Asp Thr Gly Arg Cys Leu Lys Cys Leu Tyr His Thr Glu
    930                 935                 940
Gly Asp His Cys Gln Leu Cys Gln Tyr Gly Tyr Tyr Gly Asp Ala Leu
945                 950                 955                 960
Arg Gln Asp Cys Arg Lys Cys Val Cys Asn Tyr Leu Gly Thr Val Lys
                965                 970                 975
Glu His Cys Asn Gly Ser Asp Cys His Cys Asp Lys Ala Thr Gly Gln
            980                 985                 990
Cys Ser Cys Leu Pro Asn Val Ile Gly Gln Asn Cys Asp Arg Cys Ala
        995                 1000                1005
Pro Asn Thr Trp Gln Leu Ala Ser Gly Thr Gly Cys Gly Pro Cys Asn
    1010                1015                1020
Cys Asn Ala Ala His Ser Phe Gly Pro Ser Cys Asn Glu Phe Thr Gly
1025                1030                1035                1040
Gln Cys Gln Cys Met Pro Gly Phe Gly Gly Arg Thr Cys Ser Glu Cys
                1045                1050                1055
Gln Glu Leu Phe Trp Gly Asp Pro Asp Val Glu Cys Arg Ala Cys Asp
            1060                1065                1070
Cys Asp Pro Arg Gly Ile Glu Thr Pro Gln Cys Asp Gln Ser Thr Gly
        1075                1080                1085
Gln Cys Val Cys Val Glu Gly Val Gly Pro Arg Cys Asp Lys Cys
    1090                1095                1100
Thr Arg Gly Tyr Ser Gly Val Phe Pro Asp Cys Thr Pro Cys His Gln
1105                1110                1115                1120
Cys Phe Ala Leu Trp Asp Ala Ile Ile Gly Glu Leu Thr Asn Arg Thr
                1125                1130                1135
His Lys Phe Leu Glu Lys Ala Lys Ala Leu Lys Ile Ser Gly Val Ile
            1140                1145                1150
Gly Pro Tyr Arg Glu Thr Val Asp Ser Val Glu Lys Lys Val Asn Glu
        1155                1160                1165
Ile Lys Asp Ile Leu Ala Gln Ser Pro Ala Ala Glu Pro Leu Lys Asn
    1170                1175                1180
Ile Gly Ile Leu Phe Glu Glu Ala Glu Lys Leu Thr Lys Asp Val Thr
1185                1190                1195                1200
Glu Lys Met Ala Gln Val Glu Val Lys Leu Thr Asp Thr Ala Ser Gln
            1205                1210                1215
Ser Asn Ser Thr Ala Gly Glu Leu Gly Ala Leu Gln Ala Glu Ala Glu
        1220                1225                1230
Ser Leu Asp Lys Thr Val Lys Glu Leu Ala Glu Gln Leu Glu Phe Ile
    1235                1240                1245
Lys Asn Ser Asp Ile Gln Gly Ala Leu Asp Ser Ile Thr Lys Tyr Phe
    1250                1255                1260
Gln Met Ser Leu Glu Ala Glu Lys Arg Val Asn Ala Ser Thr Thr Asp
1265                1270                1275                1280
Pro Asn Ser Thr Val Glu Gln Ser Ala Leu Thr Arg Asp Arg Val Glu
            1285                1290                1295
Asp Leu Met Leu Glu Arg Glu Ser Pro Phe Lys Glu Gln Gln Glu Glu
        1300                1305                1310
```

```
Gln Ala Arg Leu Leu Asp Glu Leu Ala Gly Lys Leu Gln Ser Leu Asp
         1315                1320                1325
Leu Ser Ala Ala Ala Gln Met Thr Cys Gly Thr Pro Pro Gly Ala Asp
     1330                1335                1340
Cys Ser Glu Ser Glu Cys Gly Gly Pro Asn Cys Arg Thr Asp Glu Gly
1345                1350                1355                1360
Glu Lys Lys Cys Gly Gly Pro Gly Cys Gly Gly Leu Val Thr Val Ala
             1365                1370                1375
His Ser Ala Trp Gln Lys Ala Met Asp Phe Asp Arg Asp Val Leu Ser
         1380                1385                1390
Ala Leu Ala Glu Val Glu Gln Leu Ser Lys Met Val Ser Glu Ala Lys
     1395                1400                1405
Val Arg Ala Asp Glu Ala Lys Gln Asn Ala Gln Asp Val Leu Leu Lys
 1410                1415                1420
Thr Asn Ala Thr Lys Glu Lys Val Asp Lys Ser Asn Glu Asp Leu Arg
1425                1430                1435                1440
Asn Leu Ile Lys Gln Ile Arg Asn Phe Leu Thr Glu Asp Ser Ala Asp
             1445                1450                1455
Leu Asp Ser Ile Glu Ala Val Ala Asn Glu Val Leu Lys Ser Gly Asn
         1460                1465                1470
Ala Ser Thr Pro Gln Gln Leu Gln Asn Leu Thr Glu Asp Ile Arg Glu
     1475                1480                1485
Arg Val Glu Thr Leu Ser Gln Val Glu Val Ile Leu Gln Gln Ser Ala
 1490                1495                1500
Ala Asp Ile Ala Arg Ala Glu Leu Leu Leu Glu Glu Ala Lys Arg Ala
1505                1510                1515                1520
Ser Lys Ser Ala Thr Asp Val Lys Val Thr Ala Asp Met Val Lys Glu
             1525                1530                1535
Ala Leu Glu Glu Ala Glu Lys Ala Gln Val Ala Ala Glu Lys Ala Ile
         1540                1545                1550
Lys Gln Ala Asp Glu Asp Ile Gln Gly Thr Gln Asn Leu Leu Thr Ser
     1555                1560                1565
Ile Glu Ser Glu Thr Ala Ala Ser Glu Glu Thr Leu Thr Asn Ala Ser
 1570                1575                1580
Gln Arg Ile Ser Lys Leu Glu Arg Asn Val Glu Glu Leu Lys Arg Lys
1585                1590                1595                1600
Ala Ala Gln Asn Ser Gly Glu Ala Glu Tyr Ile Glu Lys Val Val Tyr
             1605                1610                1615
Ser Val Lys Gln Asn Ala Asp Asp Val Lys Lys Thr Leu Asp Gly Glu
         1620                1625                1630
Leu Asp Glu Lys Tyr Lys Lys Val Glu Ser Leu Ile Ala Gln Lys Thr
     1635                1640                1645
Glu Glu Ser Ala Asp Ala Arg Arg Lys Ala Glu Leu Leu Gln Asn Glu
 1650                1655                1660
Ala Lys Thr Leu Leu Ala Gln Ala Asn Ser Lys Leu Gln Leu Leu Glu
1665                1670                1675                1680
Asp Leu Glu Arg Lys Tyr Glu Asp Asn Gln Lys Tyr Leu Glu Asp Lys
             1685                1690                1695
Ala Gln Glu Leu Val Arg Leu Glu Gly Glu Val Arg Ser Leu Leu Lys
         1700                1705                1710
Asp Ile Ser Glu Lys Val Ala Val Tyr Ser Thr Cys Leu
     1715                1720                1725
```

```
<210> SEQ ID NO 21
<211> LENGTH: 5306
<212> TYPE: DNA
<213> ORGANISM: Homo sapiens
<220> FEATURE:
<221> NAME/KEY: CDS
<222> LOCATION: (260)..(5086)
<221> NAME/KEY: sig_peptide
<222> LOCATION: (260)..(358)

<400> SEQUENCE: 21
cggggcaggc tgctcccggg gtaggtgagg gaagcgcgga ggcggcgcgc gggggcagtg      60
gtcggcgagc agcgcggtcc tcgctagggg cgcccacccg tcagtctctc cggcgcgagc     120
cgccgccacc gcccgcgccg gagtcaggcc cctgggcccc caggctcaag cagcgaagcg     180
gcctccgggg gacgccgcta ggcgagagga acgcgccggt gcccttgcct tcgccgtgac     240
ccagcgtgcg ggcggcggg atg aga ggg agc cat cgg gcc gcg ccg gcc ctg      292
                    Met Arg Gly Ser His Arg Ala Ala Pro Ala Leu
                      1               5                  10 cgg ccc cgg ggg cgg ctc tgg ccc gtg ctg gcc gtg ctg gcg gcg gcc       340
Arg Pro Arg Gly Arg Leu Trp Pro Val Leu Ala Val Leu Ala Ala Ala
             15                  20                  25 gcc gcg gcg ggc tgt gcc cag gca gcc atg gac gag tgc acg gac gag       388
Ala Ala Ala Gly Cys Ala Gln Ala Ala Met Asp Glu Cys Thr Asp Glu
         30                  35                  40 ggc ggg cgg ccg cag cgc tgc atg ccc gag ttc gtc aac gcc gct ttc       436
Gly Gly Arg Pro Gln Arg Cys Met Pro Glu Phe Val Asn Ala Ala Phe
     45                  50                  55 aac gtg act gtg gtg gcc acc aac acg tgt ggg act ccg ccc gag gaa       484
Asn Val Thr Val Val Ala Thr Asn Thr Cys Gly Thr Pro Pro Glu Glu
 60                  65                  70                  75 tac tgt gtg cag acc ggg gtg acc ggg gtc acc aag tcc tgt cac ctg       532
Tyr Cys Val Gln Thr Gly Val Thr Gly Val Thr Lys Ser Cys His Leu
                 80                  85                  90 tgc gac gcc ggg cag ccc cac ctg cag cac ggg gca gcc ttc ctg acc       580
Cys Asp Ala Gly Gln Pro His Leu Gln His Gly Ala Ala Phe Leu Thr
             95                 100                 105 gac tac aac aac cag gcc gac acc acc tgg tgg caa agc cag acc atg       628
Asp Tyr Asn Asn Gln Ala Asp Thr Thr Trp Trp Gln Ser Gln Thr Met
        110                 115                 120 ctg gcc ggg gtg cag tac ccc agc tcc atc aac ctc acg ctg cac ctg       676
Leu Ala Gly Val Gln Tyr Pro Ser Ser Ile Asn Leu Thr Leu His Leu
    125                 130                 135 gga aaa gct ttt gac atc acc tat gtg cgt ctc aag ttc cac acc agc       724
Gly Lys Ala Phe Asp Ile Thr Tyr Val Arg Leu Lys Phe His Thr Ser
140                 145                 150                 155 cgc ccg gag agc ttt gcc att tac aag cgc aca cgg gaa gac ggg ccc       772
Arg Pro Glu Ser Phe Ala Ile Tyr Lys Arg Thr Arg Glu Asp Gly Pro
                160                 165                 170 tgg att cct tac cag tac tac agt ggt tcc tgc gag aac acc tac tcc       820
Trp Ile Pro Tyr Gln Tyr Tyr Ser Gly Ser Cys Glu Asn Thr Tyr Ser
            175                 180                 185 aag gca aac cgc ggc ttc atc agg aca gga ggg gac gag cag cag gcc       868
Lys Ala Asn Arg Gly Phe Ile Arg Thr Gly Gly Asp Glu Gln Gln Ala
        190                 195                 200 ttg tgt act gat gaa ttc agt gac att tct ccc ctc act ggg ggc aac       916
Leu Cys Thr Asp Glu Phe Ser Asp Ile Ser Pro Leu Thr Gly Gly Asn
    205                 210                 215 gtg gcc ttt tct acc ctg gaa gga agg ccc agc gcc tat aac ttt gac       964
Val Ala Phe Ser Thr Leu Glu Gly Arg Pro Ser Ala Tyr Asn Phe Asp
220                 225                 230                 235
```

```
aat agc cct gtg ctg cag gaa tgg gta act gcc act gac atc aga gta      1012
Asn Ser Pro Val Leu Gln Glu Trp Val Thr Ala Thr Asp Ile Arg Val
            240                 245                 250 act ctt aat cgc ctg aac act ttt gga gat gaa gtg ttt aac gat ccc      1060
Thr Leu Asn Arg Leu Asn Thr Phe Gly Asp Glu Val Phe Asn Asp Pro
            255                 260                 265 aaa gtt ctc aag tcc tat tat tat gcc atc tct gat ttt gct gta ggt      1108
Lys Val Leu Lys Ser Tyr Tyr Tyr Ala Ile Ser Asp Phe Ala Val Gly
            270                 275                 280 ggc aga tgt aaa tgt aat gga cac gca agc gag tgt atg aag aac gaa      1156
Gly Arg Cys Lys Cys Asn Gly His Ala Ser Glu Cys Met Lys Asn Glu
285                 290                 295 ttt gat aag ctg gtg tgt aat tgc aaa cat aac aca tat gga gta gac      1204
Phe Asp Lys Leu Val Cys Asn Cys Lys His Asn Thr Tyr Gly Val Asp
300                 305                 310                 315 tgt gaa aag tgt ctt cct ttc ttc aat gac cgg ccg tgg agg agg gca      1252
Cys Glu Lys Cys Leu Pro Phe Phe Asn Asp Arg Pro Trp Arg Arg Ala
            320                 325                 330 act gcg gaa agt gcc agt gaa tgc ctg ccc tgt gat tgc aat ggt cga      1300
Thr Ala Glu Ser Ala Ser Glu Cys Leu Pro Cys Asp Cys Asn Gly Arg
            335                 340                 345 tcc cag gaa tgc tac ttc gac cct gaa ctc tat cgt tcc act ggc cat      1348
Ser Gln Glu Cys Tyr Phe Asp Pro Glu Leu Tyr Arg Ser Thr Gly His
            350                 355                 360 ggg ggc cac tgt acc aac tgc cag gat aac aca gat ggc gcc cac tgt      1396
Gly Gly His Cys Thr Asn Cys Gln Asp Asn Thr Asp Gly Ala His Cys
            365                 370                 375 gag agg tgc cga gag aac ttc ttc cgc ctt ggc aac aat gaa gcc tgc      1444
Glu Arg Cys Arg Glu Asn Phe Phe Arg Leu Gly Asn Asn Glu Ala Cys
380                 385                 390                 395 tct tca tgc cac tgt agt cct gtg ggc tct cta agc aca cag tgt gat      1492
Ser Ser Cys His Cys Ser Pro Val Gly Ser Leu Ser Thr Gln Cys Asp
            400                 405                 410 agt tac ggc aga tgc agc tgt aag cca gga gtg atg ggg gac aaa tgt      1540
Ser Tyr Gly Arg Cys Ser Cys Lys Pro Gly Val Met Gly Asp Lys Cys
            415                 420                 425 gac cgt tgc cag cct gga ttc cat tct ctc act gaa gca gga tgc agg      1588
Asp Arg Cys Gln Pro Gly Phe His Ser Leu Thr Glu Ala Gly Cys Arg
            430                 435                 440 cca tgc tct tgt gat ccc tct ggc agc ata gat gaa tgt aat gtt gaa      1636
Pro Cys Ser Cys Asp Pro Ser Gly Ser Ile Asp Glu Cys Asn Val Glu
445                 450                 455 aca gga aga tgt gtt tgc aaa gac aat gtc gaa ggc ttc aat tgt gaa      1684
Thr Gly Arg Cys Val Cys Lys Asp Asn Val Glu Gly Phe Asn Cys Glu
460                 465                 470                 475 aga tgc aaa cct gga ttt ttt aat ctg gaa tca tct aat cct cgg ggt      1732
Arg Cys Lys Pro Gly Phe Phe Asn Leu Glu Ser Ser Asn Pro Arg Gly
            480                 485                 490 tgc aca ccc tgc ttc tgc ttt ggg cat tct tct gtc tgt aca aac gct      1780
Cys Thr Pro Cys Phe Cys Phe Gly His Ser Ser Val Cys Thr Asn Ala
            495                 500                 505 gtt ggc tac agt gtt tat tct atc tcc tct acc ttt cag att gat gag      1828
Val Gly Tyr Ser Val Tyr Ser Ile Ser Ser Thr Phe Gln Ile Asp Glu
            510                 515                 520 gat ggg tgg cgt gcg gaa cag aga gat ggc tct gaa gca tct ctc gag      1876
Asp Gly Trp Arg Ala Glu Gln Arg Asp Gly Ser Glu Ala Ser Leu Glu
            525                 530                 535 tgg tcc tct gag agg caa gat atc gcc gtg atc tca gac agc tac ttt      1924
Trp Ser Ser Glu Arg Gln Asp Ile Ala Val Ile Ser Asp Ser Tyr Phe
```

```
540                 545                 550                 555 cct cgg tac ttc att gct cct gca aag ttc ttg ggc aag cag gtg ttg    1972
Pro Arg Tyr Phe Ile Ala Pro Ala Lys Phe Leu Gly Lys Gln Val Leu
                560                 565                 570 agt tat ggt cag aac ctc tcc ttc tcc ttt cga gtg gac agg cga gat    2020
Ser Tyr Gly Gln Asn Leu Ser Phe Ser Phe Arg Val Asp Arg Arg Asp
            575                 580                 585 act cgc ctc tct gcc gaa gac ctt gtg ctt gag gga gct ggc tta aga    2068
Thr Arg Leu Ser Ala Glu Asp Leu Val Leu Glu Gly Ala Gly Leu Arg
        590                 595                 600 gta tct gta ccc ttg atc gct cag ggc aat tcc tat cca agt gag acc    2116
Val Ser Val Pro Leu Ile Ala Gln Gly Asn Ser Tyr Pro Ser Glu Thr
    605                 610                 615 act gtg aag tat gtc ttc agg ctc cat gaa gca aca gat tac cct tgg    2164
Thr Val Lys Tyr Val Phe Arg Leu His Glu Ala Thr Asp Tyr Pro Trp
620                 625                 630                 635 agg cct gct ctt acc cct ttt gaa ttt cag aag ctc cta aac aac ttg    2212
Arg Pro Ala Leu Thr Pro Phe Glu Phe Gln Lys Leu Leu Asn Asn Leu
                640                 645                 650 acc tct atc aag ata cgt ggg aca tac agt gag aga agt gct gga tat    2260
Thr Ser Ile Lys Ile Arg Gly Thr Tyr Ser Glu Arg Ser Ala Gly Tyr
            655                 660                 665 ttg gat gat gtc acc ctg gca agt gct cgt cct ggg cct gga gtc cct    2308
Leu Asp Asp Val Thr Leu Ala Ser Ala Arg Pro Gly Pro Gly Val Pro
        670                 675                 680 gca act tgg gtg gag tcc tgc acc tgt cct gtg gga tat gga ggg cag    2356
Ala Thr Trp Val Glu Ser Cys Thr Cys Pro Val Gly Tyr Gly Gly Gln
    685                 690                 695 ttt tgt gag atg tgc ctc tca ggt tac aga aga gaa act cct aat ctt    2404
Phe Cys Glu Met Cys Leu Ser Gly Tyr Arg Arg Glu Thr Pro Asn Leu
700                 705                 710                 715 gga cca tac agt cca tgt gtg ctt tgc gcc tgc aat gga cac agc gag    2452
Gly Pro Tyr Ser Pro Cys Val Leu Cys Ala Cys Asn Gly His Ser Glu
                720                 725                 730 acc tgt gat cct gag aca ggt gtt tgt aac tgc aga gac aat acg gct    2500
Thr Cys Asp Pro Glu Thr Gly Val Cys Asn Cys Arg Asp Asn Thr Ala
            735                 740                 745 ggc ccg cac tgt gag aag tgc agt gat ggg tac tat gga gat tca act    2548
Gly Pro His Cys Glu Lys Cys Ser Asp Gly Tyr Tyr Gly Asp Ser Thr
        750                 755                 760 gca ggc acc tcc tcc gat tgc caa ccc tgt ccg tgt cct gga ggt tca    2596
Ala Gly Thr Ser Ser Asp Cys Gln Pro Cys Pro Cys Pro Gly Gly Ser
    765                 770                 775 agt tgt gct gtt gtt ccc aag aca aag gag gtg gtg tgc acc aac tgt    2644
Ser Cys Ala Val Val Pro Lys Thr Lys Glu Val Val Cys Thr Asn Cys
780                 785                 790                 795 cct act ggc acc act ggt aag aga tgt gag ctc tgt gat gat ggc tac    2692
Pro Thr Gly Thr Thr Gly Lys Arg Cys Glu Leu Cys Asp Asp Gly Tyr
                800                 805                 810 ttt gga gac ccc ctg ggt aga aac ggc cct gtg aga ctt tgc cgc ctg    2740
Phe Gly Asp Pro Leu Gly Arg Asn Gly Pro Val Arg Leu Cys Arg Leu
            815                 820                 825 tgc cag tgc agt gac aac atc gat ccc aac gca gtt gga aat tgc aat    2788
Cys Gln Cys Ser Asp Asn Ile Asp Pro Asn Ala Val Gly Asn Cys Asn
        830                 835                 840 cgc ttg acg gga gaa tgc ctg aag tgc atc tat aac act gct ggc ttc    2836
Arg Leu Thr Gly Glu Cys Leu Lys Cys Ile Tyr Asn Thr Ala Gly Phe
    845                 850                 855 tat tgt gac cgg tgc aaa gac gga ttt ttt gga aat ccc ctg gct ccc    2884
```

```
                                                              -continued

Tyr Cys Asp Arg Cys Lys Asp Gly Phe Phe Gly Asn Pro Leu Ala Pro
860                 865                 870                 875 aat cca gca gac aaa tgc aaa gcc tgc aat tgc aat ccg tat ggg acc   2932
Asn Pro Ala Asp Lys Cys Lys Ala Cys Asn Cys Asn Pro Tyr Gly Thr
                    880                 885                 890 atg aag cag cag agc agc tgt aac ccc gtg acg ggg cag tgt gaa tgt   2980
Met Lys Gln Gln Ser Ser Cys Asn Pro Val Thr Gly Gln Cys Glu Cys
            895                 900                 905 ttg cct cac gtg act ggc cag gac tgt ggt gct tgt gac cct gga ttc   3028
Leu Pro His Val Thr Gly Gln Asp Cys Gly Ala Cys Asp Pro Gly Phe
        910                 915                 920 tac aat ctg cag agt ggg caa ggc tgt gag agg tgt gac tgc cat gcc   3076
Tyr Asn Leu Gln Ser Gly Gln Gly Cys Glu Arg Cys Asp Cys His Ala
    925                 930                 935 ttg ggc tcc acc aat ggg cag tgt gac atc cgc acc ggc cag tgt gag   3124
Leu Gly Ser Thr Asn Gly Gln Cys Asp Ile Arg Thr Gly Gln Cys Glu
940                 945                 950                 955 tgc cag ccc ggc atc act ggt cag cac tgt gag cgc tgt gag gtc aac   3172
Cys Gln Pro Gly Ile Thr Gly Gln His Cys Glu Arg Cys Glu Val Asn
                960                 965                 970 cac ttt ggg ttt gga cct gaa ggc tgc aaa ccc tgt gac tgt cat cct   3220
His Phe Gly Phe Gly Pro Glu Gly Cys Lys Pro Cys Asp Cys His Pro
            975                 980                 985 gag gga tct ctt tca ctt cag tgc aaa gat gat ggt cgc tgt gaa tgc   3268
Glu Gly Ser Leu Ser Leu Gln Cys Lys Asp Asp Gly Arg Cys Glu Cys
        990                 995                 1000 aga gaa ggc ttt gtg gga aat cgc tgt gac cag tgt gaa gaa aac tat   3316
Arg Glu Gly Phe Val Gly Asn Arg Cys Asp Gln Cys Glu Glu Asn Tyr
    1005                1010                1015 ttc tac aat cgg tct tgg cct ggc tgc cag gaa tgt cca gct tgt tac   3364
Phe Tyr Asn Arg Ser Trp Pro Gly Cys Gln Glu Cys Pro Ala Cys Tyr
1020                1025                1030                1035 cgg ctg gta aag gat aag gtt gct gat cat aga gtg aag ctc cag gaa   3412
Arg Leu Val Lys Asp Lys Val Ala Asp His Arg Val Lys Leu Gln Glu
                1040                1045                1050 tta gag agt ctc ata gca aac ctt gga act ggg gat gag atg gtg aca   3460
Leu Glu Ser Leu Ile Ala Asn Leu Gly Thr Gly Asp Glu Met Val Thr
            1055                1060                1065 gat caa gcc ttc gag gat aga cta aag gaa gca gag agg gaa gtt atg   3508
Asp Gln Ala Phe Glu Asp Arg Leu Lys Glu Ala Glu Arg Glu Val Met
        1070                1075                1080 gac ctc ctt cgt gag gcc cag gat gtc aaa gat gtt gac cag aat ttg   3556
Asp Leu Leu Arg Glu Ala Gln Asp Val Lys Asp Val Asp Gln Asn Leu
    1085                1090                1095 atg gat cgc cta cag aga gtg aat aac act ctg tcc agc caa att agc   3604
Met Asp Arg Leu Gln Arg Val Asn Asn Thr Leu Ser Ser Gln Ile Ser
1100                1105                1110                1115 cgt tta cag aat atc cgg aat acc att gaa gag act gga aac ttg gct   3652
Arg Leu Gln Asn Ile Arg Asn Thr Ile Glu Glu Thr Gly Asn Leu Ala
                1120                1125                1130 gaa caa gcg cgt gcc cat gta gag aac aca gag cgg ttg att gaa atc   3700
Glu Gln Ala Arg Ala His Val Glu Asn Thr Glu Arg Leu Ile Glu Ile
            1135                1140                1145 gca tcc aga gaa ctt gag aaa gca aaa gtc gct gct gcc aat gtg tca   3748
Ala Ser Arg Glu Leu Glu Lys Ala Lys Val Ala Ala Ala Asn Val Ser
        1150                1155                1160 gtc act cag cca gaa tct aca ggg gac cca aac aac atg act ctt ttg   3796
Val Thr Gln Pro Glu Ser Thr Gly Asp Pro Asn Asn Met Thr Leu Leu
    1165                1170                1175
```

-continued

| | |
|---|---|
| gca gaa gag gct cga aag ctt gct gaa cgt cat aaa cag gaa gct gat<br>Ala Glu Glu Ala Arg Lys Leu Ala Glu Arg His Lys Gln Glu Ala Asp<br>1180                      1185                      1190                      1195 | 3844 |
| gac att gtt cga gtg gca aag aca gcc aat gat acg tca act gag gca<br>Asp Ile Val Arg Val Ala Lys Thr Ala Asn Asp Thr Ser Thr Glu Ala<br>            1200                      1205                      1210 | 3892 |
| tac aac ctg ctt ctg agg aca ctg gca gga gaa aat caa aca gca ttt<br>Tyr Asn Leu Leu Leu Arg Thr Leu Ala Gly Glu Asn Gln Thr Ala Phe<br>                1215                      1220                      1225 | 3940 |
| gag att gaa gag ctt aat agg aag tat gaa caa gcg aag aac atc tca<br>Glu Ile Glu Glu Leu Asn Arg Lys Tyr Glu Gln Ala Lys Asn Ile Ser<br>                      1230                      1235                      1240 | 3988 |
| cag gat ctg gaa aaa caa gct gcc cga gta cat gag gag gcc aaa agg<br>Gln Asp Leu Glu Lys Gln Ala Ala Arg Val His Glu Glu Ala Lys Arg<br>        1245                      1250                      1255 | 4036 |
| gcc ggt gac aaa gct gtg gag atc tat gcc agc gtg gct cag ctg agc<br>Ala Gly Asp Lys Ala Val Glu Ile Tyr Ala Ser Val Ala Gln Leu Ser<br>1260                      1265                      1270                      1275 | 4084 |
| cct ttg gac tct gag aca ctg gag aat gaa gca aat aac ata aag atg<br>Pro Leu Asp Ser Glu Thr Leu Glu Asn Glu Ala Asn Asn Ile Lys Met<br>            1280                      1285                      1290 | 4132 |
| gaa gct gag aat ctg gaa caa ctg att gac cag aaa tta aaa gat tat<br>Glu Ala Glu Asn Leu Glu Gln Leu Ile Asp Gln Lys Leu Lys Asp Tyr<br>                1295                      1300                      1305 | 4180 |
| gag gac ctc aga gaa gat atg aga ggg aag gaa ctt gaa gtc aag aac<br>Glu Asp Leu Arg Glu Asp Met Arg Gly Lys Glu Leu Glu Val Lys Asn<br>                      1310                      1315                      1320 | 4228 |
| ctt ctg gag aaa ggc aag act gaa cag cag acc gca gac caa ctc cta<br>Leu Leu Glu Lys Gly Lys Thr Glu Gln Gln Thr Ala Asp Gln Leu Leu<br>        1325                      1330                      1335 | 4276 |
| gcc cga gct gat gct gcc aag gcc ctc gct gaa gaa gct gca aag aag<br>Ala Arg Ala Asp Ala Ala Lys Ala Leu Ala Glu Glu Ala Ala Lys Lys<br>1340                      1345                      1350                      1355 | 4324 |
| gga cgg gat acc tta caa gaa gct aat gac att ctc aac aac ctg aaa<br>Gly Arg Asp Thr Leu Gln Glu Ala Asn Asp Ile Leu Asn Asn Leu Lys<br>            1360                      1365                      1370 | 4372 |
| gat ttt gat agg cgc gtg aac gat aac aag acg gcc gca gag gag gca<br>Asp Phe Asp Arg Arg Val Asn Asp Asn Lys Thr Ala Ala Glu Glu Ala<br>                1375                      1380                      1385 | 4420 |
| cta agg aag att cct gcc atc aac cag acc atc act gaa gcc aat gaa<br>Leu Arg Lys Ile Pro Ala Ile Asn Gln Thr Ile Thr Glu Ala Asn Glu<br>                      1390                      1395                      1400 | 4468 |
| aag acc aga gaa gcc cag cag gcc ctg ggc agt gct gcg gcg gat gcc<br>Lys Thr Arg Glu Ala Gln Gln Ala Leu Gly Ser Ala Ala Ala Asp Ala<br>        1405                      1410                      1415 | 4516 |
| aca gag gcc aag aac aag gcc cat gag gcg gag agg atc gca agc gct<br>Thr Glu Ala Lys Asn Lys Ala His Glu Ala Glu Arg Ile Ala Ser Ala<br>1420                      1425                      1430                      1435 | 4564 |
| gtc caa aag aat gcc acc agc acc aag gca gaa gct gaa aga act ttt<br>Val Gln Lys Asn Ala Thr Ser Thr Lys Ala Glu Ala Glu Arg Thr Phe<br>            1440                      1445                      1450 | 4612 |
| gca gaa gtt aca gat ctg gat aat gag gtg aac aat atg ttg aag caa<br>Ala Glu Val Thr Asp Leu Asp Asn Glu Val Asn Asn Met Leu Lys Gln<br>                1455                      1460                      1465 | 4660 |
| ctg cag gaa gca gaa aaa gag cta aag aga aaa caa gat gac gct gac<br>Leu Gln Glu Ala Glu Lys Glu Leu Lys Arg Lys Gln Asp Asp Ala Asp<br>                      1470                      1475                      1480 | 4708 |
| cag gac atg atg atg gca ggg atg gct tca cag gct gct caa gaa gcc<br>Gln Asp Met Met Met Ala Gly Met Ala Ser Gln Ala Ala Gln Glu Ala<br>        1485                      1490                      1495 | 4756 |

-continued

```
gag atc aat gcc aga aaa gcc aaa aac tct gtt act agc ctc ctc agc      4804
Glu Ile Asn Ala Arg Lys Ala Lys Asn Ser Val Thr Ser Leu Leu Ser
1500                1505                1510                1515 att att aat gac ctc ttg gag cag ctg ggg cag ctg gat aca gtg gac      4852
Ile Ile Asn Asp Leu Leu Glu Gln Leu Gly Gln Leu Asp Thr Val Asp
            1520                1525                1530 ctg aat aag cta aac gag att gaa ggc acc cta aac aaa gcc aaa gat      4900
Leu Asn Lys Leu Asn Glu Ile Glu Gly Thr Leu Asn Lys Ala Lys Asp
        1535                1540                1545 gaa atg aag gtc agc gat ctt gat agg aaa gtg tct gac ctg gag aat      4948
Glu Met Lys Val Ser Asp Leu Asp Arg Lys Val Ser Asp Leu Glu Asn
    1550                1555                1560 gaa gcc aag aag cag gag gct gcc atc atg gac tat aac cga gat atc      4996
Glu Ala Lys Lys Gln Glu Ala Ala Ile Met Asp Tyr Asn Arg Asp Ile
1565                1570                1575 gag gag atc atg aag gac att cgc aat ctg gag gac atc agg aag acc      5044
Glu Glu Ile Met Lys Asp Ile Arg Asn Leu Glu Asp Ile Arg Lys Thr
1580                1585                1590                1595 tta cca tct ggc tgc ttc aac acc ccg tcc att gaa aag ccc              5086
Leu Pro Ser Gly Cys Phe Asn Thr Pro Ser Ile Glu Lys Pro
                1600                1605 tagtgtctt agggctggaa ggcagcatcc ctctgacagg ggggcagttg tgaggccaca     5146
gagtgccttg acacaaagat tacattttc agaccccac tcctctgctg ctgtccatca      5206 ctgtccttt gaaccaggaa aagtcacaga gtttaaagag aagcaaatta aacatcctga    5266
atcgggaaca aagggtttta tctaataaag tgtctcttcc                          5306

<210> SEQ ID NO 22
<211> LENGTH: 1609
<212> TYPE: PRT
<213> ORGANISM: Homo sapiens

<400> SEQUENCE: 22

Met Arg Gly Ser His Arg Ala Ala Pro Ala Leu Arg Pro Arg Gly Arg
1               5                   10                  15

Leu Trp Pro Val Leu Ala Val Leu Ala Ala Ala Ala Ala Gly Cys
            20                  25                  30

Ala Gln Ala Ala Met Asp Glu Cys Thr Asp Glu Gly Gly Arg Pro Gln
        35                  40                  45

Arg Cys Met Pro Glu Phe Val Asn Ala Ala Phe Asn Val Thr Val Val
    50                  55                  60

Ala Thr Asn Thr Cys Gly Thr Pro Pro Glu Glu Tyr Cys Val Gln Thr
65                  70                  75                  80

Gly Val Thr Gly Val Thr Lys Ser Cys His Leu Cys Asp Ala Gly Gln
                85                  90                  95

Pro His Leu Gln His Gly Ala Ala Phe Leu Thr Asp Tyr Asn Asn Gln
            100                 105                 110

Ala Asp Thr Thr Trp Trp Gln Ser Gln Thr Met Leu Ala Gly Val Gln
        115                 120                 125

Tyr Pro Ser Ser Ile Asn Leu Thr Leu His Leu Gly Lys Ala Phe Asp
    130                 135                 140

Ile Thr Tyr Val Arg Leu Lys Phe His Thr Ser Arg Pro Glu Ser Phe
145                 150                 155                 160

Ala Ile Tyr Lys Arg Thr Arg Glu Asp Gly Pro Trp Ile Pro Tyr Gln
                165                 170                 175

Tyr Tyr Ser Gly Ser Cys Glu Asn Thr Tyr Ser Lys Ala Asn Arg Gly
```

-continued

```
                180                 185                 190
Phe Ile Arg Thr Gly Gly Asp Glu Gln Gln Ala Leu Cys Thr Asp Glu
            195                 200                 205
Phe Ser Asp Ile Ser Pro Leu Thr Gly Gly Asn Val Ala Phe Ser Thr
210                 215                 220
Leu Glu Gly Arg Pro Ser Ala Tyr Asn Phe Asp Asn Ser Pro Val Leu
225                 230                 235                 240
Gln Glu Trp Val Thr Ala Thr Asp Ile Arg Val Thr Leu Asn Arg Leu
                245                 250                 255
Asn Thr Phe Gly Asp Glu Val Phe Asn Asp Pro Lys Val Leu Lys Ser
            260                 265                 270
Tyr Tyr Tyr Ala Ile Ser Asp Phe Ala Val Gly Gly Arg Cys Lys Cys
        275                 280                 285
Asn Gly His Ala Ser Glu Cys Met Lys Asn Glu Phe Asp Lys Leu Val
    290                 295                 300
Cys Asn Cys Lys His Asn Thr Tyr Gly Val Asp Cys Glu Lys Cys Leu
305                 310                 315                 320
Pro Phe Phe Asn Asp Arg Pro Trp Arg Arg Ala Thr Ala Glu Ser Ala
                325                 330                 335
Ser Glu Cys Leu Pro Cys Asp Cys Asn Gly Arg Ser Gln Glu Cys Tyr
            340                 345                 350
Phe Asp Pro Glu Leu Tyr Arg Ser Thr Gly His Gly Gly His Cys Thr
        355                 360                 365
Asn Cys Gln Asp Asn Thr Asp Gly Ala His Cys Glu Arg Cys Arg Glu
    370                 375                 380
Asn Phe Phe Arg Leu Gly Asn Asn Glu Ala Cys Ser Ser Cys His Cys
385                 390                 395                 400
Ser Pro Val Gly Ser Leu Ser Thr Gln Cys Asp Ser Tyr Gly Arg Cys
                405                 410                 415
Ser Cys Lys Pro Gly Val Met Gly Asp Lys Cys Asp Arg Cys Gln Pro
            420                 425                 430
Gly Phe His Ser Leu Thr Glu Ala Gly Cys Arg Pro Cys Ser Cys Asp
        435                 440                 445
Pro Ser Gly Ser Ile Asp Glu Cys Asn Val Glu Thr Gly Arg Cys Val
    450                 455                 460
Cys Lys Asp Asn Val Glu Gly Phe Asn Cys Glu Arg Cys Lys Pro Gly
465                 470                 475                 480
Phe Phe Asn Leu Glu Ser Ser Asn Pro Arg Gly Cys Thr Pro Cys Phe
                485                 490                 495
Cys Phe Gly His Ser Ser Val Cys Thr Asn Ala Val Gly Tyr Ser Val
            500                 505                 510
Tyr Ser Ile Ser Ser Thr Phe Gln Ile Asp Glu Asp Gly Trp Arg Ala
        515                 520                 525
Glu Gln Arg Asp Gly Ser Glu Ala Ser Leu Glu Trp Ser Ser Glu Arg
    530                 535                 540
Gln Asp Ile Ala Val Ile Ser Asp Ser Tyr Phe Pro Arg Tyr Phe Ile
545                 550                 555                 560
Ala Pro Ala Lys Phe Leu Gly Lys Gln Val Leu Ser Tyr Gly Gln Asn
                565                 570                 575
Leu Ser Phe Ser Phe Arg Val Asp Arg Arg Asp Thr Arg Leu Ser Ala
            580                 585                 590
Glu Asp Leu Val Leu Glu Gly Ala Gly Leu Arg Val Ser Val Pro Leu
        595                 600                 605
```

-continued

```
Ile Ala Gln Gly Asn Ser Tyr Pro Ser Glu Thr Thr Val Lys Tyr Val
        610                 615                 620
Phe Arg Leu His Glu Ala Thr Asp Tyr Pro Trp Arg Pro Ala Leu Thr
625                 630                 635                 640
Pro Phe Glu Phe Gln Lys Leu Leu Asn Asn Leu Thr Ser Ile Lys Ile
                645                 650                 655
Arg Gly Thr Tyr Ser Glu Arg Ser Ala Gly Tyr Leu Asp Asp Val Thr
                660                 665                 670
Leu Ala Ser Ala Arg Pro Gly Pro Gly Val Pro Ala Thr Trp Val Glu
                675                 680                 685
Ser Cys Thr Cys Pro Val Gly Tyr Gly Gly Gln Phe Cys Glu Met Cys
        690                 695                 700
Leu Ser Gly Tyr Arg Arg Glu Thr Pro Asn Leu Gly Pro Tyr Ser Pro
705                 710                 715                 720
Cys Val Leu Cys Ala Cys Asn Gly His Ser Glu Thr Cys Asp Pro Glu
                725                 730                 735
Thr Gly Val Cys Asn Cys Arg Asp Asn Thr Ala Gly Pro His Cys Glu
                740                 745                 750
Lys Cys Ser Asp Gly Tyr Tyr Gly Asp Ser Thr Ala Gly Thr Ser Ser
        755                 760                 765
Asp Cys Gln Pro Cys Pro Cys Pro Gly Gly Ser Ser Cys Ala Val Val
        770                 775                 780
Pro Lys Thr Lys Glu Val Val Cys Thr Asn Cys Pro Thr Gly Thr Thr
785                 790                 795                 800
Gly Lys Arg Cys Glu Leu Cys Asp Asp Gly Tyr Phe Gly Asp Pro Leu
                805                 810                 815
Gly Arg Asn Gly Pro Val Arg Leu Cys Arg Leu Cys Gln Cys Ser Asp
                820                 825                 830
Asn Ile Asp Pro Asn Ala Val Gly Asn Cys Asn Arg Leu Thr Gly Glu
        835                 840                 845
Cys Leu Lys Cys Ile Tyr Asn Thr Ala Gly Phe Tyr Cys Asp Arg Cys
        850                 855                 860
Lys Asp Gly Phe Phe Gly Asn Pro Leu Ala Pro Asn Pro Ala Asp Lys
865                 870                 875                 880
Cys Lys Ala Cys Asn Cys Asn Pro Tyr Gly Thr Met Lys Gln Gln Ser
                885                 890                 895
Ser Cys Asn Pro Val Thr Gly Gln Cys Glu Cys Leu Pro His Val Thr
        900                 905                 910
Gly Gln Asp Cys Gly Ala Cys Asp Pro Gly Phe Tyr Asn Leu Gln Ser
        915                 920                 925
Gly Gln Gly Cys Glu Arg Cys Asp Cys His Ala Leu Gly Ser Thr Asn
930                 935                 940
Gly Gln Cys Asp Ile Arg Thr Gly Gln Cys Glu Cys Gln Pro Gly Ile
945                 950                 955                 960
Thr Gly Gln His Cys Glu Arg Cys Glu Val Asn His Phe Gly Phe Gly
                965                 970                 975
Pro Glu Gly Cys Lys Pro Cys Asp Cys His Pro Glu Gly Ser Leu Ser
                980                 985                 990
Leu Gln Cys Lys Asp Asp Gly Arg Cys Glu Cys Arg Glu Gly Phe Val
            995                 1000                1005
Gly Asn Arg Cys Asp Gln Cys Glu Glu Asn Tyr Phe Tyr Asn Arg Ser
        1010                1015                1020
```

-continued

```
Trp Pro Gly Cys Gln Glu Cys Pro Ala Cys Tyr Arg Leu Val Lys Asp
1025                1030                1035                1040

Lys Val Ala Asp His Arg Val Lys Leu Gln Glu Leu Glu Ser Leu Ile
            1045                1050                1055

Ala Asn Leu Gly Thr Gly Asp Glu Met Val Thr Asp Gln Ala Phe Glu
                1060                1065                1070

Asp Arg Leu Lys Glu Ala Glu Arg Glu Val Met Asp Leu Leu Arg Glu
            1075                1080                1085

Ala Gln Asp Val Lys Asp Val Asp Gln Asn Leu Met Asp Arg Leu Gln
        1090                1095                1100

Arg Val Asn Asn Thr Leu Ser Ser Gln Ile Ser Arg Leu Gln Asn Ile
1105                1110                1115                1120

Arg Asn Thr Ile Glu Glu Thr Gly Asn Leu Ala Glu Gln Ala Arg Ala
            1125                1130                1135

His Val Glu Asn Thr Glu Arg Leu Ile Glu Ile Ala Ser Arg Glu Leu
            1140                1145                1150

Glu Lys Ala Lys Val Ala Ala Ala Asn Val Ser Val Thr Gln Pro Glu
        1155                1160                1165

Ser Thr Gly Asp Pro Asn Asn Met Thr Leu Leu Ala Glu Glu Ala Arg
    1170                1175                1180

Lys Leu Ala Glu Arg His Lys Gln Glu Ala Asp Ile Val Arg Val
1185                1190                1195                1200

Ala Lys Thr Ala Asn Asp Thr Ser Thr Glu Ala Tyr Asn Leu Leu Leu
            1205                1210                1215

Arg Thr Leu Ala Gly Glu Asn Gln Thr Ala Phe Glu Ile Glu Glu Leu
            1220                1225                1230

Asn Arg Lys Tyr Glu Gln Ala Lys Asn Ile Ser Gln Asp Leu Glu Lys
            1235                1240                1245

Gln Ala Ala Arg Val His Glu Glu Ala Lys Arg Ala Gly Asp Lys Ala
    1250                1255                1260

Val Glu Ile Tyr Ala Ser Val Ala Gln Leu Ser Pro Leu Asp Ser Glu
1265                1270                1275                1280

Thr Leu Glu Asn Glu Ala Asn Asn Ile Lys Met Glu Ala Glu Asn Leu
            1285                1290                1295

Glu Gln Leu Ile Asp Gln Lys Leu Lys Asp Tyr Glu Asp Leu Arg Glu
            1300                1305                1310

Asp Met Arg Gly Lys Glu Leu Glu Val Lys Asn Leu Leu Glu Lys Gly
        1315                1320                1325

Lys Thr Glu Gln Gln Thr Ala Asp Gln Leu Leu Ala Arg Ala Asp Ala
    1330                1335                1340

Ala Lys Ala Leu Ala Glu Glu Ala Ala Lys Lys Gly Arg Asp Thr Leu
1345                1350                1355                1360

Gln Glu Ala Asn Asp Ile Leu Asn Asn Leu Lys Asp Phe Asp Arg Arg
            1365                1370                1375

Val Asn Asp Asn Lys Thr Ala Ala Glu Glu Ala Leu Arg Lys Ile Pro
            1380                1385                1390

Ala Ile Asn Gln Thr Ile Thr Glu Ala Asn Glu Lys Thr Arg Glu Ala
        1395                1400                1405

Gln Gln Ala Leu Gly Ser Ala Ala Ala Asp Ala Thr Glu Ala Lys Asn
    1410                1415                1420

Lys Ala His Glu Ala Glu Arg Ile Ala Ser Ala Val Gln Lys Asn Ala
1425                1430                1435                1440

Thr Ser Thr Lys Ala Glu Ala Glu Arg Thr Phe Ala Glu Val Thr Asp
```

1445                1450                1455
Leu Asp Asn Glu Val Asn Asn Met Leu Lys Gln Leu Gln Glu Ala Glu
            1460                1465                1470

Lys Glu Leu Lys Arg Lys Gln Asp Asp Ala Asp Gln Asp Met Met Met
        1475                1480                1485

Ala Gly Met Ala Ser Gln Ala Ala Gln Glu Ala Glu Ile Asn Ala Arg
    1490                1495                1500

Lys Ala Lys Asn Ser Val Thr Ser Leu Leu Ser Ile Ile Asn Asp Leu
1505                1510                1515                1520

Leu Glu Gln Leu Gly Gln Leu Asp Thr Val Asp Leu Asn Lys Leu Asn
                1525                1530                1535

Glu Ile Glu Gly Thr Leu Asn Lys Ala Lys Asp Glu Met Lys Val Ser
            1540                1545                1550

Asp Leu Asp Arg Lys Val Ser Asp Leu Glu Asn Glu Ala Lys Lys Gln
        1555                1560                1565

Glu Ala Ala Ile Met Asp Tyr Asn Arg Asp Ile Glu Glu Ile Met Lys
    1570                1575                1580

Asp Ile Arg Asn Leu Glu Asp Ile Arg Lys Thr Leu Pro Ser Gly Cys
1585                1590                1595                1600

Phe Asn Thr Pro Ser Ile Glu Lys Pro
            1605

<210> SEQ ID NO 23
<211> LENGTH: 4948
<212> TYPE: DNA
<213> ORGANISM: Homo sapiens
<220> FEATURE:
<221> NAME/KEY: CDS
<222> LOCATION: (1)..(4728)

<400> SEQUENCE: 23

| | | |
|---|---|---|
| cag gca gcc atg gac gag tgc acg gac gag ggc ggg cgg ccg cag cgc<br>Gln Ala Ala Met Asp Glu Cys Thr Asp Glu Gly Gly Arg Pro Gln Arg<br>1               5                  10                  15 | 48 |
| tgc atg ccc gag ttc gtc aac gcc gct ttc aac gtg act gtg gtg gcc<br>Cys Met Pro Glu Phe Val Asn Ala Ala Phe Asn Val Thr Val Val Ala<br>            20                  25                  30 | 96 |
| acc aac acg tgt ggg act ccg ccc gag gaa tac tgt gtg cag acc ggg<br>Thr Asn Thr Cys Gly Thr Pro Pro Glu Glu Tyr Cys Val Gln Thr Gly<br>        35                  40                  45 | 144 |
| gtg acc ggg gtc acc aag tcc tgt cac ctg tgc gac gcc ggg cag ccc<br>Val Thr Gly Val Thr Lys Ser Cys His Leu Cys Asp Ala Gly Gln Pro<br>    50                  55                  60 | 192 |
| cac ctg cag cac ggg gca gcc ttc ctg acc gac tac aac aac cag gcc<br>His Leu Gln His Gly Ala Ala Phe Leu Thr Asp Tyr Asn Asn Gln Ala<br>65                  70                  75                  80 | 240 |
| gac acc acc tgg tgg caa agc cag acc atg ctg gcc ggg gtg cag tac<br>Asp Thr Thr Trp Trp Gln Ser Gln Thr Met Leu Ala Gly Val Gln Tyr<br>                85                  90                  95 | 288 |
| ccc agc tcc atc aac ctc acg ctg cac ctg gga aaa gct ttt gac atc<br>Pro Ser Ser Ile Asn Leu Thr Leu His Leu Gly Lys Ala Phe Asp Ile<br>            100                 105                 110 | 336 |
| acc tat gtg cgt ctc aag ttc cac acc agc cgc ccg gag agc ttt gcc<br>Thr Tyr Val Arg Leu Lys Phe His Thr Ser Arg Pro Glu Ser Phe Ala<br>        115                 120                 125 | 384 |
| att tac aag cgc aca cgg gaa gac ggg ccc tgg att cct tac cag tac<br>Ile Tyr Lys Arg Thr Arg Glu Asp Gly Pro Trp Ile Pro Tyr Gln Tyr<br>    130                 135                 140 | 432 |

```
tac agt ggt tcc tgc gag aac acc tac tcc aag gca aac cgc ggc ttc      480
Tyr Ser Gly Ser Cys Glu Asn Thr Tyr Ser Lys Ala Asn Arg Gly Phe
145                 150                 155                 160 atc agg aca gga ggg gac gag cag cag gcc ttg tgt act gat gaa ttc      528
Ile Arg Thr Gly Gly Asp Glu Gln Gln Ala Leu Cys Thr Asp Glu Phe
                165                 170                 175 agt gac att tct ccc ctc act ggg ggc aac gtg gcc ttt tct acc ctg      576
Ser Asp Ile Ser Pro Leu Thr Gly Gly Asn Val Ala Phe Ser Thr Leu
            180                 185                 190 gaa gga agg ccc agc gcc tat aac ttt gac aat agc cct gtg ctg cag      624
Glu Gly Arg Pro Ser Ala Tyr Asn Phe Asp Asn Ser Pro Val Leu Gln
        195                 200                 205 gaa tgg gta act gcc act gac atc aga gta act ctt aat cgc ctg aac      672
Glu Trp Val Thr Ala Thr Asp Ile Arg Val Thr Leu Asn Arg Leu Asn
210                 215                 220 act ttt gga gat gaa gtg ttt aac gat ccc aaa gtt ctc aag tcc tat      720
Thr Phe Gly Asp Glu Val Phe Asn Asp Pro Lys Val Leu Lys Ser Tyr
225                 230                 235                 240 tat tat gcc atc tct gat ttt gct gta ggt ggc aga tgt aaa tgt aat      768
Tyr Tyr Ala Ile Ser Asp Phe Ala Val Gly Gly Arg Cys Lys Cys Asn
                245                 250                 255 gga cac gca agc gag tgt atg aag aac gaa ttt gat aag ctg gtg tgt      816
Gly His Ala Ser Glu Cys Met Lys Asn Glu Phe Asp Lys Leu Val Cys
            260                 265                 270 aat tgc aaa cat aac aca tat gga gta gac tgt gaa aag tgt ctt cct      864
Asn Cys Lys His Asn Thr Tyr Gly Val Asp Cys Glu Lys Cys Leu Pro
        275                 280                 285 ttc ttc aat gac cgg ccg tgg agg agg gca act gcg gaa agt gcc agt      912
Phe Phe Asn Asp Arg Pro Trp Arg Arg Ala Thr Ala Glu Ser Ala Ser
290                 295                 300 gaa tgc ctg ccc tgt gat tgc aat ggt cga tcc cag gaa tgc tac ttc      960
Glu Cys Leu Pro Cys Asp Cys Asn Gly Arg Ser Gln Glu Cys Tyr Phe
305                 310                 315                 320 gac cct gaa ctc tat cgt tcc act ggc cat ggg ggc cac tgt acc aac     1008
Asp Pro Glu Leu Tyr Arg Ser Thr Gly His Gly Gly His Cys Thr Asn
                325                 330                 335 tgc cag gat aac aca gat ggc gcc cac tgt gag agg tgc cga gag aac     1056
Cys Gln Asp Asn Thr Asp Gly Ala His Cys Glu Arg Cys Arg Glu Asn
            340                 345                 350 ttc ttc cgc ctt ggc aac aat gaa gcc tgc tct tca tgc cac tgt agt     1104
Phe Phe Arg Leu Gly Asn Asn Glu Ala Cys Ser Ser Cys His Cys Ser
        355                 360                 365 cct gtg ggc tct cta agc aca cag tgt gat agt tac ggc aga tgc agc     1152
Pro Val Gly Ser Leu Ser Thr Gln Cys Asp Ser Tyr Gly Arg Cys Ser
370                 375                 380 tgt aag cca gga gtg atg ggg gac aaa tgt gac cgt tgc cag cct gga     1200
Cys Lys Pro Gly Val Met Gly Asp Lys Cys Asp Arg Cys Gln Pro Gly
385                 390                 395                 400 ttc cat tct ctc act gaa gca gga tgc agg cca tgc tct tgt gat ccc     1248
Phe His Ser Leu Thr Glu Ala Gly Cys Arg Pro Cys Ser Cys Asp Pro
                405                 410                 415 tct ggc agc ata gat gaa tgt aat gtt gaa aca gga aga tgt gtt tgc     1296
Ser Gly Ser Ile Asp Glu Cys Asn Val Glu Thr Gly Arg Cys Val Cys
            420                 425                 430 aaa gac aat gtc gaa ggc ttc aat tgt gaa aga tgc aaa cct gga ttt     1344
Lys Asp Asn Val Glu Gly Phe Asn Cys Glu Arg Cys Lys Pro Gly Phe
        435                 440                 445 ttt aat ctg gaa tca tct aat cct cgg ggt tgc aca ccc tgc ttc tgc     1392
Phe Asn Leu Glu Ser Ser Asn Pro Arg Gly Cys Thr Pro Cys Phe Cys
450                 455                 460
```

```
ttt ggg cat tct tct gtc tgt aca aac gct gtt ggc tac agt gtt tat      1440
Phe Gly His Ser Ser Val Cys Thr Asn Ala Val Gly Tyr Ser Val Tyr
465                 470                 475                 480 tct atc tcc tct acc ttt cag att gat gag gat ggg tgg cgt gcg aa       1488
Ser Ile Ser Ser Thr Phe Gln Ile Asp Glu Asp Gly Trp Arg Ala Glu
                485                 490                 495 cag aga gat ggc tct gaa gca tct ctc gag tgg tcc tct gag agg caa      1536
Gln Arg Asp Gly Ser Glu Ala Ser Leu Glu Trp Ser Ser Glu Arg Gln
            500                 505                 510 gat atc gcc gtg atc tca gac agc tac ttt cct cgg tac ttc att gct      1584
Asp Ile Ala Val Ile Ser Asp Ser Tyr Phe Pro Arg Tyr Phe Ile Ala
        515                 520                 525 cct gca aag ttc ttg ggc aag cag gtg ttg agt tat ggt cag aac ctc      1632
Pro Ala Lys Phe Leu Gly Lys Gln Val Leu Ser Tyr Gly Gln Asn Leu
    530                 535                 540 tcc ttc tcc ttt cga gtg gac agg cga gat act cgc ctc tct gcc gaa      1680
Ser Phe Ser Phe Arg Val Asp Arg Arg Asp Thr Arg Leu Ser Ala Glu
545                 550                 555                 560 gac ctt gtg ctt gag gga gct ggc tta aga gta tct gta ccc ttg atc      1728
Asp Leu Val Leu Glu Gly Ala Gly Leu Arg Val Ser Val Pro Leu Ile
                565                 570                 575 gct cag ggc aat tcc tat cca agt gag acc act gtg aag tat gtc ttc      1776
Ala Gln Gly Asn Ser Tyr Pro Ser Glu Thr Thr Val Lys Tyr Val Phe
            580                 585                 590 agg ctc cat gaa gca aca gat tac cct tgg agg cct gct ctt acc cct      1824
Arg Leu His Glu Ala Thr Asp Tyr Pro Trp Arg Pro Ala Leu Thr Pro
        595                 600                 605 ttt gaa ttt cag aag ctc cta aac aac ttg acc tct atc aag ata cgt      1872
Phe Glu Phe Gln Lys Leu Leu Asn Asn Leu Thr Ser Ile Lys Ile Arg
    610                 615                 620 ggg aca tac agt gag aga agt gct gga tat ttg gat gat gtc acc ctg      1920
Gly Thr Tyr Ser Glu Arg Ser Ala Gly Tyr Leu Asp Asp Val Thr Leu
625                 630                 635                 640 gca agt gct cgt cct ggg cct gga gtc cct gca act tgg gtg gag tcc      1968
Ala Ser Ala Arg Pro Gly Pro Gly Val Pro Ala Thr Trp Val Glu Ser
                645                 650                 655 tgc acc tgt cct gtg gga tat gga ggg cag ttt tgt gag atg tgc ctc      2016
Cys Thr Cys Pro Val Gly Tyr Gly Gly Gln Phe Cys Glu Met Cys Leu
            660                 665                 670 tca ggt tac aga aga gaa act cct aat ctt gga cca tac agt cca tgt      2064
Ser Gly Tyr Arg Arg Glu Thr Pro Asn Leu Gly Pro Tyr Ser Pro Cys
        675                 680                 685 gtg ctt tgc gcc tgc aat gga cac agc gag acc tgt gat cct gag aca      2112
Val Leu Cys Ala Cys Asn Gly His Ser Glu Thr Cys Asp Pro Glu Thr
    690                 695                 700 ggt gtt tgt aac tgc aga gac aat acg gct ggc ccg cac tgt gag aag      2160
Gly Val Cys Asn Cys Arg Asp Asn Thr Ala Gly Pro His Cys Glu Lys
705                 710                 715                 720 tgc agt gat ggg tac tat gga gat tca act gca ggc acc tcc tcc gat      2208
Cys Ser Asp Gly Tyr Tyr Gly Asp Ser Thr Ala Gly Thr Ser Ser Asp
                725                 730                 735 tgc caa ccc tgt ccg tgt cct gga ggt cca agt tgt gct gtt gtt ccc      2256
Cys Gln Pro Cys Pro Cys Pro Gly Gly Ser Ser Cys Ala Val Val Pro
            740                 745                 750 aag aca aag gag gtg gtg tgc acc aac tgt cct act ggc acc act ggt      2304
Lys Thr Lys Glu Val Val Cys Thr Asn Cys Pro Thr Gly Thr Thr Gly
        755                 760                 765 aag aga tgt gag ctc tgt gat gat ggc tac ttt gga gac ccc ctg ggt      2352
Lys Arg Cys Glu Leu Cys Asp Asp Gly Tyr Phe Gly Asp Pro Leu Gly
```

```
     770                 775                 780
aga aac ggc cct gtg aga ctt tgc cgc ctg tgc cag tgc agt gac aac    2400
Arg Asn Gly Pro Val Arg Leu Cys Arg Leu Cys Gln Cys Ser Asp Asn
785                 790                 795                 800 atc gat ccc aac gca gtt gga aat tgc aat cgc ttg acg gga gaa tgc    2448
Ile Asp Pro Asn Ala Val Gly Asn Cys Asn Arg Leu Thr Gly Glu Cys
                805                 810                 815 ctg aag tgc atc tat aac act gct ggc ttc tat tgt gac cgg tgc aaa    2496
Leu Lys Cys Ile Tyr Asn Thr Ala Gly Phe Tyr Cys Asp Arg Cys Lys
            820                 825                 830 gac gga ttt ttt gga aat ccc ctg gct ccc aat cca gca gac aaa tgc    2544
Asp Gly Phe Phe Gly Asn Pro Leu Ala Pro Asn Pro Ala Asp Lys Cys
        835                 840                 845 aaa gcc tgc aat tgc aat ccg tat ggg acc atg aag cag cag agc agc    2592
Lys Ala Cys Asn Cys Asn Pro Tyr Gly Thr Met Lys Gln Gln Ser Ser
850                 855                 860 tgt aac ccc gtg acg ggg cag tgt gaa tgt ttg cct cac gtg act ggc    2640
Cys Asn Pro Val Thr Gly Gln Cys Glu Cys Leu Pro His Val Thr Gly
865                 870                 875                 880 cag gac tgt ggt gct tgt gac cct gga ttc tac aat ctg cag agt ggg    2688
Gln Asp Cys Gly Ala Cys Asp Pro Gly Phe Tyr Asn Leu Gln Ser Gly
                885                 890                 895 caa ggc tgt gag agg tgt gac tgc cat gcc ttg ggc tcc acc aat ggg    2736
Gln Gly Cys Glu Arg Cys Asp Cys His Ala Leu Gly Ser Thr Asn Gly
            900                 905                 910 cag tgt gac atc cgc acc ggc cag tgt gag tgc cag ccc ggc atc act    2784
Gln Cys Asp Ile Arg Thr Gly Gln Cys Glu Cys Gln Pro Gly Ile Thr
        915                 920                 925 ggt cag cac tgt gag cgc tgt gag gtc aac cac ttt ggg ttt gga cct    2832
Gly Gln His Cys Glu Arg Cys Glu Val Asn His Phe Gly Phe Gly Pro
    930                 935                 940 gaa ggc tgc aaa ccc tgt gac tgt cat cct gag gga tct ctt tca ctt    2880
Glu Gly Cys Lys Pro Cys Asp Cys His Pro Glu Gly Ser Leu Ser Leu
945                 950                 955                 960 cag tgc aaa gat gat ggt cgc tgt gaa tgc aga gaa ggc ttt gtg gga    2928
Gln Cys Lys Asp Asp Gly Arg Cys Glu Cys Arg Glu Gly Phe Val Gly
                965                 970                 975 aat cgc tgt gac cag tgt gaa gaa aac tat ttc tac aat cgg tct tgg    2976
Asn Arg Cys Asp Gln Cys Glu Glu Asn Tyr Phe Tyr Asn Arg Ser Trp
            980                 985                 990 cct ggc tgc cag gaa tgt cca gct tgt tac cgg ctg gta aag gat aag    3024
Pro Gly Cys Gln Glu Cys Pro Ala Cys Tyr Arg Leu Val Lys Asp Lys
        995                 1000                1005 gtt gct gat cat aga gtg aag ctc cag gaa tta gag agt ctc ata gca    3072
Val Ala Asp His Arg Val Lys Leu Gln Glu Leu Glu Ser Leu Ile Ala
    1010                1015                1020 aac ctt gga act ggg gat gag atg gtg aca gat caa gcc ttc gag gat    3120
Asn Leu Gly Thr Gly Asp Glu Met Val Thr Asp Gln Ala Phe Glu Asp
1025                1030                1035                1040 aga cta aag gaa gca gag agg gaa gtt atg gac ctc ctt cgt gag gcc    3168
Arg Leu Lys Glu Ala Glu Arg Glu Val Met Asp Leu Leu Arg Glu Ala
                1045                1050                1055 cag gat gtc aaa gat gtt gac cag aat ttg atg gat cgc cta cag aga    3216
Gln Asp Val Lys Asp Val Asp Gln Asn Leu Met Asp Arg Leu Gln Arg
            1060                1065                1070 gtg aat aac act ctg tcc agc caa att agc cgt tta cag aat atc cgg    3264
Val Asn Asn Thr Leu Ser Ser Gln Ile Ser Arg Leu Gln Asn Ile Arg
        1075                1080                1085 aat acc att gaa gag act gga aac ttg gct gaa caa gcg cgt gcc cat    3312
```

```
Asn Thr Ile Glu Glu Thr Gly Asn Leu Ala Glu Gln Ala Arg Ala His
    1090                1095                1100 gta gag aac aca gag cgg ttg att gaa atc gca tcc aga gaa ctt gag      3360
Val Glu Asn Thr Glu Arg Leu Ile Glu Ile Ala Ser Arg Glu Leu Glu
1105                1110                1115                1120 aaa gca aaa gtc gct gct gcc aat gtg tca gtc act cag cca gaa tct      3408
Lys Ala Lys Val Ala Ala Ala Asn Val Ser Val Thr Gln Pro Glu Ser
                1125                1130                1135 aca ggg gac cca aac aac atg act ctt ttg gca gaa gag gct cga aag      3456
Thr Gly Asp Pro Asn Asn Met Thr Leu Leu Ala Glu Glu Ala Arg Lys
            1140                1145                1150 ctt gct gaa cgt cat aaa cag gaa gct gat gac att gtt cga gtg gca      3504
Leu Ala Glu Arg His Lys Gln Glu Ala Asp Asp Ile Val Arg Val Ala
        1155                1160                1165 aag aca gcc aat gat acg tca act gag gca tac aac ctg ctt ctg agg      3552
Lys Thr Ala Asn Asp Thr Ser Thr Glu Ala Tyr Asn Leu Leu Leu Arg
    1170                1175                1180 aca ctg gca gga gaa aat caa aca gca ttt gag att gaa gag ctt aat      3600
Thr Leu Ala Gly Glu Asn Gln Thr Ala Phe Glu Ile Glu Glu Leu Asn
1185                1190                1195                1200 agg aag tat gaa caa gcg aag aac atc tca cag gat ctg gaa aaa caa      3648
Arg Lys Tyr Glu Gln Ala Lys Asn Ile Ser Gln Asp Leu Glu Lys Gln
                1205                1210                1215 gct gcc cga gta cat gag gag gcc aaa agg gcc ggt gac aaa gct gtg      3696
Ala Ala Arg Val His Glu Glu Ala Lys Arg Ala Gly Asp Lys Ala Val
            1220                1225                1230 gag atc tat gcc agc gtg gct cag ctg agc cct ttg gac tct gag aca      3744
Glu Ile Tyr Ala Ser Val Ala Gln Leu Ser Pro Leu Asp Ser Glu Thr
        1235                1240                1245 ctg gag aat gaa gca aat aac ata aag atg gaa gct gag aat ctg gaa      3792
Leu Glu Asn Glu Ala Asn Asn Ile Lys Met Glu Ala Glu Asn Leu Glu
    1250                1255                1260 caa ctg att gac cag aaa tta aaa gat tat gag gac ctc aga gaa gat      3840
Gln Leu Ile Asp Gln Lys Leu Lys Asp Tyr Glu Asp Leu Arg Glu Asp
1265                1270                1275                1280 atg aga ggg aag gaa ctt gaa gtc aag aac ctt ctg gag aaa ggc aag      3888
Met Arg Gly Lys Glu Leu Glu Val Lys Asn Leu Leu Glu Lys Gly Lys
                1285                1290                1295 act gaa cag cag acc gca gac caa ctc cta gcc cga gct gat gct gcc      3936
Thr Glu Gln Gln Thr Ala Asp Gln Leu Leu Ala Arg Ala Asp Ala Ala
            1300                1305                1310 aag gcc ctc gct gaa gaa gct gca aag aag gga cgg gat acc tta caa      3984
Lys Ala Leu Ala Glu Glu Ala Ala Lys Lys Gly Arg Asp Thr Leu Gln
        1315                1320                1325 gaa gct aat gac att ctc aac aac ctg aaa gat ttt gat agg cgc gtg      4032
Glu Ala Asn Asp Ile Leu Asn Asn Leu Lys Asp Phe Asp Arg Arg Val
    1330                1335                1340 aac gat aac aag acg gcc gca gag gag gca cta agg aag att cct gcc      4080
Asn Asp Asn Lys Thr Ala Ala Glu Glu Ala Leu Arg Lys Ile Pro Ala
1345                1350                1355                1360 atc aac cag acc atc act gaa gcc aat gaa aag acc aga gaa gcc cag      4128
Ile Asn Gln Thr Ile Thr Glu Ala Asn Glu Lys Thr Arg Glu Ala Gln
                1365                1370                1375 cag gcc ctg ggc agt gct gcg gcg gat gcc aca gag gcc aag aac aag      4176
Gln Ala Leu Gly Ser Ala Ala Ala Asp Ala Thr Glu Ala Lys Asn Lys
            1380                1385                1390 gcc cat gag gcg gag agg atc gca agc gct gtc caa aag aat gcc acc      4224
Ala His Glu Ala Glu Arg Ile Ala Ser Ala Val Gln Lys Asn Ala Thr
        1395                1400                1405
```

```
agc acc aag gca gaa gct gaa aga act ttt gca gaa gtt aca gat ctg    4272
Ser Thr Lys Ala Glu Ala Glu Arg Thr Phe Ala Glu Val Thr Asp Leu
    1410                1415                1420 gat aat gag gtg aac aat atg ttg aag caa ctg cag gaa gca gaa aaa    4320
Asp Asn Glu Val Asn Asn Met Leu Lys Gln Leu Gln Glu Ala Glu Lys
1425                1430                1435                1440 gag cta aag aga aaa caa gat gac gct gac cag gac atg atg atg gca    4368
Glu Leu Lys Arg Lys Gln Asp Asp Ala Asp Gln Asp Met Met Met Ala
                1445                1450                1455 ggg atg gct tca cag gct gct caa gaa gcc gag atc aat gcc aga aaa    4416
Gly Met Ala Ser Gln Ala Ala Gln Glu Ala Glu Ile Asn Ala Arg Lys
            1460                1465                1470 gcc aaa aac tct gtt act agc ctc ctc agc att att aat gac ctc ttg    4464
Ala Lys Asn Ser Val Thr Ser Leu Leu Ser Ile Ile Asn Asp Leu Leu
1475                1480                1485 gag cag ctg ggg cag ctg gat aca gtg gac ctg aat aag cta aac gag    4512
Glu Gln Leu Gly Gln Leu Asp Thr Val Asp Leu Asn Lys Leu Asn Glu
                1490                1495                1500 att gaa ggc acc cta aac aaa gcc aaa gat gaa atg aag gtc agc gat    4560
Ile Glu Gly Thr Leu Asn Lys Ala Lys Asp Glu Met Lys Val Ser Asp
1505                1510                1515                1520 ctt gat agg aaa gtg tct gac ctg gag aat gaa gcc aag aag cag gag    4608
Leu Asp Arg Lys Val Ser Asp Leu Glu Asn Glu Ala Lys Lys Gln Glu
                1525                1530                1535 gct gcc atc atg gac tat aac cga gat atc gag gag atc atg aag gac    4656
Ala Ala Ile Met Asp Tyr Asn Arg Asp Ile Glu Glu Ile Met Lys Asp
            1540                1545                1550 att cgc aat ctg gag gac atc agg aag acc tta cca tct ggc tgc ttc    4704
Ile Arg Asn Leu Glu Asp Ile Arg Lys Thr Leu Pro Ser Gly Cys Phe
1555                1560                1565 aac acc ccg tcc att gaa aag ccc tagtgtcttt agggctggaa ggcagcatcc   4758
Asn Thr Pro Ser Ile Glu Lys Pro
                1570                1575 ctctgacagg ggggcagttg tgaggccaca gagtgccttg acacaaagat tacattttc   4818 agaccccac tcctctgctg ctgtccatca ctgtcctttt gaaccaggaa aagtcacaga   4878
gtttaaagag aagcaaatta aacatcctga atcgggaaca aagggtttta tctaataaag  4938
tgtctcttcc                                                         4948

<210> SEQ ID NO 24
<211> LENGTH: 1576
<212> TYPE: PRT
<213> ORGANISM: Homo sapiens

<400> SEQUENCE: 24

Gln Ala Ala Met Asp Glu Cys Thr Asp Glu Gly Gly Arg Pro Gln Arg
1               5                   10                  15

Cys Met Pro Glu Phe Val Asn Ala Ala Phe Asn Val Thr Val Val Ala
            20                  25                  30

Thr Asn Thr Cys Gly Thr Pro Pro Glu Glu Tyr Cys Val Gln Thr Gly
        35                  40                  45

Val Thr Gly Val Thr Lys Ser Cys His Leu Cys Asp Ala Gly Gln Pro
    50                  55                  60

His Leu Gln His Gly Ala Ala Phe Leu Thr Asp Tyr Asn Asn Gln Ala
65                  70                  75                  80

Asp Thr Thr Trp Trp Gln Ser Gln Thr Met Leu Ala Gly Val Gln Tyr
                85                  90                  95

Pro Ser Ser Ile Asn Leu Thr Leu His Leu Gly Lys Ala Phe Asp Ile
```

-continued

```
              100                 105                 110
Thr Tyr Val Arg Leu Lys Phe His Thr Ser Arg Pro Glu Ser Phe Ala
            115                 120                 125
Ile Tyr Lys Arg Thr Arg Glu Asp Gly Pro Trp Ile Pro Tyr Gln Tyr
        130                 135                 140
Tyr Ser Gly Ser Cys Glu Asn Thr Tyr Ser Lys Ala Asn Arg Gly Phe
145                 150                 155                 160
Ile Arg Thr Gly Gly Asp Glu Gln Gln Ala Leu Cys Thr Asp Glu Phe
                165                 170                 175
Ser Asp Ile Ser Pro Leu Thr Gly Gly Asn Val Ala Phe Ser Thr Leu
            180                 185                 190
Glu Gly Arg Pro Ser Ala Tyr Asn Phe Asp Asn Ser Pro Val Leu Gln
        195                 200                 205
Glu Trp Val Thr Ala Thr Asp Ile Arg Val Thr Leu Asn Arg Leu Asn
    210                 215                 220
Thr Phe Gly Asp Glu Val Phe Asn Asp Pro Lys Val Leu Lys Ser Tyr
225                 230                 235                 240
Tyr Tyr Ala Ile Ser Asp Phe Ala Val Gly Gly Arg Cys Lys Cys Asn
                245                 250                 255
Gly His Ala Ser Glu Cys Met Lys Asn Glu Phe Asp Lys Leu Val Cys
            260                 265                 270
Asn Cys Lys His Asn Thr Tyr Gly Val Asp Cys Glu Lys Cys Leu Pro
        275                 280                 285
Phe Phe Asn Asp Arg Pro Trp Arg Arg Ala Thr Ala Glu Ser Ala Ser
    290                 295                 300
Glu Cys Leu Pro Cys Asp Cys Asn Gly Arg Ser Gln Glu Cys Tyr Phe
305                 310                 315                 320
Asp Pro Glu Leu Tyr Arg Ser Thr Gly His Gly Gly His Cys Thr Asn
                325                 330                 335
Cys Gln Asp Asn Thr Asp Gly Ala His Cys Glu Arg Cys Arg Glu Asn
            340                 345                 350
Phe Phe Arg Leu Gly Asn Asn Glu Ala Cys Ser Ser Cys His Cys Ser
        355                 360                 365
Pro Val Gly Ser Leu Ser Thr Gln Cys Asp Ser Tyr Gly Arg Cys Ser
    370                 375                 380
Cys Lys Pro Gly Val Met Gly Asp Lys Cys Asp Arg Cys Gln Pro Gly
385                 390                 395                 400
Phe His Ser Leu Thr Glu Ala Gly Cys Arg Pro Cys Ser Cys Asp Pro
                405                 410                 415
Ser Gly Ser Ile Asp Glu Cys Asn Val Glu Thr Gly Arg Cys Val Cys
            420                 425                 430
Lys Asp Asn Val Glu Gly Phe Asn Cys Glu Arg Cys Lys Pro Gly Phe
        435                 440                 445
Phe Asn Leu Glu Ser Ser Asn Pro Arg Gly Cys Thr Pro Cys Phe Cys
    450                 455                 460
Phe Gly His Ser Ser Val Cys Thr Asn Ala Val Gly Tyr Ser Val Tyr
465                 470                 475                 480
Ser Ile Ser Ser Thr Phe Gln Ile Asp Glu Asp Gly Trp Arg Ala Glu
                485                 490                 495
Gln Arg Asp Gly Ser Glu Ala Ser Leu Glu Trp Ser Ser Glu Arg Gln
            500                 505                 510
Asp Ile Ala Val Ile Ser Asp Ser Tyr Phe Pro Arg Tyr Phe Ile Ala
        515                 520                 525
```

-continued

```
Pro Ala Lys Phe Leu Gly Lys Gln Val Leu Ser Tyr Gly Gln Asn Leu
    530                 535                 540

Ser Phe Ser Phe Arg Val Asp Arg Arg Asp Thr Arg Leu Ser Ala Glu
545                 550                 555                 560

Asp Leu Val Leu Glu Gly Ala Gly Leu Arg Val Ser Val Pro Leu Ile
                565                 570                 575

Ala Gln Gly Asn Ser Tyr Pro Ser Glu Thr Thr Val Lys Tyr Val Phe
                580                 585                 590

Arg Leu His Glu Ala Thr Asp Tyr Pro Trp Arg Pro Ala Leu Thr Pro
            595                 600                 605

Phe Glu Phe Gln Lys Leu Leu Asn Asn Leu Thr Ser Ile Lys Ile Arg
    610                 615                 620

Gly Thr Tyr Ser Glu Arg Ser Ala Gly Tyr Leu Asp Asp Val Thr Leu
625                 630                 635                 640

Ala Ser Ala Arg Pro Gly Pro Gly Val Pro Ala Thr Trp Val Glu Ser
                645                 650                 655

Cys Thr Cys Pro Val Gly Tyr Gly Gly Gln Phe Cys Glu Met Cys Leu
                660                 665                 670

Ser Gly Tyr Arg Arg Glu Thr Pro Asn Leu Gly Pro Tyr Ser Pro Cys
            675                 680                 685

Val Leu Cys Ala Cys Asn Gly His Ser Glu Thr Cys Asp Pro Glu Thr
    690                 695                 700

Gly Val Cys Asn Cys Arg Asp Asn Thr Ala Gly Pro His Cys Glu Lys
705                 710                 715                 720

Cys Ser Asp Gly Tyr Tyr Gly Asp Ser Thr Ala Gly Thr Ser Ser Asp
                725                 730                 735

Cys Gln Pro Cys Pro Cys Pro Gly Gly Ser Ser Cys Ala Val Val Pro
            740                 745                 750

Lys Thr Lys Glu Val Val Cys Thr Asn Cys Pro Thr Gly Thr Thr Gly
    755                 760                 765

Lys Arg Cys Glu Leu Cys Asp Asp Gly Tyr Phe Gly Asp Pro Leu Gly
770                 775                 780

Arg Asn Gly Pro Val Arg Leu Cys Arg Leu Cys Gln Cys Ser Asp Asn
785                 790                 795                 800

Ile Asp Pro Asn Ala Val Gly Asn Cys Asn Arg Leu Thr Gly Glu Cys
                805                 810                 815

Leu Lys Cys Ile Tyr Asn Thr Ala Gly Phe Tyr Cys Asp Arg Cys Lys
            820                 825                 830

Asp Gly Phe Phe Gly Asn Pro Leu Ala Pro Asn Pro Ala Asp Lys Cys
            835                 840                 845

Lys Ala Cys Asn Cys Asn Pro Tyr Gly Thr Met Lys Gln Gln Ser Ser
    850                 855                 860

Cys Asn Pro Val Thr Gly Gln Cys Glu Cys Leu Pro His Val Thr Gly
865                 870                 875                 880

Gln Asp Cys Gly Ala Cys Asp Pro Gly Phe Tyr Asn Leu Gln Ser Gly
                885                 890                 895

Gln Gly Cys Glu Arg Cys Asp Cys His Ala Leu Gly Ser Thr Asn Gly
            900                 905                 910

Gln Cys Asp Ile Arg Thr Gly Gln Cys Glu Cys Gln Pro Gly Ile Thr
    915                 920                 925

Gly Gln His Cys Glu Arg Cys Glu Val Asn His Phe Gly Phe Gly Pro
930                 935                 940
```

```
Glu Gly Cys Lys Pro Cys Asp Cys His Pro Glu Gly Ser Leu Ser Leu
945                 950                 955                 960

Gln Cys Lys Asp Asp Gly Arg Cys Glu Cys Arg Glu Gly Phe Val Gly
            965                 970                 975

Asn Arg Cys Asp Gln Cys Glu Glu Asn Tyr Phe Tyr Asn Arg Ser Trp
        980                 985                 990

Pro Gly Cys Gln Glu Cys Pro Ala Cys Tyr Arg Leu Val Lys Asp Lys
    995                 1000                1005

Val Ala Asp His Arg Val Lys Leu Gln Glu Leu Glu Ser Leu Ile Ala
1010                1015                1020

Asn Leu Gly Thr Gly Asp Glu Met Val Thr Asp Gln Ala Phe Glu Asp
1025                1030                1035                1040

Arg Leu Lys Glu Ala Glu Arg Glu Val Met Asp Leu Leu Arg Glu Ala
                1045                1050                1055

Gln Asp Val Lys Asp Val Asp Gln Asn Leu Met Asp Arg Leu Gln Arg
            1060                1065                1070

Val Asn Asn Thr Leu Ser Ser Gln Ile Ser Arg Leu Gln Asn Ile Arg
        1075                1080                1085

Asn Thr Ile Glu Glu Thr Gly Asn Leu Ala Glu Gln Ala Arg Ala His
    1090                1095                1100

Val Glu Asn Thr Glu Arg Leu Ile Glu Ile Ala Ser Arg Glu Leu Glu
1105                1110                1115                1120

Lys Ala Lys Val Ala Ala Ala Asn Val Ser Val Thr Gln Pro Glu Ser
                1125                1130                1135

Thr Gly Asp Pro Asn Asn Met Thr Leu Leu Ala Glu Glu Ala Arg Lys
            1140                1145                1150

Leu Ala Glu Arg His Lys Gln Glu Ala Asp Asp Ile Val Arg Val Ala
        1155                1160                1165

Lys Thr Ala Asn Asp Thr Ser Thr Glu Ala Tyr Asn Leu Leu Leu Arg
    1170                1175                1180

Thr Leu Ala Gly Glu Asn Gln Thr Ala Phe Glu Ile Glu Glu Leu Asn
1185                1190                1195                1200

Arg Lys Tyr Glu Gln Ala Lys Asn Ile Ser Gln Asp Leu Glu Lys Gln
                1205                1210                1215

Ala Ala Arg Val His Glu Glu Ala Lys Arg Ala Gly Asp Lys Ala Val
            1220                1225                1230

Glu Ile Tyr Ala Ser Val Ala Gln Leu Ser Pro Leu Asp Ser Glu Thr
        1235                1240                1245

Leu Glu Asn Glu Ala Asn Asn Ile Lys Met Glu Ala Glu Asn Leu Glu
    1250                1255                1260

Gln Leu Ile Asp Gln Lys Leu Lys Asp Tyr Glu Asp Leu Arg Glu Asp
1265                1270                1275                1280

Met Arg Gly Lys Glu Leu Glu Val Lys Asn Leu Leu Glu Lys Gly Lys
                1285                1290                1295

Thr Glu Gln Gln Thr Ala Asp Gln Leu Leu Ala Arg Ala Asp Ala Ala
            1300                1305                1310

Lys Ala Leu Ala Glu Glu Ala Ala Lys Lys Gly Arg Asp Thr Leu Gln
        1315                1320                1325

Glu Ala Asn Asp Ile Leu Asn Asn Leu Lys Asp Phe Asp Arg Arg Val
    1330                1335                1340

Asn Asp Asn Lys Thr Ala Ala Glu Glu Ala Leu Arg Lys Ile Pro Ala
1345                1350                1355                1360

Ile Asn Gln Thr Ile Thr Glu Ala Asn Glu Lys Thr Arg Glu Ala Gln
```

-continued

```
                 1365                1370                1375
Gln Ala Leu Gly Ser Ala Ala Ala Asp Ala Thr Glu Ala Lys Asn Lys
            1380                1385                1390
Ala His Glu Ala Glu Arg Ile Ala Ser Ala Val Gln Lys Asn Ala Thr
        1395                1400                1405
Ser Thr Lys Ala Glu Ala Glu Arg Thr Phe Ala Glu Val Thr Asp Leu
    1410                1415                1420
Asp Asn Glu Val Asn Asn Met Leu Lys Gln Leu Gln Glu Ala Glu Lys
1425                1430                1435                1440
Glu Leu Lys Arg Lys Gln Asp Asp Ala Asp Gln Asp Met Met Met Ala
                1445                1450                1455
Gly Met Ala Ser Gln Ala Ala Gln Glu Ala Glu Ile Asn Ala Arg Lys
            1460                1465                1470
Ala Lys Asn Ser Val Thr Ser Leu Leu Ser Ile Ile Asn Asp Leu Leu
        1475                1480                1485
Glu Gln Leu Gly Gln Leu Asp Thr Val Asp Leu Asn Lys Leu Asn Glu
    1490                1495                1500
Ile Glu Gly Thr Leu Asn Lys Ala Lys Asp Glu Met Lys Val Ser Asp
1505                1510                1515                1520
Leu Asp Arg Lys Val Ser Asp Leu Glu Asn Glu Ala Lys Lys Gln Glu
                1525                1530                1535
Ala Ala Ile Met Asp Tyr Asn Arg Asp Ile Glu Glu Ile Met Lys Asp
            1540                1545                1550
Ile Arg Asn Leu Glu Asp Ile Arg Lys Thr Leu Pro Ser Gly Cys Phe
        1555                1560                1565
Asn Thr Pro Ser Ile Glu Lys Pro
    1570                1575

<210> SEQ ID NO 25
<211> LENGTH: 7554
<212> TYPE: DNA
<213> ORGANISM: Mus musculus
<220> FEATURE:
<221> NAME/KEY: CDS
<222> LOCATION: (193)..(5010)
<221> NAME/KEY: sig_peptide
<222> LOCATION: (193)..(291)

<400> SEQUENCE: 25
cgcaccggga agtagcggag gcagcgcgat cttggctcgg acgcccaccc atcggctctg     60
cgtccggctc tcggcctcca gcccggtcca cagcccggcc tcggcccgca gcggaggatc    120
ggcctcggga tacgccgcta ggcgagtgca gcgcggcacc ccagcctttg ccagggggcc    180
cgccgcagcg gg atg acg ggc ggc ggg cgg gcc gcg ctg gcc ctg cag ccc    231
           Met Thr Gly Gly Gly Arg Ala Ala Leu Ala Leu Gln Pro
             1               5                  10 cgg ggg cgg ctg tgg ccg ctg ttg gct gtg ctg gcg gct gtg gcg ggc       279
Arg Gly Arg Leu Trp Pro Leu Leu Ala Val Leu Ala Ala Val Ala Gly
     15                 20                  25 tgt gtc cgg gcg gcc atg gac gag tgc gcg gat gag ggc ggg cgg ccg       327
Cys Val Arg Ala Ala Met Asp Glu Cys Ala Asp Glu Gly Gly Arg Pro
 30                 35                  40                  45 cag cgc tgc atg ccg gag ttt gtt aat gcc gcc ttc aat gtg acc gtg       375
Gln Arg Cys Met Pro Glu Phe Val Asn Ala Ala Phe Asn Val Thr Val
                50                  55                  60 gtg gct acc aac acg tgt ggg act ccg ccc gag gag tac tgc gtg cag       423
Val Ala Thr Asn Thr Cys Gly Thr Pro Pro Glu Glu Tyr Cys Val Gln
             65                  70                  75
```

-continued

```
act ggg gtg acc gga gtc act aag tcc tgt cac ctg tgc gac gcc ggc     471
Thr Gly Val Thr Gly Val Thr Lys Ser Cys His Leu Cys Asp Ala Gly
         80                  85                  90 cag cag cac ctg caa cac ggg gca gcc ttc ctg acc gac tac aac aac     519
Gln Gln His Leu Gln His Gly Ala Ala Phe Leu Thr Asp Tyr Asn Asn
 95                 100                 105 cag gcc gac acc acc tgg tgg caa agc cag act atg ctg gcc ggg gtg     567
Gln Ala Asp Thr Thr Trp Trp Gln Ser Gln Thr Met Leu Ala Gly Val
110                 115                 120                 125 cag tac ccc aac tcc atc aac ctc acg ctg cac ctg gga aag gct ttt     615
Gln Tyr Pro Asn Ser Ile Asn Leu Thr Leu His Leu Gly Lys Ala Phe
                130                 135                 140 gac atc act tac gtg cgc ctc aag ttc cac acc agc cgt cca gag agc     663
Asp Ile Thr Tyr Val Arg Leu Lys Phe His Thr Ser Arg Pro Glu Ser
        145                 150                 155 ttc gcc atc tat aag cgc act cgg gaa gac ggg ccc tgg att cct tat     711
Phe Ala Ile Tyr Lys Arg Thr Arg Glu Asp Gly Pro Trp Ile Pro Tyr
        160                 165                 170 cag tac tac agt ggg tcc tgt gag aac acg tac tca aag gct aac cgt     759
Gln Tyr Tyr Ser Gly Ser Cys Glu Asn Thr Tyr Ser Lys Ala Asn Arg
175                 180                 185 ggc ttc atc agg acc gga ggg gac gag cag cag gcc ttg tgt act gat     807
Gly Phe Ile Arg Thr Gly Gly Asp Glu Gln Gln Ala Leu Cys Thr Asp
190                 195                 200                 205 gaa ttc agt gac att tcc ccc ctc acc ggt ggc aac gtg gcc ttt tca     855
Glu Phe Ser Asp Ile Ser Pro Leu Thr Gly Gly Asn Val Ala Phe Ser
                210                 215                 220 acc ctg gaa gga cgg ccg agt gcc tac aac ttt gac aac agc cct gtg     903
Thr Leu Glu Gly Arg Pro Ser Ala Tyr Asn Phe Asp Asn Ser Pro Val
        225                 230                 235 ctc cag gaa tgg gta act gcc act gac atc aga gtg acg ctc aat cgc     951
Leu Gln Glu Trp Val Thr Ala Thr Asp Ile Arg Val Thr Leu Asn Arg
        240                 245                 250 ctg aac acc ttt gga gat gaa gtg ttt aac gac ccc aaa gtt ctc aag     999
Leu Asn Thr Phe Gly Asp Glu Val Phe Asn Asp Pro Lys Val Leu Lys
        255                 260                 265 tct tac tat tac gca atc tca gac ttt gct gtg ggc ggc agg tgt aaa    1047
Ser Tyr Tyr Tyr Ala Ile Ser Asp Phe Ala Val Gly Gly Arg Cys Lys
270                 275                 280                 285 tgt aac gga cat gcc agc gag tgt gta aag aac gag ttt gac aaa ctc    1095
Cys Asn Gly His Ala Ser Glu Cys Val Lys Asn Glu Phe Asp Lys Leu
                290                 295                 300 atg tgc aac tgc aaa cat aac aca tac gga gtt gac tgt gaa aag tgc    1143
Met Cys Asn Cys Lys His Asn Thr Tyr Gly Val Asp Cys Glu Lys Cys
        305                 310                 315 ctg cct ttc ttc aat gac cgg ccg tgg agg agg gcg act gct gag agc    1191
Leu Pro Phe Phe Asn Asp Arg Pro Trp Arg Arg Ala Thr Ala Glu Ser
        320                 325                 330 gcc agc gag tgc ctt cct tgt gac tgc aat ggc cga tcc caa gag tgc    1239
Ala Ser Glu Cys Leu Pro Cys Asp Cys Asn Gly Arg Ser Gln Glu Cys
335                 340                 345 tac ttt gat cct gaa cta tac cgt tcc act gga cat ggt ggc cac tgt    1287
Tyr Phe Asp Pro Glu Leu Tyr Arg Ser Thr Gly His Gly Gly His Cys
350                 355                 360                 365 acc aac tgc cgg gat aac aca gat ggt gcc aag tgc gag agg tgc cgg    1335
Thr Asn Cys Arg Asp Asn Thr Asp Gly Ala Lys Cys Glu Arg Cys Arg
                370                 375                 380 gag aat ttc ttc cgc ctg ggg aac act gaa gcc tgc tct ccg tgc cac    1383
Glu Asn Phe Phe Arg Leu Gly Asn Thr Glu Ala Cys Ser Pro Cys His
```

-continued

|  |  |  |  |  |  |  |  |  |  |  |  |  |  |  |  |
|--|--|--|--|--|--|--|--|--|--|--|--|--|--|--|--|
| | | | 385 | | | | | 390 | | | | | 395 | | |

```
tgc agc cct gtt ggt tct ctc agc aca cag tgt gac agt tac ggc aga     1431
Cys Ser Pro Val Gly Ser Leu Ser Thr Gln Cys Asp Ser Tyr Gly Arg
        400                 405                 410 tgc agc tgt aag cca gga gtg atg ggt gac aag tgt gac cgt tgt cag     1479
Cys Ser Cys Lys Pro Gly Val Met Gly Asp Lys Cys Asp Arg Cys Gln
    415                 420                 425 cct ggg ttc cat tcc ctc act gag gca gga tgc agg cca tgc tcc tgc     1527
Pro Gly Phe His Ser Leu Thr Glu Ala Gly Cys Arg Pro Cys Ser Cys
430                 435                 440                 445 gat cct tcg ggc agc aca gac gag tgt aat gtt gaa aca gga aga tgc     1575
Asp Pro Ser Gly Ser Thr Asp Glu Cys Asn Val Glu Thr Gly Arg Cys
                450                 455                 460 gtt tgc aaa gac aat gtt gaa ggc ttc aac tgt gag aga tgc aaa cct     1623
Val Cys Lys Asp Asn Val Glu Gly Phe Asn Cys Glu Arg Cys Lys Pro
            465                 470                 475 gga ttt ttt aat ctg gag tca tct aat cct aag ggc tgc aca ccc tgc     1671
Gly Phe Phe Asn Leu Glu Ser Ser Asn Pro Lys Gly Cys Thr Pro Cys
        480                 485                 490 ttc tgc ttt ggc cat tct tct gtg tgc aca aat gct gtt ggc tac agt     1719
Phe Cys Phe Gly His Ser Ser Val Cys Thr Asn Ala Val Gly Tyr Ser
    495                 500                 505 gtt tat gac atc tcc tcc acc ttt cag att gat gag gat ggg tgg cgc     1767
Val Tyr Asp Ile Ser Ser Thr Phe Gln Ile Asp Glu Asp Gly Trp Arg
510                 515                 520                 525 gtg gag cag aga gat ggc tcg gag gcg tct ctg gag tgg tcc tca gac     1815
Val Glu Gln Arg Asp Gly Ser Glu Ala Ser Leu Glu Trp Ser Ser Asp
                530                 535                 540 agg caa tat att gcc gta atc tca gac agt tac ttt cct aga tac ttc     1863
Arg Gln Tyr Ile Ala Val Ile Ser Asp Ser Tyr Phe Pro Arg Tyr Phe
            545                 550                 555 atc gcc cct gtg aag ttc ctg ggc aac cag gtc ctg agt tat ggg cag     1911
Ile Ala Pro Val Lys Phe Leu Gly Asn Gln Val Leu Ser Tyr Gly Gln
        560                 565                 570 aat ctt tcc ttc tcc ttc cga gtg gac aga cga gac act cgc ctc tcc     1959
Asn Leu Ser Phe Ser Phe Arg Val Asp Arg Arg Asp Thr Arg Leu Ser
    575                 580                 585 gca gag gac ctt gtg ctc gaa gga gct ggc ttg aga gta tcc gtg ccc     2007
Ala Glu Asp Leu Val Leu Glu Gly Ala Gly Leu Arg Val Ser Val Pro
590                 595                 600                 605 ttg atc gct cag ggc aac tcc tac ccc agc gag acc act gtg aag tac     2055
Leu Ile Ala Gln Gly Asn Ser Tyr Pro Ser Glu Thr Thr Val Lys Tyr
                610                 615                 620 atc ttc agg ctc cat gaa gca acg gat tac cct tgg agg ccc gct ctc     2103
Ile Phe Arg Leu His Glu Ala Thr Asp Tyr Pro Trp Arg Pro Ala Leu
            625                 630                 635 tcc ccg ttt gaa ttt cag aag ctc ctg aac aac ttg acc tct atc aag     2151
Ser Pro Phe Glu Phe Gln Lys Leu Leu Asn Asn Leu Thr Ser Ile Lys
        640                 645                 650 atc cgt ggt aca tac agc gag agg agc gct ggg tac ttg gat gat gtc     2199
Ile Arg Gly Thr Tyr Ser Glu Arg Ser Ala Gly Tyr Leu Asp Asp Val
    655                 660                 665 acc ttg caa agt gct cgc cct ggg ccc gga gtc cct gca acg tgg gtg     2247
Thr Leu Gln Ser Ala Arg Pro Gly Pro Gly Val Pro Ala Thr Trp Val
670                 675                 680                 685 gag tcc tgc acc tgt cca gtg gga tac ggg gga cag ttc tgt gag acg     2295
Glu Ser Cys Thr Cys Pro Val Gly Tyr Gly Gly Gln Phe Cys Glu Thr
                690                 695                 700 tgc ctc cca ggg tac aga aga gaa act cca agc ctt gga cct tat agc     2343
```

```
                Cys Leu Pro Gly Tyr Arg Arg Glu Thr Pro Ser Leu Gly Pro Tyr Ser
                            705                 710                 715 ccg tgt gtg ctc tgt acc tgt aat ggg cac agt gag acc tgt gac ccg        2391
Pro Cys Val Leu Cys Thr Cys Asn Gly His Ser Glu Thr Cys Asp Pro
            720                 725                 730 gag aca ggt gtc tgt gac tgc aga gac aat aca gcc ggc ccc cac tgt        2439
Glu Thr Gly Val Cys Asp Cys Arg Asp Asn Thr Ala Gly Pro His Cys
    735                 740                 745 gag aaa tgt agc gat ggg tac tat ggg gac tca acc ctg ggc acc tcc        2487
Glu Lys Cys Ser Asp Gly Tyr Tyr Gly Asp Ser Thr Leu Gly Thr Ser
750                 755                 760                 765 tct gac tgc cag cct tgt ccc tgc ccc ggt ggc tca agt tgt gcc att        2535
Ser Asp Cys Gln Pro Cys Pro Cys Pro Gly Gly Ser Ser Cys Ala Ile
                770                 775                 780 gtc cca aag aca aag gaa gtg gtg tgc acg cac tgt ccg act ggc act        2583
Val Pro Lys Thr Lys Glu Val Val Cys Thr His Cys Pro Thr Gly Thr
            785                 790                 795 gcc ggc aag aga tgt gaa ctc tgt gat gac ggc tac ttt gga gac cct        2631
Ala Gly Lys Arg Cys Glu Leu Cys Asp Asp Gly Tyr Phe Gly Asp Pro
    800                 805                 810 ctg ggc agc aat ggg ccc gtg aga ctg tgc cgc ccg tgc cag tgt aac        2679
Leu Gly Ser Asn Gly Pro Val Arg Leu Cys Arg Pro Cys Gln Cys Asn
815                 820                 825 gac aac ata gac ccc aac gcg gtt ggc aac tgc aac cgc ctg acg ggc        2727
Asp Asn Ile Asp Pro Asn Ala Val Gly Asn Cys Asn Arg Leu Thr Gly
830                 835                 840                 845 gag tgc ctg aag tgc atc tat aac acg gct ggt ttc tac tgc gac cgg        2775
Glu Cys Leu Lys Cys Ile Tyr Asn Thr Ala Gly Phe Tyr Cys Asp Arg
                850                 855                 860 tgc aag gaa ggg ttt ttc gga aat ccc ctg gct ccc aat cca gcc gac        2823
Cys Lys Glu Gly Phe Phe Gly Asn Pro Leu Ala Pro Asn Pro Ala Asp
            865                 870                 875 aaa tgc aaa gcc tgc gcc tgc aac tac ggg aca gtg cag caa cag agc        2871
Lys Cys Lys Ala Cys Ala Cys Asn Tyr Gly Thr Val Gln Gln Gln Ser
    880                 885                 890 agc tgt aac ccg gtg acc gga caa tgc cag tgt ctg cct cat gtg tct        2919
Ser Cys Asn Pro Val Thr Gly Gln Cys Gln Cys Leu Pro His Val Ser
895                 900                 905 ggc cgc gac tgc ggt act tgt gac cct ggc tac tac aac ctg cag agc        2967
Gly Arg Asp Cys Gly Thr Cys Asp Pro Gly Tyr Tyr Asn Leu Gln Ser
910                 915                 920                 925 ggg caa ggc tgc gag agg tgt gac tgc cat gct ttg ggt tcc acc aat        3015
Gly Gln Gly Cys Glu Arg Cys Asp Cys His Ala Leu Gly Ser Thr Asn
                930                 935                 940 ggg cag tgt gac atc cgc acc ggg cag tgt gag tgc cag cct ggc atc        3063
Gly Gln Cys Asp Ile Arg Thr Gly Gln Cys Glu Cys Gln Pro Gly Ile
            945                 950                 955 acc ggt cag cac tgt gag cgc tgt gag acc aac cac ttt ggg ttt gga        3111
Thr Gly Gln His Cys Glu Arg Cys Glu Thr Asn His Phe Gly Phe Gly
    960                 965                 970 cct gaa ggc tgc aaa cct tgt gac tgt cac cat gaa gga tcc ctt tcg        3159
Pro Glu Gly Cys Lys Pro Cys Asp Cys His His Glu Gly Ser Leu Ser
975                 980                 985 ctc cag tgt aaa gac gac ggc cgt tgt gaa tgc agg gaa ggc ttt gtg        3207
Leu Gln Cys Lys Asp Asp Gly Arg Cys Glu Cys Arg Glu Gly Phe Val
990                 995                 1000                1005 ggc aat cgc tgt gac cag tgt gaa gag aac tat ttc tac aat cgg tcc        3255
Gly Asn Arg Cys Asp Gln Cys Glu Glu Asn Tyr Phe Tyr Asn Arg Ser
                1010                1015                1020
```

-continued

```
tgg cct ggc tgc cag gag tgt ccg gct tgt tac cga ctt gtg aag gat     3303
Trp Pro Gly Cys Gln Glu Cys Pro Ala Cys Tyr Arg Leu Val Lys Asp
        1025                1030                1035 aag gct gct gag cat cga gtg aaa ctc cag gag tta gag agc ctc atc     3351
Lys Ala Ala Glu His Arg Val Lys Leu Gln Glu Leu Glu Ser Leu Ile
    1040                1045                1050 gcc aac ctt ggc act ggg gat gac atg gtg aca gat caa gcc ttt gag     3399
Ala Asn Leu Gly Thr Gly Asp Asp Met Val Thr Asp Gln Ala Phe Glu
1055                1060                1065 gac aga ctt aag gaa gca gaa agg gag gtg aca gac ctt ctc cgt gag     3447
Asp Arg Leu Lys Glu Ala Glu Arg Glu Val Thr Asp Leu Leu Arg Glu
1070                1075                1080                1085 gct cag gaa gtc aaa gat gta gat caa aat ctg atg gat cgc ctt cag     3495
Ala Gln Glu Val Lys Asp Val Asp Gln Asn Leu Met Asp Arg Leu Gln
        1090                1095                1100 aga gta aat agc agc ctg cat agc caa att agc cga ctg cag aat atc     3543
Arg Val Asn Ser Ser Leu His Ser Gln Ile Ser Arg Leu Gln Asn Ile
            1105                1110                1115 cgg aat act atc gaa gag acc ggg atc ttg gct gag cga gca cgg tcc     3591
Arg Asn Thr Ile Glu Glu Thr Gly Ile Leu Ala Glu Arg Ala Arg Ser
    1120                1125                1130 cga gtg gag agt aca gag cag ctg att gag atc gcc tcc agg gag ctc     3639
Arg Val Glu Ser Thr Glu Gln Leu Ile Glu Ile Ala Ser Arg Glu Leu
        1135                1140                1145 gag aaa gca aaa atg gcc gcc aat gtg tca atc act cag cca gag tct     3687
Glu Lys Ala Lys Met Ala Ala Asn Val Ser Ile Thr Gln Pro Glu Ser
1150                1155                1160                1165 aca ggg gag cca aac aac atg acc ctc ttg gca gaa gaa gcc cga agg     3735
Thr Gly Glu Pro Asn Asn Met Thr Leu Leu Ala Glu Glu Ala Arg Arg
            1170                1175                1180 ctt gca gag cgt cat aaa cag gaa gcc gat gac att gta cga gtg gca     3783
Leu Ala Glu Arg His Lys Gln Glu Ala Asp Asp Ile Val Arg Val Ala
        1185                1190                1195 aag aca gcc aac gag act tca gct gag gca tat aat ctg ctt ttg agg     3831
Lys Thr Ala Asn Glu Thr Ser Ala Glu Ala Tyr Asn Leu Leu Leu Arg
    1200                1205                1210 acc ctg gca gga gaa aat caa act gcg ctg gag att gaa gaa ctt aac     3879
Thr Leu Ala Gly Glu Asn Gln Thr Ala Leu Glu Ile Glu Glu Leu Asn
1215                1220                1225 cgg aag tac gaa caa gca aag aac atc tct cag gac ctg gag aag cag     3927
Arg Lys Tyr Glu Gln Ala Lys Asn Ile Ser Gln Asp Leu Glu Lys Gln
1230                1235                1240                1245 gct gcc cga gtc cat gag gaa gcc aag cgt gca ggt gac aaa gcc gta     3975
Ala Ala Arg Val His Glu Glu Ala Lys Arg Ala Gly Asp Lys Ala Val
        1250                1255                1260 gag atc tat gcc agt gtg gcc cag ctg acc cct gtg gac tct gag gcc     4023
Glu Ile Tyr Ala Ser Val Ala Gln Leu Thr Pro Val Asp Ser Glu Ala
            1265                1270                1275 ctg gag aat gaa gca aat aaa atc aag aaa gaa gct gca gac ctg gac     4071
Leu Glu Asn Glu Ala Asn Lys Ile Lys Lys Glu Ala Ala Asp Leu Asp
        1280                1285                1290 cgt ctg att gac cag aag cta aag gat tac gag gac ctc agg gaa gac     4119
Arg Leu Ile Asp Gln Lys Leu Lys Asp Tyr Glu Asp Leu Arg Glu Asp
    1295                1300                1305 atg aga gga aag gaa cat gaa gtg aag aac ctt cta gag aag ggg aaa     4167
Met Arg Gly Lys Glu His Glu Val Lys Asn Leu Leu Glu Lys Gly Lys
1310                1315                1320                1325 gct gaa cag cag acc gcc gac caa ctc cta gct cga gcc gat gct gcc     4215
Ala Glu Gln Gln Thr Ala Asp Gln Leu Leu Ala Arg Ala Asp Ala Ala
        1330                1335                1340
```

```
aag gcc ctt gct gaa gaa gct gct aag aag gga cgc agt acc tta caa      4263
Lys Ala Leu Ala Glu Glu Ala Ala Lys Lys Gly Arg Ser Thr Leu Gln
            1345                1350                1355 gaa gcc aat gac att ctc aac aac ctg aaa gat ttt gat aga cgt gtg      4311
Glu Ala Asn Asp Ile Leu Asn Asn Leu Lys Asp Phe Asp Arg Arg Val
1360                1365                1370 aac gat aac aag aca gcc gcg gaa gaa gct cta agg aga att ccc gcc      4359
Asn Asp Asn Lys Thr Ala Ala Glu Glu Ala Leu Arg Arg Ile Pro Ala
        1375                1380                1385 atc aac cgg acc ata gct gaa gcc aat gag aag aca agg gag gcc cag      4407
Ile Asn Arg Thr Ile Ala Glu Ala Asn Glu Lys Thr Arg Glu Ala Gln
    1390                1395                1400                1405 cta gcg ctg ggc aat gct gcc gct gac gcc acg gag gcc aag aac aag      4455
Leu Ala Leu Gly Asn Ala Ala Ala Asp Ala Thr Glu Ala Lys Asn Lys
                1410                1415                1420 gcc cat gag gca gag agg atc gcc agc gcc gcg cag aag aat gcc acc      4503
Ala His Glu Ala Glu Arg Ile Ala Ser Ala Ala Gln Lys Asn Ala Thr
            1425                1430                1435 agt acc aag gcg gac gca gaa aga acc ttc ggg gaa gtt aca gat ctg      4551
Ser Thr Lys Ala Asp Ala Glu Arg Thr Phe Gly Glu Val Thr Asp Leu
        1440                1445                1450 gat aat gag gtg aac ggt atg ctg agg cag cta gag gag gca gag aat      4599
Asp Asn Glu Val Asn Gly Met Leu Arg Gln Leu Glu Glu Ala Glu Asn
    1455                1460                1465 gag ctg aag agg aag caa gat gac gcc gac cag gac atg atg atg gcg      4647
Glu Leu Lys Arg Lys Gln Asp Asp Ala Asp Gln Asp Met Met Met Ala
1470                1475                1480                1485 ggg atg gct tcg caa gcc gct cag gag gct gag ctc aat gcc aga aag      4695
Gly Met Ala Ser Gln Ala Ala Gln Glu Ala Glu Leu Asn Ala Arg Lys
                1490                1495                1500 gcc aaa aac tct gtc agc agc ctc ctc agc cag ctg aac aac ctc ttg      4743
Ala Lys Asn Ser Val Ser Ser Leu Leu Ser Gln Leu Asn Asn Leu Leu
            1505                1510                1515 gat cag cta gga cag ctg gac aca gtg gac ctg aac aag ctc aat gag      4791
Asp Gln Leu Gly Gln Leu Asp Thr Val Asp Leu Asn Lys Leu Asn Glu
        1520                1525                1530 atc gaa ggc tcc ctg aac aaa gcc aaa gac gaa atg aag gcc agc gac      4839
Ile Glu Gly Ser Leu Asn Lys Ala Lys Asp Glu Met Lys Ala Ser Asp
    1535                1540                1545 ctg gac agg aag gtg tct gac ctg gag agc gag gct cgg aag cag gaa      4887
Leu Asp Arg Lys Val Ser Asp Leu Glu Ser Glu Ala Arg Lys Gln Glu
1550                1555                1560                1565 gca gcc atc atg gac tat aac cgg gac ata gca gag atc att aag gat      4935
Ala Ala Ile Met Asp Tyr Asn Arg Asp Ile Ala Glu Ile Ile Lys Asp
                1570                1575                1580 att cac aac ctg gag gac atc aag aag acc cta cca acc ggc tgc ttc      4983
Ile His Asn Leu Glu Asp Ile Lys Lys Thr Leu Pro Thr Gly Cys Phe
            1585                1590                1595 aac acc ccg tct atc gag aag ccc tag tggcgagagg gctgtaaggc            5030
Asn Thr Pro Ser Ile Glu Lys Pro
        1600                1605 agtgtccctg acaggggacc ctgtgaggcc tcggtgcctt gacacaaaga ttacactttt    5090
cagaccccca cttctctgct gctctccatc actgtccttt tgacccaaga aaagtcagag    5150
tttaaagaga agcaagttaa acatctttaa ccaggaacaa agggttttgc ctaataaagt    5210
ctctcctcca cttctgtcag caccctaccg gaactttccc ttgtttgcct gaagtcacgg    5270
catcttccag gggcctaccc acatcatgtg aaccttttaa tgccagggca gacccagccc    5330
```

```
cctcccctct ctcaacacca gcaggaccta tctcagtact catgtttcta tgaaggaaat      5390
ctttggctcc tcatcgtagc attgagatgg ccagtatgtc cgctctgcat cttctgcctc      5450
ctctttgaaa ggaaataaac atcctcgtgc caaaggtatt ggtcatttag aatagtggtg      5510
gccatccatc agacatgctg gctggctgag cataggacac agagccgtcg tgggtgagcg      5570
tagttacatg tgggtcccca ggagaacatg gctcaaagat gcttagggtt cctcctgttt      5630
tcattgacta ggaagatgaa tgtttcccaa atcctcaggc agctgataaa aagtctggat      5690
gggcagctcg cacgcaccac tacgtgaggt agcttttgat attttttataa gcaggactta      5750 atgcagaaga aacagatgtg ataaccactc aagttttttt ccccaagtag tactaattct      5810
taaagctttg ttagtgttag tcttggaact gttggtaaga tagctgtcaa acagttgtc       5870 ctctaaggtc atgaccaatg aaagaagagc aaatctcctt ttccccatat tttctgggaa      5930
gtggctgtaa tcgggatgta accgctctca ttaggattcc atgagtgcat ttctttttct      5990 cttttttcttg gagagagatg tgacgtttgg cccttagctc cattctcttc tgatgtttcc      6050
gttcttctta gaactcttca gagcacatcg ttgtttgcca ggtcctggtg gcaaacaccc      6110
gctcacagtg tttctcaagg ctgccaaccc catctagttc ctgcactttg tcggtccgcc      6170
cactccaagc ctttcctctg tgtggagagg gaagatccat acgtggcatt tcctagtggg      6230
cttctcaacc tctgatcctc agctcggtgg tctccttaag accacactgt gacagttccc      6290
tgccacacat cccctttcctc ctacctacct gcctctgaga ttcatattta gcctttaaca      6350
ctatgcaatt ttgtactttg cgtacggggg gaaagaaact attatctgac acactggtgc      6410
tattatttga aatttatatt ttttgtgtga atggattttg tttatcatga ttatagagta      6470
aggaatttat gtaaatatcc ccggtcctcc tagaacggca ctgtctgctc acgtctctgc      6530
tcagttgtcc ctctcactgg cacaggaacc tgtaccatgc ctggtcacgt cgtgcctggt      6590
ccccagtgtt ttgctccacc tctgccttgt gtttgcagca ccttcactgt ctgaccggaa      6650
gcctgctcac ctccacaact tgactgaaga gggccctctt ccccgtggct ctgaccatct      6710
gagctgcagc tcctcaaggt tctcatgcct gcccggagca gtagccaagc tgacagggta      6770
aagggattag gaacgtttgt ttgtggaacc ttcccacacg ggtcagtttt ctaagggagc      6830
atgtgatgac tgaacacttg agggcatcag caccgtgcta ctgatgacag aggggaggct      6890
ctgttcagcc tgtctccatc tcggagattg ccacaaaatc tcagcttggc atcctccgag      6950
gccttttgtg ccacggcaag aaggcgtggc ctcaccaagt tcagtgctga ttggctagtt      7010
cctctattcc gagctcacca ccttaacatt ttggtcacag ttgcaagaaa atggctgaaa      7070
cagaccacca ccagcatcct ttgggtcaac tccactccag caggcccgag gcgctggtgg      7130
gtggggtgtt ttggtttgtt ttctccagct tttgtggtat attttttaaac agaattttat      7190 tttttaaaat gaaagttatt tacaagatga taccttatta cgctccttcg acacagccat      7250
tgctttattg tatagttcca ataatctgta ttttatgtaa tgaaatggac agaatggctg      7310
ctgtagaatg cggggtgccg cacagaacag attgttttat ccctcccccg ccccgcccca      7370
tggaattttc ctttgattcc aactgtggcc cttttcaatg tgccttcact ttagctgttt      7430
gccttaatct ctacagcctt cccccctcag ggagggcaat aaagcgcaac acttggcatt      7490
tttttatgtt taaaagaaa acagtatttt atttataata aaatctgaat atttgtaacc       7550
cttt                                                                   7554
```

<210> SEQ ID NO 26
<211> LENGTH: 1605

```
<212> TYPE: PRT
<213> ORGANISM: Mus musculus

<400> SEQUENCE: 26

Met Thr Gly Gly Gly Arg Ala Ala Leu Ala Leu Gln Pro Arg Gly Arg
 1               5                  10                  15

Leu Trp Pro Leu Leu Ala Val Leu Ala Ala Val Ala Gly Cys Val Arg
            20                  25                  30

Ala Ala Met Asp Glu Cys Ala Asp Glu Gly Gly Arg Pro Gln Arg Cys
        35                  40                  45

Met Pro Glu Phe Val Asn Ala Ala Phe Asn Val Thr Val Ala Thr
    50                  55                  60

Asn Thr Cys Gly Thr Pro Pro Glu Glu Tyr Cys Val Gln Thr Gly Val
65                  70                  75                  80

Thr Gly Val Thr Lys Ser Cys His Leu Cys Asp Ala Gly Gln Gln His
                85                  90                  95

Leu Gln His Gly Ala Ala Phe Leu Thr Asp Tyr Asn Asn Gln Ala Asp
            100                 105                 110

Thr Thr Trp Trp Gln Ser Gln Thr Met Leu Ala Gly Val Gln Tyr Pro
        115                 120                 125

Asn Ser Ile Asn Leu Thr Leu His Leu Gly Lys Ala Phe Asp Ile Thr
    130                 135                 140

Tyr Val Arg Leu Lys Phe His Thr Ser Arg Pro Glu Ser Phe Ala Ile
145                 150                 155                 160

Tyr Lys Arg Thr Arg Glu Asp Gly Pro Trp Ile Pro Tyr Gln Tyr Tyr
                165                 170                 175

Ser Gly Ser Cys Glu Asn Thr Tyr Ser Lys Ala Asn Arg Gly Phe Ile
            180                 185                 190

Arg Thr Gly Gly Asp Glu Gln Gln Ala Leu Cys Thr Asp Glu Phe Ser
        195                 200                 205

Asp Ile Ser Pro Leu Thr Gly Gly Asn Val Ala Phe Ser Thr Leu Glu
    210                 215                 220

Gly Arg Pro Ser Ala Tyr Asn Phe Asp Asn Ser Pro Val Leu Gln Glu
225                 230                 235                 240

Trp Val Thr Ala Thr Asp Ile Arg Val Thr Leu Asn Arg Leu Asn Thr
                245                 250                 255

Phe Gly Asp Glu Val Phe Asn Asp Pro Lys Val Leu Lys Ser Tyr Tyr
            260                 265                 270

Tyr Ala Ile Ser Asp Phe Ala Val Gly Gly Arg Cys Lys Cys Asn Gly
        275                 280                 285

His Ala Ser Glu Cys Val Lys Asn Glu Phe Asp Lys Leu Met Cys Asn
    290                 295                 300

Cys Lys His Asn Thr Tyr Gly Val Asp Cys Glu Lys Cys Leu Pro Phe
305                 310                 315                 320

Phe Asn Asp Arg Pro Trp Arg Arg Ala Thr Ala Glu Ser Ala Ser Glu
                325                 330                 335

Cys Leu Pro Cys Asp Cys Asn Gly Arg Ser Gln Glu Cys Tyr Phe Asp
            340                 345                 350

Pro Glu Leu Tyr Arg Ser Thr Gly His Gly Gly His Cys Thr Asn Cys
        355                 360                 365

Arg Asp Asn Thr Asp Gly Ala Lys Cys Glu Arg Cys Arg Glu Asn Phe
    370                 375                 380

Phe Arg Leu Gly Asn Thr Glu Ala Cys Ser Pro Cys His Cys Ser Pro
385                 390                 395                 400
```

-continued

```
Val Gly Ser Leu Ser Thr Gln Cys Asp Ser Tyr Gly Arg Cys Ser Cys
            405                 410                 415
Lys Pro Gly Val Met Gly Asp Lys Cys Asp Arg Cys Gln Pro Gly Phe
            420                 425                 430
His Ser Leu Thr Glu Ala Gly Cys Arg Pro Cys Ser Cys Asp Pro Ser
            435                 440                 445
Gly Ser Thr Asp Glu Cys Asn Val Glu Thr Gly Arg Cys Val Cys Lys
            450                 455                 460
Asp Asn Val Glu Gly Phe Asn Cys Glu Arg Cys Lys Pro Gly Phe Phe
465                 470                 475                 480
Asn Leu Glu Ser Ser Asn Pro Lys Gly Cys Thr Pro Cys Phe Cys Phe
            485                 490                 495
Gly His Ser Ser Val Cys Thr Asn Ala Val Gly Tyr Ser Val Tyr Asp
            500                 505                 510
Ile Ser Ser Thr Phe Gln Ile Asp Glu Asp Gly Trp Arg Val Glu Gln
            515                 520                 525
Arg Asp Gly Ser Glu Ala Ser Leu Glu Trp Ser Ser Asp Arg Gln Tyr
            530                 535                 540
Ile Ala Val Ile Ser Asp Ser Tyr Phe Pro Arg Tyr Phe Ile Ala Pro
545                 550                 555                 560
Val Lys Phe Leu Gly Asn Gln Val Leu Ser Tyr Gly Gln Asn Leu Ser
            565                 570                 575
Phe Ser Phe Arg Val Asp Arg Arg Asp Thr Arg Leu Ser Ala Glu Asp
            580                 585                 590
Leu Val Leu Glu Gly Ala Gly Leu Arg Val Ser Val Pro Leu Ile Ala
            595                 600                 605
Gln Gly Asn Ser Tyr Pro Ser Glu Thr Thr Val Lys Tyr Ile Phe Arg
            610                 615                 620
Leu His Glu Ala Thr Asp Tyr Pro Trp Arg Pro Ala Leu Ser Pro Phe
625                 630                 635                 640
Glu Phe Gln Lys Leu Leu Asn Asn Leu Thr Ser Ile Lys Ile Arg Gly
            645                 650                 655
Thr Tyr Ser Glu Arg Ser Ala Gly Tyr Leu Asp Asp Val Thr Leu Gln
            660                 665                 670
Ser Ala Arg Pro Gly Pro Gly Val Pro Ala Thr Trp Val Glu Ser Cys
            675                 680                 685
Thr Cys Pro Val Gly Tyr Gly Gly Gln Phe Cys Glu Thr Cys Leu Pro
            690                 695                 700
Gly Tyr Arg Arg Glu Thr Pro Ser Leu Gly Pro Tyr Ser Pro Cys Val
705                 710                 715                 720
Leu Cys Thr Cys Asn Gly His Ser Glu Thr Cys Asp Pro Glu Thr Gly
            725                 730                 735
Val Cys Asp Cys Arg Asp Asn Thr Ala Gly Pro His Cys Glu Lys Cys
            740                 745                 750
Ser Asp Gly Tyr Tyr Gly Asp Ser Thr Leu Gly Thr Ser Ser Asp Cys
            755                 760                 765
Gln Pro Cys Pro Cys Pro Gly Gly Ser Ser Cys Ala Ile Val Pro Lys
            770                 775                 780
Thr Lys Glu Val Val Cys Thr His Cys Pro Thr Gly Thr Ala Gly Lys
785                 790                 795                 800
Arg Cys Glu Leu Cys Asp Asp Gly Tyr Phe Gly Asp Pro Leu Gly Ser
            805                 810                 815
```

-continued

```
Asn Gly Pro Val Arg Leu Cys Arg Pro Cys Gln Cys Asn Asp Asn Ile
            820                 825                 830

Asp Pro Asn Ala Val Gly Asn Cys Asn Arg Leu Thr Gly Glu Cys Leu
            835                 840                 845

Lys Cys Ile Tyr Asn Thr Ala Gly Phe Tyr Cys Asp Arg Cys Lys Glu
            850                 855                 860

Gly Phe Phe Gly Asn Pro Leu Ala Pro Asn Pro Ala Asp Lys Cys Lys
865                 870                 875                 880

Ala Cys Ala Cys Asn Tyr Gly Thr Val Gln Gln Gln Ser Ser Cys Asn
                    885                 890                 895

Pro Val Thr Gly Gln Cys Gln Cys Leu Pro His Val Ser Gly Arg Asp
                    900                 905                 910

Cys Gly Thr Cys Asp Pro Gly Tyr Tyr Asn Leu Gln Ser Gly Gln Gly
            915                 920                 925

Cys Glu Arg Cys Asp Cys His Ala Leu Gly Ser Thr Asn Gly Gln Cys
            930                 935                 940

Asp Ile Arg Thr Gly Gln Cys Glu Cys Gln Pro Gly Ile Thr Gly Gln
945                 950                 955                 960

His Cys Glu Arg Cys Glu Thr Asn His Phe Gly Phe Gly Pro Glu Gly
                    965                 970                 975

Cys Lys Pro Cys Asp Cys His Glu Gly Ser Leu Ser Leu Gln Cys
                    980                 985                 990

Lys Asp Asp Gly Arg Cys Glu Cys Arg Glu Gly Phe Val Gly Asn Arg
            995                 1000                1005

Cys Asp Gln Cys Glu Glu Asn Tyr Phe Tyr Asn Arg Ser Trp Pro Gly
    1010                1015                1020

Cys Gln Glu Cys Pro Ala Cys Tyr Arg Leu Val Lys Asp Lys Ala Ala
1025                1030                1035                1040

Glu His Arg Val Lys Leu Gln Glu Leu Glu Ser Leu Ile Ala Asn Leu
            1045                1050                1055

Gly Thr Gly Asp Asp Met Val Thr Asp Gln Ala Phe Glu Asp Arg Leu
            1060                1065                1070

Lys Glu Ala Glu Arg Glu Val Thr Asp Leu Leu Arg Glu Ala Gln Glu
        1075                1080                1085

Val Lys Asp Val Asp Gln Asn Leu Met Asp Arg Leu Gln Arg Val Asn
    1090                1095                1100

Ser Ser Leu His Ser Gln Ile Ser Arg Leu Gln Asn Ile Arg Asn Thr
1105                1110                1115                1120

Ile Glu Glu Thr Gly Ile Leu Ala Glu Arg Ala Arg Ser Arg Val Glu
            1125                1130                1135

Ser Thr Glu Gln Leu Ile Glu Ile Ala Ser Arg Glu Leu Glu Lys Ala
        1140                1145                1150

Lys Met Ala Ala Asn Val Ser Ile Thr Gln Pro Glu Ser Thr Gly Glu
        1155                1160                1165

Pro Asn Asn Met Thr Leu Leu Ala Glu Glu Ala Arg Arg Leu Ala Glu
    1170                1175                1180

Arg His Lys Gln Glu Ala Asp Asp Ile Val Arg Val Ala Lys Thr Ala
1185                1190                1195                1200

Asn Glu Thr Ser Ala Glu Ala Tyr Asn Leu Leu Leu Arg Thr Leu Ala
            1205                1210                1215

Gly Glu Asn Gln Thr Ala Leu Glu Ile Glu Glu Leu Asn Arg Lys Tyr
            1220                1225                1230

Glu Gln Ala Lys Asn Ile Ser Gln Asp Leu Glu Lys Gln Ala Ala Arg
```

```
                    1235                1240                1245
Val His Glu Ala Lys Arg Ala Gly Asp Lys Ala Val Glu Ile Tyr
        1250                1255                1260

Ala Ser Val Ala Gln Leu Thr Pro Val Asp Ser Glu Ala Leu Glu Asn
1265                1270                1275                1280

Glu Ala Asn Lys Ile Lys Lys Glu Ala Ala Asp Leu Asp Arg Leu Ile
            1285                1290                1295

Asp Gln Lys Leu Lys Asp Tyr Glu Asp Leu Arg Glu Asp Met Arg Gly
        1300                1305                1310

Lys Glu His Glu Val Lys Asn Leu Leu Glu Lys Gly Lys Ala Glu Gln
    1315                1320                1325

Gln Thr Ala Asp Gln Leu Leu Ala Arg Ala Asp Ala Ala Lys Ala Leu
1330                1335                1340

Ala Glu Glu Ala Ala Lys Lys Gly Arg Ser Thr Leu Gln Glu Ala Asn
1345                1350                1355                1360

Asp Ile Leu Asn Asn Leu Lys Asp Phe Asp Arg Arg Val Asn Asp Asn
            1365                1370                1375

Lys Thr Ala Ala Glu Glu Ala Leu Arg Arg Ile Pro Ala Ile Asn Arg
        1380                1385                1390

Thr Ile Ala Glu Ala Asn Glu Lys Thr Arg Glu Ala Gln Leu Ala Leu
    1395                1400                1405

Gly Asn Ala Ala Ala Asp Ala Thr Glu Ala Lys Asn Lys Ala His Glu
1410                1415                1420

Ala Glu Arg Ile Ala Ser Ala Ala Gln Lys Asn Ala Thr Ser Thr Lys
1425                1430                1435                1440

Ala Asp Ala Glu Arg Thr Phe Gly Glu Val Thr Asp Leu Asp Asn Glu
            1445                1450                1455

Val Asn Gly Met Leu Arg Gln Leu Glu Glu Ala Glu Asn Glu Leu Lys
        1460                1465                1470

Arg Lys Gln Asp Asp Ala Asp Gln Asp Met Met Met Ala Gly Met Ala
    1475                1480                1485

Ser Gln Ala Ala Gln Glu Ala Glu Leu Asn Ala Arg Lys Ala Lys Asn
1490                1495                1500

Ser Val Ser Ser Leu Leu Ser Gln Leu Asn Asn Leu Leu Asp Gln Leu
1505                1510                1515                1520

Gly Gln Leu Asp Thr Val Asp Leu Asn Lys Leu Asn Glu Ile Glu Gly
            1525                1530                1535

Ser Leu Asn Lys Ala Lys Asp Glu Met Lys Ala Ser Asp Leu Asp Arg
        1540                1545                1550

Lys Val Ser Asp Leu Glu Ser Glu Ala Arg Lys Gln Glu Ala Ala Ile
    1555                1560                1565

Met Asp Tyr Asn Arg Asp Ile Ala Glu Ile Ile Lys Asp Ile His Asn
    1570                1575                1580

Leu Glu Asp Ile Lys Lys Thr Leu Pro Thr Gly Cys Phe Asn Thr Pro
1585                1590                1595                1600

Ser Ile Glu Lys Pro
            1605

<210> SEQ ID NO 27
<211> LENGTH: 7263
<212> TYPE: DNA
<213> ORGANISM: Mus musculus
<220> FEATURE:
<221> NAME/KEY: CDS
<222> LOCATION: (1)..(4716)
```

<400> SEQUENCE: 27

| | | | | | | | | | | | | | | | | |
|---|---|---|---|---|---|---|---|---|---|---|---|---|---|---|---|---|
| gcc | atg | gac | gag | tgc | gcg | gat | gag | ggc | ggg | cgg | ccg | cag | cgc | tgc | atg | 48 |
| Ala | Met | Asp | Glu | Cys | Ala | Asp | Glu | Gly | Gly | Arg | Pro | Gln | Arg | Cys | Met | |
| 1 | | | | 5 | | | | | 10 | | | | | 15 | | |
| ccg | gag | ttt | gtt | aat | gcc | gcc | ttc | aat | gtg | acc | gtg | gtg | gct | acc | aac | 96 |
| Pro | Glu | Phe | Val | Asn | Ala | Ala | Phe | Asn | Val | Thr | Val | Val | Ala | Thr | Asn | |
| | | | 20 | | | | | 25 | | | | | 30 | | | |
| acg | tgt | ggg | act | ccg | ccc | gag | gag | tac | tgc | gtg | cag | act | ggg | gtg | acc | 144 |
| Thr | Cys | Gly | Thr | Pro | Pro | Glu | Glu | Tyr | Cys | Val | Gln | Thr | Gly | Val | Thr | |
| | | 35 | | | | | 40 | | | | | 45 | | | | |
| gga | gtc | act | aag | tcc | tgt | cac | ctg | tgc | gac | gcc | ggc | cag | cag | cac | ctg | 192 |
| Gly | Val | Thr | Lys | Ser | Cys | His | Leu | Cys | Asp | Ala | Gly | Gln | Gln | His | Leu | |
| | 50 | | | | | 55 | | | | | 60 | | | | | |
| caa | cac | ggg | gca | gcc | ttc | ctg | acc | gac | tac | aac | aac | cag | gcc | gac | acc | 240 |
| Gln | His | Gly | Ala | Ala | Phe | Leu | Thr | Asp | Tyr | Asn | Asn | Gln | Ala | Asp | Thr | |
| 65 | | | | | 70 | | | | | 75 | | | | | 80 | |
| acc | tgg | tgg | caa | agc | cag | act | atg | ctg | gcc | ggg | gtg | cag | tac | ccc | aac | 288 |
| Thr | Trp | Trp | Gln | Ser | Gln | Thr | Met | Leu | Ala | Gly | Val | Gln | Tyr | Pro | Asn | |
| | | | | 85 | | | | | 90 | | | | | 95 | | |
| tcc | atc | aac | ctc | acg | ctg | cac | ctg | gga | aag | gct | ttt | gac | atc | act | tac | 336 |
| Ser | Ile | Asn | Leu | Thr | Leu | His | Leu | Gly | Lys | Ala | Phe | Asp | Ile | Thr | Tyr | |
| | | | 100 | | | | | 105 | | | | | 110 | | | |
| gtg | cgc | ctc | aag | ttc | cac | acc | agc | cgt | cca | gag | agc | ttc | gcc | atc | tat | 384 |
| Val | Arg | Leu | Lys | Phe | His | Thr | Ser | Arg | Pro | Glu | Ser | Phe | Ala | Ile | Tyr | |
| | | 115 | | | | | 120 | | | | | 125 | | | | |
| aag | cgc | act | cgg | gaa | gac | ggg | ccc | tgg | att | cct | tat | cag | tac | tac | agt | 432 |
| Lys | Arg | Thr | Arg | Glu | Asp | Gly | Pro | Trp | Ile | Pro | Tyr | Gln | Tyr | Tyr | Ser | |
| | 130 | | | | | 135 | | | | | 140 | | | | | |
| ggg | tcc | tgt | gag | aac | acg | tac | tca | aag | gct | aac | cgt | ggc | ttc | atc | agg | 480 |
| Gly | Ser | Cys | Glu | Asn | Thr | Tyr | Ser | Lys | Ala | Asn | Arg | Gly | Phe | Ile | Arg | |
| 145 | | | | | 150 | | | | | 155 | | | | | 160 | |
| acc | gga | ggg | gac | gag | cag | cag | gcc | ttg | tgt | act | gat | gaa | ttc | agt | gac | 528 |
| Thr | Gly | Gly | Asp | Glu | Gln | Gln | Ala | Leu | Cys | Thr | Asp | Glu | Phe | Ser | Asp | |
| | | | | 165 | | | | | 170 | | | | | 175 | | |
| att | tcc | ccc | ctc | acc | ggt | ggc | aac | gtg | gcc | ttt | tca | acc | ctg | gaa | gga | 576 |
| Ile | Ser | Pro | Leu | Thr | Gly | Gly | Asn | Val | Ala | Phe | Ser | Thr | Leu | Glu | Gly | |
| | | | 180 | | | | | 185 | | | | | 190 | | | |
| cgg | ccg | agt | gcc | tac | aac | ttt | gac | aac | agc | cct | gtg | ctc | cag | gaa | tgg | 624 |
| Arg | Pro | Ser | Ala | Tyr | Asn | Phe | Asp | Asn | Ser | Pro | Val | Leu | Gln | Glu | Trp | |
| | | 195 | | | | | 200 | | | | | 205 | | | | |
| gta | act | gcc | act | gac | atc | aga | gtg | acg | ctc | aat | cgc | ctg | aac | acc | ttt | 672 |
| Val | Thr | Ala | Thr | Asp | Ile | Arg | Val | Thr | Leu | Asn | Arg | Leu | Asn | Thr | Phe | |
| | 210 | | | | | 215 | | | | | 220 | | | | | |
| gga | gat | gaa | gtg | ttt | aac | gac | ccc | aaa | gtt | ctc | aag | tct | tac | tat | tac | 720 |
| Gly | Asp | Glu | Val | Phe | Asn | Asp | Pro | Lys | Val | Leu | Lys | Ser | Tyr | Tyr | Tyr | |
| 225 | | | | | 230 | | | | | 235 | | | | | 240 | |
| gca | atc | tca | gac | ttt | gct | gtg | ggc | ggc | agg | tgt | aaa | tgt | aac | gga | cat | 768 |
| Ala | Ile | Ser | Asp | Phe | Ala | Val | Gly | Gly | Arg | Cys | Lys | Cys | Asn | Gly | His | |
| | | | | 245 | | | | | 250 | | | | | 255 | | |
| gcc | agc | gag | tgt | gta | aag | aac | gag | ttt | gac | aaa | ctc | atg | tgc | aac | tgc | 816 |
| Ala | Ser | Glu | Cys | Val | Lys | Asn | Glu | Phe | Asp | Lys | Leu | Met | Cys | Asn | Cys | |
| | | | 260 | | | | | 265 | | | | | 270 | | | |
| aaa | cat | aac | aca | tac | gga | gtt | gac | tgt | gaa | aag | tgc | ctg | cct | ttc | ttc | 864 |
| Lys | His | Asn | Thr | Tyr | Gly | Val | Asp | Cys | Glu | Lys | Cys | Leu | Pro | Phe | Phe | |
| | | 275 | | | | | 280 | | | | | 285 | | | | |
| aat | gac | cgg | ccg | tgg | agg | agg | gcg | act | gct | gag | agc | gcc | agc | gag | tgc | 912 |
| Asn | Asp | Arg | Pro | Trp | Arg | Arg | Ala | Thr | Ala | Glu | Ser | Ala | Ser | Glu | Cys | |
| | 290 | | | | | 295 | | | | | 300 | | | | | |

| | |
|---|---|
| ctt cct tgt gac tgc aat ggc cga tcc caa gag tgc tac ttt gat cct<br>Leu Pro Cys Asp Cys Asn Gly Arg Ser Gln Glu Cys Tyr Phe Asp Pro<br>305                     310                     315                   320 | 960 |
| gaa cta tac cgt tcc act gga cat ggt ggc cac tgt acc aac tgc cgg<br>Glu Leu Tyr Arg Ser Thr Gly His Gly Gly His Cys Thr Asn Cys Arg<br>                     325                     330                   335 | 1008 |
| gat aac aca gat ggt gcc aag tgc gag agg tgc cgg gag aat ttc ttc<br>Asp Asn Thr Asp Gly Ala Lys Cys Glu Arg Cys Arg Glu Asn Phe Phe<br>                 340                     345                   350 | 1056 |
| cgc ctg ggg aac act gaa gcc tgc tct ccg tgc cac tgc agc cct gtt<br>Arg Leu Gly Asn Thr Glu Ala Cys Ser Pro Cys His Cys Ser Pro Val<br>             355                     360                   365 | 1104 |
| ggt tct ctc agc aca cag tgt gac agt tac ggc aga tgc agc tgt aag<br>Gly Ser Leu Ser Thr Gln Cys Asp Ser Tyr Gly Arg Cys Ser Cys Lys<br>370                     375                     380 | 1152 |
| cca gga gtg atg ggt gac aag tgt gac cgt tgt cag cct ggg ttc cat<br>Pro Gly Val Met Gly Asp Lys Cys Asp Arg Cys Gln Pro Gly Phe His<br>385                     390                     395                   400 | 1200 |
| tcc ctc act gag gca gga tgc agg cca tgc tcc tgc gat cct tcg ggc<br>Ser Leu Thr Glu Ala Gly Cys Arg Pro Cys Ser Cys Asp Pro Ser Gly<br>                       405                     410                   415 | 1248 |
| agc aca gac gag tgt aat gtt gaa aca gga aga tgc gtt tgc aaa gac<br>Ser Thr Asp Glu Cys Asn Val Glu Thr Gly Arg Cys Val Cys Lys Asp<br>             420                     425                   430 | 1296 |
| aat gtt gaa ggc ttc aac tgt gag aga tgc aaa cct gga ttt ttt aat<br>Asn Val Glu Gly Phe Asn Cys Glu Arg Cys Lys Pro Gly Phe Phe Asn<br>435                     440                     445 | 1344 |
| ctg gag tca tct aat cct aag ggc tgc aca ccc tgc ttc tgc ttt ggc<br>Leu Glu Ser Ser Asn Pro Lys Gly Cys Thr Pro Cys Phe Cys Phe Gly<br>450                     455                     460 | 1392 |
| cat tct tct gtg tgc aca aat gct gtt ggc tac agt gtt tat gac atc<br>His Ser Ser Val Cys Thr Asn Ala Val Gly Tyr Ser Val Tyr Asp Ile<br>465                     470                     475                   480 | 1440 |
| tcc tcc acc ttt cag att gat gag gat ggg tgg cgc gtg gag cag aga<br>Ser Ser Thr Phe Gln Ile Asp Glu Asp Gly Trp Arg Val Glu Gln Arg<br>                     485                     490                   495 | 1488 |
| gat ggc tcg gag gcg tct ctg gag tgg tcc tca gac agg caa tat att<br>Asp Gly Ser Glu Ala Ser Leu Glu Trp Ser Ser Asp Arg Gln Tyr Ile<br>             500                     505                   510 | 1536 |
| gcc gta atc tca gac agt tac ttt cct aga tac ttc atc gcc cct gtg<br>Ala Val Ile Ser Asp Ser Tyr Phe Pro Arg Tyr Phe Ile Ala Pro Val<br>             515                     520                   525 | 1584 |
| aag ttc ctg ggc aac cag gtc ctg agt tat ggg cag aat ctt tcc ttc<br>Lys Phe Leu Gly Asn Gln Val Leu Ser Tyr Gly Gln Asn Leu Ser Phe<br>530                     535                     540 | 1632 |
| tcc ttc cga gtg gac aga cga gac act cgc ctc tcc gca gag gac ctt<br>Ser Phe Arg Val Asp Arg Arg Asp Thr Arg Leu Ser Ala Glu Asp Leu<br>545                     550                     555                   560 | 1680 |
| gtg ctc gaa gga gct ggc ttg aga gta ccg tgc ccc ttg atc gct cag<br>Val Leu Glu Gly Ala Gly Leu Arg Val Ser Val Pro Leu Ile Ala Gln<br>                     565                     570                   575 | 1728 |
| ggc aac tcc tac ccc agc gag acc act gtg aag tac atc ttc agg ctc<br>Gly Asn Ser Tyr Pro Ser Glu Thr Thr Val Lys Tyr Ile Phe Arg Leu<br>             580                     585                   590 | 1776 |
| cat gaa gca acg gat tac cct tgg agg ccc gct ctc tcc ccg ttt gaa<br>His Glu Ala Thr Asp Tyr Pro Trp Arg Pro Ala Leu Ser Pro Phe Glu<br>595                     600                     605 | 1824 |
| ttt cag aag ctc ctg aac aac ttg acc tct atc aag atc cgt ggt aca<br>Phe Gln Lys Leu Leu Asn Asn Leu Thr Ser Ile Lys Ile Arg Gly Thr<br>             610                     615                   620 | 1872 |

```
tac agc gag agg agc gct ggg tac ttg gat gat gtc acc ttg caa agt    1920
Tyr Ser Glu Arg Ser Ala Gly Tyr Leu Asp Asp Val Thr Leu Gln Ser
625                 630                 635                 640 gct cgc cct ggg ccc gga gtc cct gca acg tgg gtg gag tcc tgc acc    1968
Ala Arg Pro Gly Pro Gly Val Pro Ala Thr Trp Val Glu Ser Cys Thr
                645                 650                 655 tgt cca gtg gga tac ggg gga cag ttc tgt gag acg tgc ctc cca ggg    2016
Cys Pro Val Gly Tyr Gly Gly Gln Phe Cys Glu Thr Cys Leu Pro Gly
            660                 665                 670 tac aga aga gaa act cca agc ctt gga cct tat agc ccg tgt gtg ctc    2064
Tyr Arg Arg Glu Thr Pro Ser Leu Gly Pro Tyr Ser Pro Cys Val Leu
        675                 680                 685 tgt acc tgt aat ggg cac agt gag acc tgt gac ccg gag aca ggt gtc    2112
Cys Thr Cys Asn Gly His Ser Glu Thr Cys Asp Pro Glu Thr Gly Val
    690                 695                 700 tgt gac tgc aga gac aat aca gcc ggc ccc cac tgt gag aaa tgt agc    2160
Cys Asp Cys Arg Asp Asn Thr Ala Gly Pro His Cys Glu Lys Cys Ser
705                 710                 715                 720 gat ggg tac tat ggg gac tca acc ctg ggc acc tcc tct gac tgc cag    2208
Asp Gly Tyr Tyr Gly Asp Ser Thr Leu Gly Thr Ser Ser Asp Cys Gln
                725                 730                 735 cct tgt ccc tgc ccc ggt ggc tca agt tgt gcc att gtc cca aag aca    2256
Pro Cys Pro Cys Pro Gly Gly Ser Ser Cys Ala Ile Val Pro Lys Thr
            740                 745                 750 aag gaa gtg gtg tgc acg cac tgt ccg act ggc act gcc ggc aag aga    2304
Lys Glu Val Val Cys Thr His Cys Pro Thr Gly Thr Ala Gly Lys Arg
        755                 760                 765 tgt gaa ctc tgt gat gac ggc tac ttt gga gac cct ctg ggc agc aat    2352
Cys Glu Leu Cys Asp Asp Gly Tyr Phe Gly Asp Pro Leu Gly Ser Asn
    770                 775                 780 ggg ccc gtg aga ctg tgc cgc ccg tgc cag tgt aac gac aac ata gac    2400
Gly Pro Val Arg Leu Cys Arg Pro Cys Gln Cys Asn Asp Asn Ile Asp
785                 790                 795                 800 ccc aac gcg gtt ggc aac tgc aac cgc ctg acg ggc gag tgc ctg aag    2448
Pro Asn Ala Val Gly Asn Cys Asn Arg Leu Thr Gly Glu Cys Leu Lys
                805                 810                 815 tgc atc tat aac acg gct ggt ttc tac tgc gac cgg tgc aag gaa ggg    2496
Cys Ile Tyr Asn Thr Ala Gly Phe Tyr Cys Asp Arg Cys Lys Glu Gly
            820                 825                 830 ttt ttc gga aat ccc ctg gct ccc aat cca gcc gac aaa tgc aaa gcc    2544
Phe Phe Gly Asn Pro Leu Ala Pro Asn Pro Ala Asp Lys Cys Lys Ala
        835                 840                 845 tgc gcc tgc aac tac ggg aca gtg cag caa cag agc agc tgt aac ccg    2592
Cys Ala Cys Asn Tyr Gly Thr Val Gln Gln Gln Ser Ser Cys Asn Pro
    850                 855                 860 gtg acc gga caa tgc cag tgt ctg cct cat gtg tct ggc cgc gac tgc    2640
Val Thr Gly Gln Cys Gln Cys Leu Pro His Val Ser Gly Arg Asp Cys
865                 870                 875                 880 ggt act tgt gac cct ggc tac tac aac ctg cag agc ggg caa ggc tgc    2688
Gly Thr Cys Asp Pro Gly Tyr Tyr Asn Leu Gln Ser Gly Gln Gly Cys
                885                 890                 895 gag agg tgt gac tgc cat gct ttg ggt tcc acc aat ggg cag tgt gac    2736
Glu Arg Cys Asp Cys His Ala Leu Gly Ser Thr Asn Gly Gln Cys Asp
            900                 905                 910 atc cgc acc ggg cag tgt gag tgc cag cct ggc atc acc ggt cag cac    2784
Ile Arg Thr Gly Gln Cys Glu Cys Gln Pro Gly Ile Thr Gly Gln His
        915                 920                 925 tgt gag cgc tgt gag acc aac cac ttt ggg ttt gga cct gaa ggc tgc    2832
Cys Glu Arg Cys Glu Thr Asn His Phe Gly Phe Gly Pro Glu Gly Cys
```

```
                930               935               940
aaa cct tgt gac tgt cac cat gaa gga tcc ctt tcg ctc cag tgt aaa    2880
Lys Pro Cys Asp Cys His His Glu Gly Ser Leu Ser Leu Gln Cys Lys
945             950              955               960 gac gac ggc cgt tgt gaa tgc agg gaa ggc ttt gtg ggc aat cgc tgt    2928
Asp Asp Gly Arg Cys Glu Cys Arg Glu Gly Phe Val Gly Asn Arg Cys
            965              970               975 gac cag tgt gaa gag aac tat ttc tac aat cgg tcc tgg cct ggc tgc    2976
Asp Gln Cys Glu Glu Asn Tyr Phe Tyr Asn Arg Ser Trp Pro Gly Cys
        980              985               990 cag gag tgt ccg gct tgt tac cga ctt gtg aag gat aag gct gct gag    3024
Gln Glu Cys Pro Ala Cys Tyr Arg Leu Val Lys Asp Lys Ala Ala Glu
        995              1000              1005 cat cga gtg aaa ctc cag gag tta gag agc ctc atc gcc aac ctt ggc    3072
His Arg Val Lys Leu Gln Glu Leu Glu Ser Leu Ile Ala Asn Leu Gly
   1010              1015              1020 act ggg gat gac atg gtg aca gat caa gcc ttt gag gac aga ctt aag    3120
Thr Gly Asp Asp Met Val Thr Asp Gln Ala Phe Glu Asp Arg Leu Lys
1025            1030              1035              1040 gaa gca gaa agg gag gtg aca gac ctt ctc cgt gag gct cag gaa gtc    3168
Glu Ala Glu Arg Glu Val Thr Asp Leu Leu Arg Glu Ala Gln Glu Val
            1045              1050              1055 aaa gat gta gat caa aat ctg atg gat cgc ctt cag aga gta aat agc    3216
Lys Asp Val Asp Gln Asn Leu Met Asp Arg Leu Gln Arg Val Asn Ser
            1060              1065              1070 agc ctg cat agc caa att agc cga ctg cag aat atc cgg aat act atc    3264
Ser Leu His Ser Gln Ile Ser Arg Leu Gln Asn Ile Arg Asn Thr Ile
        1075             1080              1085 gaa gag acc ggg atc ttg gct gag cga gca cgg tcc cga gtg gag agt    3312
Glu Glu Thr Gly Ile Leu Ala Glu Arg Ala Arg Ser Arg Val Glu Ser
    1090             1095              1100 aca gag cag ctg att gag atc gcc tcc agg gag ctc gag aaa gca aaa    3360
Thr Glu Gln Leu Ile Glu Ile Ala Ser Arg Glu Leu Glu Lys Ala Lys
1105             1110              1115              1120 atg gcc gcc aat gtg tca atc act cag cca gag tct aca ggg gag cca    3408
Met Ala Ala Asn Val Ser Ile Thr Gln Pro Glu Ser Thr Gly Glu Pro
            1125              1130              1135 aac aac atg acc ctc ttg gca gaa gaa gcc cga agg ctt gca gag cgt    3456
Asn Asn Met Thr Leu Leu Ala Glu Glu Ala Arg Arg Leu Ala Glu Arg
        1140              1145              1150 cat aaa cag gaa gcc gat gac att gta cga gtg gca aag aca gcc aac    3504
His Lys Gln Glu Ala Asp Asp Ile Val Arg Val Ala Lys Thr Ala Asn
        1155              1160              1165 gag act tca gct gag gca tat aat ctg ctt ttg agg acc ctg gca gga    3552
Glu Thr Ser Ala Glu Ala Tyr Asn Leu Leu Leu Arg Thr Leu Ala Gly
    1170              1175              1180 gaa aat caa act gcg ctg gag att gaa gaa ctt aac cgg aag tac gaa    3600
Glu Asn Gln Thr Ala Leu Glu Ile Glu Glu Leu Asn Arg Lys Tyr Glu
1185             1190              1195              1200 caa gca aag aac atc tct cag gac ctg gag aag cag gct gcc cga gtc    3648
Gln Ala Lys Asn Ile Ser Gln Asp Leu Glu Lys Gln Ala Ala Arg Val
            1205              1210              1215 cat gag gaa gcc aag cgt gca ggt gac aaa gcc gta gag atc tat gcc    3696
His Glu Glu Ala Lys Arg Ala Gly Asp Lys Ala Val Glu Ile Tyr Ala
        1220              1225              1230 agt gtg gcc cag ctg acc cct gtg gac tct gag gcc ctg gag aat gaa    3744
Ser Val Ala Gln Leu Thr Pro Val Asp Ser Glu Ala Leu Glu Asn Glu
        1235              1240              1245 gca aat aaa atc aag aaa gaa gct gca gac ctg gac cgt ctg att gac    3792
```

```
Ala Asn Lys Ile Lys Lys Glu Ala Ala Asp Leu Asp Arg Leu Ile Asp
   1250                1255                1260 cag aag cta aag gat tac gag gac ctc agg gaa gac atg aga gga aag        3840
Gln Lys Leu Lys Asp Tyr Glu Asp Leu Arg Glu Asp Met Arg Gly Lys
1265                1270                1275                1280 gaa cat gaa gtg aag aac ctt cta gag aag ggg aaa gct gaa cag cag        3888
Glu His Glu Val Lys Asn Leu Leu Glu Lys Gly Lys Ala Glu Gln Gln
                1285                1290                1295 acc gcc gac caa ctc cta gct cga gcc gat gct gcc aag gcc ctt gct        3936
Thr Ala Asp Gln Leu Leu Ala Arg Ala Asp Ala Ala Lys Ala Leu Ala
        1300                1305                1310 gaa gaa gct gct aag aag gga cgc agt acc tta caa gaa gcc aat gac        3984
Glu Glu Ala Ala Lys Lys Gly Arg Ser Thr Leu Gln Glu Ala Asn Asp
    1315                1320                1325 att ctc aac aac ctg aaa gat ttt gat aga cgt gtg aac gat aac aag        4032
Ile Leu Asn Asn Leu Lys Asp Phe Asp Arg Arg Val Asn Asp Asn Lys
 1330                1335                1340 aca gcc gcg gaa gaa gct cta agg aga att ccc gcc atc aac cgg acc        4080
Thr Ala Ala Glu Glu Ala Leu Arg Arg Ile Pro Ala Ile Asn Arg Thr
1345                1350                1355                1360 ata gct gaa gcc aat gag aag aca agg gag gcc cag cta gcg ctg ggc        4128
Ile Ala Glu Ala Asn Glu Lys Thr Arg Glu Ala Gln Leu Ala Leu Gly
                1365                1370                1375 aat gct gcc gct gac gcc acg gag gcc aag aac aag gcc cat gag gca        4176
Asn Ala Ala Ala Asp Ala Thr Glu Ala Lys Asn Lys Ala His Glu Ala
        1380                1385                1390 gag agg atc gcc agc gcc gcg cag aag aat gcc acc agt acc aag gcg        4224
Glu Arg Ile Ala Ser Ala Ala Gln Lys Asn Ala Thr Ser Thr Lys Ala
    1395                1400                1405 gac gca gaa aga acc ttc ggg gaa gtt aca gat ctg gat aat gag gtg        4272
Asp Ala Glu Arg Thr Phe Gly Glu Val Thr Asp Leu Asp Asn Glu Val
 1410                1415                1420 aac ggt atg ctg agg cag cta gag gag gca gag aat gag ctg aag agg        4320
Asn Gly Met Leu Arg Gln Leu Glu Glu Ala Glu Asn Glu Leu Lys Arg
1425                1430                1435                1440 aag caa gat gac gcc gac cag gac atg atg atg gcg ggg atg gct tcg        4368
Lys Gln Asp Asp Ala Asp Gln Asp Met Met Met Ala Gly Met Ala Ser
                1445                1450                1455 caa gcc gct cag gag gct gag ctc aat gcc aga aag gcc aaa aac tct        4416
Gln Ala Ala Gln Glu Ala Glu Leu Asn Ala Arg Lys Ala Lys Asn Ser
        1460                1465                1470 gtc agc agc ctc ctc agc cag ctg aac aac ctc ttg gat cag cta gga        4464
Val Ser Ser Leu Leu Ser Gln Leu Asn Asn Leu Leu Asp Gln Leu Gly
    1475                1480                1485 cag ctg gac aca gtg gac ctg aac aag ctc aat gag atc gaa ggc tcc        4512
Gln Leu Asp Thr Val Asp Leu Asn Lys Leu Asn Glu Ile Glu Gly Ser
 1490                1495                1500 ctg aac aaa gcc aaa gac gaa atg aag gcc agc gac ctg gac agg aag        4560
Leu Asn Lys Ala Lys Asp Glu Met Lys Ala Ser Asp Leu Asp Arg Lys
1505                1510                1515                1520 gtg tct gac ctg gag agc gag gct cgg aag cag gaa gca gcc atc atg        4608
Val Ser Asp Leu Glu Ser Glu Ala Arg Lys Gln Glu Ala Ala Ile Met
                1525                1530                1535 gac tat aac cgg gac ata gca gag atc att aag gat att cac aac ctg        4656
Asp Tyr Asn Arg Asp Ile Ala Glu Ile Ile Lys Asp Ile His Asn Leu
        1540                1545                1550 gag gac atc aag aag acc cta cca acc ggc tgc ttc aac acc ccg tct        4704
Glu Asp Ile Lys Lys Thr Leu Pro Thr Gly Cys Phe Asn Thr Pro Ser
    1555                1560                1565
```

-continued

| | |
|---|---|
| atc gag aag ccc tagtggcgag agggctgtaa ggcagtgtcc ctgacagggg<br>Ile Glu Lys Pro<br>  1570 | 4756 |
| accctgtgag gcctcggtgc cttgacacaa agattacact tttcagaccc ccacttctct | 4816 |
| gctgctctcc atcactgtcc ttttgaccca agaaaagtca gagtttaaag agaagcaagt | 4876 |
| taaacatctt taaccaggaa caaagggttt tgcctaataa agtctctcct ccacttctgt | 4936 |
| cagcacccta ccggaacttt cccttgtttg cctgaagtca cggcatcttc cagggccta | 4996 |
| cccacatcat gtgaaccttt taatgccagg gcagacccag ccccctcccc tctctcaaca | 5056 |
| ccagcaggac ctatctcagt actcatgttt ctatgaagga aatctttggc tcctcatcgt | 5116 |
| agcattgaga tggccagtat gtccgctctg catcttctgc ctcctctttg aaaggaaata | 5176 |
| aacatcctcg tgccaaaggt attggtcatt tagaatagtg gtggccatcc atcagacatg | 5236 |
| ctggctggct gagcatagga cacagagccg tcgtgggtga gcgtagttac atgtgggtcc | 5296 |
| ccaggagaac atggctcaaa gatgcttagg gttcctcctg ttttcattga ctaggaagat | 5356 |
| gaatgtttcc caaatcctca ggcagctgat aaaagtctg gatgggcagc tgcacgcac | 5416 |
| cactacgtga ggtagctttt gatatttta taagcaggac ttaatgcaga agaaacagat | 5476 |
| gtgataacca ctcaagtttt ttttccccaag tagtactaat tcttaaagct ttgttagtgt | 5536 |
| tagtcttgga actgttggta agatagctgt caaaacagtt gtcctctaag gtcatgacca | 5596 |
| atgaaagaag agcaaatctc cttttcccca tattttctgg gaagtggctg taatcgggat | 5656 |
| gtaaccgctc tcattaggat tccatgagtg catttctttt tctcttttc ttggagagag | 5716 |
| atgtgacgtt tggcccttag ctccattctc ttctgatgtt tccgttcttt ctagaactct | 5776 |
| tcagagcaca tcgttgtttg ccaggtcctg gtggcaaaca cccgctcaca gtgtttctca | 5836 |
| aggctgccaa ccccatctag ttcctgcact ttgtcggtcc gcccactcca agcctttcct | 5896 |
| ctgtgtggag agggaagatc catacgtggc atttcctagt gggcttctca acctctgatc | 5956 |
| ctcagctcgg tggtctcctt aagaccacac tgtgacagtt ccctgccaca catcccttc | 6016 |
| ctcctaccta cctgcctctg agattcatat ttagcccttta acactatgca attttgtact | 6076 |
| ttgcgtacgg ggggaaagaa actattatct gacacactgg tgctattatt tgaaatttat | 6136 |
| atttttgtg tgaatggatt ttgtttatca tgattataga gtaaggaatt tatgtaaata | 6196 |
| tccccggtcc tcctagaacg gcactgtctg ctcacgtctc tgctcagttg tccctctcac | 6256 |
| tggcacagga acctgtacca tgcctggtca cgtcgtgcct ggtccccagt gttttgctcc | 6316 |
| acctctgcct tgtgtttgca gcaccttcac tgtctgaccg gaagcctgct cacctccaca | 6376 |
| acttgactga agagggccct cttccccgtg gctctgacca tctgagctgc agctcctcaa | 6436 |
| ggttctcatg cctgcccgga gcagtagcca agctgacagg gtaaagggat taggaacgtt | 6496 |
| tgtttgtgga accttcccac acgggtcagt tttctaaggg agcatgtgat gactgaacac | 6556 |
| ttgagggcat cagcaccgtg ctactgatga cagagggggag gctctgttca gcctgtctcc | 6616 |
| atctcggaga ttgccacaaa atctcagctt ggcatcctcc gaggcctttt gtgccacggc | 6676 |
| aagaaggcgt ggcctcacca agttcagtgc tgattggcta gttcctctat tccgagctca | 6736 |
| ccaccttaac attttggtca cagttgcaag aaaatggctg aaacagacca ccaccagcat | 6796 |
| cctttgggtc aactccactc cagcaggccc gaggcgctgg tgggtggggt gttttggttt | 6856 |
| gttttctcca gcttttgtgg tatatttta aacagaattt tattttttaa aatgaaagtt | 6916 |
| atttacaaga tgatacctta ttacgctcct tcgacacagc cattgcttta ttgtatagtt | 6976 |
| ccaataatct gtatttatg taatgaaatg gacagaatgg ctgctgtaga atgcggggtg | 7036 |

-continued

```
ccgcacagaa cagattgttt tatccctccc ccgcccccgc ccatggaatt ttcctttgat      7096
tccaactgtg gccttttca atgtgccttc actttagctg tttgccttaa tctctacagc      7156
cttcccccct cagggagggc aataaagcgc aacacttgga ttttttttat gtttaaaaag     7216
aaaacagtat tttatttata ataaaatctg aatatttgta accctttt                   7263
```

<210> SEQ ID NO 28
<211> LENGTH: 1572
<212> TYPE: PRT
<213> ORGANISM: Mus musculus

<400> SEQUENCE: 28

| | | | | | | | | | | | | | | | |
|---|---|---|---|---|---|---|---|---|---|---|---|---|---|---|---|
| Ala | Met | Asp | Glu | Cys | Ala | Asp | Glu | Gly | Gly | Arg | Pro | Gln | Arg | Cys | Met |
| 1 | | | | 5 | | | | | 10 | | | | | 15 | |
| Pro | Glu | Phe | Val | Asn | Ala | Ala | Phe | Asn | Val | Thr | Val | Ala | Thr | Asn | |
| | | | 20 | | | | | 25 | | | | | 30 | | |
| Thr | Cys | Gly | Thr | Pro | Pro | Glu | Glu | Tyr | Cys | Val | Gln | Thr | Gly | Val | Thr |
| | | | 35 | | | | 40 | | | | | 45 | | | |
| Gly | Val | Thr | Lys | Ser | Cys | His | Leu | Cys | Asp | Ala | Gly | Gln | Gln | His | Leu |
| | 50 | | | | | 55 | | | | | 60 | | | | |
| Gln | His | Gly | Ala | Ala | Phe | Leu | Thr | Asp | Tyr | Asn | Asn | Gln | Ala | Asp | Thr |
| 65 | | | | | 70 | | | | | 75 | | | | | 80 |
| Thr | Trp | Trp | Gln | Ser | Gln | Thr | Met | Leu | Ala | Gly | Val | Gln | Tyr | Pro | Asn |
| | | | | 85 | | | | | 90 | | | | | 95 | |
| Ser | Ile | Asn | Leu | Thr | Leu | His | Leu | Gly | Lys | Ala | Phe | Asp | Ile | Thr | Tyr |
| | | | | 100 | | | | | 105 | | | | | 110 | |
| Val | Arg | Leu | Lys | Phe | His | Thr | Ser | Arg | Pro | Glu | Ser | Phe | Ala | Ile | Tyr |
| | | | | 115 | | | | | 120 | | | | | 125 | |
| Lys | Arg | Thr | Arg | Glu | Asp | Gly | Pro | Trp | Ile | Pro | Tyr | Gln | Tyr | Tyr | Ser |
| | | 130 | | | | | 135 | | | | | 140 | | | |
| Gly | Ser | Cys | Glu | Asn | Thr | Tyr | Ser | Lys | Ala | Asn | Arg | Gly | Phe | Ile | Arg |
| 145 | | | | | 150 | | | | | 155 | | | | | 160 |
| Thr | Gly | Gly | Asp | Glu | Gln | Gln | Ala | Leu | Cys | Thr | Asp | Glu | Phe | Ser | Asp |
| | | | | 165 | | | | | 170 | | | | | 175 | |
| Ile | Ser | Pro | Leu | Thr | Gly | Gly | Asn | Val | Ala | Phe | Ser | Thr | Leu | Glu | Gly |
| | | | | 180 | | | | | 185 | | | | | 190 | |
| Arg | Pro | Ser | Ala | Tyr | Asn | Phe | Asp | Asn | Ser | Pro | Val | Leu | Gln | Glu | Trp |
| | | | | 195 | | | | | 200 | | | | | 205 | |
| Val | Thr | Ala | Thr | Asp | Ile | Arg | Val | Thr | Leu | Asn | Arg | Leu | Asn | Thr | Phe |
| | 210 | | | | | 215 | | | | | 220 | | | | |
| Gly | Asp | Glu | Val | Phe | Asn | Asp | Pro | Lys | Val | Leu | Lys | Ser | Tyr | Tyr | Tyr |
| 225 | | | | | 230 | | | | | 235 | | | | | 240 |
| Ala | Ile | Ser | Asp | Phe | Ala | Val | Gly | Gly | Arg | Cys | Lys | Cys | Asn | Gly | His |
| | | | | 245 | | | | | 250 | | | | | 255 | |
| Ala | Ser | Glu | Cys | Val | Lys | Asn | Glu | Phe | Asp | Lys | Leu | Met | Cys | Asn | Cys |
| | | | 260 | | | | | 265 | | | | | 270 | | |
| Lys | His | Asn | Thr | Tyr | Gly | Val | Asp | Cys | Glu | Lys | Cys | Leu | Pro | Phe | Phe |
| | | 275 | | | | | 280 | | | | | 285 | | | |
| Asn | Asp | Arg | Pro | Trp | Arg | Arg | Ala | Thr | Ala | Glu | Ser | Ala | Ser | Glu | Cys |
| | 290 | | | | | 295 | | | | | 300 | | | | |
| Leu | Pro | Cys | Asp | Cys | Asn | Gly | Arg | Ser | Gln | Glu | Cys | Tyr | Phe | Asp | Pro |
| 305 | | | | | 310 | | | | | 315 | | | | | 320 |
| Glu | Leu | Tyr | Arg | Ser | Thr | Gly | His | Gly | Gly | His | Cys | Thr | Asn | Cys | Arg |
| | | | | 325 | | | | | 330 | | | | | 335 | |

```
Asp Asn Thr Asp Gly Ala Lys Cys Glu Arg Cys Arg Glu Asn Phe Phe
                340                 345                 350

Arg Leu Gly Asn Thr Glu Ala Cys Ser Pro His Cys Ser Pro Val
            355                 360             365

Gly Ser Leu Ser Thr Gln Cys Asp Ser Tyr Gly Arg Cys Ser Cys Lys
        370                 375                 380

Pro Gly Val Met Gly Asp Lys Cys Asp Arg Cys Gln Pro Gly Phe His
385                 390                 395                 400

Ser Leu Thr Glu Ala Gly Cys Arg Pro Cys Ser Cys Asp Pro Ser Gly
                405                 410                 415

Ser Thr Asp Glu Cys Asn Val Glu Thr Gly Arg Cys Val Cys Lys Asp
            420                 425                 430

Asn Val Glu Gly Phe Asn Cys Glu Arg Cys Lys Pro Gly Phe Phe Asn
            435                 440                 445

Leu Glu Ser Ser Asn Pro Lys Gly Cys Thr Pro Cys Phe Cys Phe Gly
        450                 455                 460

His Ser Ser Val Cys Thr Asn Ala Val Gly Tyr Ser Val Tyr Asp Ile
465                 470                 475                 480

Ser Ser Thr Phe Gln Ile Asp Glu Asp Gly Trp Arg Val Glu Gln Arg
                485                 490                 495

Asp Gly Ser Glu Ala Ser Leu Glu Trp Ser Ser Asp Arg Gln Tyr Ile
            500                 505                 510

Ala Val Ile Ser Asp Ser Tyr Phe Pro Arg Tyr Phe Ile Ala Pro Val
            515                 520                 525

Lys Phe Leu Gly Asn Gln Val Leu Ser Tyr Gly Gln Asn Leu Ser Phe
            530                 535                 540

Ser Phe Arg Val Asp Arg Arg Asp Thr Arg Leu Ser Ala Glu Asp Leu
545                 550                 555                 560

Val Leu Glu Gly Ala Gly Leu Arg Val Ser Val Pro Leu Ile Ala Gln
                565                 570                 575

Gly Asn Ser Tyr Pro Ser Glu Thr Thr Val Lys Tyr Ile Phe Arg Leu
            580                 585                 590

His Glu Ala Thr Asp Tyr Pro Trp Arg Pro Ala Leu Ser Pro Phe Glu
            595                 600                 605

Phe Gln Lys Leu Leu Asn Asn Leu Thr Ser Ile Lys Ile Arg Gly Thr
            610                 615                 620

Tyr Ser Glu Arg Ser Ala Gly Tyr Leu Asp Asp Val Thr Leu Gln Ser
625                 630                 635                 640

Ala Arg Pro Gly Pro Gly Val Pro Ala Thr Trp Val Glu Ser Cys Thr
                645                 650                 655

Cys Pro Val Gly Tyr Gly Gly Gln Phe Cys Glu Thr Cys Leu Pro Gly
            660                 665                 670

Tyr Arg Arg Glu Thr Pro Ser Leu Gly Pro Tyr Ser Pro Cys Val Leu
            675                 680                 685

Cys Thr Cys Asn Gly His Ser Glu Thr Cys Asp Pro Glu Thr Gly Val
            690                 695                 700

Cys Asp Cys Arg Asp Asn Thr Ala Gly Pro His Cys Glu Lys Cys Ser
705                 710                 715                 720

Asp Gly Tyr Tyr Gly Asp Ser Thr Leu Gly Thr Ser Ser Asp Cys Gln
                725                 730                 735

Pro Cys Pro Cys Pro Gly Gly Ser Ser Cys Ala Ile Val Pro Lys Thr
            740                 745                 750
```

```
Lys Glu Val Val Cys Thr His Cys Pro Thr Gly Thr Ala Gly Lys Arg
        755                 760                 765

Cys Glu Leu Cys Asp Asp Gly Tyr Phe Gly Asp Pro Leu Gly Ser Asn
        770                 775                 780

Gly Pro Val Arg Leu Cys Arg Pro Cys Gln Cys Asn Asp Asn Ile Asp
785                 790                 795                 800

Pro Asn Ala Val Gly Asn Cys Asn Arg Leu Thr Gly Glu Cys Leu Lys
                805                 810                 815

Cys Ile Tyr Asn Thr Ala Gly Phe Tyr Cys Asp Arg Cys Lys Glu Gly
            820                 825                 830

Phe Phe Gly Asn Pro Leu Ala Pro Asn Pro Ala Asp Lys Cys Lys Ala
            835                 840                 845

Cys Ala Cys Asn Tyr Gly Thr Val Gln Gln Ser Ser Cys Asn Pro
    850                 855                 860

Val Thr Gly Gln Cys Gln Cys Leu Pro His Val Ser Gly Arg Asp Cys
865                 870                 875                 880

Gly Thr Cys Asp Pro Gly Tyr Tyr Asn Leu Gln Ser Gly Gln Gly Cys
                885                 890                 895

Glu Arg Cys Asp Cys His Ala Leu Gly Ser Thr Asn Gly Gln Cys Asp
            900                 905                 910

Ile Arg Thr Gly Gln Cys Glu Cys Gln Pro Gly Ile Thr Gly Gln His
            915                 920                 925

Cys Glu Arg Cys Glu Thr Asn His Phe Gly Phe Gly Pro Glu Gly Cys
    930                 935                 940

Lys Pro Cys Asp Cys His His Glu Gly Ser Leu Ser Leu Gln Cys Lys
945                 950                 955                 960

Asp Asp Gly Arg Cys Glu Cys Arg Glu Gly Phe Val Gly Asn Arg Cys
                965                 970                 975

Asp Gln Cys Glu Glu Asn Tyr Phe Tyr Asn Arg Ser Trp Pro Gly Cys
            980                 985                 990

Gln Glu Cys Pro Ala Cys Tyr Arg Leu Val Lys Asp Lys Ala Ala Glu
            995                 1000                1005

His Arg Val Lys Leu Gln Glu Leu Glu Ser Leu Ile Ala Asn Leu Gly
   1010                1015                1020

Thr Gly Asp Asp Met Val Thr Asp Gln Ala Phe Glu Asp Arg Leu Lys
1025                1030                1035                1040

Glu Ala Glu Arg Glu Val Thr Asp Leu Leu Arg Glu Ala Gln Glu Val
                1045                1050                1055

Lys Asp Val Asp Gln Asn Leu Met Asp Arg Leu Gln Arg Val Asn Ser
        1060                1065                1070

Ser Leu His Ser Gln Ile Ser Arg Leu Gln Asn Ile Arg Asn Thr Ile
        1075                1080                1085

Glu Glu Thr Gly Ile Leu Ala Glu Arg Ala Arg Ser Arg Val Glu Ser
   1090                1095                1100

Thr Glu Gln Leu Ile Glu Ile Ala Ser Arg Glu Leu Glu Lys Ala Lys
1105                1110                1115                1120

Met Ala Ala Asn Val Ser Ile Thr Gln Pro Glu Ser Thr Gly Glu Pro
                1125                1130                1135

Asn Asn Met Thr Leu Leu Ala Glu Glu Ala Arg Arg Leu Ala Glu Arg
            1140                1145                1150

His Lys Gln Glu Ala Asp Asp Ile Val Arg Val Ala Lys Thr Ala Asn
        1155                1160                1165

Glu Thr Ser Ala Glu Ala Tyr Asn Leu Leu Leu Arg Thr Leu Ala Gly
```

```
        1170                1175                1180
Glu Asn Gln Thr Ala Leu Glu Ile Glu Glu Leu Asn Arg Lys Tyr Glu
1185                1190                1195                1200

Gln Ala Lys Asn Ile Ser Gln Asp Leu Glu Lys Gln Ala Ala Arg Val
            1205                1210                1215

His Glu Glu Ala Lys Arg Ala Gly Asp Lys Ala Val Glu Ile Tyr Ala
        1220                1225                1230

Ser Val Ala Gln Leu Thr Pro Val Asp Ser Glu Ala Leu Glu Asn Glu
    1235                1240                1245

Ala Asn Lys Ile Lys Lys Glu Ala Ala Asp Leu Asp Arg Leu Ile Asp
1250                1255                1260

Gln Lys Leu Lys Asp Tyr Glu Asp Leu Arg Glu Asp Met Arg Gly Lys
1265                1270                1275                1280

Glu His Glu Val Lys Asn Leu Leu Glu Lys Gly Lys Ala Glu Gln Gln
            1285                1290                1295

Thr Ala Asp Gln Leu Leu Ala Arg Ala Asp Ala Ala Lys Ala Leu Ala
        1300                1305                1310

Glu Glu Ala Ala Lys Lys Gly Arg Ser Thr Leu Gln Glu Ala Asn Asp
    1315                1320                1325

Ile Leu Asn Asn Leu Lys Asp Phe Asp Arg Arg Val Asn Asp Asn Lys
    1330                1335                1340

Thr Ala Glu Glu Ala Leu Arg Arg Ile Pro Ala Ile Asn Arg Thr
1345                1350                1355                1360

Ile Ala Glu Ala Asn Glu Lys Thr Arg Glu Ala Gln Leu Ala Leu Gly
            1365                1370                1375

Asn Ala Ala Ala Asp Ala Thr Glu Ala Lys Asn Lys Ala His Glu Ala
        1380                1385                1390

Glu Arg Ile Ala Ser Ala Ala Gln Lys Asn Ala Thr Ser Thr Lys Ala
    1395                1400                1405

Asp Ala Glu Arg Thr Phe Gly Glu Val Thr Asp Leu Asp Asn Glu Val
    1410                1415                1420

Asn Gly Met Leu Arg Gln Leu Glu Glu Ala Glu Asn Glu Leu Lys Arg
1425                1430                1435                1440

Lys Gln Asp Asp Ala Asp Gln Asp Met Met Met Ala Gly Met Ala Ser
            1445                1450                1455

Gln Ala Ala Gln Glu Ala Glu Leu Asn Ala Arg Lys Ala Lys Asn Ser
        1460                1465                1470

Val Ser Ser Leu Leu Ser Gln Leu Asn Asn Leu Leu Asp Gln Leu Gly
    1475                1480                1485

Gln Leu Asp Thr Val Asp Leu Asn Lys Leu Asn Glu Ile Glu Gly Ser
    1490                1495                1500

Leu Asn Lys Ala Lys Asp Glu Met Lys Ala Ser Asp Leu Asp Arg Lys
1505                1510                1515                1520

Val Ser Asp Leu Glu Ser Glu Ala Arg Lys Gln Glu Ala Ala Ile Met
            1525                1530                1535

Asp Tyr Asn Arg Asp Ile Ala Glu Ile Ile Lys Asp Ile His Asn Leu
        1540                1545                1550

Glu Asp Ile Lys Lys Thr Leu Pro Thr Gly Cys Phe Asn Thr Pro Ser
    1555                1560                1565

Ile Glu Lys Pro
    1570
```

LAMININ 8 AND METHODS FOR ITS USE

CROSS REFERENCE

This application claims priority to U.S. Provisional Patent Application Serial Nos. 60/131,720 filed Apr. 30, 1999; 60/149,738 filed August 1999; Ser. No. 60/155,945 filed Sep. 24, 1999; and Ser. No. 60/182,012 filed Feb. 11, 2000; all of which are incorporated herein by reference in their entirety.

FIELD OF THE INVENTION

This application relates to purified laminin 8 and methods for its use.

BACKGROUND OF THE INVENTION

Basal laminae (basement membranes) are sheet-like, cell-associated extracellular matrices that play a central role in cell growth, tissue development, and tissue maintenance. They are present in virtually all tissues, and appear in the earliest stages of embryonic development.

Basal laminae are central to a variety of architectural and cell-interactive functions: (See for example, Malinda and Kleinman, Int. J. Biochem. Cell Biol. 28:957–959 (1996); Aumailley and Krieg, J. Invest. Dermatology 106:209–214 (1996)).

1. They serve as architectural supports for tissues, providing adhesive substrata for cells.
2. They create perm-selective barriers between tissue compartments that impede the migration of cells and passively regulate the exchange of macromolecules. These properties are illustrated by the kidney glomerular basement membrane, which functions as an important filtration structure, creating an effective blood-tissue barrier that is not permeable to most proteins and cells.
3. Basal laminae create highly interactive surfaces that can promote cell migration and cell elongation during embryogenesis and wound repair. Following an injury, they provide a surface upon which cells regenerate to restore normal tissue function.
4. Basal laminae present information encoded in their structure to contacting cells that is important for differentiation and tissue maintenance. This information is communicated to the cells through various receptors that include the integrins, dystroglycan, and cell surface proteoglycans. Signaling is dependent not only on the presence of matrix ligands and corresponding receptors that interact with sufficient affinities, but also on such topographical factors as ligand density in a three-dimensional matrix "landscape", and on the ability of basal lamina components to cluster receptors. Because these matrix proteins can be long-lived, basal laminae create a "surface memory" in the basal lamina for resident and transient cells.

The basal lamina is largely composed of laminin and type IV collagen heterotrimers that in turn become organized into complex polymeric structures. To date, six type IV collagen chains and at least twelve laminin subunits have been identified. These chains possess shared and unique functions and are expressed with specific temporal (developmental) and spatial (tissue-site specific) patterns.

Laminins are a family of heterotrimeric glycoproteins that reside primarily in the basal lamina. They function via binding interactions with neighboring cell receptors, and by forming laminin networks, and they are important signaling molecules that can strongly influence cellular function. Laminins are important in both maintaining cell/tissue phenotype as well as promoting cell growth and differentiation in tissue repair and development.

Laminins are large, multi-domain proteins, with a common structural organization. The laminin molecule integrates various matrix and cell interactive functions into one molecule.

The laminin molecule is comprised of an $\alpha$-, $\beta$-, and $\gamma$-chain subunit joined together through a coiled-coil domain. Within this structure are identifiable domains that possess binding activity towards other laminin and basal lamina molecules, and membrane-bound receptors. Domains VI, IVb, and IVa form globular structures, and domains V, IIIb, and IIIa (which contain cysteine-rich EGF-like elements) form rod-like structures. (Kamiguchi et al., Ann. Rev. Neurosci. 21:97–125 (1998)) Domains I and II of the three chains participate in the formation of a triple-stranded coiled-coil structure (the long arm).

Table 1 shows the individual chains that each laminin type is composed of:

TABLE 1

| Known laminin family members | |
|---|---|
| Protein | Chains |
| Laminin-1 | $\alpha 1\beta 1\gamma 1$ |
| Laminin-2 | $\alpha 2\beta 1\gamma 1$ |
| Laminin-3 | $\alpha 1\beta 2\gamma 1$ |
| Laminin-4 | $\alpha 2\beta 2\gamma 1$ |
| Laminin-5 | $\alpha 3\beta 3\gamma 2$ |
| Laminin-6 | $\alpha 3\beta 1\gamma 1$ |
| Laminin-7 | $\alpha 3\beta 2\gamma 1$ |
| Laminin-8 | $\alpha 4\beta 1\gamma 1$ |
| Laminin-9 | $\alpha 4\beta 2\gamma 1$ |
| Laminin-10 | $\alpha 5\beta 1\gamma 1$ |
| Laminin-11 | $\alpha 5\beta 2\gamma 1$ |
| Laminin-12 | $\alpha 2\beta 1\gamma 3$ |

Four structurally-defined family groups of laminins have been identified. The first group of five identified laminin molecules all share the $\beta 1$ and $\gamma 1$ chains, and vary by their $\alpha$-chain composition ($\alpha 1$ to $\alpha 5$ chain). The second group of five identified laminin molecules all share the $\beta 2$ and $\gamma 1$ chain, and again vary by their $\alpha$-chain composition. The third group of identified laminin molecules has one identified member, laminin 5, with a chain composition of $\alpha 3\beta 3\gamma 2$. The fourth group of identified laminin molecules has one identified member, laminin 12, with the newly identified $\gamma 3$ chain ($\alpha 2\beta 1\gamma 3$).

Some progress has been made in elucidating the relationship between domain structure and function. (See, for example, Wewer and Engvall, Neuromusc. Disord. 6:409–418 (1996).) The overall sequence similarity among the homologous domains in different chains varies, but it is highest in domain VI (thought to play a key role in laminin polymerization), followed by domains V (possibly involved in protein-protein interactions) and III (entactin/nidogen binding; possible cell adhesion sites), and is lowest in domains I, II (both thought to be involved in intermolecular assembly, and containing possible cell adhesion sites), and G. Not all domains are present in all 3 types of chains. The globular G domain (thought to be involved in cell receptor binding) is present only in the $\alpha$ chains. Other domains may not be present in all chains within a certain chain type. For example, domain VI is absent from $\alpha 3$, $\alpha 4$, and $\gamma 2$ chains. (Wewer and Engvall, 1996)

As a result of their large size (>600 kD) and unique structure, the laminin molecules can be resolved in the electron microscope. (Wewer and Engvall, 1996) Typically, laminins appear as cross-shaped molecules in an EM. The three short arms of the cross represent the amino terminal portions of each of the three separate laminin chains (one short arm per chain). The long arm of the cross is composed of the C-terminal parts of the three chains, which together form a coiled coil structure. (Wewer and Engvall, 1996) The long arm ends with the globular G domain.

The coiled-coil domain of the long arm is crucial for assembly of the three chains of laminin. (Yurchenco et al., Proc. Natl. Acad. Sci. 94:10189–10194 (1997)). Disulfide bonds bridge and stabilize all three chains in the most proximal region of the long arm and join the β and γ chains in the most distal region of the long arm.

A model of laminin receptor-facilitated self-assembly, based on studies conducted with cultured skeletal myotubes and Schwann cells, predicts that laminins bind to their receptors, which freely diffuse in a fluidic membrane, when ligand-free. Receptor engagement forces the laminins into a high local two-dimensional concentration, facilitating their mass-action driven assembly into ordered surface polymers. In this process, the engaged receptors are also reorganized, accompanied by cytoskeletal rearrangements. (Colognato, J. Cell Biol. 145:619–631 (1999)) This reorganization activates the receptors, causing signal transduction with the alteration of cell expression, shape and/or behavior. The evidence is that laminins must possess both cell-interacting and architecture-forming sites, which are located in different protein domains and on different subunits.

One class of laminin receptors are the integrins, which are cell surface receptors that mediate many cell-matrix and cell-cell interactions. Integrins are heterodimers, consisting of an α and a β subunit. 16 α- and 8 β-subunits are known, and at least 22 combinations of α and β subunits have been identified to date. Some integrins have only one or a few known ligands, whereas others appear to be very promiscuous. Binding to integrins is generally of low affinity, and is dependent on divalent cations. Integrins, activated through binding to their ligands, transduce signals via kinase activation cascades, such as focal adhesion and mitogen-activated kinases. Several different integrins bind different laminin isoforms more or less specifically. (Aumailley et al., In The Laminins, Timpl and Ekblom, eds., Harwood Academic Publishers, Amsterdam. pp. 127–158 (1996))

Laminin 8, a recently identified laminin, is composed of α4, β1, and γ1 laminin chains. The laminin α4 chain is widely distributed both in adults and during development. (Iivanainen et al., J. Biol. Chem. 272:27862–27868 (1997)) In adults it is found in the basement membrane surrounding cardiac, skeletal, and smooth muscle fibers, and in lung alveolar septa. Furthermore, it is found in the endothelial basement membrane both in capillaries and larger vessels, and in the perineurial basement membrane of peripheral nerves, as well as in intersinusoidal spaces, large arteries, and smaller arterioles of bone marrow. (Frieser et al., Eur. J. Biochemistry 246:727–735 (1997); Miner et al., J. Cell Biol. 137:685–701 (1997); Geberhiwot et al., Exptl. Cell Res. 253:723–732 (1999); Gu et al., Blood 93:2533–2542 (1999); Iivanainen et al., J. Biol. Chem. 272:27862–27868 (1997)).

Laminin 8 is a major laminin isoform in the vascular endothelium (Iivanainen et al., J. Biol. Chem. 272:27862–27868 (1997); Frieser et al., 1997), is expressed and adhered to by platelets (Geberhiwot et al., Exptl. Cell Res. 253:723–732 (1999)), and is the only laminin isoform synthesized in 3T3-L1 adipocytes, with its level of synthesis shown to increase upon adipose conversion of the cells. (Niimi et al., Matrix Biology 16:223–230 (1997)) Laminin 8 was further speculated to be the laminin isoform generally expressed in mesenchymal cell lineages to induce microvessels in connective tissues. (Niimi et al., 1997).

Laminin 8 has also been identified in mouse bone marrow primary cell cultures, arteriolar walls, and intersinusoidal spaces where data indicated that it is the major laminin isoform in the developing bone marrow. (Gu et al., Blood 93:2533–2542 (1999). The investigators concluded that, due to its localization in adult bone marrow adjacent to hematopoietic cells, laminin isoforms containing the α4 chain are the most likely to have biologically relevant interactions with developing hematopoietic cells. (Gu et al., 1999)

Despite the broad tissue distribution of the laminin α4 chain and laminin 8, there is not a means to prepare substantially purified laminin 8 from cell or tissue sources for research and therapeutic purposes, nor has a means for recombinant expression of laminin 8 been developed. Such research and therapeutic purposes include, but are not limited to, methods for treating-injuries to tissue of mesenchymal origin, such as bone, cartilage, tendon, and ligament, treating injuries to vascular tissue, promoting cell attachment and migration, promoting therapeutic angiogenesis and neural regeneration, ex vivo cell therapy, improving the biocompatibility of medical devices, and preparing improved cell culture devices and media.

Thus, there is a need in the art for adequate amounts of substantially purified laminin-8 for research and therapeutic purposes, and methods for making laminin 8. Such laminin 8 could be prepared either from cell lines in culture, or via recombinant DNA technology.

A preferred method of production is the use of recombinant DNA technology to engineer a human cell line of choice to produce recombinant laminin-8 ("r-laminin 8"). A recombinant-based method of laminin-8 production has several advantages over purification from human tissue or isolation from human cell lines in culture:

1. The recombinant produced protein is free of human pathogens. While this is also true for endogenous cell culture produced protein, protein derived from human tissue carries a risk for contamination by HIV, hepatitis, and other infectious agents.

2. Expression levels of the protein, and hence yields, can be improved through the use of genetically engineered genes/vectors that enhance the production of the encoded protein.

3. It is possible to engineer additional peptide sequences to the protein chain that provides a binding site for a commercially viable affinity purification procedure.

4. The method can provide for the modification of protein structure/function through the addition, substitution, elimination, and/or other modifications of protein domain structures. For example, it may be desirable to introduce an integrin binding site (e.g. RGD), switch integrin recognition sites, or engineer in a stable binding site to a synthetic substrate. Thus, the creation of expression vectors that express laminin chains generates enormous flexibility for future uses and creates a basis for creating second generation "designer" laminins.

SUMMARY OF THE INVENTION

The present invention fulfills the need in the art for a source of substantially purified laminin 8 protein, methods for making substantially purified recombinant laminin 8 (hereinafter referred to as r-laminin 8), pharmaceutical compositions comprising laminin 8, and methods of using laminin 8 for treating injuries to tissue of mesenchymal origin, such as bone, cartilage, tendon, and ligament, treating injuries to vascular tissue, promoting cell attachment and migration, ex vivo cell therapy, improving the biocompatibility of medical devices, and preparing improved cell culture devices and media.

In one aspect, the present invention provides recombinant host cells that express laminin 8 chains and secrete r-laminin 8. In another aspect, the present invention provides substantially purified laminin 8, and methods for producing substantially purified r-laminin 8.

In a further aspect, the present invention provides pharmaceutical compositions, comprising laminin 8 together with a pharmaceutically acceptable carrier. Such pharmaceutical compositions can optionally be provided with other extracellular matrix components.

In further aspect, the present invention provides methods and kits for accelerating the healing of injuries to tissue of mesenchymal origin, such as bone, cartilage, tendon, and ligament, treating injuries to vascular tissue, and for improving the biocompatibility of grafts used for treating such injuries. In specific examples, laminin 8 or pharmaceutical compositions thereof are used to:

a. promote re-endothelialization at the site of vascular injuries;
 b. improve the "take" of grafts;
 c. improve the biocompatibility of medical devices;
 d. treat neural injuries (neural regeneration);
 e. regulate angiogenesis; and
 d. promote cell attachment and migration
   by providing an amount effective of r-laminin 8 for the various methods. In preferred embodiments of all of these methods, recombinant laminin 8 is used. The kits comprise an amount of laminin 8 effective for the desired effect, and instructions for the use thereof.

In a further aspect, the present invention provides improved medical devices and grafts, and methods for preparing improved medical devices and grafts, wherein the improvement comprises applying an amount effective of laminin 8 or the pharmaceutical compositions of the invention to the device or graft for the desired application.

In a further aspect, the invention provides improved cell culture devices, and methods for preparing improved cell culture devices, for the growth and maintenance of cells in culture, by providing an amount effective of laminin 8 for the attachment of cells to a cell culture device for the subsequent proliferation/differentiation/stasis of the cells.

In another aspect, the invention provides a cell culture growth supplement, comprising laminin 8. In another aspect, the invention provides an improved cell culture growth media, wherein the improvement comprises the addition of r-laminin 8.

BRIEF DESCRIPTION OF THE FIGURES

FIG. 4 is a graph depicting HT-1080 cell adhesion to r-laminin 8 or laminin 1 coated at 10 μg/ml on 96 well plates in the presence and absence of various function-blocking integrin antibodies and other compounds.

FIG. 5 is a graph depicting bovine capillary endothelial (BCE) cell adhesion to r-laminin 8 or laminin 1 coated at 10 μg/ml on 96 well plates in the presence and absence of various function-blocking integrin antibodies and other compounds.

FIG. 6 is a graph depicting immortomouse brain endothelial (IBE) cell adhesion to r-laminin 8 or laminin 1 coated at 10 μg/ml on 96 well plates in the presence and absence of various function-blocking integrin antibodies and other compounds.

FIG. 7 is a graph depicting integrin α6β4-transfected K562 cell adhesion to r-laminin 8 or laminin 1 coated at 10 μg/ml on 96 well plates in the presence and absence of various function-blocking integrin antibodies and other compounds.

FIG. 8 is a graph depicting integrin α6-transfected K562 cell adhesion to r-laminin 8 or laminin 1 coated at 10 μg/ml on 96 well plates in the presence and absence of various function-blocking integrin antibodies and other compounds.

DETAILED DESCRIPTION OF THE PREFERRED EMBODIMENTS

Figure 1:
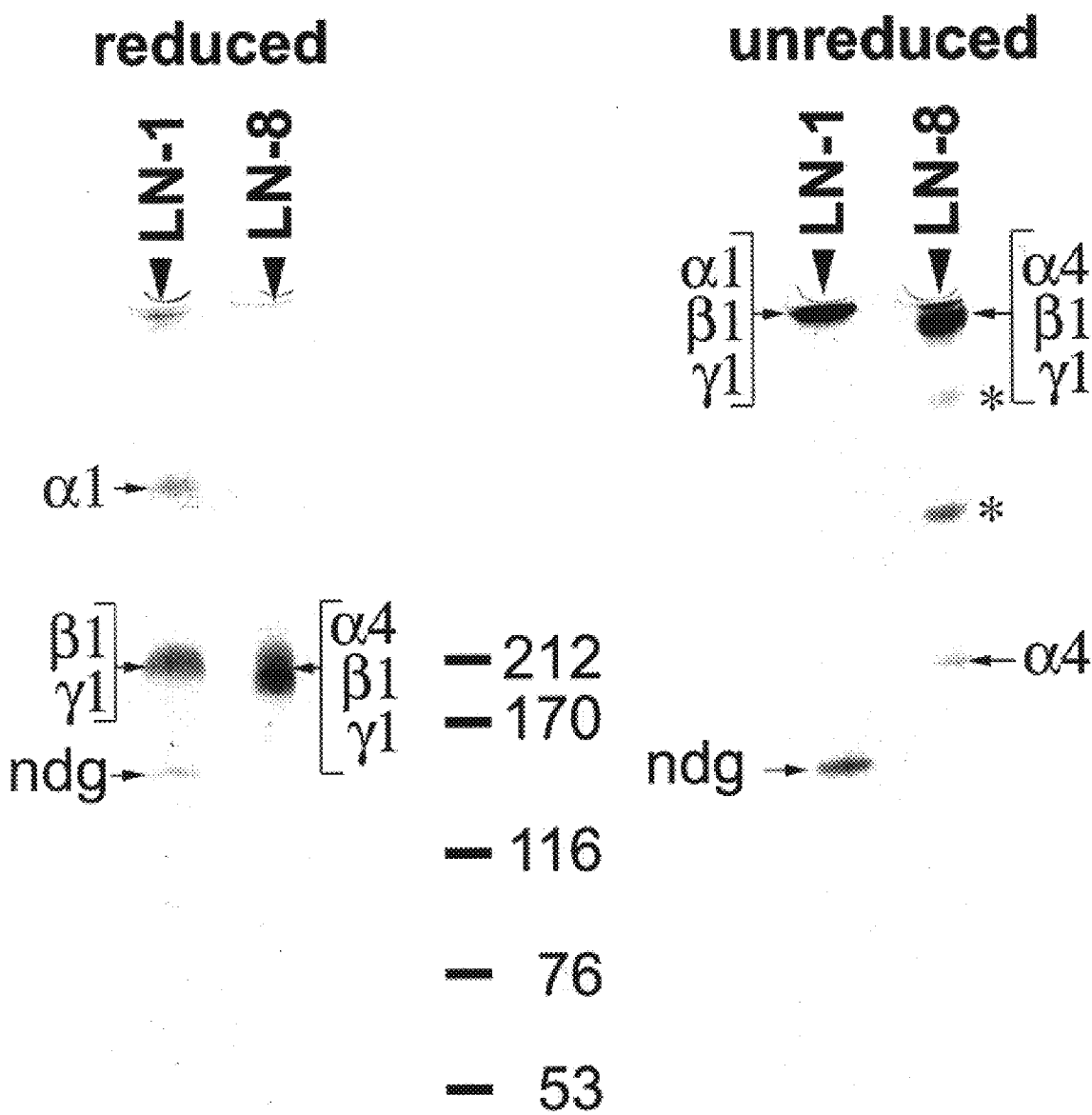
FIG. 1 is a photograph of a 3–12% gradient SDS-PAGE gel. LN-1 is laminin 1/nidogen (ndg) complex with component chain identities indicated on the left; LN-8 is recombinant laminin 8. Interpretation of r-laminin 8 protein band identities are indicated based on western blotting data: α4=reactivity with anti-human laminin α4 and also anti-FLAG monoclonal antibody (mAb); β1=reactivity with polyclonal anti-murine laminin α1/γ1/γ1; γ1=reactivity with anti-human laminin γ1 mAb; *=reactivity with both anti-laminin γ1 mAb and anti-murine α1/β1/γ1. Both samples were run on the same gel which was subsequently silver stained.

All references, patents and patent applications are hereby incorporated by reference in their entirety.

Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, $2^{nd}$ Ed. (R. I. Fresliney. 1987. Liss, Inc. New York, N.Y.), *Gene Transfer and Expression Protocols*, pp. 109–128, ed. E. J. Murray, The Humana Press Inc., Clifton, N.J.), and the Ambion 1998 Catalog (Ambion, Austin, Tex.).

As used herein "laminin 8" encompasses both r-laminin 8 and heterotrimeric laminin 8 from naturally occurring sources.

As used herein, the term "r-laminin 8" refers to recombinant heterotrimeric laminin 8, expressed by a cell that has been transfected with one or more expression vectors comprising at least one nucleic acid sequence encoding a laminin 8 chain selected from the α4, β1 and γ1 chains, or a portion of the chains that are capable of forming a heterotrimeric laminin 8 and maintaining laminin 8 activity, or processed forms thereof. Such r-laminin 8 can thus comprise α4, β1, and γ1 sequences from a single organism, or from different organisms. Various laminin 8 chain DNA sequences are known in the art, and the use of each to prepare the r-laminin 8 of the invention is contemplated. (See, for example, Iivanainen et al., FEBS Letters 365:183–188 (1995); Frieser et al., Eur. J. Biochem. 246:727–735 (1997); Richards et al., Eur. J. Biochem. 238:813–821 (1996); Liu and Mayne, 15:433–437 (1996); Vuolteenaho et al., J. Biol. Chem. 265:15611–15616 (1990); Kallunki et al., J. Biol. Chem. 266:221–228 (1991); Sasaki et al., J. Biol. Chem. 263:16536–16544 (1988); Sasaki and Yamada, J. Biol. Chem. 262:17111–17117 (1987); Sasaki et al., Proc. Natl. Acad. Sci. 84:935–939 (1987); Pikkarainen et al., J. Biol. Chem. 262:10454–10462 (1987); all references incorporated by reference herein in their entirety).

The invention encompasses those laminin molecules wherein one or two of the chains that make up the recombinant heterotrimeric laminin 8 are encoded by endogenous laminin 8 chains. In a preferred embodiment, cells are transfected with one or more expression vectors comprising nucleic acid sequences encoding each of the α4, β1 and γ1 chains, or a portion of each of the chains that are capable of forming a heterotrimeric laminin 8 and maintaining laminin 8 activity.

In the present invention, laminin 8 is a secreted protein, which is capable of being directed to the ER, secretory vesicles, and the extracellular space as a result of a signal sequence, as well as those proteins released into the extracellular space without necessarily containing a signal sequence. If the secreted protein is released into the extracellular space, the secreted protein can undergo extracellular processing to produce a "mature" protein. Such processing event can be variable, and thus may yield different versions of the final "mature protein". The substantially purified laminin 8 of the present invention includes heterotrimers comprising both the full length and any such processed laminin 8 chains.

As used herein, the term "substantially purified" means that the laminin 8 so designated has been separated from its in vivo cellular environment.

As used herein, a laminin 8 polypeptide chain refers to a polypeptide chain according to one or more of the following:

(a) comprises a polypeptide structure selected from the group consisting of:
1. R1-R2-R3
2. R1-R2R3(e)
3. R3
4. R3(e)
5. R1-R3
6. R1-R3(e)
7. R2-R3
8. R2-R3(e)

wherein R1 is an amino terminal methionine; R2 is a signal sequence that is capable of directing secretion of the polypeptide, wherein the signal sequence may be the natural signal sequence for the particular laminin chain, that of another secreted protein, or an artificial sequence; R3 is a secreted laminin chain selected from the α4, β1, and γ1 chains; and R3(e) is a secreted laminin chain selected from the α4, β1, and γ1 chains that further comprises an epitope tag (such as those described below), which can be placed at any position within the laminin chain amino acid sequence; and/or (b) is encoded by a polynucleotide that is substantially similar to one or more of the disclosed laminin chain polynucleotide sequences or portions thereof (SEQ ID NOS.: 1, 3, 5, 7, 9, 11, 13, 15, 17, 19, 21, 23, 25, or 27); and/or (c) is encoded by a polynucleotide that hybridizes under high or low stringency conditions to the coding regions, or portions thereof, of one or more of the recombinant laminin 8 chain DNA sequences disclosed herein (SEQ ID NOS.: 1, 3, 5, 7, 9, 11, 13, 15, 17, 19, 21, 23, 25, 27), or complementary sequences thereof; and/or (d) has at least 70% identity to one or more of the disclosed laminin 8 polypeptide chain amino acid sequences (SEQ ID NOS.: 2, 4, 6, 8, 10, 12, 14, 16, 18, 20, 22, 24, 26, or 28), preferably at least 80% identity, and most preferably at least about 90% identity.

The phrase "substantially similar" is used herein in reference to polynucleotide or polypeptide sequences having one or more conservative variations from the laminin 8 sequences disclosed herein, including but not limited to deletions, insertions, inversions, repeats, and substitutions, wherein the resulting laminin chain is functionally equivalent to those disclosed herein.

For example, conservative polynucleotide variants may contain alterations in coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5–10, 1–5, or 1–2 amino acids are substituted, deleted, or added in any combination are also preferred. Polynucleotide variants can be produced for a variety of reasons, including but not limited to optimizing codon expression for a particular host (change codons in the human mRNA to those preferred by a bacterial host such as *E. coli*).

Naturally occurring conservative variants are called "allelic variants," and refer to one of several alternate forms of a gene occupying a given locus on a chromosome of an organism. (Genes II, Lewin, B., ed., John Wiley & Sons, New York (1985).) These allelic variants can vary at either the polynucleotide and/or polypeptide level. Alternatively, non-naturally occurring conservative variants may be produced by mutagenesis techniques or by direct synthesis.

Using known methods of protein engineering and recombinant DNA technology, conservative polynucleotide variants may be generated to improve or alter the characteristics of the expressed laminin chain polypeptides. For instance, one or more amino acids can be deleted from the N-terminus or C-terminus of the secreted protein. (See, for example, Ron et al., J. Biol. Chem. 268: 2984–2988 (1993); Dobeli et al., J. Biotechnology 7:199–216 (1988)) Ample evidence demonstrates that variants often retain a biological activity similar to that of the naturally occurring protein. (See, for example, Gayleet al., J. Biol. Chem 268:22105–22111 (1993)) Furthermore, even if deleting one or more amino acids from the N-terminus or C-terminus of a polypeptide results in modification or loss of one or more biological functions, other biological activities may still be retained.

Guidance concerning how to make phenotypically silent amino acid substitutions is provided in Bowie, J. U. et al., Science 247:1306–1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, Science 244:1081–1085 (1989).) The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved. Moreover, tolerated conservative amino acid substitutions involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

The "substantially similar" polypeptides of the present invention also include (i) substitutions with one or more of the non-conserved amino acid residues, where the substituted amino acid residues may or may not be one encoded by the genetic code, or (ii) substitution with one or more amino acid residues having substituents groups, or (iii) fusion of the mature polypeptide with another compound, such as a compound to increase the stability and/or solubility of the polypeptide (for example, polyethylene glycol), or (iv) fusion of the polypeptide with additional amino acids, such as an IgG Fc fusion region peptide, or leader or secretory sequence, or a sequence facilitating purification. Such variant polypeptides are deemed to be within the scope of those skilled in the art from the teachings herein.

For example, polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., Clin. Exp. Immunol. 2:331–340 (1967); Robbins et al., Diabetes 36: 838–845 (1987); Cleland et al., Crit. Rev. Therapeutic Drug Carrier Systems 10:307–377 (1993).)

"Stringency of hybridization" is used herein to refer to conditions under which nucleic acid hybrids are stable. The invention also includes nucleic acids that hybridize under high stringency conditions (as defined herein) to all or a portion of the coding sequences of the laminin chain polynucleotides disclosed herein, or their complements. The hybridizing portion of the hybridizing nucleic acids is typically at least 50 nucleotides in length. As known to those of skill in the art, the stability of hybrids is reflected in the melting temperature ($T_M$) of the hybrids. $T_M$ decreases approximately 1–1.5° C. with every 1% decrease in sequence homology. In general, the stability of a hybrid is a function of sodium ion concentration and temperature. Typically, the hybridization reaction is performed under conditions of lower stringency, followed by washes of varying, but higher, stringency. Reference to hybridization stringency relates to such washing conditions. Thus, as used herein, high stringency refers to an overnight incubation at 42° C. in a solution comprising 50% formamide, 5×SSC (750 mM NaCl, 75 mM sodium citrate), 50 mM sodium phosphate (pH 7.6), 5× Denhardt's solution, 10% dextran sulfate, and 20 μg/ml denatured, sheared salmon sperm DNA, followed by washing the filters in 0.1×SSC at about 65° C.

Also contemplated are laminin 8-encoding nucleic acid sequences that hybridize to the polynucleotides of the present invention at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37° C. in a solution comprising 6×SSPE (20×SSPE=3M NaCl; 0.2M $NaH_2PO_4$; 0.02M EDTA, pH 7.4), 0.5% SDS, 30% formamide, 100 ug/ml salmon sperm blocking DNA; followed by washes at 50° C. with 1×SSPE, 0.1% SDS. In addition, to achieve even lower stringency, washes performed following stringent hybridization can be done at higher salt concentrations (e.g. 5×SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

As used herein, "percent identity" of two amino acids or of two nucleic acids is determined using the algorithm of Karlin and Altschul (Proc. Natl. Acad. Sci. USA 87:2264–2268, 1990), modified as in Karlin and Altschul (Proc. Natl. Acad. Sci. USA 90:5873–5877, 1993). Such an algorithm is incorporated into the NBLAST and XBLAST programs of Altschul et al. (J. Mol. Biol. 215:403–410, 1990). BLAST nucleotide searches are performed with the NBLAST program, score=100, wordlength=12, to obtain nucleotide sequences homologous to the nucleic acid molecules of the invention. BLAST protein searches are performed with the XBLAST program, score=50, wordlength= 3, to obtain an amino acid sequence homologus to a polypeptide of the invention. To obtain gapped alignments for comparison purposes, Gapped BLAST is utilized as described in Altschul et al. (Nucleic Acids. Res. 25:3389–3402, 1997). When utilizing BLAST and Gapped BLAST programs, the default parameters of the respective programs (e.g., XBLAST and NBLAST) are used. See http://www.ncbi.nlm.nih.gov.

Further embodiments of the present invention include polynucleotides encoding laminin 8 chain polypeptides having at least 70% identity, preferably at least 80% identity, and most preferably at least 90% identity to one or more of the polypeptide sequences contained in SEQ ID NO:2, 4, 6, 8, 10, 12, 14, 16, 18, 20, 22, 24, 26, 28, or fragments thereof.

As used herein, "α4 polynucleotide" refers to polynucleotides encoding an α4 laminin chain of the same name. Such polynucleotides can be characterized by one or more of the following: (a) the nucleotides of said polynucleotide may encode an amino acid sequence substantially similar to the sequence set forth in SEQ ID NO: 2, 4, 6, 8, 10, 12 or fragments thereof; (b) polynucleotides that encode polypeptides which share at least 70% identity, preferably 80% identity, and most preferably at least 90% identity with the sequence set forth in SEQ ID NO: 2, 4, 6, 8, 10, 12, or fragments thereof; (c) the α4 polynucleotides hybridize under low or high stringency conditions to the coding sequence set forth in one or more of SEQ ID NO: 1, 3, 5, 7, 9, 11, or fragments thereof, or complementary sequences thereof; or (d) the α4 polynucleotides encode a polypeptide with a general structure selected from (1) R1-R2-R3; (2) R1-R2-R3(e); (3) R3; (4) R3(e); (5) R1-R3; (6) R1-R3(e); (7) R2-R3(e), and (8) R2-R3(e); wherein R1 and R2 are as described above, and R3 and R3(e) are as described above but comprise secreted α4 chain polypeptides.

As used herein, "β1 polynucleotides" refers to polynucleotides encoding a βB1 laminin chain of the same name. Such polynucleotides can be characterized by one or more of the following: (a) the nucleotides of said polynucleotides may encode an amino acid sequence substantially similar to the sequence set forth in SEQ ID NO: 14, 16, 18, 20 or fragments thereof; (b) polynucleotides that encode polypeptides which share at least 70% identity, preferably at least 80%, and most preferably at least 90% identity with one or more of the sequences set forth in SEQ ID NO: 14, 16, 18, 20 or fragments thereof; (c) the β1 polynucleotides hybridize under low or high stringency conditions to the coding sequence set forth in one or more of SEQ ID NO: 13, 15, 17, 19, fragments thereof, or complementary sequences thereof; or (d) the β1 polynucleotides encode a polypeptide with a general structure selected from (1) R1-R2-R3; (2) R1-R2-R3(e); (3) R3; (4) R3(e); (5) R1-R3; (6) R1-R3(e); (7) R2-R3; and (8) R2-R3(e); wherein R1 and R2 are as described above, and R3 and R3(e) are as described above but comprise secreted β1 chain polypeptides.

As used herein, "γ1 polynucleotides" refers to polynucleotides encoding a γ1 laminin chain of the same name. Such polynucleotides can be characterized by one or more of the following: (a) the nucleotides of said polynucleotides may encode an amino acid that is substantially similar to one or more of the sequences set forth in SEQ ID NO: 22, 24, 26, 28 or fragments thereof; (b) polynucleotides that encode polypeptides which share at least 70% identity, preferably at least 80%, and most preferably at least 90% identity with at one or more of the sequences set forth in SEQ ID NO: 22, 24, 26, 28 or fragments thereof; (c) the γ1 polynucleotides hybridize under low or high stringency conditions to the coding sequence set forth in one or more of SEQ ID NO: 21, 23, 25, 27 or complementary sequences thereof; or (d) the γ1 polynucleotides encode a polypeptide with a general structure selected from (1) R1-R2-R3; (2) R1-R2-R3(e); (3) R3; (4) R3(e); (5) R1-R3; (6) R1-R3(e); (7) R2-R3; and (8) R2-R3(e); wherein R1 and R2 are as described above, and R3 and R3(e) are as described above but comprise secreted γ1 chain polypeptides.

As used herein, the term "epitope tag" refers to a polypeptide sequence that is expressed as part of a chimeric protein, where the epitope tag serves as a recognition site for binding of antibodies generated against the epitope tag, or for binding of other molecules that can be used for affinity purification of sequences containing the tag.

As used herein, the term "increased biocompatibility" refers to reduced induction of acute or chronic inflammatory response, and reduced disruption of the proper differentiation of implant-surrounding tissues for laminin 8-coated biomaterials relative to an analogous, non-coated biomaterial.

As used herein the term "graft" refers to both natural and prosthetic grafts and implants.

In one aspect, the present invention provides r-laminin 8 expressing-cells that have been transfected with an expression vector containing promoter sequences that are operatively linked to nucleic acid sequences encoding at least one polypeptide sequence comprising the α4, β1 and γ1 chains of laminin 8, or fragments thereof, wherein the transfected cells secrete heterotrimeric laminin 8 containing the recombinant laminin chain. In a preferred embodiment, the cells are systematically transfected with recombinant expression vectors containing promoter sequences that are operatively linked to nucleic acid sequences encoding polypeptide sequences comprising the α4, β1 and γ1 chains of laminin 8 After the multiple transfections, the cells express each of the recombinant laminin 8 chains, which form the heterotrimer, before r-laminin 8 secretion into the media.

In a preferred embodiment, cDNAs encoding the α4, γ1 and γ1 chains, or fragments thereof, are subcloned into an expression vector. Alternatively, laminin 8 α4, β1 and/or γ1 gene sequences, including one or more introns, can be used.

Any cell capable of expressing and secreting the r-laminin 8 can be used. Preferably, eukaryotic cells are used, and most preferably mammalian cells are used, including but not limited to kidney and epithelial cell lines. In a most preferred embodiment, the mammalian cells do not express all of the laminin 8 chains endogenously. Carbohydrate and disulfide post-translational modifications are believed to be required for laminin 8 protein folding and function. This makes the use of eukaryotic cells preferable for producing functional r-laminin 8, although other systems are useful for obtaining, for example, antigens for antibody production.

"Recombinant expression vector" includes vectors that operatively link a nucleic acid coding region or gene to any promoter capable of effecting expression of the gene product. The promoter sequence used to drive expression of the individual chains or r-laminin 8 may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). The expression vector must be replicable in the host organisms either as an episome or by integration into host chromosomal DNA. In a preferred embodiment, the expression vector comprises a plasmid. However, the invention is intended to include other expression vectors that serve equivalent functions, such as viruses.

In one embodiment, at least one of the laminin chain polypeptide sequences, or fragments thereof, is operatively linked to a nucleic acid sequence encoding an "epitope tag", so that at least one of the chains is expressed as a fusion protein with an expressed epitope tag. The epitope tag may be expressed as the amino terminus, the carboxy terminus, or internal to any of the polypeptide chains comprising r-laminin 8, so long as the resulting r-laminin 8 remains functional. Any epitope tag may be utilized, so long as it can be used as the basis for affinity purification of the resulting r-laminin 8. Examples of such epitope tags include, but are not limited to FLAG (Sigma Chemical, St. Louis, Mo.), myc (9E10) (Invitrogen, Carlsbad, Calif.), 6-His (Invitrogen; Novagen, Madison, Wis.), and HA (Boehringer Manheim Biochemicals).

In another embodiment, one of the r-laminin 8 chains is expressed as a fusion protein with a first epitope tag, and at least one other r-laminin chain is expressed as a fusion protein with a second epitope tag. This permits multiple rounds of purification to be carried out. Alternatively, the same epitope tag can be used to create fusion proteins with more than one of the r-laminin chains.

In a further embodiment, the epitope tag can be engineered to be cleavable from the r-laminin 8 chain(s). Alternatively, no epitope tag is fused to any of the r-laminin 8 chains, and the r-laminin 8 is purified by standard techniques, including but not limited to affinity chromatography using laminin 8 specific antibodies or other laminin 8 binding molecules.

Transfection of the expression vectors into eukaryotic cells can be accomplished via any technique known in the art, including but not limited to calcium phosphate co-precipitation, electroporation, or liposome mediated-, DEAE dextran mediated-, polycationic mediated-, or viral mediated transfection. Transfection of bacterial cells can be done by standard methods.

In a preferred embodiment, the cells are stably transfected. Methods for stable transfection and selection of appropriate transfected cells are known in the art. In a most preferred embodiment, a CMV promoter driven expression vector is used in a human kidney embryonic 293 cell line.

Media from cells transfected with a single laminin chain are initially analyzed on Western blots using laminin chain-specific antibodies. The expression of single laminin chains following transfection is generally intracellular. Clones showing reactivity against individual transfected chain(s) are verified by any appropriate method, such as PCR, reverse transcription-PCR, or nucleic acid hybridization, to confirm incorporation of the transfected gene. Preferably, analysis of genomic DNA preparations from such clones is done by PCR using laminin chain-specific primer pairs. Media from transfected clones producing all three chains are further analyzed for r-laminin 8 secretion and/or activity, by any appropriate method, including Western blot analysis and cell binding assays. Activity of the r-laminin 8 is preferably analyzed in a cell adhesion assay.

In another aspect, the present invention provides substantially purified laminin 8, preferably r-laminin 8. In one embodiment, the substantially purified laminin 8 comprises a first chain comprising an α4 chain polypeptide; a second chain comprising a β1 chain polypeptide; and a third chain comprising a γ1 chain polypeptide. Alternatively, the r-laminin 8 comprises a first chain that is substantially similar to at least one of the sequences shown in SEQ ID NO: 2, 4, 6, 8, 10, 12 or fragments thereof, a second chain that is substantially similar to at least one of the sequence shown in SEQ ID NO: 14, 16, 18, 20 or fragments thereof, and a third chain that is substantially similar to the sequence shown in SEQ ID NO: 22, 24, 26, 28 or fragments thereof.

In another embodiment, the substantially purified r-laminin 8 comprises a first chain comprising a polypeptide that is at least about 70% identical to at least one of the sequences shown in SEQ ID NO: 2, 4, 6, 8, 10, 12 or fragments thereof; a second chain comprising a polypeptide that is at least 70% identical to at least one of the sequences shown in SEQ ID NO: 14, 16, 18, 20 or fragments thereof, and a third chain comprising a polypeptide that is at least 70% identical to at least one of the sequences shown in SEQ ID NO: 22, 24, 26, 28 or fragments thereof, wherein the first, second, and third polypeptides are produced recombinantly, and wherein the first, second, and third chains assemble into a recombinant heterotrimeric laminin 8.

In a preferred embodiment, at least one of the first, second, or third chains of the substantially purified human r-laminin 8 is expressed as a fusion protein with an epitope tag.

Alternatively, the r-laminin 8 comprises a heterotrimeric polypeptide structure, wherein each individual chain comprises a general structure selected from the group consisting of: (1) R1-R2-R3; (2) R1-R2-R3(e); (3) R3; (4) R3(e); (5) R1-R3; (6) R1-R3(e); (7) R2-R3; and (8) R2-R3(e)

wherein R1 is a amino terminal methionine; R2 is a signal sequence that is capable of directing secretion of the polypeptide, wherein the signal sequence may be the natural signal sequence for the particular laminin chain, that of another secreted protein, or an artificial sequence; R3 is a secreted α4, β1, or γ1 laminin chain; and R3(e) is a secreted laminin α4, β1, and γ1 chain that further comprises an epitope tag (such as those described above), which can be placed at any position within the laminin chain amino acid sequence.

In a preferred embodiment, purification of r-laminin 8 is accomplished by passing media from the transfected cells through an antibody affinity column. In one embodiment, antibodies against a peptide epitope expressed on at least one of the recombinant chains are attached to an affinity column, and bind the r-laminin 8 that has been secreted into the media. The r-laminin 8 is removed from the column by passing excess peptide over the column. Eluted fractions are analyzed by any appropriate method, including gel electrophoresis and Western blot analysis. In a further embodiment, the peptide epitope can be cleaved after purification. In other embodiments, two or three separate r-laminin chains are expressed as fusion proteins, each with a different epitope tag, permitting two or three rounds of purification and a doubly or triply purified r-laminin 8. The epitope tag can be engineered so as to be cleavable from the r-laminin 8 chain(s) after purification. Alternatively, no epitope tag is fused to any of the r-laminin 8 chains, and the r-laminin 8 is purified by standard techniques, including but not limited to affinity chromatography using laminin 8 specific antibodies or other laminin 8 binding molecules.

The present invention further provides pharmaceutical compositions comprising substantially purified laminin 8 and a pharmaceutically acceptable carrier. In a preferred embodiment, the pharmaceutical composition comprises substantially purified r-laminin 8. According to this aspect of the invention, other agents can be included in the pharmaceutical compositions, depending on the condition being treated. The pharmaceutical composition may further comprise one or more other compounds, including but not limited to any of the collagens, other laminin types, fibronectin, vitronectin, cadherins, integrins, α-dystroglycan, entactin/nidogen, α-dystroglycan, glycoproteins, proteoglycans, heparan sulfate proteoglycan, glycosaminoglycans, epidermal growth factor, vascular endothelial growth factor, fibroblast growth factor, or nerve growth factors, and peptide fragments thereof.

Pharmaceutical preparations comprising substantially purified laminin 8 can be prepared in any suitable form, and generally comprise the laminin 8 in combination with any of the well known pharmaceutically acceptable carriers. The carriers can be injectable carriers, topical carriers, transdermal carriers, and the like. The preparation may advantageously be in a form for topical administration, such as an ointment, gel, cream, spray, dispersion, suspension or paste. The preparations may further advantageously include preservatives, antibacterials, antifungals, antioxidants, osmotic agents, and similar materials in composition and quantity as is conventional. Suitable solutions for use in accordance with the invention are sterile, are not harmful for the proposed application, and may be subjected to conventional pharmaceutical operations such as sterilization and/or may contain conventional adjuvants, such as preservatives, stabilizers, wetting agents, emulsifiers, buffers etc. For assistance in formulating the compositions of the present invention, one may refer to Remington's Pharmaceutical Sciences, 15th Ed., Mack Publishing Co., Easton, Pa. (1975).

In further aspect, the present invention provides methods and kits comprising laminin 8, or pharmaceutical compositions thereof (and instructions for using the laminin 8 in the kits) for accelerating the healing of injuries to tissue of mesenchymal origin, such as bone, cartilage, tendon, and ligament, treating injuries to vascular and neural tissue, and for improving the biocompatibility of grafts used for treating such injuries. In a preferred embodiment of each of the methods disclosed below, r-laminin 8 is used. In specific examples, substantially purified laminin 8, r-laminin 8, or pharmaceutical compositions thereof are used to:

a. promote re-endothelialization at the site of vascular injuries;
  b. improve the "take" of grafts;
  c. improve the biocompatibility of medical devices;
  d. treat neural injuries (neural regeneration);
  e. regulate angiogenesis; and
  d. promote cell attachment and migration
     by providing an amount effective of laminin 8 or pharmaceutical compositions thereof for the various methods.

In one embodiment, laminin 8 is used to promote re-endothelialization, and to thus inhibit abnormal smooth muscle cell proliferation, at the site of a vascular injury. The α4 chain is associated with mesenchymally derived cell populations, including but not limited to endothelium and smooth muscle cells, and laminin 8 has been shown to be a primary laminin of the vascular endothelium.

The value of angioplasty in clearing occluded coronary arteries is limited by a restenosis/reocclusion rate of 50–70%. Several studies have indicated that the insertion of a vascular stent following angioplasty appears to decrease the occurrence of restenosis, but the problem still limits the effectiveness of this treatment. Restenosis appears to arise in part from the proliferation of vascular smooth muscle cells in response to the angioplasty treatment. It is likely that the scraping action of angioplasty removes not only the problematic occlusion, but also sections of the vascular basal lamina. The discontinuous basal lamina that results could contribute to what appears to be abnormal growth of the vascular smooth muscle cells that leads to restenosis.

The attachment of laminin 8 to vascular stents can be used to limit restenosis, by promoting re-endothelialization. The interaction of vascular endothelial cells with the laminin 8 coated stents promotes their adhesion and attachment, thereby leading to homeostasis and a normal cell growth response, instead of the injury/activation endothelial cell response seen with restenosis. While activated platelets adhere to laminin 8, non-activated platelets do not. Furthermore, is has been shown that soluble laminin 8 does not cause platelet activation, but has an inhibitory effect on platelet activation by classical activators such as thrombin, collagen I, and ADP (unpublished observations). A more normal and controlled rate of re-endothelialization will decrease the incidence of re-occlusions, and improve the outcome of the angioplasty procedure.

Similarly, synthetic vascular grafts can induce blood clotting and thrombosis through interactions of blood clotting factors with the synthetic graft material. Coating vascular grafts with laminin 8 promotes endothelialization of the synthetic vessel, thereby providing for a non-thrombogenic surface. Vascular endothelial cells, like other cells that sit upon a basement membrane, prefer to adhere to an appropriate basement membrane substrate. Laminin-8 has been identified as a component of the vascular basal lamina, and is suspected to be involved in the attachment of vascular endothelial cells to the supporting basal lamina. Providing this substrate in a graft material creates a non-thrombogenic surface, promotes endothelialization, and inhibits intravascular thrombosis and vascular obstruction.

Administration to the injured blood vessel can be accomplished in some cases by simply coating laminin 8 or pharmaceutical compositions thereof into an injured area. In other embodiments, delivery can be accomplished by:
  1. Coating a stent;
  2. Coating a biodegradable sleeve over the stent; or
  3. Forcing a liquid preparation of the laminin 8 or pharmaceutical compositions thereof through a porous catheter to the injured site.

In another embodiment, the present invention provides methods to promote bone and connective tissue repair in a subject. The incorporation of laminin 8 or pharmaceutical compositions thereof into wound repair dressings and matrices as well as tissue grafts to accelerate the healing of bone and connective tissue repair provides a natural ligand interactive surface to promote normal cell adherence, cell growth and tissue development. Many grafts are used to replace connective tissue that has a cell layer adherent to a basal lamina. When an inappropriate surface is provided to these cells following grafting, the graft is at risk for failure of restoration of the normal cell layer. The advantage of coating these grafts with laminin 8 is to create a surface that sufficiently recapitulates a normal basal lamina surface to promote cell re-population. As used herein the term "graft" refers to both natural and prosthetic grafts.

The methods of the present invention have application in the healing of tendon, cartilage, or ligament tears, deformities and defects, bone fractures, defects, as well as use in the improved fixation of tendon, cartilage, or ligament to bone or other tissues. In addition, bony in-growth into various prosthetic devices can be greatly enhanced so that such artificial parts are firmly and permanently anchored into the surrounding skeletal tissue through a natural osseous bridge.

In a further aspect, the present invention comprises medical devices with improved biocompatibility, wherein the devices are coated with laminin 8 or pharmaceutical compositions thereof, alone or in combination with other proteins or agents that serve to increase the biocompatibility of the device surface. The coated device stimulates cell attachment and provides for diminished inflammation and/or infection at the site of entry of the appliance.

Such medical devices can be of any material used for implantation into the body, and preferably are made of or coated with a biocompatible metal that may be either stainless steel or titanium. Alternatively, the device is made of or coated with a ceramic material, or a polymer including but not limited to polyester, polyglycolic acid or a polygalactose-polyglycolic acid copolymer.

One particular use of the present invention is to increase cell adhesion to target surfaces, including but not limited to endothelial, skeletal muscle, smooth muscle, and other mesenchymally-derived cells. For example, vascular grafts and stents may be coated with laminin 8 or pharmaceutical compositions thereof to stimulate endothelial cell attachment. Alternatively, bone or connective tissue grafts or prostheses may be coated with laminin 8 or pharmaceutical compositions thereof to stimulate adhesion of the appropriate cell type and improved grafting efficiency.

If the device is made of a natural or synthetic biodegradable material in the form of a mesh, sheet or fabric, laminin 8 or pharmaceutical compositions thereof may be applied directly to the surface thereof. Appropriate cells may then be cultured on the matrix to form transplantable or implantable devices, including dental abutment pieces, needles, metal pins or rods, indwelling catheters, colostomy tubes, surgical meshes and any other appliance for which coating with laminin 8 is desirable. Alternatively, the devices may be implanted and cells may be permitted to attach in vivo.

Coupling of the substantially purified laminin 8 may be non-covalent (such as by adsorption), or by covalent means. The device may be immersed in, incubated in, or sprayed with the laminin 8 or pharmaceutical compositions thereof.

The dosage regimen for various treatments using the laminin 8 of the present invention is based on a variety of factors, including the type of injury or condition, the age, weight, sex, medical condition of the individual, the severity of the condition, and the route of administration. Thus, the dosage regimen may vary widely, but can be determined routinely by a physician using standard methods. Laminins are extremely potent molecules, and one or a few molecules per cell could produce an effect. Thus, effective doses in the pico-gram per milliliter range are possible if the delivery is optimized. Laminins are sometimes present in an insoluble form in the basement membrane and have the capability of polymerizing at concentrations as low as about 50 $\mu$g/ml, depending on the laminin isoform and the conditions. Laminins can also polymerize into a gel at a concentration of about 2–3 mg/ml. Dosage levels of the order of between 1 ng/ml and 10 mg/ml are thus useful for all methods disclosed herein, preferably between about 1 $\mu$g/ml and about 3 mg/ml.

The present invention also provides a method for inducing cell attachment to the device (as disclosed above), comprising coating the appliance with laminin 8 or pharmaceutical compositions thereof prior to incubation with cells appropriate for the desired application.

Laminin preparations are known to induce the growth and differentiation of neurons (U.S. Pat. No. 5,229,365), and have been used in combination with Type I collagen to coat a hollow conduit and promote nerve regeneration across a gap of severed nerve. (U.S. Pat. No. 5,019,087).

Thus, in another embodiment, a method is provided for nerve regeneration, comprising administering to a subject in need thereof an amount effective of laminin 8 or pharmaceutical compositions thereof to promote nerve regeneration. The graft can comprise a nerve graft, or a prosthetic graft. Both bioresorbable and non-resorbable materials have been used in tubes for bridging nerve gaps. (See for example, Nyilas, et al., (Trans. Soc. Biomater., 6, 85, 1983), Molander, et al. (Biomaterials, Vol. 4, pp. 276–280, October, 1983), Colin, et al., (Journal of Dental Research July, 1984, pp. 987–993). The method can be used to treat diseases and injuries characterized by the loss of function and or/degeneration of neurons and nerves.

Laminins, or cell extracts containing laminins have been shown to regulate angiogenesis in a biphasic manner. (See, for example, Nicosia et al., Dev. Biol. 164:197–206 (1994); Bonfil et al., Int. J. Cancer 58:233–239 (1994)). At lower concentrations (30–300 $\mu$g/ml), a laminin-entactin complex stimulated angiogenesis in a three-dimensional culture, while at 3000 $\mu$g/ml the same complex was inhibitory to angiogenesis. Thus, in another aspect, the present invention provides methods for regulating angiogenesis, comprising contacting a tissue or culture substrate with an amount effective of laminin 8 or pharmaceutical compositions thereof to regulate angiogenesis. In one embodiments, the laminin 8 is used to promote angiogenesis by contacting a tissue or culture substrate with an amount effective of laminin 8 to promote angiogenesis. In another embodiment, the laminin 8 is used to inhibit angiogenesis, by contacting the tissue or culture substrate with an amount effective of laminin 8 to inhibit angiogenesis. An example of culture substrates to be contacted with laminin 8 to regulate angiogenesis are those used for tissue engineering purposes.

In another aspect of the present invention, laminin 8 is used for the culture of cells, including but not limited to endothelial cells, nerve cells, cells of hematopoietic lineage, and mesenchymally-derived cells including but not limited to cells derived from bone, connective tissue, and adipose tissue, skeletal muscle cells, and smooth muscle cells, by contacting the cells with an amount effective of laminin 8 to stimulate attachment and proliferation/differentiation/stasis of cells. The laminin 8 can either be provided in the cell culture medium, or as a cell culture medium supplement, or may be coated on the surface of a cell growth substrate. In a preferred embodiment, the method further includes contacting the cells with other compounds, including but not limited to any of the collagens, other laminin types, fibronectin, $\alpha$-dystroglycan, cadherins, integrins, entactin/nidogen, $\alpha$-dystroglycan, glycoproteins, proteoglycans, heparan sulfate proteoglycan, glycosaminoglycans, epidermal growth factor or nerve growth factors, vascular endothelial growth factor, fibroblast growth factor, and peptide fragments thereof.

The cells may comprise primary cells or cell culture cell lines. The methods of this aspect of the invention can be used in vivo, ex vivo, or in vitro.

In a preferred embodiment, laminin 8 is used to coat the surface of a substrate, to promote cell adhesion to the substrate, and to stimulate cell proliferation/differentiation/stasis. The substrate used herein may be any desired substrate. For laboratory use, the substrate may be as simple as glass or plastic. For use in vivo, the substrate may be any biologically compatible material capable of supporting cell adhesion. Suitable substrate materials include shaped articles made of or coated with such materials as collagen, regenerated collagen, polyglycolic acid, polygalactose, polylactic acid or derivatives thereof; biocompatible metals such as titanium and stainless steel; ceramic materials including prosthetic material such as hydroxylapatite; synthetic polymers including polyesters and nylons; polystyrene; polyacrylates; polytetrafluoroethylene and virtually any other material to which biological molecules can readily adhere. The determination of the ability of a particular material to support adhesion of the r-laminin 8 of the invention requires only routine experimentation by the skilled artisan.

In a further aspect, the present invention provides cell growth substrates for adhesion and culturing of cells, by providing an amount effective of laminin 8 for the attachment of cells to a cell culture device for the attachment and subsequent proliferation/differentiation/stasis of the cells. The substrates may comprise any of the substrates discussed above.

In another aspect of the present invention, an improved cell culture medium is provided, wherein the improvement comprises addition to the cell culture medium of an effective amount of laminin 8 to the cell culture medium to promote the adherence, proliferation, and/or maintenance of cells. Any cell culture media that can support the growth of cells can be used with the present invention. Such cell culture media include, but are not limited to Basal Media Eagle, Dulbecco's Modified Eagle Medium, Iscove's Modified Dulbecco's Medium, McCoy's Medium, Minimum Essential Medium, F-10 Nutrient Mixtures, Opti-MEM® Reduced-Serum Medium, RPMI Medium, and Macrophage-SFM Medium or combinations thereof.

The improved cell culture medium can be supplied in either a concentrated (ie: 10×) or non-concentrated form, and may be supplied as either a liquid, a powder, or a lyophilizate. The cell culture may be either chemically defined, or may contain a serum supplement. Culture media is commercially available from many sources, such as GIBCO BRL (Gaithersburg, Md.) and Sigma (St. Louis, Mo.). In an alternative embodiment, the laminin 8 is used as a cell culture supplement.

The laminin 8 or pharmaceutical compositions thereof of the present invention can be used for the treatment of a variety of conditions and diseases as described herein, including but not limited to various vascular, neural, and mesenchymal tissue injuries, including but not limited to angioplasty restenosis, tissue ischemia, neural damage, vascular surgical procedures, atherosclerosis, bone fractures, defects, and disorders which result in weakened bones such as osteoporosis, osteoarthritis, and periodontal disease; bone loss resulting from cancer or side effects of other medical treatment; age-related loss of bone mass; articular cartilage tears, deformities and other cartilage defects such as arthritis and cartilaginous tissue damage, tendon or ligament tears, deformities and other tendon or ligament defects such as tendinitis and carpal tunnel syndrome, periodontal ligament injury, and tendon-to-bone detachment.

The amount of laminin 8 or pharmaceutical compositions thereof used in such treatments will, of course, depend upon the type and severity of the condition or disease being treated, the route of administration chosen, and will be determined by the attending physician or veterinarian. The term "therapeutically effective amount" of laminin 8 or pharmaceutical compositions thereof refers to the amount of laminin 8 or pharmaceutical compositions thereof, in the absence of other exogenously applied factors, determined to produce a therapeutic response in a mammal. Such therapeutically effective amounts are readily ascertained by one of ordinary skill in the art.

The present invention may be better understood with reference to the accompanying examples that are intended for purposes of illustration only and should not be construed to limit the scope of the invention, as defined by the claims appended hereto.

EXAMPLES

Expression Constructs

For expression of the human laminin α4 chain containing a C-terminal FLAG epitope, the full length cDNA was constructed and modified as follows. Complementary DNA lambda clones subcloned into pBluescript™ or pCRscript™ (Stratagene) plasmid vectors from an earlier study (Iivanainen et al., 1995) were used as cDNA source, except for clone FL136. The EcoRI insert from FL136 lambda DNA was cloned into the pBluescript™ EcoRI site to make FL136E. The 0.78 kb SacI-BamHI fragment from clone FL76 was ligated into SacI-BamHI digested pSL1180 (Pharmacia) to make FL76SB. A sequence corresponding to nucleotides 2378–4274 of human laminin α4 cDNA was PCR-amplified using cDNA library as a template, digested with SacI and cloned into the FL76SB SacI site and its orientation confirmed to make HL4-SB. The FL64 BamHI-SalI fragment was cloned into HL4-SB BamHI-SalI to make HL4-3'.

The Eco72I-XhoI fragment from clone FL117 was ligated into the Eco72I-XhoI sites of FL136E to make HL4-5'. Both mouse and human laminin α4 cDNAs have poorly conserved Kozak-sequences at the translation initiation site, as well as several extra 5' untranslated region (UTR) ATG sequences. To ensure efficient and correct translation initiation, the Kozak sequence was edited to match the consensus and the rest of the 5' UTR was deleted using standard molecular biology techniques. The resulting product was EcoRI-EagI-digested and cloned to the EcoRI-EagI-digested HL4-5' to make HL4Mut-5'. The SpeI-XhoI fragment from HL4Mut-5' was cloned into HL4-3' to make clone HL4-Full with full length cDNA. The EcoRI insert from HL4-Full was cloned into pcDNA3.1/Zeo(−) expression vector (Invitrogen) to make HL4-Full.pcDNA. (SEQ ID NO: 1).

The sequence encoding the FLAG epitope (SEQ ID NO:3) was inserted as follows. The FL64 BamHI-HindIII fragment was cloned into pUC19 to make FL64BH. PCR was performed using primers to introduce the FLAG epitope, using HL4-3' as template. The product was digested with XbaI and HindIII and cloned in XbaI-HindIII digested FL64BH to make HL4FLAG-3'. This also resulted in deletion of the original 3' UTR. The BamHI-HindIII fragment from HL4FLAG-3' was cloned into BamHI-HindIII-digested HL4-Full.pcDNA vector, replacing the original BamHI-HindIII fragment to make HL4FLAG-B, which lacked the BamHI-HindIII fragment. The final expression construct named HL4FLAG-Full was made by inserting the missing BamHI fragment in the correct orientation. All PCR-derived parts of the cDNA sequence were sequenced to ensure that no mutations had occurred during amplification.

The construct used for expression of the mouse laminin β1 chain (SEQ ID NO: 17) has been previously described (Yurchenco et al., Proc. Natl. Acad. Sci. U.S.A. 94(19), 10189–94 (1997)).

To make the construct named HG1 for expression of the human laminin γ1 chain, full length cDNA (SEQ ID NO:21) encoding the human laminin γ1 chain was released with BamHI from a baculovirus expression vector pVL941 (unpublished) and cloned into the BamHI site of a pcDNA3.1/Hygro(−) mammalian expression vector (Invitrogen).

Antibodies, Control Proteins, and Cell Lines

Affinity purified polyclonal anti-laminin α4 antibody (Ab) S8 was prepared as described previously. (Iivanainen et al., 1997, J. Biol. Chem. 272(44), 27862–8) Polyclonal anti-EHS-laminin Ab, anti-FLAG M2 monoclonal Ab (mAb), purified control mouse IgG, RGDS-peptide and heparin (grade I-A) were purchased from Sigma Chemical Company (St. Louis, Mo.). Anti-laminin γ1 (clone 22) mAb was from Transduction Laboratories (Lexington, Ky.). Mouse function blocking mAbs against integrin α1 (clone FB12), integrin α2 (clone P1E6), and integrin α3 (clone P1B5) were obtained from Chemicon (Temecula, Calif.). Rat function blocking mAbs anti-integrin α6 (clone GoH3) and control rat IgG$_{2a}$ were also from Chemicon. Rat function blocking mAbs against integrin α5 (clone BIIG2) and integrin β1 (clone AIIB2) were provided by Dr. C. Damsky (Univ. of California, San Francisco) as hybridoma supernatants. Immunoglobulins were purified from the supernatants using GAMMABIND PLUS™ Sepharose (Pharmacia; Stockholm, Sweden) according to the manufacturer's instructions. Secondary Ab conjugates anti-rabbit IgG-HRP and anti-mouse IgG-HRP were from Dakopatts (Denmark). Laminin 1 from EHS-tumor, collagen type IV from EHS-tumor, and human placental laminin were obtained from Sigma. Fibronectin and some of the laminin 1 from EHS-tumor were purchased from Gibco BRL (Rockville, Md.) EHS-derived laminin 1/nidogen complex was kindly provided by Dr. J. Engel (Univ. of Basel, Switzerland). Human fibrosarcoma HT-1080 (CCL-121) cells were from the American Type Tissue Collection. (Manassas, Va.) IMMORTOMOUSE™ brain capillary endothelial (IBE, Kanda et al., 1999, *Exp. Cell Res.* 248(1), 203–13) and bovine adrenal microvascular (BCE, Folkman et al., 1979) cells were kindly provided by Dr. L. Claesson-Welsh (Medical Biochemistry and Microbiology, Univ. of Uppsala) and K. Olausson (Medical Cell Biology, Univ. of Uppsala). Three human erythroleukemic K562 cell lines transfected to express integrins $\alpha 3$ (Delwel et al., 1994, *Mol. Biol. Cell* 5(2),203–15), $\alpha 6$ (Delwel et al., 1993, *J. Biol. Chem.* 268(34), 25865–75), or both $\alpha 6$ and $\alpha 4$ (Niessen et al., 1994, *Exp. Cell Res.* 211(2), 360–7 *Mol. Biol. Cell*) were provided by Dr. A. Sonnenberg (Netherlands Cancer Institute, Amsterdam, Netherlands).

Production and Purification of Recombinant Laminin 8

Recombinant laminin 8 ("r-laminin 8") was produced in human embryonic kidney cells (HEK-293, ATCC CRL-1573) cultured in DME/pyruvate/10% fetal calf serum (FCS) at 37° C. in a humidified 5% $CO_2$ atmosphere. Wild-type cells were stably transfected with the laminin $\beta 1$ expression construct as previously described (Yurchenco et al., 1997) and selected using 500 µg/ml G418. All further cell culture and clonal expansion was carried out in the continuous presence of relevant selection antibiotics. A highly expressing clone was then transfected with the HL4FLAG-Full construct using standard calcium-phosphate transfection methods, and stable colonies were selected using 300 µg/ml Zeocin. Clones were isolated using cloning rings, expanded, and analyzed for laminin $\alpha 4$ secretion by Western blotting of medium using the anti-laminin $\alpha 4$ Ab S8. The clone with the highest expression was transfected with the HG1 construct, and stable clones were selected using 100 µg/ml hygromycin. These clones were then screened via Western blotting using a mAb against laminin $\gamma 1$, and clones showing the highest secretion were expanded further.

For production of r-laminin 8, cells were grown in the culture medium for up to four days, after which the medium was collected and centrifuged to remove cell debris. After collection, Tris-Cl pH 7.5 was added to 50 mM and EDTA was added to a concentration of 10 mM. If not used immediately, the medium was stored at −70° C. For protein production into serum-free medium, confluent cultures were washed twice with PBS and the medium was changed to DME supplemented with pyruvate, insulin-transferrin-selen supplement (Sigma) and 1 µg/ml aprotinin (Sigma).

r-laminin 8 was affinity purified using an anti-FLAG M2 matrix (Sigma). Before use, the matrix was washed with 0.1M glycine (pH 3.5) and TBS (50 mM Tris-HCl pH 7.5/150 mM NaCl) according to the manufacturer's instructions. Brij-20 (Fluka, Milwaukee, Wis.) was added to the medium to a final concentration of 0.05% (v/v), and the medium was incubated in batch mode with the matrix (25 µl matrix/ml) overnight at 4° C. with agitation. The matrix was collected by passing the medium through a sintered column, and washed extensively in the column first with TBS/1 mM EDTA and then PBS/1 mM EDTA. Bound r-laminin 8 was competitively eluted with 100 µg/ml FLAG peptide (Sigma) in PBS/1 mM EDTA at room temperature. The matrix was then regenerated as recommended by the manufacturer. The eluate was diluted 1:1 with 20 mM $NaPO_4$/1 mM EDTA (pH 7.5), and injected into a UNO-Q ion-exchange column (Bio-Rad, Hercules, Calif.). At this salt concentration, the FLAG peptide passes through, but r-laminin 8 is bound. The column was then washed with 20 mM phosphate/1 mM EDTA, and the r-laminin 8 was eluted with 20 mM $NaPO_4$/1.5M NaCl/1 mM EDTA. The eluate was diluted 1:10 with 20 mM $NaPO_4$ (pH 7.5)/1 mM EDTA to a final salt concentration of 150 mM and concentrated using 100 kD cut-off ultrafiltration (Gelman; Ann Arbor, Mich.) to approximately 0.5 mg/ml.

Characterization of r-laminin 8

Secreted r-laminin 8 in cell medium and after purification was characterized using linear 5% or 6% SDS-PAGE and 3–12% gradient SDS-PAGE under reducing and non-reducing conditions. Proteins were visualized using silver staining or blotted to PVDF membranes using a semi-dry blotting system (Bio-Rad). For immunodetection, Renaissance ECL-System (Dupont, Waltham, Mass.) was used in conjunction with the Abs described above. Protein quantitation was done by measuring absorbance at 280 nm or using the Bradford method (Bio-Rad protein assay kit).

Rotary shadowing electron micrography (EM) was performed as described previously. (Yurchenco and Chen, 1993) When purifying for rotary shadowing, the matrix was equilibrated with 0.15 M $NH_4HCO_3$-acetate buffer (pH 7.4), and the r-laminin 8 was then eluted with FLAG-peptide in the same buffer.

Adhesion Assays and Cell Culture

For adhesion assays, flat-bottom 96 well plates (Maxi-Sorp, Nunc; Rochester, N.Y.) were coated by incubating with proteins diluted in PBS overnight at 4° C. (50 µl/well). The remaining protein-binding capacity was saturated by addition of 2% heat-inactivated BSA in PBS (50 µl/well) and further incubation for at least 4 hours. Prior to assaying, the coating/blocking solution was aspirated, and the wells were washed with the binding medium (100 µl/well). Drying of coated protein was avoided, since this was found to be detrimental to adhesion in some cases.

All cells were cultured in humidified 5% $CO_2$ atmosphere. HT-1080 and BCE cells were cultured in DME/10% FCS/pyruvate at 37° C., BCE on gelatin-coated plastic. IBE cells were cultured in F12/10% FCS/2 U/ml $\gamma$-interferon on gelatin-coated plastic at 33° C. Transfected K562 cells were grown in suspension in RPMI/10% FCS supplemented with 1 mg/ml G418 at 37° C. For K562 cells transfected with both $\alpha 4$ and $\beta 4$ integrins, 0.7 mg/ml hygromycin was included in the medium. Prior to dissociation, the cells were washed twice with PBS. HT-1080 cells were disassociated using 5 mM EDTA in PBS, while the others were disassociated using trypsin-EDTA (Gibco-BRL). To remove trypsin, cells were pelleted and resuspended twice in serum-free medium. Cells were counted and suspended in buffered serum-free medium at $2-3\times10^5$ cells/ml. K562 cells were washed twice with serum-free medium and resuspended at $10^6$ cells/ml. DME/25 mM HEPES/pyruvate was used for HT-1080 cells; F12/25 mM HEPES/0.25% BSA was used for other cell types.

K562 cell stimulation was done using 5 ng/ml PMA (Sigma). Antibodies or other test compounds were added to the cell suspension and the cells were allowed to recover at 37° C. for 30 minutes. The cells were then added to the protein-coated 96-well plates (100 µl/well) and allowed to adhere for 30 (K562) or 60 (other cells) minutes at 37° C. To remove unbound cells, wells were washed by two or three cycles of careful addition of 100 µl of binding medium followed by aspiration. The remaining cells were fixed with 1% glutaraldehyde in PBS for 10 minutes at room temperature. Cells were stained with 0.1% crystal violet (Sigma) for 30 minutes and unbound stain was removed by four washes with water. Bound stain was solubilized in 2% SDS (100 µl/well) and quantitated by measuring the absorbance at 595 nm using a microplate reader.

None of the cell lines bound appreciably to BSA. When the quantitative results were calculated, binding to BSA was given a value of zero, while the relevant control was given the value of 100. The mean and SEM were calculated from results obtained from parallel wells.

RESULTS

Production and Characterization of r-laminin 8

Unconcentrated medium from wild-type HEK-293 cells did not react in Western blots with the anti-laminin α4, anti-laminin γ1, anti-EHS-laminin, or anti-FLAG antibodies, indicating that these cells express endogenous laminins at very low amounts if at all. The transfected α4 chain could be secreted to some extent even when expressed alone, but secretion of the other chains required simultaneous expression of all three chains. Cells transfected with laminin α4, β1, and γ1 chain expression constructs secreted large amounts of all three chains to the medium. The best cell clones ("G1–2" and "G1–3") were estimated to produce 3–5 milligrams or r-laminin 8 per liter of medium.

The r-laminin 8 bound to anti-FLAG M2 matrix with high specificity. When eluted competitively with the FLAG peptide, only laminin α4, β1, and γ1 bands were seen in silver-stained 3–12% gradient SDS-PAGE gels. (FIG. 1) Under non-reducing conditions, the purified protein hardly entered the gel, which was to be expected as the predicted molecular weight for the mature trimer is at least 570 kD. A minor fraction of the purified trimer appeared as non-covalently associated (see discussion). In this fraction, the β1 and γ1 chains appeared as covalently associated dimers, whereas the α4 chain was non-covalently associated. Under reducing conditions, the protein appeared as a broad band at around 200 kD, which reacted on Western blots with α4, EHS, γ1, and anti-FLAG antibodies. The predicted molecular weights for mature α4, β1, and γ1 polypeptides are 200, 195, and 174 kD respectively. Laminins are heavily glycosylated, which may account for the slight discrepancy in molecular weight observed in SDS-PAGE. The β1 and γ1 chains of laminin 1 purified from EHS-tumor showed similar or slightly slower mobility than those of r-laminin 8.

Figure 2:
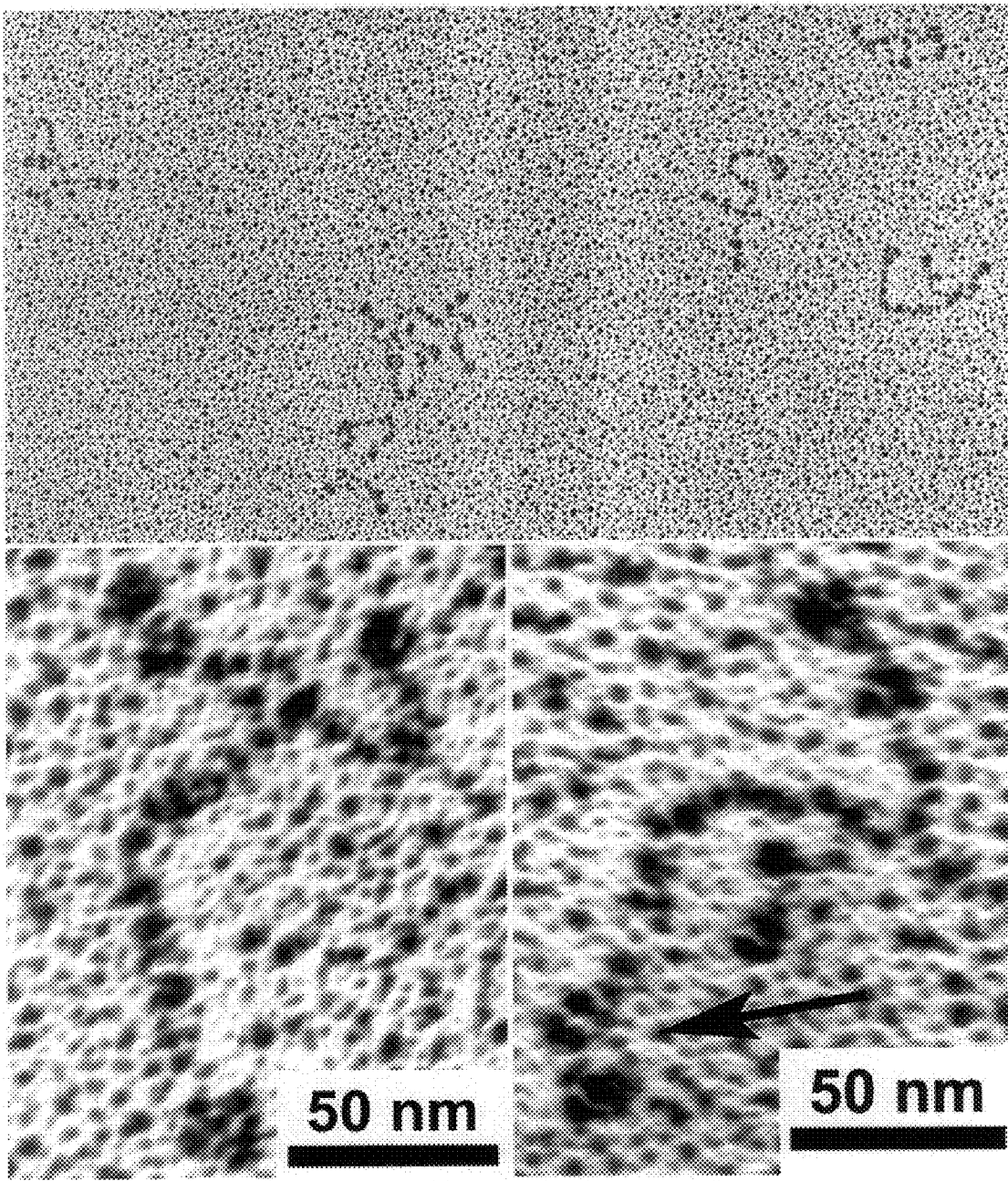
FIG. 2 is a rotary shadowed electron micrograph or r-laminin 8. Top: low magnification field showing several r-laminin 8 molecules. Bottom: Individual molecules. Each molecule has two short arms and one long arm. In some molecules, a very short (5–10 nm) rod-like stub can be seen at the junction of the arms. Arrow: G-domain can be seen as consisting of two moieties in some molecules. (Bar=50 nm).

Rotary shadowing EM revealed r-laminin 8 to be a Y-shaped molecule with two short and one long arm in accordance with the predicted structure. (FIG. 2) In many cases, a very short (5–10 nm) rod-like stub could be seen at the junction of the arms. The G-domains could sometimes be seen as consisting of two moieties.

Cell Binding to r-laminin 8 and Receptor Identification

We assayed the binding of human fibrosarcoma (HT-1080) and transfected K562 cells to r-laminin 8 in the presence of different blocking anti-integrin antibodies to identify integrin receptors binding to r-laminin 8. Immortomouse brain capillary endothelial (IBE) and bovine adrenal microvascular endothelial (BCE) cells were also used to study the adhesion of endothelial cells to r-laminin 8. The BCE cells express at least integrins α6β1, α6β4, α1β1, α2β1, α3β1, α5β1, αvβ1, αvβ3, and α5β5 (Klein et al., 1993, Mol. Biol. Cell 4(10), 973–82), whereas IBE cells have been reported to express integrins α3, α5 and β1, but not α1, α2, or α6 (Kanda et al., 1999).

Figure 3:
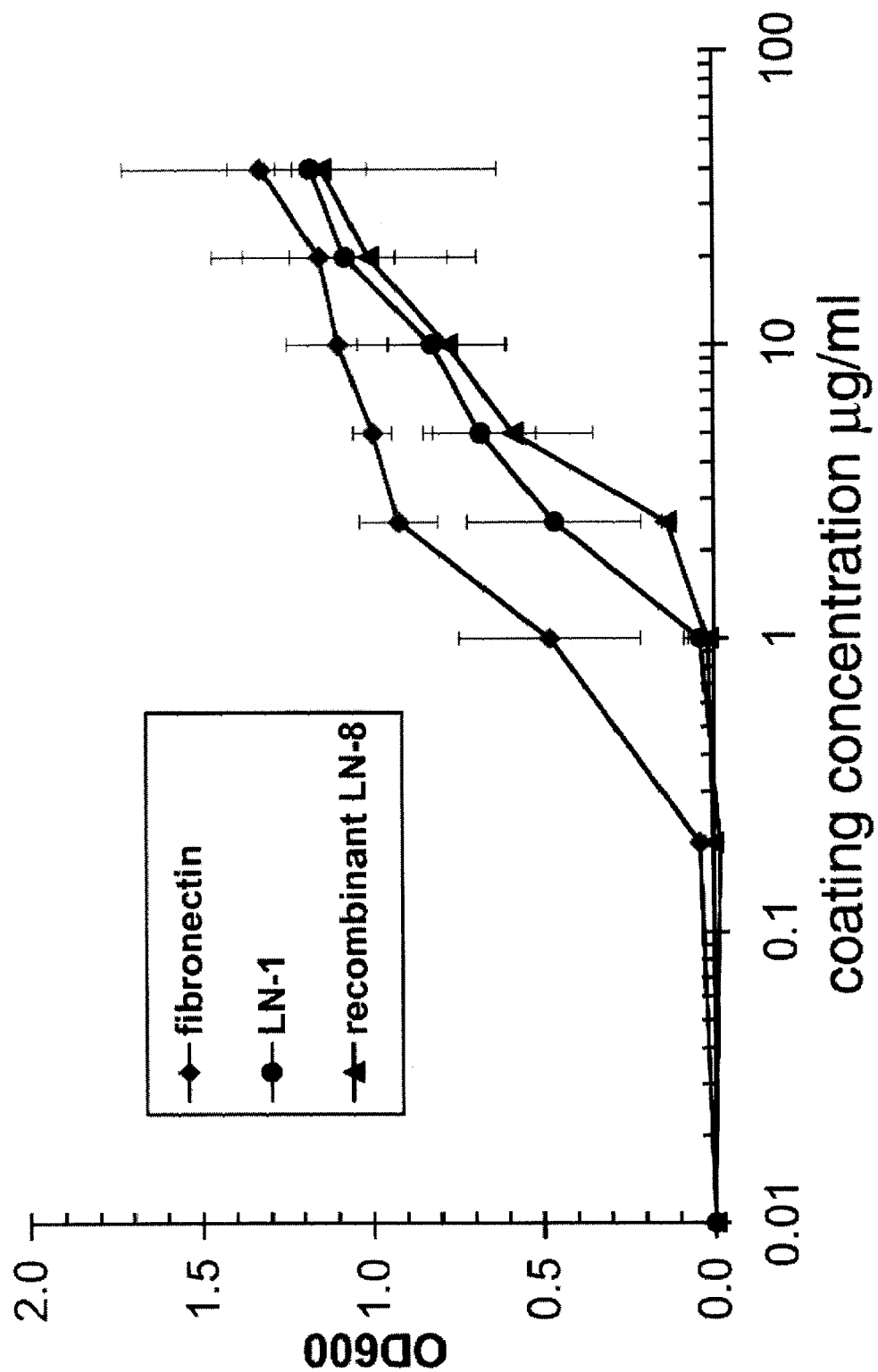
FIG. 3 is a graph depicting a titration of cell adhesion to r-laminin 8 or laminin 1.

When compared to laminin 1, the adhesiveness of r-laminin 8 was quantitatively similar or slightly weaker for the cell lines studied, as approximately the same number of cells bound to both substrates after washing. (FIG. 3) Similar results were obtained with IBE and BCE cells (data not shown). In further cell adhesion assays (FIGS. 4–8), cells were allowed to bind to either-laminin 8 or laminin 1 coated at 10 µg/ml on 96 well plates. Prior to the assay, different components were added to the cell medium. Values indicated are relative to that of control antibody (normal mouse IgG for mouse antibodies and rat $IgG_{2a}$ for rat monoclonal antibodies), which was designated as 100. For other substances, the same volume of buffer was added. Adhesion to bovine serum albumin (BSA) was designated zero. The text under the columns indicate the integrin subunit blocked or the added substance. Error bars indicate SEM. Integrin monoclonal antibodies were used at 10 µg/ml, heparin at 2 mg/ml, and EDTA at 5 mM.

Monoclonal antibodies against integrins α1 and β2 were tested only in the HT-1080 cell line, where they had no or only small effects on cell binding, indicating that these integrins were not major mediators of adhesion to r-laminin 8 (FIG. 4). Adhesion to Type IV collagen was reduced to about 50% by the anti-integrin α2 mAb, demonstrating the presence of active α2 integrin (data not shown). Integrin α1 mAb had only a slight effect on adhesion to collagen IV when used alone, but it had a synergistic effect when used in combination with the α2 mAb (not shown). The Ab against integrin α3 had only minor effects on adhesion of HT-1080 when used alone, but it had a synergistic effect when used in combination with the α2 mAb (data not shown). The monoclonal antibody to α2 integrin had only minor effects on adhesion of HT 1080 (FIG. 4) cells to fibronectin or laminin, even though the cells have been shown to express high levels of α3β1 (Wayner et al., 1993, J. Cell Biol. 121(5), 1141–52). The blocking of integrin α5 had a slight stimulating effect on HT-1080 adhesion to both laminin 1 and laminin 8 (FIG. 4), whereas adhesion of BCE cells to r-laminin 8 was slightly reduced (FIG. 5). The mAb did block adhesion of HT-1080 cells to fibronectin almost completely, indicating the presence of active α5 integrin in these cells (not shown).

α-6 subunit containing integrin(s) were identified as the major mediators of adhesion to r-laminin 8. The integrin α6 subunit is known to associate with either β1 or β4 (Sonnenberg et al., 1990, J. Cell Sci. 96(Pt 2), 207–17). By using a mAb (GoH3) that blocks α6β1- and α6β4-mediated binding, we could completely abolish binding of HT-1080 and BCE cells to r-laminin 8. An anti-β1 integrin mAb (AIIB2) also completely blocked the binding of HT-1080 cells to r-laminin 8 indicating that integrin α6β1 is crucial for adhesion of these cells to r-laminin 8 (FIG. 4). In contrast, binding of BCE cells was blocked only partially (about 70%) by the anti-β1 mAb, suggesting that these endothelial cells use both α6β1 and α6β4 to adhere to r-laminin 8 (FIG. 5). In another endothelial cell line, the mouse IBE cells, the anti-α6 subunit mAb blocked the binding to r-laminin 8 only partially (about 60%), suggesting that the cells are using, in addition to α6-subunit containing integrins, also other receptors (FIG. 6).

Interestingly, when adhesion to r-laminin 8 was compared to that of laminin 1, it was observed that the adhesion was quite differently affected by the blocking anti-α6 and anti-α1 integrin mAbs. HT-1080 cells interacted with laminin 1 not only via α6β1 integrin, but also via other β1-subunit-containing integrin(s), since the blocking was only partial with anti-α6, but complete with anti-β1. (FIG. 4) Furthermore, the adhesion of BCE cells to laminin 1 was mediated by β1 integrin(s) other than α6β1, since the adhesion was completely blocked by anti-β1, but was only minimally affected by anti-α6. (FIG. 5) Similarly, in IBE cells, the adhesion to laminin 1 was mediated by receptors other than α6 integrin(s), since it was not affected by anti-α6. (FIG. 6).

To verify the role of α6β1 and α6β4 integrins as r-laminin 8 receptors, transfected K562 cells were used. Parental K562 cells endogenously express only integrin α5β1, which is in an inactive state. The cells normally grow in suspension but can be made adherent with an activating anti-β1 Ab or stimulation with PMA. K562 cells transfected with the α6 subunit express α6β1 on the cell surface (Delwel et al., 1993). Interestingly, while these cells bound laminin 1 efficiently only after stimulation with PMA, they bound r-laminin 8 strongly even without stimulation (FIG. 8). This finding demonstrates that the adhesive properties of r-laminin 8 are different from those of laminin 1. The cell adhesion to both laminin isoforms could be blocked with either anti-integrin α6 or β1 mAbs, which agrees with results obtained with other cell lines (FIG. 4–5). In addition to inactive α6β1, K562 cells transfected with α6 and β4 subunits express constitutively active α6β4 complex, and can bind laminin 1 even without stimulation (Niessen et al., 1994). We found that these cells bound to both laminin 1 and laminin 8 without stimulation, although activation of the β1 integrins with PMA resulted in increased adhesion. The adhesion of non-stimulated cells could be completely inhibited with anti-integrin α6, but only partially with anti-β1, again indicating that α6β4 is able to mediate adhesion to r-laminin 8 (FIG. 7). In contrast, K562 cells expressing α3β1 adhered poorly to both laminin isoforms (not shown). This agrees with an earlier study where α3-transfected K562 cells were found to bind efficiently to laminin 8, but poorly to laminin 1 (Delwel et al., 1994).

Cell adhesion to both laminin 1 and r-laminin 8 was found to be dependent on divalent cations, since it could be abolished by 5 mM EDTA in all cell lines tested (FIGS. 4–8). Heparin, when used at 2 mg/ml, had no effect on the adhesion of HT-1080, BCE, and IBE to r-laminin 8 (FIGS. 4–6). On laminin 1, however, there was a slight decrease in adhesion of BCE cells (FIG. 5), while the other cell lines were unaffected (FIGS. 4,6). The RGDS-peptide that is reported to block the function of various integrins (Pierschbacher and Ruoslahti, 1984, *Nature* 309(5963), 30–3) had no effect at 1 mM concentration on adhesion of HT-1080, BCE, or IBE cells to the laminins (data not shown).

It was further observed that the cell-binding activity of r-laminin 8 was sensitive to air-drying. When the coated protein was allowed to air dry for 15 minutes at room temperature before adding the cells, the cell-binding activity of r-laminin 8 was completely lost (FIG. 4). Even shorter than a 15 minute exposure could abolish the cell-binding activity (not shown). A drop of buffer was allowed to sit on the plastic, while the rest of the well was briefly exposed to air drying. On the dried area, the BCE cells were rounded, and only a few of them showed any signs of spreading. On the area kept wet, practically all cells were well spread and tightly adhered to the surface. Accordingly, all cells on the dried area were lost during washing.

Laminin 1 was not as sensitive to this effect, but drying still reduced the cell binding activity by half (FIG. 4).

DISCUSSION

The present work provides significant advances concerning the recently described laminin 8 isoform and its α4 chain. Large quantities or r-laminin 8 could be produced as native trimeric protein in cultured human cells, and the r-laminin 8 was shown to be biologically active and to have cell adhesive properties. Furthermore, r-laminin 8 was shown to have a preference for binding to the α6 integrins.

The r-laminin 8 produced in this study is a species hybrid of two human (α4 and γ1) and one mouse (β1) chains, and it contained a FLAG epitope tag attached to the C-terminus of the α4 chain. Despite these modifications, r-laminin 8 assembled into trimers in a manner expected from a native laminin protein, as demonstrated by rotary shadowing EM. The amount of r-laminin 8 produced by the HEK-293 cells in monolayer cultures was quite high considering the size and complexity of the protein. An amount of 3–5 mg/L of culture medium is similar to what is frequently obtained in eukaryotic systems, such as the baculovirus insect cell system.

Similarly to other laminin isoforms characterized to date, all the chains of the r-laminin 8 trimer were disulfide linked to each other. Only a minor fraction consisted of disulfide-linked γ1/γ1 containing dimers and non-crosslinked α4. These chains were also associated into trimers, since the dimers followed the FLAG-tagged α4 chain in immunoprecipitations using the anti-FLAG mAb. The presence of the α4 chain in r-laminin 8 trimers was also demonstrated by showing that all of the α4 could be immunoprecipitated after several rounds of immunoprecipitation with the anti-laminin 1 Ab that recognizes the α1, β1, and γ1 chains (data not shown).

The reason for the two minor r-laminin 8 bands of different size reacting with EHS and γ1 antibodies is unclear. The larger one agrees with the size for a dimer, but the smaller one could not be accounted for. The size difference could be as large as 100 kD. It is possible that these dimers and non-covalent trimers are the products of incomplete or incorrect post-translational processing due to overexpression.

The purified r-laminin 8 was shown to have biological activity, as all cell lines tested in this study adhered to and spread equally well on r-laminin 8 as on laminin 1. This activity could be abolished by drying the protein, suggesting that native conformation was important for full cell binding activity. The cell binding in all cases be abolished by EDTA, indicating dependence on divalent cations.

A large variety of integrins have been implicated as receptors for different laminin isoforms. In this study, we demonstrated that integrins α6β1 and α6β4 were major mediators of cell adhesion to r-laminin 8. The adhesion of HT-1080 and BCE cells was completely blocked by anti-integrin α6 mAb, despite the fact that both cell lines express a wide spectrum of β1 and αv integrins, including several of those shown to bind to other laminin isoforms. (Conforti et. al., 1994, *Cell Adhes. Commun.* 1(4), 279–93) HT-1080 cell adhesion to r-laminin 8 is mediated solely by integrin α6β1, since the adhesion could be blocked not only by anti-α6 mAb, but also by the β1 antibody. In contrast, the β1 mAb only partially blocked adhesion to BCE cells, suggesting that α6β4 contributed to the binding of BCE cells to r-laminin 8. The role of α6β4 as a r-laminin 8 receptor was confirmed by assaying the binding of α6 and β4 transfected K562 cells that express both α6β1 and α6β4 on the cell surface. Indeed, adhesion was completely blocked with α6 mAb, but only partially with β1 mAb, indicating that the α6β4 complex also binds to r-laminin 8. K562 cells expressing α6β1 bound r-laminin 8 while α3β1 expressing cells did not, thus confirming that integrin α6β1 binds r-laminin 8. Our results somewhat contradict the reported lack of integrin α6 subunit in IBE cells (Kanda et al, 1999), since the adhesion to r-laminin 8 was severely perturbed by the anti-integrin α6 mAb. The result suggests that these cells use yet another receptor(s) in addition to α6 integrins for binding to r-laminin 8. However, in certain cases GoH3 is not able to completely block integrin α6 in α6β4 complexes (Sonnenberg et al., 1993, *J. Cell Sci.* 106(Pt 4), 1083–102). Thus, the remaining adhesion could be due to incompletely blocked α6β4 complexes.

Interestingly, adhesion of the cell lines tested to r-laminin 8 was found to be more dependent on integrin α6 than adhesion of the cell lines to laminin 1. Another indication of the different adhesive properties of r-laminin 8 and laminin 1 was the finding that α6β1-expressing K562 cells did bind to r-laminin 8 without stimulation, but, as also previously reported (Delwel et al., 1993), needed to be stimulated by PMA to efficiently bind to laminin 1 coated surfaces. Thus, r-laminin 8 appears to have a higher avidity or affinity than laminin 1 to α6β1. The α6β1 integrin might bind r-laminin 8 even in the conformation that makes it unable to bind to laminin 1, or the cells could be stimulated by the presence of r-laminin 8 via an unknown mechanism. It could be that the avidity/affinity difference is of biological significance, and may well be one reason for the existence of large numbers of laminin isoforms.

In addition to integrins, several other cell surface proteins have been reported to function as laminin receptors. Alpha-dystroglycan is a component of the dystrophin-dystroglycan complex in the skeletal muscle thought to connect the contractile cytoskeleton to the extracellular matrix. Dystroglycan has also been shown to bind laminin 2 and dystrophin, forming a link between the two. (Ervasti and Campbell, 1993, *J. Cell Biol.* 122(4), 809–23) Indirect evidence suggests that laminin 8 might bind to α-dystroglycan; it has been shown that laminin from laminin αd-deficient dystrophic muscle bound dystroglycan, but, in contrast to laminin from normal muscle, in a manner that was sensitive to inhibition by heparin. (McDearmon et al., 1998, *J. Biol. Chem.* 273(37), 24139–44) Since upregulation of laminin α4 has been observed in laminin α2 deficient muscular dystrophy (Patton et al, 1997; Ringelmann et al., 1999), it can be assumed that the laminin α4 chain is involved in the observed interaction. Alpha-dystroglycan is not restricted to skeletal muscle. (Durbeej et al. 1998, *J. Histochem. Cytochem.* 46(4), 449–57) It was recently shown to be a receptor for laminin 1 in bovine aorta endothelial cells, binding in a manner sensitive to heparin, dextran sulfate, and fucoidan. (Shimizu et al., 1999, *J. Biol. Chem.* 274(17), 11995–2000) Heparin-sensitive interactions were not detected in this study, but this does not rule out the possibility of such interactions in other cell types or in vivo. We did observe that the r-laminin 8 binds heparin-sepharose at physiological salt concentration (data not shown).

In this study, integrins α6β1 and α6β4 were identified as receptors for r-laminin 8 in cultured cells, and thus it is likely that these integrins mediate binding of laminin 8 in vivo, such as to endothelial and muscle cells. Endothelial cells express a wide variety of integrins depending on developmental stage, activation state, and location. At least integrins α6β1, α5β1, α6β1, α6β4, and αvβ3 have been found in endothelial cells in vivo (Sonnenberg 1990; Conforti 1992), whereas the main laminin isoforms in endothelial basement membranes (BM) are laminins 8 and 10. Other cells besides endothelial cells are likely to interact with the laminin 8 in endothelial BM; platelets contain and secrete laminin 8 when stimulated and adhere to it using the α6β1 intregrin.

Laminins 8 and 9 are also found in developing muscle and in the peripheral nervous system, overlapping in expression with integrin α6. In laminin α2-deficient muscle, both the laminin α4 and integrin α6 are upregulated. (Vachon et al, 1997, *J. Clin. Invest.* 100(7), 1870–81) Interestingly, integrin α6 and integrin β4 knock-outs result in epidemolysis bullosa (Georges-Labouesse et al, 1996, *Nat. Genet.* 13(3), 370–3; van der Neut et al., 1996, *Nat. Genet.* 13(3), 366–9), but no muscular or vascular phenotype was reported.

The present invention is not limited by the aforementioned particular preferred embodiments. It will occur to those ordinarily skilled in the art that various modifications may be made to the disclosed preferred embodiments without diverting from the concept of the invention. All such modifications are intended to be within the scope of the present invention.

We claim:

1. A pharmaceutical composition comprising:

a) a substantially purified laminin 8, comprising:
- a first polypeptide chain comprising an amino acid sequence selected from the group consisting of SEQ ID NO: 2, SEQ ID NO: 4, SEQ ID NO: 6, or SEQ ID NO: 8, or a secreted form thereof;
- a second polypeptide chain comprising an amino acid sequence selected from the group consisting of SEQ ID NO: 14, and SEQ ID NO: 16, or a secreted form thereof; and
- a third polypeptide chain comprising an amino acid sequence selected from the group consisting of SEQ ID NO: 22 or SEQ ID NO: 24, or a secreted form thereof; and b) a pharmaceutically acceptable carrier.

2. The pharmaceutical composition of claim 1, wherein at least one of the first polypeptide chain, the second polypeptide chain, and the third polypeptide chain further comprise an epitope tag.

3. The pharmaceutical composition of claim 1, wherein at least two of the first polypeptide chain, the second polypeptide chain, and the third polypeptide chain further comprise an epitope tag.

* * * * *